US008361968B2

(12) United States Patent
Kitada et al.

(10) Patent No.: US 8,361,968 B2
(45) Date of Patent: Jan. 29, 2013

(54) METASTIN DERIVATIVES AND USE THEREOF

(75) Inventors: Chieko Kitada, Osaka (JP); Taiji Asami, Tsukuba (JP); Naoko Nishizawa, Ibaraki (JP); Tetsuya Ohtaki, Tsukuba (JP); Naoki Tarui, Osaka (JP); Hirokazu Matsumoto, Ibaraki (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/135,230

(22) Filed: Jun. 29, 2011

(65) Prior Publication Data

US 2012/0015868 A1 Jan. 19, 2012

Related U.S. Application Data

(60) Division of application No. 12/455,563, filed on Jun. 2, 2009, now abandoned, which is a continuation of application No. 10/540,494, filed as application No. PCT/JP03/16978 on Dec. 26, 2003, now abandoned.

(30) Foreign Application Priority Data

Dec. 26, 2002 (JP) ................................ 2002-377179

(51) Int. Cl.
*A61P 35/04* (2006.01)
*A61P 35/00* (2006.01)
*A61K 38/08* (2006.01)

(52) U.S. Cl. ..................... 514/19.8; 514/19.3; 514/21.6; 530/328; 530/323

(58) Field of Classification Search ................. None
See application file for complete search history.

(56) References Cited

U.S. PATENT DOCUMENTS

| | | | |
|---|---|---|---|
| 6,800,611 B2 | 10/2004 | Fujii et al. | |
| 7,625,869 B2 | 12/2009 | Kitada et al. | |
| 2004/0142875 A1 | 7/2004 | Fujii et al. | |
| 2009/0215700 A1 | 8/2009 | Asami et al. | |
| 2010/0286035 A1 | 11/2010 | Ohtaki et al. | |

FOREIGN PATENT DOCUMENTS

| | | |
|---|---|---|
| EP | 162 575 | 11/1985 |
| EP | 0472220 A1 | 2/1992 |
| EP | 1 577 323 | 9/2005 |
| EP | 1577323 A1 | 9/2005 |
| EP | 1604682 A1 | 12/2005 |
| JP | 9-169735 A | 6/1997 |
| JP | 2003-026601 | 1/2003 |
| JP | 2003300906 A | 10/2003 |
| JP | 2004217651 A | 8/2004 |
| RU | 2002102081 | 9/2003 |
| RU | 2005135739 A | 3/2006 |
| RU | 2306147 C2 | 9/2007 |
| RU | 2311920 C2 | 12/2007 |
| RU | 2006/145886 A | 6/2008 |
| RU | 2333221 C2 | 9/2008 |
| RU | 2344831 C2 | 1/2009 |
| RU | 2008125063 A | 12/2009 |
| WO | WO-9611953 A1 | 4/1996 |
| WO | WO-97/40071 | 10/1997 |
| WO | WO-98/39448 | 9/1998 |
| WO | WO-00/24890 | 5/2000 |
| WO | WO-00/24890 A1 | 5/2000 |
| WO | WO-0100228 | 1/2001 |
| WO | WO-01/44469 A1 | 6/2001 |
| WO | WO-0141812 | 6/2001 |
| WO | WO-01/74377 A1 | 10/2001 |
| WO | WO-01/75104 | 10/2001 |
| WO | WO-01/75104 A1 | 10/2001 |
| WO | WO-0172295 | 10/2001 |
| WO | WO-0179286 | 10/2001 |
| WO | WO-02/085399 A1 | 10/2002 |
| WO | WO-02/092829 A1 | 11/2002 |
| WO | WO-02/092829 A1 | 11/2002 |
| WO | WO-03/027149 A1 | 4/2003 |
| WO | WO-03/060125 A1 | 7/2003 |
| WO | WO-2004/038021 A1 | 5/2004 |
| WO | WO-2004/060264 | 7/2004 |
| WO | WO-2004/060264 A2 | 7/2004 |
| WO | WO 2004/063221 A1 | 7/2004 |
| WO | WO-2004/073730 A1 | 9/2004 |
| WO | WO-2004/080749 A2 | 9/2004 |
| WO | WO-2004/087622 A2 | 10/2004 |
| WO | WO-2004/093894 A2 | 11/2004 |
| WO | WO-2004/096855 A2 | 11/2004 |
| WO | WO-2004/101747 A2 | 11/2004 |
| WO | WO-2004/106289 A1 | 12/2004 |
| WO | WO-2005/042744 A1 | 5/2005 |
| WO | WO-2005/095973 A2 | 10/2005 |
| WO | WO-2006/001499 A2 | 1/2006 |
| WO | WO-2007/072997 A1 | 6/2007 |
| WO | WO-2007/072997 A1 | 6/2007 |
| WO | WO-2007/084211 A2 | 7/2007 |

(Continued)

OTHER PUBLICATIONS

A.S. Dutta et al., "Polypeptides, Part 15.[1,2] Synthesis and Biological Activity of α-Aza-analogues of Luliberin modified in Positions 6 and 10," *Journal of the Chemical Society*, 1(2), pp. 379-388 (1978).

M.L. Gottsch et al., "A Role for Kisspeptins in the Regulation of Gonadotropin Secretion in the Mouse", *Endocrinology*, 145(9), pp. 4073-4077 (2004).

M.D. Ringel et at, "Metastin receptor is overexpressed in Papillary Thyroid Cancer and Activates MAP Kinase in Thyroid Cancer Cells", *The Journal of Clinical Endocrinology & Metabolism*, 87(5), pp. 2399-2402 (May 2002).

(Continued)

*Primary Examiner* — Christina Bradley
(74) *Attorney, Agent, or Firm* — Edwards Wildman Palmer LLP; David G. Conlin, Esq.; Kathryn A. Piffat, Esq.

(57) ABSTRACT

The present invention provides a metastin derivative in which the amino acids comprising metastin were modified by alternative chemical substituents resulting in metastin derivitives, having excellent blood stability and exhibiting cancer metastasis inhibiting action or cancer growth inhibiting action.

2 Claims, 10 Drawing Sheets

FOREIGN PATENT DOCUMENTS

| WO | WO-2007/109135 A2 | 9/2007 |
|---|---|---|
| WO | WO-2008/050897 A1 | 5/2008 |
| WO | WO-2009/131191 A1 | 10/2009 |
| WO | WO-2010/033224 A1 | 3/2010 |

OTHER PUBLICATIONS

N. Venkatesan et al., "Synthesis and Enzyme Inhibitory Activities of Novel Peptide Isosteres", *Current Medicinal Chemistry*, vol. 9, pp. 2243-2270 (2002).

K. Tomita et al., "Structure-activity relationship study on small peptidic GPR54 agonists", *Bioorganic & Medicinal Chemistry*, vol. 14, pp. 7595-7603 (2006).

A. Niida et al., "Design and synthesis of downsized metastin (45-54) analogs with maintenance of high GPR54 agonistic activity", *Bioorganic & Medicinal Chemistry*, vol. 16, pp. 134-137 (2006).

Harms et al., "KISS1 metastasis suppression and emergent pathways", *Clinical and Experimental Metastasis*, vol. 20, pp. 11-18 (2003).

Masui et al., "Metastin and its variant forms suppress migration of pancreatic cancer cells", *Biochem. Biophys. Res. Com.*, vol. 315, pp. 85-92 (2004).

Jiang et al., "KISS1 Suppresses Metastasis in Human Ovarian Cancer via Inhibition of Protein Kinase C Alpha", *Clinical and Experimental Metastasis*, vol. 22, pp. 369-376 (2005).

Nash et al., "The KISS1 metastasis suppressor: mechanistic insights and clinical utility", *Front. Biosci.* vol. 11, pp. 647-659 (2006).

S. Han et al., "Orphan G protein-coupled receptors MrgA1 and MrgC11 are distinctively activated by RF-amide-related peptides through the Gαq/11 pathway", *PNAS*, 99(23), pp. 14740-14745 (2000).

M. Kotsani et al., "The Metastasis Suppressor Gene KiSS-1 Encodes Kisspeptins, the Natural Ligands of the Orphan G Protein-coupled Receptor GPR54", *The Journal of Biological Chemistry*, 276(37), pp. 34631-34636 (2001).

The gist of speech of the 53rd Pharmaceutical Society of Japan, 2003, Organic 2,m B-13-2, p. 68.

European Search Report dated Mar. 4, 2008 for EPO 03768337.2-2406 corresponding to this US application.

M.K. Clements et al., "FMRF amide-related neuropeptides are agonists of the orphan G-protein-coupled receptor GPR54", *Biochemical and Biophysical Research Communications*, 284(5), pp. 1189-1193 (2001).

A.I. Muir et al., "AXOR12, a Novel Human G Protein-coupled Receptor, Activated by the Peptide KiSS-1", *Journal of Biological Chemistry, American Society of Biochemical Biologists*, 276(31), pp. 28969-28975 (2001).

C. Frochot et al., "A Solid-Phase Synthesis of Three AZA-, Iminoaza- and Reduced AZA-Peptides From the Same Precursor", *Letters in Peptide Science* 4(4-6), pp. 219-225 (1997).

Journal of the Chemical Socieity, Perkin Transactions 1, No. 2, pp. 379-388.

*Nature*, vol. 411, pp. 613617 (2001).

*The Journal of Clinical Endocrinology & Metabolism*, vol. 88, pp. 914-919 (2003).

T. Masui et al., *Biochemical and Biophysical Research Communications*, vol. 315, pp. 85-92 (2004).

Y. Terao et al., *Biochemical and Biophysical Acta*, 1678, pp. 102-110 (2004).

M.L. Gottisch et al., *Endocrinology* 145, pp. 4073-4077.

Notification of Transmittal of Translation of the International Preliminary Report on Patentability (PCT/IB/338) mailed Aug. 25, 2005.

English translation of the International Preliminary Report on Patentability (PCT/IPEA/409) dated Sep. 13, 2004.

"A prolactin-releasing peptide in the brain", Hinuma et al.; Letters to Nature, vol. 393, pp. 272-276, May 21, 1998.

"Working backwards to find answers", Jean-Claude Meunier; Nature vol. 393, pp. 211-212, May 21, 1998.

"Characterization of a cDNA encoding a novel avian hypothalamic neuropeptide exerting an inhibitory effect on gonadotropin release"; Satake et al., pp. 379-385; Biochem J. (2001) 354.

Bruehlmeier M. et al., "Stabilization of neurotensin analogues: effect on peptide catabolism, biodistribution and tumor binding"; Nuclear Medicine and Biology, vol. 29, No. 3; Apr. 1, 2002, pp. 321-327.

Cudic M et al., "Development of novel antibacterial peptides that kill resistant isolates"; Peptides, Elsevier; vol. 23, Jan. 1, 2002, pp. 2071-2083.

Stafford, L.J. et al., Frochot, C. et al., "Identification and Characterization of mouse metastatis-suppressor KiSS1 and its G-protein-coupled receptor", Cancer Research, American Association for Cancer Research, vol. 62, No. 19, pp. 5399-5404 (2002).

Search Report for Georgian Patent Applicaton AP2007011265 (Nov. 16, 2010).

Extended European Search Report, 4 pages (dated Oct. 6, 2010).

Search Report, along with English Translation of Seach Report for Georgian Patent Application No. AP2006010770 (dated Nov. 30, 2009).

Makri at al., The kisspeptin (KiSS-1)/GPR54 system in cancer biology, Cancer Treatment Reviews (2008) 34, 682-692.

W.S. Dhillo, 2008, Kisspeptin: A Novel Regulator of Reproductive Function, Journal of Neuroendocrinology 20, 963-970.

EJ Mead et al., Kisspeptins: a multifunctional peptide system with a role in reproduction, cancer and the cardiovascular system; British Journal of Pharmacology (2007) 151, 1143-1153.

```
                       SEQUENCE LISTING

<160> NUMBER OF SEQ ID NOS: 229

<210> SEQ ID NO 1
<211> LENGTH: 54
<212> TYPE: PRT
<213> ORGANISM: Homo sapiens

<400> SEQUENCE: 1

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 2
<211> LENGTH: 162
<212> TYPE: DNA
<213> ORGANISM: Homo sapiens

<400> SEQUENCE: 2
ggtacttctc tgtctccgcc gccggaatct tctggttctc gtcagcagcc gggtctgtct    60
gctccgcact ctcgtcagat cccggctccg cagggtgctg ttctggttca gcgtgaaaaa   120
gacctgccga actacaactg gaactctttc ggtctgcgtt tc                      162

<210> SEQ ID NO 3
<211> LENGTH: 152
<212> TYPE: PRT
<213> ORGANISM: Mus musculus

<400> SEQUENCE: 3

Met Tyr Leu Arg Phe Gly Val Asp Val Cys Ser Leu Ser Pro Trp Lys
1               5                   10                  15

Glu Thr Val Asp Leu Pro Leu Pro Pro Arg Met Ile Ser Met Ala Ser
            20                  25                  30

Trp Gln Leu Leu Leu Leu Leu Cys Val Ala Thr Tyr Gly Glu Pro Leu
        35                  40                  45

Ala Lys Val Ala Pro Gly Ser Thr Gly Gln Gln Ser Gly Pro Gln Glu
    50                  55                  60

Leu Val Asn Ala Trp Glu Lys Glu Ser Arg Tyr Ala Glu Ser Lys Pro
65                  70                  75                  80

Gly Ser Ala Gly Leu Arg Ala Arg Arg Ser Ser Pro Cys Pro Pro Val
            85                  90                  95

Glu Gly Pro Ala Gly Arg Gln Arg Pro Leu Cys Ala Ser Arg Ser Arg
            100                 105                 110

Leu Ile Pro Ala Pro Arg Gly Ala Val Leu Val Gln Arg Glu Lys Asp
            115                 120                 125

Leu Ser Thr Tyr Asn Trp Asn Ser Phe Gly Leu Arg Tyr Gly Arg Arg
        130                 135                 140

Gln Ala Ala Arg Ala Ala Arg Gly
```

<210> SEQ ID NO 4
<211> LENGTH: 456
<212> TYPE: DNA
<213> ORGANISM: Mus musculus

<400> SEQUENCE: 4

```
atgtatctga gatttggcgt tgatgtctgc agcctgagtc cctggaagga gactgtagac    60
ctgccccttc ctcccagaat gatctcaatg gcttcttggc agctgctgct tctcctctgt   120
gtcgccacct atggggagcc gctggcaaaa gtgaagcctg gatccacagg ccagcagtcc   180
ggaccccagg aactcgttaa tgcctgggaa aggaatcgc ggtatgcaga gagcaagcct   240
gggtctgcag gctgcgcgc tcgtaggtcg tcgccatgcc cgccggttga gggccccgcg   300
gggcgccagc ggcccctgtg tgcctcccgc agtcgcctga tccctgcgcc ccgcggagcg   360
gtgctggtgc agcgggagaa ggacctgtcc acctacaact ggaactcctt cggcctgcgc   420
tacggcagga ggcaggcggc gcgggcagca cggggc                             456
```

<210> SEQ ID NO 5
<211> LENGTH: 156
<212> TYPE: PRT
<213> ORGANISM: Mus musculus

<400> SEQUENCE: 5

```
Met Tyr Leu Arg Phe Gly Val Asp Val Cys Ser Leu Ser Pro Trp Lys
1               5                   10                  15
Glu Thr Val Asp Leu Pro Leu Pro Pro Arg Met Ile Ser Met Ala Ser
                20                  25                  30
Trp Gln Leu Leu Leu Leu Leu Cys Val Ala Thr Tyr Gly Glu Pro Leu
            35                  40                  45
Ala Lys Val Ala Pro Leu Val Lys Pro Gly Ser Thr Gly Gln Gln Ser
        50                  55                  60
Gly Pro Gln Glu Leu Val Asn Ala Trp Glu Lys Glu Ser Arg Tyr Ala
65                  70                  75                  80
Glu Ser Lys Pro Gly Ser Ala Gly Leu Arg Ala Arg Arg Ser Ser Pro
                85                  90                  95
Cys Pro Pro Val Glu Gly Pro Ala Gly Arg Gln Arg Pro Leu Cys Ala
            100                 105                 110
Ser Arg Ser Arg Leu Ile Pro Ala Pro Arg Gly Ala Val Leu Val Gln
        115                 120                 125
Arg Glu Lys Asp Leu Ser Thr Tyr Asn Trp Asn Ser Phe Gly Leu Arg
    130                 135                 140
Tyr Gly Arg Arg Gln Ala Ala Arg Ala Ala Arg Gly
145                 150                 155
```

<210> SEQ ID NO 6
<211> LENGTH: 468
<212> TYPE: DNA
<213> ORGANISM: Mus musculus

<400> SEQUENCE: 6

```
atgtatctga gatttggcgt tgatgtctgc agcctgagtc cctggaagga gactgtagac    60
ctgccccttc ctcccagaat gatctcaatg gcttcttggc agctgctgct tctcctctgt   120
gtcgccacct atggggagcc gctggcaaaa gtggcacctt tggtgaagcc tggatccaca   180
ggccagcagt ccggacccca ggaactcgtt aatgcctggg aaaaggaatc gcggtatgca   240
```

-continued

```
gagagcaagc ctgggtctgc agggctgcgc gctcgtaggt cgtcgccatg cccgccggtt      300
gagggccccg cggggcgcca gcggcccctg tgtgcctccc gcagtcgcct gatccctgcg      360
ccccgcggag cggtgctggt gcagcgggag aaggacctgt ccacctacaa ctggaactcc      420
ttcggcctgc gctacggcag gaggcaggcg gcgcgggcag cacggggc                    468
```

<210> SEQ ID NO 7
<211> LENGTH: 130
<212> TYPE: PRT
<213> ORGANISM: Rattus sp.

<400> SEQUENCE: 7

```
Met Thr Ser Leu Ala Ser Trp Gln Leu Leu Leu Leu Cys Val Ala
1               5                   10                  15

Ser Phe Gly Glu Pro Leu Ala Lys Met Ala Pro Val Val Asn Pro Glu
                20                  25                  30

Pro Thr Gly Gln Gln Ser Gly Pro Gln Glu Leu Val Asn Ala Trp Gln
            35                  40                  45

Lys Gly Pro Arg Tyr Ala Glu Ser Lys Pro Gly Ala Ala Gly Leu Arg
        50                  55                  60

Ala Arg Arg Thr Ser Pro Cys Pro Pro Val Glu Asn Pro Thr Gly His
65                  70                  75                  80

Gln Arg Pro Pro Cys Ala Thr Arg Ser Arg Leu Ile Pro Ala Pro Arg
                85                  90                  95

Gly Ser Val Leu Val Gln Arg Glu Lys Asp Met Ser Ala Tyr Asn Trp
            100                 105                 110

Asn Ser Phe Gly Leu Arg Tyr Gly Arg Arg Gln Val Ala Arg Ala Ala
        115                 120                 125

Arg Gly
    130
```

<210> SEQ ID NO 8
<211> LENGTH: 390
<212> TYPE: DNA
<213> ORGANISM: Rattus sp.

<400> SEQUENCE: 8

```
atgacctcgc tggcttcttg gcagctgctg cttctcctct gtgtggcctc ttttggggag      60
ccactggcaa aaatggcacc tgtggtgaac cctgaaccca caggccaaca gtccggaccc     120
caggaactcg ttaatgcctg caaaagggc ccgcggtatg cagagagcaa gcctggggct      180
gcaggactgc gcgctcgccg aacatcgcca tgcccgccgg tggagaaccc cacggggcac     240
cagcggcccc cgtgtgccac ccgcagtcgc ctgatccctg cgccccgcgg atcggtgctg     300
gtgcagcgcg agaaggacat gtcagcctac aactggaact cctttggcct cgctacggc      360 aggaggcagg tggcgcgggc ggcacggggc                                       390
```

<210> SEQ ID NO 9
<211> LENGTH: 398
<212> TYPE: PRT
<213> ORGANISM: Homo sapiens

<400> SEQUENCE: 9

```
Met His Thr Val Ala Thr Ser Gly Pro Asn Ala Ser Trp Gly Ala Pro
1               5                   10                  15

Ala Asn Ala Ser Gly Cys Pro Gly Cys Gly Ala Asn Ala Ser Asp Gly
                20                  25                  30

Pro Val Pro Ser Pro Arg Ala Val Asp Ala Trp Leu Val Pro Leu Phe
```

```
              35                  40                  45
Phe Ala Ala Leu Met Leu Gly Leu Val Gly Asn Ser Leu Val Ile
 50                  55                  60

Tyr Val Ile Cys Arg His Lys Pro Met Arg Thr Val Thr Asn Phe Tyr
 65                  70                  75                  80

Ile Ala Asn Leu Ala Ala Thr Asp Val Thr Phe Leu Leu Cys Cys Val
                 85                  90                  95

Pro Phe Thr Ala Leu Leu Tyr Pro Leu Pro Gly Trp Val Leu Gly Asp
                100                 105                 110

Phe Met Cys Lys Phe Val Asn Tyr Ile Gln Gln Val Ser Val Gln Ala
                115                 120                 125

Thr Cys Ala Thr Leu Thr Ala Met Ser Val Asp Arg Trp Tyr Val Thr
                130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Val Ser Ala Pro
                165                 170                 175

Val Leu Ala Leu His Arg Leu Ser Pro Gly Pro Arg Ala Tyr Cys Ser
                180                 185                 190

Glu Ala Phe Pro Ser Arg Ala Leu Glu Arg Ala Phe Ala Leu Tyr Asn
                195                 200                 205

Leu Leu Ala Leu Tyr Leu Leu Pro Leu Leu Ala Thr Cys Ala Cys Tyr
210                 215                 220

Ala Ala Met Leu Arg His Leu Gly Arg Val Ala Val Arg Pro Ala Pro
225                 230                 235                 240

Ala Asp Ser Ala Leu Gln Gly Gln Val Leu Ala Glu Arg Ala Gly Ala
                245                 250                 255

Val Arg Ala Lys Val Ser Arg Leu Val Ala Ala Val Val Leu Leu Phe
                260                 265                 270

Ala Ala Cys Trp Gly Pro Ile Gln Leu Phe Leu Val Leu Gln Ala Leu
                275                 280                 285

Gly Pro Ala Gly Ser Trp His Pro Arg Ser Tyr Ala Ala Tyr Ala Leu
290                 295                 300

Lys Thr Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Arg Arg
                325                 330                 335

Val Cys Pro Cys Ala Pro Arg Arg Pro Arg Arg Pro Arg Pro Gly
                340                 345                 350

Pro Ser Asp Pro Ala Ala Pro His Ala Glu Leu His Arg Leu Gly Ser
                355                 360                 365

His Pro Ala Pro Ala Arg Ala Gln Lys Pro Gly Ser Ser Gly Leu Ala
                370                 375                 380

Ala Arg Gly Leu Cys Val Leu Gly Glu Asp Asn Ala Pro Leu
385                 390                 395

<210> SEQ ID NO 10
<211> LENGTH: 1194
<212> TYPE: DNA
<213> ORGANISM: Homo sapiens

<400> SEQUENCE: 10
atgcacaccg tggctacgtc cggacccaac gcgtcctggg gggcaccggc caacgcctcc      60
ggctgcccgg gctgtggcgc caacgcctcg gacggcccag tcccttcgcc gcgggccgtg     120
```

```
gacgcctggc tcgtgccgct cttcttcgcg gcgctgatgc tgctgggcct ggtggggaac    180
tcgctggtca tctacgtcat ctgccgccac aagccgatgc ggaccgtgac caacttctac    240
atcgccaacc tggcggccac ggacgtgacc ttcctcctgt gctgcgtccc cttcacggcc    300
ctgctgtacc cgctgcccgg ctgggtgctg ggcgacttca tgtgcaagtt cgtcaactac    360
atccagcagg tctcggtgca ggccacgtgt gccactctga ccgccatgag tgtggaccgc    420
tggtacgtga cggtgttccc gttgcgcgcc ctgcaccgcc gcacgccccg cctggcgctg    480
gctgtcagcc tcagcatctg ggtaggctct gcggcggtgt ctgcgccggt gctcgccctg    540
caccgcctgt cacccgggcc gcgcgcctac tgcagtgagg ccttccccag ccgcgccctg    600
gagcgcgcct tcgcactgta caacctgctg gcgctgtacc tgctgccgct gctcgccacc    660
tgcgcctgct atgcggccat gctgcgccac ctgggccggg tcgccgtgcg ccccgcgccc    720
gccgatagcg ccctgcaggg gcaggtgctg gcagagcgcg caggcgccgt gcgggccaag    780
gtctcgcggc tggtggcggc cgtggtcctg ctcttcgccg cctgctgggg ccccatccag    840
ctgttcctgg tgctgcaggc gctgggcccc gcgggctcct ggcacccacg cagctacgcc    900
gcctacgcgc ttaagacctg gctcactgc atgtcctaca gcaactccgc gctgaacccg    960
ctgctctacg ccttcctggg ctcgcacttc cgacaggcct tccgccgcgt ctgcccctgc   1020
gcgccgcgcc gccccgcgg ccccgcggg ccggaccct cggaccccgc agccccacac   1080
gcggagctgc accgcctggg gtcccacccg gccccgcca gggcgcagaa gccagggagc   1140
agtgggctgg ccgcgcgcgg gctgtgcgtc ctgggggagg acaacgcccc tctc         1194

<210> SEQ ID NO 11
<211> LENGTH: 396
<212> TYPE: PRT
<213> ORGANISM: Rattus sp.

<400> SEQUENCE: 11

Met Ala Ala Glu Ala Thr Leu Gly Pro Asn Val Ser Trp Trp Ala Pro
1               5                   10                  15

Ser Asn Ala Ser Gly Cys Pro Gly Cys Gly Val Asn Ala Ser Asp Gly
            20                  25                  30

Pro Gly Ser Ala Pro Arg Pro Leu Asp Ala Trp Leu Val Pro Leu Phe
        35                  40                  45

Phe Ala Ala Leu Met Leu Leu Gly Leu Val Gly Asn Ser Leu Val Ile
    50                  55                  60

Phe Val Ile Cys Arg His Lys His Met Gln Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Thr Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Thr Val Ser Leu Ser Ile Trp Val Gly Ser Ala Ala Val Ser Ala Pro
                165                 170                 175

Val Leu Ala Leu His Arg Leu Ser Pro Gly Pro His Thr Tyr Cys Ser
            180                 185                 190
```

```
Glu Ala Phe Pro Ser Arg Ala Leu Glu Arg Ala Phe Ala Leu Tyr Asn
            195                 200                 205

Leu Leu Ala Leu Tyr Leu Leu Pro Leu Leu Ala Thr Cys Ala Cys Tyr
    210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
                245                 250                 255

Val Arg Thr Lys Val Ser Arg Leu Val Ala Ala Val Leu Leu Phe
            260                 265                 270

Ala Ala Cys Trp Gly Pro Ile Gln Leu Phe Leu Val Leu Gln Ala Leu
            275                 280                 285

Gly Pro Ser Gly Ala Trp His Pro Arg Ser Tyr Ala Ala Tyr Ala Leu
290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Gly Pro Gln Arg Gln Arg Arg Pro His Ala Ser Ala
            340                 345                 350

His Ser Asp Arg Ala Ala Pro His Ser Val Pro His Ser Arg Ala Ala
            355                 360                 365

His Pro Val Arg Val Arg Thr Pro Glu Pro Gly Asn Pro Val Val Arg
370                 375                 380

Ser Pro Ser Val Gln Asp Glu His Thr Ala Pro Leu
385                 390                 395

<210> SEQ ID NO 12
<211> LENGTH: 1188
<212> TYPE: DNA
<213> ORGANISM: Rattus sp.

<400> SEQUENCE: 12
atggccgcag aggcgacgtt gggtccgaac gtgagctggt gggctccgtc caacgcttcg      60
ggatgcccgg gctgcggtgt caatgcctcg gatggcccag gctccgcgcc aaggcccctg     120
gatgcctggc tggtgcccct gttttcgct gccctaatgt tgctggggct agtcgggaac      180
tcactggtca tcttcgttat ctgccgccac aagcacatgc agaccgtcac caatttctac     240
atcgctaacc tggcggccac agatgtcact ttccttctgt gctgcgtacc cttcaccgcg     300
ctcctctatc cgctgcccac ctgggtgctg ggagacttca tgtgcaaatt cgtcaactac     360
atccagcagg tctcggtgca agccacatgt gccactttga cagccatgag tgtggaccgc     420
tggtacgtga ctgtgttccc gctgcgtgca cttcaccgcc gcactccgcg cctggccctg     480
actgtcagcc ttagcatctg ggtgggttcc gcagctgttt ccgccccggt gctggctctg     540
caccgcctgt cgcccgggcc tcacacctac tgcagtgagg cgtttcccag ccgtgccctg     600
gagcgcgctt tcgcgctcta caacctgctg gccctatacc tgctgccgct gctcgccacc     660
tgcgcctgct acggtgccat gctgcgccac ctggccgcg ccgctgtacg ccccgcaccc      720
actgatggcg ccctgcaggg gcagctgcta gcacagcgcg ctggagcagt gcgcaccaag     780
gtctcccggc tggtggccgc tgtcgtcctg ctcttcgccg cctgctgggg cccgatccag     840
ctgttcctgg tgcttcaagc cctgggcccc tcggggcct ggcaccctcg aagctatgcc      900
gcctacgcgc tcaagatctg gctcactgc atgtcctaca gcaattctgc gctcaacccg      960
ctgctctatg ccttcctggg ttcccacttc agacaggcct tctgccgcgt gtgccctgc     1020
```

```
ggcccgcaac gccagcgtcg gccccacgcg tcagcgcact cggaccgagc cgcacccccat    1080 agtgtgccgc acagccgggc tgcgcaccct gtccgggtca ggaccccga gcctgggaac     1140 cctgtggtgc gctcgccctc tgttcaggat gaacacactg ccccactc                 1188
```

<210> SEQ ID NO 13
<211> LENGTH: 396
<212> TYPE: PRT
<213> ORGANISM: Mus musculus

<400> SEQUENCE: 13

```
Met Ala Thr Glu Ala Thr Leu Ala Pro Asn Val Thr Trp Trp Ala Pro
1               5                   10                  15

Ser Asn Ala Ser Gly Cys Pro Gly Cys Gly Val Asn Ala Ser Asp Asp
            20                  25                  30

Pro Gly Ser Ala Pro Arg Pro Leu Asp Ala Trp Leu Val Pro Leu Phe
        35                  40                  45

Phe Ala Thr Leu Met Leu Leu Gly Leu Val Gly Asn Ser Leu Val Ile
    50                  55                  60

Tyr Val Ile Cys Arg His Lys His Met Gln Thr Val Thr Asn Phe Tyr
65                  70                  75                  80

Ile Ala Asn Leu Ala Ala Thr Asp Val Thr Phe Leu Leu Cys Cys Val
                85                  90                  95

Pro Phe Thr Ala Leu Leu Tyr Pro Leu Pro Ala Trp Val Leu Gly Asp
            100                 105                 110

Phe Met Cys Lys Phe Val Asn Tyr Ile Gln Gln Val Ser Val Gln Ala
        115                 120                 125

Thr Cys Ala Thr Leu Thr Ala Met Ser Val Asp Arg Trp Tyr Val Thr
    130                 135                 140

Val Phe Pro Leu Arg Ala Leu His Arg Arg Thr Pro Arg Leu Ala Leu
145                 150                 155                 160

Ala Val Ser Leu Ser Ile Trp Val Gly Ser Ala Ala Val Ser Ala Pro
                165                 170                 175

Val Leu Ala Leu His Arg Leu Ser Pro Gly Pro Arg Thr Tyr Cys Ser
            180                 185                 190

Glu Ala Phe Pro Ser Arg Ala Leu Glu Arg Ala Phe Ala Leu Tyr Asn
        195                 200                 205

Leu Leu Ala Leu Tyr Leu Leu Pro Leu Leu Ala Thr Cys Ala Cys Tyr
    210                 215                 220

Gly Ala Met Leu Arg His Leu Gly Arg Ala Ala Val Arg Pro Ala Pro
225                 230                 235                 240

Thr Asp Gly Ala Leu Gln Gly Gln Leu Leu Ala Gln Arg Ala Gly Ala
                245                 250                 255

Val Arg Thr Lys Val Ser Arg Leu Val Ala Ala Val Val Leu Leu Phe
            260                 265                 270

Ala Ala Cys Trp Gly Pro Ile Gln Leu Phe Leu Val Leu Gln Ala Leu
        275                 280                 285

Gly Pro Ser Gly Ala Trp His Pro Arg Ser Tyr Ala Ala Tyr Ala Val
    290                 295                 300

Lys Ile Trp Ala His Cys Met Ser Tyr Ser Asn Ser Ala Leu Asn Pro
305                 310                 315                 320

Leu Leu Tyr Ala Phe Leu Gly Ser His Phe Arg Gln Ala Phe Cys Arg
                325                 330                 335

Val Cys Pro Cys Cys Arg Gln Arg Gln Arg Arg Pro His Thr Ser Ala
            340                 345                 350
```

```
His Ser Asp Arg Ala Ala Thr His Thr Val Pro His Ser Arg Ala Ala
        355                 360                 365

His Pro Val Arg Ile Arg Ser Pro Glu Pro Gly Asn Pro Val Val Arg
        370                 375                 380

Ser Pro Cys Ala Gln Ser Glu Arg Thr Ala Ser Leu
385                 390                 395

<210> SEQ ID NO 14
<211> LENGTH: 1188
<212> TYPE: DNA
<213> ORGANISM: Mus musculus

<400> SEQUENCE: 14
atggccaccg aggcgacatt ggctcccaat gtgacctggt gggctccgtc caacgcttca      60
ggatgcccag gctgcggtgt caacgcctcg gatgacccag gctctgcgcc aaggcccctg     120
gatgcctggc tggttcccct gttttttcgct acactcatgt tgcttgggct ggtcggaaac    180
tcattggtca tctacgttat ctgccgccac aagcacatgc agacagttac caacttctac    240
atcgctaacc tggctgccac agacgtcact ttcctactgt gctgcgtgcc cttcaccgca    300
ctcctctacc cgctgcccgc ctgggtgctg ggagacttca tgtgcaaatt cgtcaactac    360
atccagcagg tctcggtgca agccacatgt gccactctga cggccatgag tgtgaccgc     420
tggtatgtga ctgtgttccc gctgcgtgca cttcaccgcc gcactccgcg cctggccctg    480
gctgtcagcc tcagcatctg ggtggggtca gcagctgtgt ccgcccccggt gctggccctg   540
caccgcctgt cgccagggcc tcgcacctac tgcagcgagg cgtttcccag ccgcgccctg    600
gagcgcgcct tcgcgctcta caacctgctg gctctatatc tgctgccgct gctcgccacc    660
tgcgcctgct acggcgccat gctgcgccac ctgggccgtg cggctgtacg ccccgcaccc   720
actgacggcg ccctgcaggg acagctgcta gcacagcgcg ccggagcagt gcgcaccaag   780
gtctcccggc tggtggccgc tgtcgtcctg ctcttcgccg cctgctgggg cccgatccag    840
ctgttcctgg tgcttcaagc cctgggcccc tcggggggcct ggcaccctcg aagctatgcc   900
gcctacgcgg tcaagatctg gctcactgc atgtcctaca gcaactcggc gctcaatccg    960
ctgctctatg ccttcctggg ttcacacttc agacaggcct tctgccgcgt gtgcccctgc   1020
tgccggcaac gccagcgccg gccccacacg tcagcgcact cggaccgagc tgcaactcac   1080
actgtgccgc acagccgtgc tgcgcaccct gtgcggatca ggagcccgga gcctgggaac   1140
cctgtggtgc gctcgccctg cgctcagagt gaacgcactg cctcactc                1188

<210> SEQ ID NO 15
<211> LENGTH: 15
<212> TYPE: PRT
<213> ORGANISM: Homo sapiens
<220> FEATURE:
<223> OTHER INFORMATION: C-term amidated

<400> SEQUENCE: 15

Lys Asp Leu Pro Asn Tyr Asn Trp Asn Ser Phe Gly Leu Arg Phe
1               5                   10                  15

<210> SEQ ID NO 16
<211> LENGTH: 10
<212> TYPE: PRT
<213> ORGANISM: Homo sapiens
<220> FEATURE:
<223> OTHER INFORMATION: C-term amidated

<400> SEQUENCE: 16
```

-continued

Tyr Asn Trp Asn Ser Phe Gly Leu Arg Phe
1               5                   10

<210> SEQ ID NO 17
<211> LENGTH: 9
<212> TYPE: PRT
<213> ORGANISM: Homo sapiens
<220> FEATURE:
<223> OTHER INFORMATION: C-term amidated

<400> SEQUENCE: 17

Asn Trp Asn Ser Phe Gly Leu Arg Phe
1               5

<210> SEQ ID NO 18
<211> LENGTH: 8
<212> TYPE: PRT
<213> ORGANISM: Homo sapiens
<220> FEATURE:
<223> OTHER INFORMATION: C-term amidated

<400> SEQUENCE: 18

Trp Asn Ser Phe Gly Leu Arg Phe
1               5

<210> SEQ ID NO 19
<211> LENGTH: 45
<212> TYPE: DNA
<213> ORGANISM: Homo sapiens

<400> SEQUENCE: 19
aaggacctgc cgaactacaa ctggaactcc ttcggcctgc gcttc            45

<210> SEQ ID NO 20
<211> LENGTH: 30
<212> TYPE: DNA
<213> ORGANISM: Homo sapiens

<400> SEQUENCE: 20
tacaactgga actccttcgg cctgcgcttc                             30

<210> SEQ ID NO 21
<211> LENGTH: 27
<212> TYPE: DNA
<213> ORGANISM: Homo sapiens

<400> SEQUENCE: 21
aactggaact ccttcggcct gcgcttc                                27

<210> SEQ ID NO 22
<211> LENGTH: 24
<212> TYPE: DNA
<213> ORGANISM: Homo sapiens

<400> SEQUENCE: 22
tggaactcct tcggcctgcg cttc                                   24

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (1)..(1)
<223> OTHER INFORMATION: 3-(3-Indolyl)propionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 23

Asn Ser Phe Gly Leu Arg Phe
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Phenylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 24

Asn Ser Phe Gly Leu Arg Phe
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-(indol-3-yl)ethylcarbamoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 25

Asn Ser Phe Gly Leu Arg Phe
1               5

<210> SEQ ID NO 26
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Pyridylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 26

Asn Ser Phe Gly Leu Arg Phe
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-Imidazoleacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 27

Asn Ser Phe Gly Leu Arg Phe
1               5

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Asn Trp Asn
1

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Tyr Asn Trp Asn
1               5

<210> SEQ ID NO 30
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Pro Asn Tyr Asn Trp Asn
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Leu Pro Asn Tyr Asn Trp Asn
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Leu Pro Asn Tyr Asn Trp Asn
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Asp Leu Pro Asn Tyr Asn Trp Asn
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Glu Lys Asp Leu Pro Asn Tyr Asn Trp Asn
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Glu Lys Asp Leu Pro Asn Tyr Asn Trp Asn
```

```
<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Arg Glu Lys Asp Leu Pro Asn Tyr Asn Trp Asn
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Val Gln Arg Glu Lys Asp Leu Pro Asn Tyr Asn Trp Asn
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Leu Val Gln Arg Glu Lys Asp Leu Pro Asn Tyr Asn Trp Asn
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Val Leu Val Gln Arg Glu Lys Asp Leu Pro Asn Tyr Asn Trp Asn
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Val Leu Val Gln Arg Glu Lys Asp Leu Pro Asn Tyr Asn Trp Asn
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 41

Gly Ala Val Leu Val Gln Arg Glu Lys Asp Leu Pro Asn Tyr Asn Trp
1               5                   10                  15
Asn

<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gly Ala Val Leu Val Gln Arg Glu Lys Asp Leu Pro Asn Tyr Asn
1               5                   10                  15
Trp Asn

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Pro Gln Gly Ala Val Leu Val Gln Arg Glu Lys Asp Leu Pro Asn Tyr
1               5                   10                  15
Asn Trp Asn

<210> SEQ ID NO 44
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ala Pro Gln Gly Ala Val Leu Val Gln Arg Glu Lys Asp Leu Pro Asn
1               5                   10                  15
Tyr Asn Trp Asn
            20

<210> SEQ ID NO 45
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Pro Ala Pro Gln Gly Ala Val Leu Val Gln Arg Glu Lys Asp Leu Pro
1               5                   10                  15
Asn Tyr Asn Trp Asn
            20

<210> SEQ ID NO 46
<211> LENGTH: 22
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 46

Ile Pro Ala Pro Gln Gly Ala Val Leu Val Gln Arg Glu Lys Asp Leu
1               5                   10                  15

Pro Asn Tyr Asn Trp Asn
            20

<210> SEQ ID NO 47
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Pro Ala Pro Gln Gly Ala Val Leu Val Gln Arg Glu Lys Asp
1               5                   10                  15

Leu Pro Asn Tyr Asn Trp Asn
            20

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Gln Ile Pro Ala Pro Gln Gly Ala Val Leu Val Gln Arg Glu Lys
1               5                   10                  15

Asp Leu Pro Asn Tyr Asn Trp Asn
            20

<210> SEQ ID NO 49
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Arg Gln Ile Pro Ala Pro Gln Gly Ala Val Leu Val Gln Arg Glu
1               5                   10                  15

Lys Asp Leu Pro Asn Tyr Asn Trp Asn
            20                  25

<210> SEQ ID NO 50
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Ser Arg Gln Ile Pro Ala Pro Gln Gly Ala Val Leu Val Gln Arg
1               5                   10                  15

Glu Lys Asp Leu Pro Asn Tyr Asn Trp Asn
            20                  25
```

```
<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Pro His Ser Arg Gln Ile Pro Ala Pro Gln Gly Ala Val Leu Val Gln
1               5                   10                  15

Arg Glu Lys Asp Leu Pro Asn Tyr Asn Trp Asn
            20                  25

<210> SEQ ID NO 52
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ala Pro His Ser Arg Gln Ile Pro Ala Pro Gln Gly Ala Val Leu Val
1               5                   10                  15

Gln Arg Glu Lys Asp Leu Pro Asn Tyr Asn Trp Asn
            20                  25

<210> SEQ ID NO 53
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Ala Pro His Ser Arg Gln Ile Pro Ala Pro Gln Gly Ala Val Leu
1               5                   10                  15

Val Gln Arg Glu Lys Asp Leu Pro Asn Tyr Asn Trp Asn
            20                  25

<210> SEQ ID NO 54
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Leu Ser Ala Pro His Ser Arg Gln Ile Pro Ala Pro Gln Gly Ala Val
1               5                   10                  15

Leu Val Gln Arg Glu Lys Asp Leu Pro Asn Tyr Asn Trp Asn
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Leu Ser Ala Pro His Ser Arg Gln Ile Pro Ala Pro Gln Gly Ala
1               5                   10                  15
```

```
Val Leu Val Gln Arg Glu Lys Asp Leu Pro Asn Tyr Asn Trp Asn
        20                  25                  30
```

<210> SEQ ID NO 56
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

```
Pro Gly Leu Ser Ala Pro His Ser Arg Gln Ile Pro Ala Pro Gln Gly
1               5                   10                  15

Ala Val Leu Val Gln Arg Glu Lys Asp Leu Pro Asn Tyr Asn Trp Asn
            20                  25                  30
```

<210> SEQ ID NO 57
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Gln Pro Gly Leu Ser Ala Pro His Ser Arg Gln Ile Pro Ala Pro Gln
1               5                   10                  15

Gly Ala Val Leu Val Gln Arg Glu Lys Asp Leu Pro Asn Tyr Asn Trp
            20                  25                  30

Asn
```

<210> SEQ ID NO 58
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Gln Gln Pro Gly Leu Ser Ala Pro His Ser Arg Gln Ile Pro Ala Pro
1               5                   10                  15

Gln Gly Ala Val Leu Val Gln Arg Glu Lys Asp Leu Pro Asn Tyr Asn
            20                  25                  30

Trp Asn
```

<210> SEQ ID NO 59
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

```
Arg Gln Gln Pro Gly Leu Ser Ala Pro His Ser Arg Gln Ile Pro Ala
1               5                   10                  15

Pro Gln Gly Ala Val Leu Val Gln Arg Glu Lys Asp Leu Pro Asn Tyr
            20                  25                  30

Asn Trp Asn
        35
```

```
<210> SEQ ID NO 60
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ser Arg Gln Gln Pro Gly Leu Ser Ala Pro His Ser Arg Gln Ile Pro
1               5                   10                  15

Ala Pro Gln Gly Ala Val Leu Val Gln Arg Glu Lys Asp Leu Pro Asn
            20                  25                  30

Tyr Asn Trp Asn
        35

<210> SEQ ID NO 61
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gly Ser Arg Gln Gln Pro Gly Leu Ser Ala Pro His Ser Arg Gln Ile
1               5                   10                  15

Pro Ala Pro Gln Gly Ala Val Leu Val Gln Arg Glu Lys Asp Leu Pro
            20                  25                  30

Asn Tyr Asn Trp Asn
        35

<210> SEQ ID NO 62
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ser Gly Ser Arg Gln Gln Pro Gly Leu Ser Ala Pro His Ser Arg Gln
1               5                   10                  15

Ile Pro Ala Pro Gln Gly Ala Val Leu Val Gln Arg Glu Lys Asp Leu
            20                  25                  30

Pro Asn Tyr Asn Trp Asn
        35

<210> SEQ ID NO 63
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ser Ser Gly Ser Arg Gln Gln Pro Gly Leu Ser Ala Pro His Ser Arg
1               5                   10                  15

Gln Ile Pro Ala Pro Gln Gly Ala Val Leu Val Gln Arg Glu Lys Asp
            20                  25                  30

Leu Pro Asn Tyr Asn Trp Asn
        35
```

-continued

```
<210> SEQ ID NO 64
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Ser Ser Gly Ser Arg Gln Gln Pro Gly Leu Ser Ala Pro His Ser
1               5                   10                  15

Arg Gln Ile Pro Ala Pro Gln Gly Ala Val Leu Val Gln Arg Glu Lys
            20                  25                  30

Asp Leu Pro Asn Tyr Asn Trp Asn
        35                  40

<210> SEQ ID NO 65
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Pro Glu Ser Ser Gly Ser Arg Gln Gln Pro Gly Leu Ser Ala Pro His
1               5                   10                  15

Ser Arg Gln Ile Pro Ala Pro Gln Gly Ala Val Leu Val Gln Arg Glu
            20                  25                  30

Lys Asp Leu Pro Asn Tyr Asn Trp Asn
        35                  40

<210> SEQ ID NO 66
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Pro Pro Glu Ser Ser Gly Ser Arg Gln Gln Pro Gly Leu Ser Ala Pro
1               5                   10                  15

His Ser Arg Gln Ile Pro Ala Pro Gln Gly Ala Val Leu Val Gln Arg
            20                  25                  30

Glu Lys Asp Leu Pro Asn Tyr Asn Trp Asn
        35                  40

<210> SEQ ID NO 67
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Pro Pro Pro Glu Ser Ser Gly Ser Arg Gln Gln Pro Gly Leu Ser Ala
1               5                   10                  15

Pro His Ser Arg Gln Ile Pro Ala Pro Gln Gly Ala Val Leu Val Gln
            20                  25                  30

Arg Glu Lys Asp Leu Pro Asn Tyr Asn Trp Asn
        35                  40
```

<210> SEQ ID NO 68
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ser Pro Pro Pro Glu Ser Ser Gly Ser Arg Gln Gln Pro Gly Leu Ser
1               5                   10                  15

Ala Pro His Ser Arg Gln Ile Pro Ala Pro Gln Gly Ala Val Leu Val
            20                  25                  30

Gln Arg Glu Lys Asp Leu Pro Asn Tyr Asn Trp Asn
        35                  40

<210> SEQ ID NO 69
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Leu Ser Pro Pro Pro Glu Ser Ser Gly Ser Arg Gln Gln Pro Gly Leu
1               5                   10                  15

Ser Ala Pro His Ser Arg Gln Ile Pro Ala Pro Gln Gly Ala Val Leu
            20                  25                  30

Val Gln Arg Glu Lys Asp Leu Pro Asn Tyr Asn Trp Asn
        35                  40                  45

<210> SEQ ID NO 70
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ser Leu Ser Pro Pro Pro Glu Ser Ser Gly Ser Arg Gln Gln Pro Gly
1               5                   10                  15

Leu Ser Ala Pro His Ser Arg Gln Ile Pro Ala Pro Gln Gly Ala Val
            20                  25                  30

Leu Val Gln Arg Glu Lys Asp Leu Pro Asn Tyr Asn Trp Asn
        35                  40                  45

<210> SEQ ID NO 71
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Thr Ser Leu Ser Pro Pro Pro Glu Ser Ser Gly Ser Arg Gln Gln Pro
1               5                   10                  15

Gly Leu Ser Ala Pro His Ser Arg Gln Ile Pro Ala Pro Gln Gly Ala
            20                  25                  30

Val Leu Val Gln Arg Glu Lys Asp Leu Pro Asn Tyr Asn Trp Asn
        35                  40                  45

```
<210> SEQ ID NO 72
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gly Thr Ser Leu Ser Pro Pro Glu Ser Ser Gly Ser Arg Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Tyr Lys Trp Asn
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Tyr Asp Trp Asn
1

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Tyr Trp Asn
1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Leu Trp Asn
1

<210> SEQ ID NO 77
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 77

Tyr Asn Ala Asn
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Tyr Asn Leu Asn
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Tyr Asn Ser Asn
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Tyr Asn Asp Asn
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Tyr Asn Lys Asn
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Asn Trp Asn
1
```

```
<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Leu Asn Trp Asn
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Asn Trp Asn
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Asp Asn Trp Asn
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Asn Trp Asn
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp(For)

<400> SEQUENCE: 87

Tyr Asn Trp Asn
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                peptide
<220> FEATURE:
<221> NAME/KEY: misc_feature
<222> LOCATION: (1)..(2)
<223> OTHER INFORMATION: CH2NH bond

<400> SEQUENCE: 88

Tyr Asn Trp Asn
1

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 89

Tyr Asn Trp Asn Ser Phe Gly Leu Arg Phe
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Pya(4)
<220> FEATURE:
<223> OTHER INFORMATION: C-term amidated

<400> SEQUENCE: 90

Tyr Asn Trp Asn Ser Phe Gly Leu Arg Xaa
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Tyr(Me)
<220> FEATURE:
<223> OTHER INFORMATION: C-term amidated

<400> SEQUENCE: 91

Tyr Asn Trp Asn Ser Phe Gly Leu Arg Tyr
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(2F)
<220> FEATURE:
```

<223> OTHER INFORMATION: C-term amidated

<400> SEQUENCE: 92

Tyr Asn Trp Asn Ser Phe Gly Leu Arg Phe
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 93

Tyr Asn Trp Asn Tyr Phe Gly Leu Arg Phe
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 94

Tyr Asn Trp Asn Leu Phe Gly Leu Arg Phe
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 95

Tyr Asn Trp Asn Ser Phe Gly Leu Arg Phe
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Tyr
<220> FEATURE:
<223> OTHER INFORMATION: C-term amidated

<400> SEQUENCE: 96

Tyr Asn Trp Asn Ser Phe Gly Leu Arg Phe
1               5                   10

<210> SEQ ID NO 97
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 97

Tyr Asn Trp Asn Ser Phe Gly Leu Lys Phe
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 98

Tyr Asn Trp Asn Ser Phe Gly Ala Arg Phe
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 99

Tyr Asn Trp Asn Ser Phe Ala Leu Arg Phe
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: NMePhe
<220> FEATURE:
<223> OTHER INFORMATION: C-term amidated

<400> SEQUENCE: 100

Tyr Asn Trp Asn Ser Phe Gly Leu Arg Phe
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn
<220> FEATURE:
<223> OTHER INFORMATION: C-term amidated
```

```
<400> SEQUENCE: 101

Asn Ser Phe Gly Leu Arg Phe
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Trp
<220> FEATURE:
<223> OTHER INFORMATION: C-term amidated

<400> SEQUENCE: 102

Trp Asn Ser Phe Gly Leu Arg Phe
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn
<220> FEATURE:
<223> OTHER INFORMATION: C-term amidated

<400> SEQUENCE: 103

Asn Trp Asn Ser Phe Gly Leu Arg Phe
1               5

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 104

Tyr Lys Trp Asn Ser Phe Gly Leu Arg Phe
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 105

Tyr Asp Trp Asn Ser Phe Gly Leu Arg Phe
1               5                   10

<210> SEQ ID NO 106
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 106

Tyr Tyr Trp Asn Ser Phe Gly Leu Arg Phe
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 107

Tyr Leu Trp Asn Ser Phe Gly Leu Arg Phe
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Pya(3)
<220> FEATURE:
<223> OTHER INFORMATION: C-term amidated

<400> SEQUENCE: 108

Tyr Asn Trp Asn Ser Phe Gly Leu Arg Xaa
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4F)
<220> FEATURE:
<223> OTHER INFORMATION: C-term amidated

<400> SEQUENCE: 109

Tyr Asn Trp Asn Ser Phe Gly Leu Arg Phe
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

```
<400> SEQUENCE: 110

Tyr Asn Ala Asn Ser Phe Gly Leu Arg Phe
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 111

Tyr Asn Leu Asn Ser Phe Gly Leu Arg Phe
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 112

Tyr Asn Ser Asn Ser Phe Gly Leu Arg Phe
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 113

Tyr Asn Asp Asn Ser Phe Gly Leu Arg Phe
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 114

Tyr Asn Lys Asn Ser Phe Gly Leu Arg Phe
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

-continued

```
<400> SEQUENCE: 115

Ala Asn Trp Asn Ser Phe Gly Leu Arg Phe
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 116

Leu Asn Trp Asn Ser Phe Gly Leu Arg Phe
1               5                   10

<210> SEQ ID NO 117
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 117

Ser Asn Trp Asn Ser Phe Gly Leu Arg Phe
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 118

Asp Asn Trp Asn Ser Phe Gly Leu Arg Phe
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 119

Lys Asn Trp Asn Ser Phe Gly Leu Arg Phe
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
```

```
<223> OTHER INFORMATION: Phe(4CN)
<220> FEATURE:
<223> OTHER INFORMATION: C-term amidated

<400> SEQUENCE: 120

Tyr Asn Trp Asn Ser Phe Gly Leu Arg Phe
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Trp(For)
<220> FEATURE:
<221> NAME/KEY: MOD_RES
<222> LOCATION: (10)..(10)
<223> OTHER INFORMATION: Phe(4CN)
<220> FEATURE:
<223> OTHER INFORMATION: C-term amidated

<400> SEQUENCE: 121

Tyr Asn Trp Asn Ser Phe Gly Leu Arg Phe
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Hph
<220> FEATURE:
<223> OTHER INFORMATION: C-term amidated

<400> SEQUENCE: 122

Tyr Asn Trp Asn Ser Phe Gly Leu Arg Phe
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: NMeArg
<220> FEATURE:
<223> OTHER INFORMATION: C-term amidated

<400> SEQUENCE: 123

Tyr Asn Trp Asn Ser Phe Gly Leu Arg Phe
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
```

```
                              peptide
<220> FEATURE:
<221> NAME/KEY: MOD_RES
<222> LOCATION: (9)..(9)
<223> OTHER INFORMATION: Arg(Me)
<220> FEATURE:
<223> OTHER INFORMATION: C-term amidated

<400> SEQUENCE: 124

Tyr Asn Trp Asn Ser Phe Gly Leu Arg Phe
1               5                   10

<210> SEQ ID NO 125
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(asy Me2)
<220> FEATURE:
<223> OTHER INFORMATION: C-term amidated

<400> SEQUENCE: 125

Tyr Asn Trp Asn Ser Phe Gly Leu Arg Phe
1               5                   10

<210> SEQ ID NO 126
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr
<220> FEATURE:
<223> OTHER INFORMATION: C-term amidated

<400> SEQUENCE: 126

Tyr Asn Trp Phe Gly Leu Arg Phe
1               5

<210> SEQ ID NO 127
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 127

Tyr Asn Trp Phe Gly Leu Arg Phe
1               5

<210> SEQ ID NO 128
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(10)
```

```
<223> OTHER INFORMATION: CH2NH bond
<220> FEATURE:
<223> OTHER INFORMATION: C-term amidated

<400> SEQUENCE: 128

Tyr Asn Trp Asn Ser Phe Gly Leu Arg Phe
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (8)..(9)
<223> OTHER INFORMATION: CH2NH bond
<220> FEATURE:
<223> OTHER INFORMATION: C-term amidated

<400> SEQUENCE: 129

Tyr Asn Trp Asn Ser Phe Gly Leu Arg Phe
1               5                   10

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Har
<220> FEATURE:
<223> OTHER INFORMATION: C-term amidated

<400> SEQUENCE: 130

Tyr Asn Trp Asn Ser Phe Gly Leu Arg Phe
1               5                   10

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Lys(Me2)
<220> FEATURE:
<223> OTHER INFORMATION: C-term amidated

<400> SEQUENCE: 131

Tyr Asn Trp Asn Ser Phe Gly Leu Lys Phe
1               5                   10

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

```
<400> SEQUENCE: 132

Tyr Asn Trp Asn Ser Phe Ser Leu Arg Phe
1               5                   10

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Nle
<220> FEATURE:
<223> OTHER INFORMATION: C-term amidated

<400> SEQUENCE: 133

Tyr Asn Trp Asn Ser Phe Gly Leu Arg Phe
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 134

Tyr Asn Trp Asn Ser Phe Gly Val Arg Phe
1               5                   10

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 135

Tyr Asn Trp Asn Ser Phe Gly Leu Arg Tyr
1               5                   10

<210> SEQ ID NO 136
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nal(2)
<220> FEATURE:
<223> OTHER INFORMATION: C-term amidated

<400> SEQUENCE: 136

Tyr Asn Trp Asn Ser Phe Gly Leu Arg Ala
1               5                   10

<210> SEQ ID NO 137
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(F5)
<220> FEATURE:
<223> OTHER INFORMATION: C-term amidated

<400> SEQUENCE: 137

Tyr Asn Trp Asn Ser Phe Gly Leu Arg Phe
1               5                   10

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Cha
<220> FEATURE:
<223> OTHER INFORMATION: C-term amidated

<400> SEQUENCE: 138

Tyr Asn Trp Asn Ser Phe Gly Leu Arg Ala
1               5                   10

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(3-Indolyl)propionyl-Asn
<220> FEATURE:
<223> OTHER INFORMATION: C-term amidated

<400> SEQUENCE: 139

Asn Ser Phe Gly Leu Arg Phe
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 140

Trp Phe Gly Leu Arg Phe
1               5

<210> SEQ ID NO 141
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide
<220> FEATURE:
<221> NAME/KEY: MOD_RES
<222> LOCATION: (8)..(8)
<223> OTHER INFORMATION: NMeLeu
<220> FEATURE:
<223> OTHER INFORMATION: C-term amidated

<400> SEQUENCE: 141

Tyr Asn Trp Asn Ser Phe Gly Leu Arg Phe
1               5                   10

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: NMeSer
<220> FEATURE:
<223> OTHER INFORMATION: C-term amidated

<400> SEQUENCE: 142

Tyr Asn Trp Asn Ser Phe Gly Leu Arg Phe
1               5                   10

<210> SEQ ID NO 143
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe-psi(CSNH)
<220> FEATURE:
<223> OTHER INFORMATION: C-term amidated

<400> SEQUENCE: 143

Tyr Asn Trp Asn Ser Phe Gly Leu Arg Phe
1               5                   10

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(symMe2)
<220> FEATURE:
<223> OTHER INFORMATION: C-term amidated

<400> SEQUENCE: 144

Tyr Asn Trp Asn Ser Phe Gly Leu Arg Phe
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (10)..(10)
<223> OTHER INFORMATION: Phe(4Cl)
<220> FEATURE:
<223> OTHER INFORMATION: C-term amidated

<400> SEQUENCE: 145

Tyr Asn Trp Asn Ser Phe Gly Leu Arg Phe
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4NH2)
<220> FEATURE:
<223> OTHER INFORMATION: C-term amidated

<400> SEQUENCE: 146

Tyr Asn Trp Asn Ser Phe Gly Leu Arg Phe
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(4NO2)
<220> FEATURE:
<223> OTHER INFORMATION: C-term amidated

<400> SEQUENCE: 147

Tyr Asn Trp Asn Ser Phe Gly Leu Arg Phe
1               5                   10

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Nal(1)
<220> FEATURE:
<223> OTHER INFORMATION: C-term amidated

<400> SEQUENCE: 148

Tyr Asn Trp Asn Ser Phe Gly Leu Arg Ala
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<223> OTHER INFORMATION: C-term amidated

<400> SEQUENCE: 149

Tyr Asn Trp Asn Ser Phe Gly Leu Arg Trp
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Nle
<220> FEATURE:
<223> OTHER INFORMATION: C-term amidated

<400> SEQUENCE: 150

Tyr Asn Trp Asn Ser Phe Gly Leu Leu Phe
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Cit
<220> FEATURE:
<223> OTHER INFORMATION: C-term amidated

<400> SEQUENCE: 151

Tyr Asn Trp Asn Ser Phe Gly Leu Xaa Phe
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(Me)
<220> FEATURE:
<221> NAME/KEY: MOD_RES
<222> LOCATION: (10)..(10)
<223> OTHER INFORMATION: NMePhe
<220> FEATURE:
<223> OTHER INFORMATION: C-term amidated

<400> SEQUENCE: 152

Tyr Asn Trp Asn Ser Phe Gly Leu Arg Phe
1               5                   10

<210> SEQ ID NO 153
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (1)..(1)
<223> OTHER INFORMATION: Fmoc-Asn
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 153

Asn Ser Phe Gly Leu Arg Phe
1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Trp
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 154

Trp Asn Ser Phe Gly Leu Arg Phe
1               5

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 155

Tyr Asn Trp Asn Ser Tyr Gly Leu Arg Phe
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Nal(1)
<220> FEATURE:
<223> OTHER INFORMATION: C-term amidated

<400> SEQUENCE: 156

Tyr Asn Trp Asn Ser Ala Gly Leu Arg Phe
1               5                   10

<210> SEQ ID NO 157
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Nal(2)
<220> FEATURE:
<223> OTHER INFORMATION: C-term amidated

<400> SEQUENCE: 157

Tyr Asn Trp Asn Ser Ala Gly Leu Arg Phe
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe(F5)
<220> FEATURE:
<223> OTHER INFORMATION: C-term amidated

<400> SEQUENCE: 158

Tyr Asn Trp Asn Ser Phe Gly Leu Arg Phe
1               5                   10

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phe(4F)
<220> FEATURE:
<223> OTHER INFORMATION: C-term amidated

<400> SEQUENCE: 159

Tyr Asn Trp Asn Ser Phe Gly Leu Arg Phe
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cha
<220> FEATURE:
<223> OTHER INFORMATION: C-term amidated

<400> SEQUENCE: 160

Tyr Asn Trp Asn Ser Ala Gly Leu Arg Phe
1               5                   10

<210> SEQ ID NO 161
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(7)
<223> OTHER INFORMATION: CH2NH bond
<220> FEATURE:
<223> OTHER INFORMATION: C-term amidated

<400> SEQUENCE: 161

Tyr Asn Trp Asn Ser Phe Gly Leu Arg Phe
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Nbeta-glycyldiaminopropionic acid
<220> FEATURE:
<223> OTHER INFORMATION: C-term amidated

<400> SEQUENCE: 162

Tyr Asn Trp Asn Ser Phe Gly Leu Gly Phe
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(7)
<223> OTHER INFORMATION: CSNH bond
<220> FEATURE:
<223> OTHER INFORMATION: C-term amidated

<400> SEQUENCE: 163

Tyr Asn Trp Asn Ser Phe Gly Leu Arg Phe
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: AzaGly
<220> FEATURE:
<223> OTHER INFORMATION: C-term amidated

<400> SEQUENCE: 164

Tyr Asn Trp Asn Ser Phe Gly Leu Arg Phe
1               5                   10

<210> SEQ ID NO 165
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phe(4NH2)
<220> FEATURE:
<223> OTHER INFORMATION: C-term amidated

<400> SEQUENCE: 165

Tyr Asn Trp Asn Ser Phe Gly Leu Phe Phe
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phe(4-Guanidino)
<220> FEATURE:
<223> OTHER INFORMATION: C-term amidated

<400> SEQUENCE: 166

Tyr Asn Trp Asn Ser Phe Gly Leu Phe Phe
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Nbeta-(N-guanidinoglycyl)diaminopropionic acid
<220> FEATURE:
<223> OTHER INFORMATION: C-term amidated

<400> SEQUENCE: 167

Tyr Asn Trp Asn Ser Phe Gly Leu Gly Phe
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Trp(For)
<220> FEATURE:
<223> OTHER INFORMATION: C-term amidated

<400> SEQUENCE: 168

Tyr Asn Trp Asn Ser Phe Gly Leu Arg Trp
1               5                   10

<210> SEQ ID NO 169
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Abu
<220> FEATURE:
<223> OTHER INFORMATION: C-term amidated

<400> SEQUENCE: 169

Tyr Asn Trp Asn Ser Phe Gly Xaa Arg Phe
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ala(3-Bzt)
<220> FEATURE:
<223> OTHER INFORMATION: C-term amidated

<400> SEQUENCE: 170

Tyr Asn Trp Asn Ser Phe Gly Leu Arg Ala
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3F)
<220> FEATURE:
<223> OTHER INFORMATION: C-term amidated

<400> SEQUENCE: 171

Tyr Asn Trp Asn Ser Phe Gly Leu Arg Phe
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3,4F2)
<220> FEATURE:
<223> OTHER INFORMATION: C-term amidated

<400> SEQUENCE: 172

Tyr Asn Trp Asn Ser Phe Gly Leu Arg Phe
1               5                   10

<210> SEQ ID NO 173
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3,4Cl2)
<220> FEATURE:
<223> OTHER INFORMATION: C-term amidated

<400> SEQUENCE: 173

Tyr Asn Trp Asn Ser Phe Gly Leu Arg Phe
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phe(3CF3)
<220> FEATURE:
<223> OTHER INFORMATION: C-term amidated

<400> SEQUENCE: 174

Tyr Asn Trp Asn Ser Phe Gly Leu Arg Phe
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ala(2-Qui)
<220> FEATURE:
<223> OTHER INFORMATION: C-term amidated

<400> SEQUENCE: 175

Tyr Asn Trp Asn Ser Phe Gly Leu Arg Ala
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: N((CH2(3Gn)Gly
<220> FEATURE:
<223> OTHER INFORMATION: C-term amidated

<400> SEQUENCE: 176

Tyr Asn Trp Asn Ser Phe Gly Leu Gly Phe
1               5                   10

<210> SEQ ID NO 177
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Arg(Et)
<220> FEATURE:
<223> OTHER INFORMATION: C-term amidated

<400> SEQUENCE: 177

Tyr Asn Trp Asn Ser Phe Gly Leu Arg Phe
1               5                   10

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(3-Indolyl)propionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 178

Asn Ser Phe Gly Leu Arg Phe
1               5

<210> SEQ ID NO 179
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(8)
<223> OTHER INFORMATION: CH2NH bond
<220> FEATURE:
<223> OTHER INFORMATION: C-term amidated

<400> SEQUENCE: 179

Tyr Asn Trp Asn Ser Phe Gly Leu Arg Phe
1               5                   10

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Indole-3-carbonyl-Asn
<220> FEATURE:
<221> NAME/KEY: MOD_RES
<222> LOCATION: (4)..(4)
```

```
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 180

Asn Ser Phe Gly Leu Arg Phe
1               5

<210> SEQ ID NO 181
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Indol-3-acetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 181

Asn Ser Phe Gly Leu Arg Phe
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-(3-Indolyl)butyryl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 182

Asn Ser Phe Gly Leu Arg Phe
1               5

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Diphenylacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 183

Asn Ser Phe Gly Leu Arg Phe
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Phenylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 184

Asn Ser Phe Gly Leu Arg Phe
1               5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 185

Trp Asn Ser Phe Gly Leu Arg Phe
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
```

```
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 186

Trp Asn Ser Phe Gly Leu Arg Phe
1               5

<210> SEQ ID NO 187
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Amidino-Trp
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 187

Trp Asn Ser Phe Gly Leu Arg Phe
1               5

<210> SEQ ID NO 188
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 188

Ala Asn Ser Phe Gly Leu Arg Phe
1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
```

```
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 189

Arg Asn Ser Phe Gly Leu Arg Phe
1               5

<210> SEQ ID NO 190
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Me)
<220> FEATURE:
<223> OTHER INFORMATION: C-term amidated

<400> SEQUENCE: 190

Thr Asn Ser Phe Gly Leu Arg Phe
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: n-Hexanoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 191

Asn Ser Phe Gly Leu Arg Phe
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Cyclohexanecarbonyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 192

Asn Ser Phe Gly Leu Arg Phe
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 2-(indol-3-yl)ethylcarbamoyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 193

Asn Ser Phe Gly Leu Arg Phe
1               5

<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (4)..(5)
<223> OTHER INFORMATION: CH2NH bond
<220> FEATURE:
<223> OTHER INFORMATION: C-term amidated

<400> SEQUENCE: 194

Tyr Asn Trp Asn Ser Phe Gly Leu Arg Phe
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: CH2NH bond
<220> FEATURE:
<223> OTHER INFORMATION: C-term amidated
```

<400> SEQUENCE: 195

Tyr Asn Trp Asn Ser Phe Gly Leu Arg Phe
1               5                   10

<210> SEQ ID NO 196
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(3)
<223> OTHER INFORMATION: CH2NH bond
<220> FEATURE:
<223> OTHER INFORMATION: C-term amidated

<400> SEQUENCE: 196

Tyr Asn Trp Asn Ser Phe Gly Leu Arg Phe
1               5                   10

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(2)
<223> OTHER INFORMATION: CH2NH bond
<220> FEATURE:
<221> NAME/KEY: MOD_RES
<222> LOCATION: (7)..(7)
<223> OTHER INFORMATION: AzaGly
<220> FEATURE:
<221> NAME/KEY: MOD_RES
<222> LOCATION: (9)..(9)
<223> OTHER INFORMATION: Arg(Me)
<220> FEATURE:
<223> OTHER INFORMATION: C-term amidated

<400> SEQUENCE: 197

Tyr Asn Trp Asn Ser Phe Gly Leu Arg Phe
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Nar
<220> FEATURE:
<223> OTHER INFORMATION: C-term amidated

<400> SEQUENCE: 198

Tyr Asn Trp Asn Ser Phe Gly Leu Arg Phe
1               5                   10

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic

```
        peptide
<220> FEATURE:
<221> NAME/KEY: MOD_RES
<222> LOCATION: (9)..(9)
<223> OTHER INFORMATION: Nar(Me)
<220> FEATURE:
<223> OTHER INFORMATION: C-term amidated

<400> SEQUENCE: 199

Tyr Asn Trp Asn Ser Phe Gly Leu Arg Phe
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Har(Me)
<220> FEATURE:
<223> OTHER INFORMATION: C-term amidated

<400> SEQUENCE: 200

Tyr Asn Trp Asn Ser Phe Gly Leu Arg Phe
1               5                   10

<210> SEQ ID NO 201
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Dab
<220> FEATURE:
<223> OTHER INFORMATION: C-term amidated

<400> SEQUENCE: 201

Tyr Asn Trp Asn Ser Phe Gly Leu Xaa Phe
1               5                   10

<210> SEQ ID NO 202
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Orn
<220> FEATURE:
<223> OTHER INFORMATION: C-term amidated

<400> SEQUENCE: 202

Tyr Asn Trp Asn Ser Phe Gly Leu Xaa Phe
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: 3-Pyridylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 203

Asn Ser Phe Gly Leu Arg Phe
1               5

<210> SEQ ID NO 204
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 4-Imidazoleacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 204

Asn Ser Phe Gly Leu Arg Phe
1               5

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Piperidinecarbonyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 205

Asn Ser Phe Gly Leu Arg Phe
1               5

<210> SEQ ID NO 206
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Piperidineacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 206

Asn Ser Phe Gly Leu Arg Phe
1               5

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Methylpiperidino-1-acetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 207

Asn Ser Phe Gly Leu Arg Phe
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 1-Pyridinoacetyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 208

Asn Ser Phe Gly Leu Arg Phe
1               5
```

```
<210> SEQ ID NO 209
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Glucuronyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 209

Asn Ser Phe Gly Leu Arg Phe
1               5

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-Pyridylpropionyl-Asn
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Me)
<220> FEATURE:
<223> OTHER INFORMATION: C-term amidated

<400> SEQUENCE: 210

Asn Ser Phe Gly Leu Arg Trp
1               5

<210> SEQ ID NO 211
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
```

```
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (9)..(9)
<223> OTHER INFORMATION: Arg(Pbf)
<220> FEATURE:
<221> NAME/KEY: MOD_RES
<222> LOCATION: (10)..(10)
<223> OTHER INFORMATION: Hph-PAL

<400> SEQUENCE: 211

Tyr Asn Trp Asn Ser Phe Gly Leu Arg Phe
1               5                   10

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (9)..(9)
<223> OTHER INFORMATION: Arg(Pbf)-O-Clt

<400> SEQUENCE: 212

Tyr Asn Trp Asn Ser Phe Gly Leu Arg
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
```

```
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (9)..(9)
<223> OTHER INFORMATION: Arg(Pbf)

<400> SEQUENCE: 213

Tyr Asn Trp Asn Ser Phe Gly Leu Arg
1               5

<210> SEQ ID NO 214
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (9)..(9)
<223> OTHER INFORMATION: Arg(Pbf)
<220> FEATURE:
<221> NAME/KEY: MOD_RES
<222> LOCATION: (10)..(10)
<223> OTHER INFORMATION: Trp(For)
<220> FEATURE:
<223> OTHER INFORMATION: C-term amidated

<400> SEQUENCE: 214

Tyr Asn Trp Asn Ser Phe Gly Leu Arg Trp
1               5                   10

<210> SEQ ID NO 215
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
```

```
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)

<400> SEQUENCE: 215

Tyr Asn Trp Asn Ser Phe Gly
1               5

<210> SEQ ID NO 216
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Gly
<220> FEATURE:
<221> NAME/KEY: MOD_RES
<222> LOCATION: (3)..(3)
<223> OTHER INFORMATION: Arg(Pbf)
<220> FEATURE:
<221> NAME/KEY: MOD_RES
<222> LOCATION: (4)..(4)
<223> OTHER INFORMATION: Phe-PAL

<400> SEQUENCE: 216

Gly Leu Arg Phe
1

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: misc_feature
<222> LOCATION: (6)..(7)
<223> OTHER INFORMATION: CH2NH bond
<220> FEATURE:
<221> NAME/KEY: MOD_RES
<222> LOCATION: (9)..(9)
<223> OTHER INFORMATION: Arg(Pbf)
<220> FEATURE:
<221> NAME/KEY: MOD_RES
<222> LOCATION: (10)..(10)
<223> OTHER INFORMATION: Phe-PAL
```

```
<400> SEQUENCE: 217

Tyr Asn Trp Asn Ser Phe Gly Leu Arg Phe
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (9)..(9)
<223> OTHER INFORMATION: Orn(Mtt)
<220> FEATURE:
<221> NAME/KEY: MOD_RES
<222> LOCATION: (10)..(10)
<223> OTHER INFORMATION: Phe-Rink Amide MBHA

<400> SEQUENCE: 218

Tyr Asn Trp Asn Ser Phe Gly Leu Xaa Phe
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (9)..(9)
<223> OTHER INFORMATION: Arg(Boc2,Me)
<220> FEATURE:
```

```
<221> NAME/KEY: MOD_RES
<222> LOCATION: (10)..(10)
<223> OTHER INFORMATION: Phe-Rink Amide MBHA

<400> SEQUENCE: 219

Tyr Asn Trp Asn Ser Phe Gly Leu Arg Phe
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: misc_feature
<222> LOCATION: (6)..(7)
<223> OTHER INFORMATION: CSNH bond
<220> FEATURE:
<221> NAME/KEY: MOD_RES
<222> LOCATION: (9)..(9)
<223> OTHER INFORMATION: Arg(Pbf)
<220> FEATURE:
<221> NAME/KEY: MOD_RES
<222> LOCATION: (10)..(10)
<223> OTHER INFORMATION: Phe-PAL

<400> SEQUENCE: 220

Tyr Asn Trp Asn Ser Phe Gly Leu Arg Phe
1               5                   10

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Boc-Tyr(But)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
```

```
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (7)..(7)
<223> OTHER INFORMATION: AzaGly
<220> FEATURE:
<221> NAME/KEY: MOD_RES
<222> LOCATION: (9)..(9)
<223> OTHER INFORMATION: Arg(Pbf)
<220> FEATURE:
<221> NAME/KEY: MOD_RES
<222> LOCATION: (10)..(10)
<223> OTHER INFORMATION: Phe-PAL

<400> SEQUENCE: 221

Tyr Asn Trp Asn Ser Phe Gly Leu Arg Phe
1               5                   10

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Trt-Phe
<220> FEATURE:
<221> NAME/KEY: MOD_RES
<222> LOCATION: (2)..(2)
<223> OTHER INFORMATION: AzaGly
<220> FEATURE:
<221> NAME/KEY: MOD_RES
<222> LOCATION: (4)..(4)
<223> OTHER INFORMATION: Arg(Boc2,Me)
<220> FEATURE:
<221> NAME/KEY: MOD_RES
<222> LOCATION: (5)..(5)
<223> OTHER INFORMATION: Phe-Rink Amide MBHA

<400> SEQUENCE: 222

Phe Gly Leu Arg Phe
1               5

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn(Trt)
<220> FEATURE:
<221> NAME/KEY: MOD_RES
<222> LOCATION: (2)..(2)
<223> OTHER INFORMATION: Ser(But)
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Boc2,Me)
<220> FEATURE:
<221> NAME/KEY: MOD_RES
<222> LOCATION: (7)..(7)
<223> OTHER INFORMATION: Phe-Rink Amide MBHA
```

```
<400> SEQUENCE: 223

Asn Ser Phe Gly Leu Arg Phe
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Asn(Trt)
<220> FEATURE:
<221> NAME/KEY: MOD_RES
<222> LOCATION: (2)..(2)
<223> OTHER INFORMATION: Ser(But)
<220> FEATURE:
<221> NAME/KEY: MOD_RES
<222> LOCATION: (4)..(4)
<223> OTHER INFORMATION: AzaGly
<220> FEATURE:
<221> NAME/KEY: MOD_RES
<222> LOCATION: (6)..(6)
<223> OTHER INFORMATION: Arg(Boc2,Me)
<220> FEATURE:
<221> NAME/KEY: MOD_RES
<222> LOCATION: (7)..(7)
<223> OTHER INFORMATION: Phe-Rink Amide MBHA

<400> SEQUENCE: 224

Asn Ser Phe Gly Leu Arg Phe
1               5

<210> SEQ ID NO 225
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: H-Trp(Boc)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Ser(But)
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Boc2,Me)
<220> FEATURE:
<221> NAME/KEY: MOD_RES
<222> LOCATION: (8)..(8)
<223> OTHER INFORMATION: Phe-Rink Amide MBHA

<400> SEQUENCE: 225

Trp Asn Ser Phe Gly Leu Arg Phe
1               5

<210> SEQ ID NO 226
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Amidino-Trp(Boc)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Ser(But)
<220> FEATURE:
<221> NAME/KEY: MOD_RES
<222> LOCATION: (5)..(5)
<223> OTHER INFORMATION: AzaGly
<220> FEATURE:
<221> NAME/KEY: MOD_RES
<222> LOCATION: (7)..(7)
<223> OTHER INFORMATION: Arg(Boc2,Me)
<220> FEATURE:
<221> NAME/KEY: MOD_RES
<222> LOCATION: (8)..(8)
<223> OTHER INFORMATION: Phe-Rink Amide MBHA

<400> SEQUENCE: 226

Trp Asn Ser Phe Gly Leu Arg Phe
1               5

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Benzyloxycarbonyl-Tyr(Bzl)
<220> FEATURE:
<221> NAME/KEY: MOD_RES
<222> LOCATION: (2)..(2)
<223> OTHER INFORMATION: Asn(Trt)
<220> FEATURE:
<221> NAME/KEY: MOD_RES
<222> LOCATION: (3)..(3)
<223> OTHER INFORMATION: Trp(Boc)
<220> FEATURE:
<221> NAME/KEY: MOD_RES
<222> LOCATION: (4)..(4)
<223> OTHER INFORMATION: Asn(Trt)
<220> FEATURE:
<221> NAME/KEY: MOD_RES
<222> LOCATION: (5)..(5)
<223> OTHER INFORMATION: Ser(But)
<220> FEATURE:
<221> NAME/KEY: MOD_RES
<222> LOCATION: (9)..(9)
<223> OTHER INFORMATION: N((CH2)3NHBoc)Gly
<220> FEATURE:
<221> NAME/KEY: MOD_RES
<222> LOCATION: (10)..(10)
<223> OTHER INFORMATION: Phe-Rink Amide MBHA

<400> SEQUENCE: 227

Tyr Asn Trp Asn Ser Phe Gly Leu Gly Phe
1               5                   10

<210> SEQ ID NO 228
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Lys Asp Leu Pro Asn
1               5

<210> SEQ ID NO 229
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: (Cy-5)-Lys
<220> FEATURE:
<223> OTHER INFORMATION: C-term amidated

<400> SEQUENCE: 229

Lys Asp Leu Pro Asn Tyr Asn Trp Asn Ser Phe Gly Leu Arg Phe
1               5                  10                  15
```

METASTIN DERIVATIVES AND USE THEREOF

CROSS-REFERENCES TO RELATED APPLICATIONS

The present application is a divisional of U.S. Ser. No. 12/455,563, filed Jun. 2, 2009 now abandoned, which is a continuation of U.S. Ser. No. 10/540,494, filed May 30, 2006, now abandoned, which is a 35 U.S.C. §371 national stage of PCT application PCT/JP03/16978, filed Dec. 26, 2003, which claims priority of Japanese Application Serial Number 2002-377179, filed Dec. 26, 2002, the disclosures of all of which are incorporated herein by reference.

TECHNICAL FIELD

The present invention relates to metastin derivatives and use thereof.

BACKGROUND ART

Human-derived metastin (also termed KiSS-1 peptide) (WO 00/24890) and mouse or rat-derived metastin (WO 01/75104 2) are known. Also, sustained released preparations containing metastin are known ((WO 02/85399).

Reportedly, metastin has an effect of suppressing cancer metastasis and is therefore effective for preventing/treating cancers (for example, lung cancer, gastric cancer, liver cancer, pancreatic cancer, colorectal cancer, rectal cancer, colonic cancer, prostate cancer, ovarian cancer, cervical cancer, breast cancer, renal cancer, bladder cancer, brain tumor, etc.); metastin also has an effect of regulating a function of the pancreas and is effective for preventing/treating pancreatic diseases (e.g., acute or chronic pancreatitis, pancreatic cancer, etc.); and metastin further has an effect of regulating a function of the placenta and is effective for preventing/treating choriocarcinoma, hydatid moles, invasive moles, miscarriage, fetal hypoplasia, sugar dysbolism, lipid dysbolism or abnormal delivery (WO00/24890; WO01/75104 2; WO 02/85399).

DISCLOSURE OF THE INVENTION

The present invention aims at providing stable metastin derivatives having excellent biological activities such as a cancer metastasis suppressing activity, and a cancer proliferation suppressing activity, etc.

The present inventors have made extensive studies to solve the foregoing problems. As a result, the inventors have found that by modifying the metastin-constituting amino acids with a specific modifying group, metastin derivatives unexpectedly show improved blood stability, etc. as compared to native metastin and exhibit an excellent cancer metastasis suppressing activity or a cancer proliferation suppressing activity. In addition, the inventors have found that unexpectedly, these metastin derivatives have an effect of suppressing gonadotropic hormone secretion, an effect of suppressing sex hormone secretion, etc., which are totally different from the effects known so far. Based on these findings, the inventors have continued further investigations and come to accomplish the present invention.

That is, the present invention provides the following features.

[1] A metastin derivative represented by formula (I):

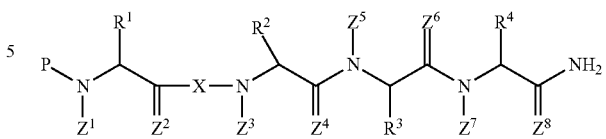

[wherein,
each of $Z^1$, $Z^3$, $Z^5$ and $Z^7$ represents hydrogen atom or a $C_{1-3}$ alkyl group; each of $Z^2$, $Z^4$, $Z^6$ and $Z^8$ represents hydrogen atom, O or S;

$R^1$ represents (1) hydrogen atom, or (2) a $C_{1-8}$ alkyl group optionally substituted with a substituent selected from the group consisting of an optionally substituted carbamoyl group, an optionally substituted hydroxyl group and an optionally substituted aromatic cyclic group;

$R^2$ represents (1) hydrogen atom or (2) a cyclic or linear $C_{1-10}$ alkyl group, or (3) a $C_{1-10}$ alkyl group consisting of a cyclic alkyl group and a linear alkyl group;

$R^3$ represents:
(1) a $C_{1-8}$ alkyl group having an optionally substituted basic group and optionally having an additional substituent,
(2) an aralkyl group having an optionally substituted basic group and optionally having an additional substituent,
(3) a $C_{1-4}$ alkyl group having a non-aromatic cyclic hydrocarbon group of carbon atoms not greater than 7 having an optionally substituted basic group, and optionally having an additional substituent, or,
(4) a $C_{1-4}$ alkyl group having a non-aromatic heterocyclic group of carbon atoms not greater than 7 having an optionally substituted basic group, and optionally having an additional substituent;

$R^4$ represents a $C_{1-4}$ alkyl group, which may optionally be substituted with a substituent selected from the group consisting of:
(1) an optionally substituted $C_{6-12}$ aromatic hydrocarbon group,
(2) an optionally substituted 5- to 14-membered aromatic heterocyclic group consisting of 1 to 7 carbon atoms and hetero atoms selected from the group consisting of nitrogen, oxygen and sulfur atoms,
(3) an optionally substituted $C_{8-14}$ aromatic fused-ring group,
(4) an optionally substituted 5- to 14-membered aromatic fused heterocyclic group consisting of 3 to 11 carbon atoms and hetero atoms selected from the group consisting of nitrogen, oxygen and sulfur atoms,
(5) an optionally substituted non-aromatic cyclic hydrocarbon group having carbon atoms not greater than 7, and,
(6) an optionally substituted non-aromatic heterocyclic group having carbon atoms not greater than 7;

X represents a group shown by formula: —NHCH($Q^1$)YQ$^2$C(=$Z^9$)— (wherein, $Q^1$ represents a $C_{1-4}$ alkyl group, which may optionally be substituted with a substituent selected from the group consisting of:
(1) an optionally substituted $C_{6-12}$ aromatic hydrocarbon group,
(2) an optionally substituted 5- to 14-membered aromatic heterocyclic group consisting of 1 to 7 carbon atoms and hetero atoms selected from the group consisting of nitrogen, oxygen and sulfur atoms,
(3) an optionally substituted $C_{8-14}$ aromatic fused-ring group, (4) an optionally substituted 5- to 14-membered aromatic fused heterocyclic group consisting of 3 to 11 carbon atoms and hetero atoms selected from the group consisting of nitrogen, oxygen and sulfur atoms, (5) an optionally substituted non-aromatic cyclic hydrocarbon group having carbon atoms not greater than 7, and, (6) an optionally substituted non-aromatic heterocyclic group having carbon atoms not greater than 7;

$Q^2$ represents (1) $CH_2$, which may optionally be substituted with a $C_{1-4}$ alkyl group optionally substituted with a substituent selected from the group consisting of carbamoyl group and hydroxyl group, (2) NH, which may optionally be substituted with a $C_{1-4}$ alkyl group optionally substituted with a substituent selected from the group consisting of carbamoyl group and hydroxyl group, or (3) O;

Y represents a group shown by formula: —CONH—, —CSNH—, —CH$_2$NH—, —NHCO—, —CH$_2$O—, —CH$_2$S— or —CH$_2$CH$_2$—, which may optionally be substituted with a $C_{1-6}$ alkyl group; and, $Z^9$ represents hydrogen atom, O or S); and, P represents:
(1) hydrogen atom;
(2) an optional amino acid residue continuously or discontinuously bound from the C-terminal end of the 1-48 amino acid sequence in the amino acid sequence represented by SEQ ID NO: 1;
(3) a group represented by formula:

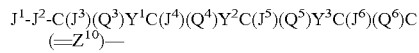

(wherein,
$J^1$ represents (a) hydrogen atom or (b) (i) a $C_{1-15}$ acyl group, (ii) a $C_{1-15}$ alkyl group, (iii) a $C_{6-14}$ aryl group, (iv) a carbamoyl group, (v) a carboxyl group, (vi) a sulfino group, (vii) an amidino group or (viii) a glyoxyloyl group, which group may optionally be substituted with (a) hydrogen atom, or (b) a substituent containing an optionally substituted cyclic group;

$J^2$ represents (1) NH optionally substituted with a $C_{1-6}$ alkyl group, (2) $CH_2$ optionally substituted with a $C_{1-6}$ alkyl group, (3) O or (4) S;

each of $J^3$ through $J^6$ represents hydrogen atom or a $C_{1-3}$ alkyl group;

each of $Q^3$ through $Q^6$ represents a $C_{1-4}$ alkyl group, which may optionally be substituted with a substituent selected from the group consisting of:
(1) an optionally substituted $C_{6-12}$ aromatic hydrocarbon group,
(2) an optionally substituted 5- to 14-membered aromatic heterocyclic group consisting of 1 to 7 carbon atoms and hetero atoms selected from the group consisting of nitrogen, oxygen and sulfur atoms,
(3) an optionally substituted $C_{8-14}$ aromatic fused-ring group,
(4) an optionally substituted 5- to 14-membered aromatic fused heterocyclic group consisting of 3 to 11 carbon atoms and hetero atoms selected from the group consisting of nitrogen, oxygen and sulfur atoms,
(5) an optionally substituted non-aromatic cyclic hydrocarbon group having carbon atoms not greater than 7,
(6) an optionally substituted non-aromatic heterocyclic group having carbon atoms not greater than 7,
(7) an optionally substituted amino group,
(8) an optionally substituted guanidino group,
(9) an optionally substituted hydroxyl group,
(10) an optionally substituted carboxyl group,
(11) an optionally substituted carbamoyl group, and
(12) an optionally substituted sulfhydryl group, or hydrogen atom;

$J^3$ and $Q^3$, $J^4$ and $Q^4$, $J^5$ and $Q^5$ or $J^6$ and $Q^6$ may be combined together, or, $J^2$ and $Q^3$, $Y^1$ and $Q^4$, $Y^2$ and $Q^5$, or $Y^3$ and $Q^6$ may be combined together, to form a ring; each of $Y^1$ through $Y^3$ represents a group represented by formula:
—CON($J^{13}$)-, —CSN($J^{13}$)-, —C($J^{14}$)N($J^{13}$)- or —N($J^{13}$)CO— (wherein each of $J^{13}$ and $J^{14}$ represents hydrogen atom or a $C_{1-3}$ alkyl group); and, $Z^{10}$ represents hydrogen atom, O or S);

(4) a group represented by formula:

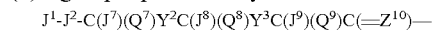

(wherein,
$J^1$ and $J^2$ have the same significance as described above;
$J^7$ through $J^9$ have the same significance as $J^3$;
$Q^7$ through $Q^9$ have the same significance as $Q^3$;
$Y^2$ and $Y^3$ have the same significance as described above;
$Z^{10}$ has the same significance as described above;
$J^7$ and $Q^7$, $J^8$ and $Q^8$ or $J^9$ and $Q^9$ may be combined together, or, $J^2$ and $Q^7$, $Y^2$ and $Q^8$ or $Y^3$ and $Q^9$ may be combined together, to form a ring);

(5) a group represented by formula:

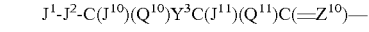

(wherein,
$J^1$ and $J^2$ have the same significance as described above represents;
$J^{10}$ and $J^{11}$ have the same significance as $J^3$;
$Q^{10}$ and $Q^{11}$ have the same significance as $Q^3$;
$Y^3$ has the same significance as described above;
$Z^{10}$ has the same significance as described above; and,
$J^{10}$ and $Q^{10}$ or $J^{11}$ and $Q^{11}$ may be combined together, or $J^2$ and $Q^{10}$ or $Y^3$ and $Q^{11}$ may be combined together, to form a ring);

(6) a group represented by formula: $J^1$-$J^2$-C($J^{12}$)($Q^{12}$)C(=$Z^{10}$)—

(wherein,
$J^1$ and $J^2$ have the same significance as described above;
$J^{12}$ has the same significance as $J^3$;
$Q^{12}$ has the same significance as $Q^3$;
$Z^{10}$ has the same significance as described above; and,
$J^{12}$ and $Q^{12}$ may be combined together, or $J^2$ and $Q^{12}$ may be combined together, to form a ring); or, (7) a group represented by formula: $J^1$- (wherein, $J^1$ has the same significance as described above)] (provided that a peptide consisting of the amino acid sequence of 1-54, 2-54, 3-54, 4-54, 5-54, 6-54, 7-54, 8-54, 9-54, 10-54, 11-54, 12-54, 13-54, 14-54, 15-54, 16-54, 17-54, 18-54, 19-54, 20-54, 21-54, 22-54, 23-54, 24-54, 25-54, 26-54, 27-54, 28-54, 29-54, 30-54, 31-54, 32-54, 33-54, 34-54, 35-54, 36-54, 37-54, 38-54, 39-54, 40-54, 41-54, 42-54, 43-54, 44-54, 45-54, 46-54, 47-54, 48-54 or 49-54 in the amino acid sequence represented by SEQ ID NO: 1 is excluded), or a salt thereof.

[2] The metastin derivative (I) according to claim 1 or a salt thereof, which is:

(i) D-Tyr-Asn-Trp-Asn-Ser-Phe-Gly-Leu-Arg(Me)-Phe-NH$_2$ (Compound No. 141), (ii) D-Tyr-Asn-Trp-Asn-Ser-Phe-Gly-Leu-Arg(Me)-Trp-NH$_2$ (Compound No. 174), (SEQ ID NO: 23)
(iii) 3-(3-Indolyl)propionyl-Asn-Ser-Phe-AzaGly-Leu-Arg(Me)-Phe-NH$_2$ (Compound No. 260), -continued (iv) 3-Phenylpropionyl-Asn-Ser-Phe-AzaGly-Leu-
Arg(Me)-Phe-NH$_2$ (Compound No. 269),
(SEQ ID NO: 24)

(v) 2-(indol-3-yl)ethylcarbamoyl-Asn-Ser-Phe-
AzaGly-Leu-Arg(Me)-Phe-NH$_2$ (Compound No. 279),
(SEQ ID NO: 25)

(vi) D-Tyr-Asn-Pya(4)-Asn-Ser-Phe-AzaGly-Leu-
Arg(Me)-Phe-NH$_2$ (Compound No. 286), (vii) D-Tyr-Asn-Trp-Asn-Ser-PheΨ(CSNH)Gly-
Leu-Arg(Me)-Phe-NH$_2$ (Compound No. 296), (viii) TyrΨ(CH$_2$NH)Asn-D-Trp-Asn-Ser-
Phe-AzaGly-Leu-Arg(Me)-Phe-NH$_2$ (Compound
No. 300), (ix) D-Tyr-D-Asn-Pya(4)-Asn-Ser-Phe-AzaGly-Leu-
Arg(Me)-Phe-NH$_2$ (Compound No. 303), (x) D-Tyr-D-Pya(4)-Asn-Ser-Phe-AzaGly-Leu-
Arg(Me)-Phe-NH$_2$ (Compound No. 305), (xi) D-Tyr-Asn-Trp-Asn-Ser-Phe-AzaGly-Leu-
Arg(Me)-Phe(4F)—NH$_2$ (Compound No. 318), (xii) D-Tyr-Asn-Trp-Asn-Ser-PheΨ(NHCO)Gly-
Leu-Arg(Me)-Phe-NH$_2$ (Compound No. 319), (xiii) 3-Pyridylpropionyl-Asn-Ser-Phe-AzaGly-Leu-
Arg(Me)-Phe-NH$_2$ (Compound No. 322),
(SEQ ID NO: 26)

(xiv) 4-Imidazoleacetyl-Asn-Ser-Phe-AzaGly-Leu-
Arg(Me)-Phe-NH$_2$ (Compound No. 323),
(SEQ ID NO: 27)

(xv) D-Tyr-D-Pya(4)-Asn-Ser-Phe-AzaGly-Leu-
Arg(Me)-Trp-NH$_2$ (Compound No. 385),
or (xvi) D-Tyr-D-Pya(4)-Asn-Ser-Phe-AzaGly-Leu-
Arg(Me)-Trp-NH$_2$ (Compound No. 386).

[3] A prodrug of the metastin derivative (I) according to (1) or a salt thereof.

[4] A pharmaceutical comprising the metastin derivative (I) according to (1) or a salt thereof, or a prodrug thereof.

[5] The pharmaceutical according to [4], which is an agent for suppressing cancer metastasis or an agent for suppressing cancer proliferation.

[6] The pharmaceutical according to [4], which is an agent for preventing/treating cancer.

[7] The pharmaceutical according to [4], which is an agent for regulating a function of the pancreas.

[8] The pharmaceutical according to [4], which is an agent for preventing/treating acute or chronic pancreatitis or pancreatic cancer.

[9] The pharmaceutical according to [4], which is an agent for regulating a function of the placenta.

[10] The pharmaceutical according to [4], which is an agent for preventing/treating choriocarcinoma, hydatid mole, invasive mole, miscarriage, fetal hypoplasia, abnormal glucose metabolism, abnormal lipid metabolism or labor induction.

[11] The pharmaceutical according to [4], which is an agent for improving gonadal function.

[12] The pharmaceutical according to [4], which is an agent for preventing/treating hormone-dependent cancer (e.g., prostate cancer, breast cancer), infertility, endometriosis or myoma of the uterus.

[13] The pharmaceutical according to [4], which is an agent for inducing or stimulating ovulation.

[14] The pharmaceutical according to [4], which is a gonadotropic hormone secretagogue agent or a sex hormone secretagogue agent.

[15] The pharmaceutical according to [4], which is an agent for preventing/treating Alzheimer's disease or mild cognitive impairment.

[16] A method for suppressing cancer metastasis or cancer proliferation, which comprises administering to a mammal an effective dose of the metastin derivative (I) according to [1] or a salt thereof, or a prodrug thereof.

[17] A method for preventing/treating cancer, which comprises administering to a mammal an effective dose of the metastin derivative (I) according to [1] or a salt thereof, or a prodrug thereof.

[18] A method for regulating a function of the pancreas, which comprises administering to a mammal an effective dose of the metastin derivative (I) according to [1] or a salt thereof, or a prodrug thereof.

[19] A method for preventing/treating acute or chronic pancreatitis or pancreatic cancer, which comprises administering to a mammal an effective dose of the metastin derivative (I) according to [1] or a salt thereof, or a prodrug thereof.

[20] A method for regulating a function of the placenta, which comprises administering to a mammal an effective dose of the metastin derivative (I) according to [1] or a salt thereof, or a prodrug thereof.

[21] A method for preventing/treating choriocarcinoma, hydatid mole, invasive mole, miscarriage, fetal hypoplasia, abnormal glucose metabolism, abnormal lipid metabolism or labor induction, which comprises administering to a mammal an effective dose of the metastin derivative (I) according to [1] or a salt thereof, or a prodrug thereof.

[22] A method for improving gonadal function, which comprises administering to a mammal an effective dose of the metastin derivative (I) according to [1] or a salt thereof, or a prodrug thereof.

[23] A method for preventing/treating hormone-dependent cancer (e.g., prostate cancer, breast cancer), infertility, endometriosis or myoma of the uterus, which comprises administering to a mammal an effective dose of the metastin derivative (I) according to [1] or a salt thereof, or a prodrug thereof.

[24] A method for inducing or stimulating ovulation, which comprises administering to a mammal an effective dose of the metastin derivative (I) according to [1] or a salt thereof, or a prodrug thereof.

[25] A method for promoting gonadotropic hormone secretion or promoting sex hormone secretion, which comprises administering to a mammal an effective dose of the metastin derivative (I) according to [1] or a salt thereof, or a prodrug thereof.

[26] A method for preventing/treating Alzheimer's disease or mild cognitive impairment, which comprises administering to a mammal an effective dose of the metastin derivative (I) according to [1] or a salt thereof, or a prodrug thereof.

[27] Use of the metastin derivative (I) according to [1] or a salt thereof, or a prodrug thereof to manufacture an agent for suppressing cancer metastasis or an agent for suppressing cancer proliferation.

[28] Use of the metastin derivative (I) according to [1] or a salt thereof, or a prodrug thereof to manufacture an agent for preventing/treating cancer.

[29] Use of the metastin derivative (I) according to [1] or a salt thereof, or a prodrug thereof to manufacture an agent for regulating a function of the pancreas.

[30] Use of the metastin derivative (I) according to [1] or a salt thereof, or a prodrug thereof to manufacture an agent for preventing/treating acute or chronic pancreatitis or pancreatic cancer.

[31] Use of the metastin derivative (I) according to [1] or a salt thereof, or a prodrug thereof to manufacture an agent for regulating a function of the placenta.

[32] Use of the metastin derivative (I) according to [1] or a salt thereof, or a prodrug thereof to manufacture an agent for preventing/treating choriocarcinoma, hydatid mole, invasive mole, miscarriage, fetal hypoplasia, abnormal glucose metabolism, abnormal lipid metabolism or labor induction.

[33] Use of the metastin derivative (I) according to [1] or a salt thereof, or a prodrug thereof to manufacture an agent for improving gonadal function.

[34] Use of the metastin derivative (I) according to [1] or a salt thereof, or a prodrug thereof to manufacture an agent for preventing/treating hormone-dependent cancer (e.g., prostate cancer, breast cancer), infertility, endometriosis or myoma of the uterus.

[35] Use of the metastin derivative (I) according to [1] or a salt thereof, or a prodrug thereof to manufacture an agent for inducing or stimulating ovulation.

[36] Use of the metastin derivative (I) according to [1] or a salt thereof, or a prodrug thereof to manufacture a gonadotropic hormone secretagogue agent or a sex hormone secretagogue agent.

[37] Use of the metastin derivative (I) according to [1] or a salt thereof, or a prodrug thereof to manufacture an agent for preventing/treating Alzheimer's disease or mild cognitive impairment.

[38] A pancreatic glucagon secretagogue agent, comprising an agonist for a metastin receptor.

[39] An agent for promoting urine formation, comprising an agonist for a metastin receptor.

[40] An agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising an agonist for a metastin receptor.

[41] The agent according to [38] through [40], wherein the agonist for a metastin receptor is the metastin derivative (I) according to [1] or a salt thereof, or a prodrug thereof.

[42] A method for promoting pancreatic glucagon secretion, which comprises administering to a mammal an effective dose of the agonist for a metastin receptor.

[43] A method for promoting urine formation, which comprises administering to a mammal an effective dose of the agonist for a metastin receptor.

[44] A method for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, which comprises administering to a mammal an effective dose of the agonist for a metastin receptor.

[45] Use of the agonist for a metastin receptor to manufacture a pancreatic glucagon secretagogue agent.

[46] Use of the agonist for a metastin receptor to manufacture an agent for promoting urine formation.
and,

[47] Use of the agonist for a metastin receptor to manufacture an agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

The present invention further provides the following features.

[1] A hyperglycemic agent, comprising metastin or a salt thereof.

[2] A pancreatic glucagon secretagogue agent, comprising metastin or a salt thereof.

[3] An agent for promoting urine formation, comprising metastin or a salt thereof.

[4] An agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising metastin or a salt thereof.

[5] A hyperglycemic agent, comprising a DNA comprising a DNA encoding metastin.

[6] A pancreatic glucagon secretagogue agent, comprising a DNA comprising a DNA encoding metastin.

[7] An agent for promoting urine formation, comprising a DNA comprising a DNA encoding metastin.

[8] An agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising a DNA comprising a DNA encoding metastin.

[9] A diagnostic agent for obesity, hyperlipemia, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders, lipotoxicity, diabetes mellitus, impaired glucose tolerance, ketosis, acidosis, pollakiuria, nocturnal enuresis, sexual dysfunction, skin disorders, arthropathy, osteopenia, arteriosclerosis, thrombotic disorders, dyspepsia or deficits in memory and learning, comprising a DNA comprising a DNA encoding metastin.

[10] A hypoglycemic agent, comprising an antibody to metastin or a salt thereof.

[11] An agent for suppressing pancreatic glucagon secretion, comprising an antibody to metastin or a salt thereof.

[12] An agent for suppressing urine formation, comprising an antibody to metastin or a salt thereof.

[13] An agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, comprising an antibody to metastin or a salt thereof.

[14] A diagnostic agent for obesity, hyperlipemia, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders, lipotoxicity, diabetes mellitus, impaired glucose tolerance, ketosis, acidosis, pollakiuria, nocturnal enuresis, sexual dysfunction, skin disorders, arthropathy, osteopenia, arteriosclerosis, thrombotic disorders, dyspepsia or deficits in memory and learning, comprising an antibody to metastin or a salt thereof.

[15] A hypoglycemic agent, comprising an antisense DNA to a DNA comprising a DNA encoding metastin.

[16] An agent for suppressing pancreatic glucagon secretion, comprising an antisense DNA to a DNA comprising a DNA encoding metastin.

[17] An agent for suppressing urine formation, comprising an antisense DNA to a DNA comprising a DNA encoding metastin.

[18] An agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, comprising an antisense DNA to a DNA comprising a DNA encoding metastin.

[19] The agent according to [1] through [18], wherein metastin is:
(1) a peptide containing the N-terminal 47-54 amino acid sequence in the amino acid sequence represented by SEQ ID NO: 1 and consisting of 8 to 54 amino acid residues,
(2) a peptide containing the N-terminal 134-141 amino acid sequence in the amino acid sequence represented by SEQ ID NO: 3 and consisting of 8 to 54 amino acid residues,
(3) a peptide containing the N-terminal 138-145 amino acid sequence in the amino acid sequence represented by SEQ ID NO: 5 and consisting of 8 to 54 amino acid residues, or,
(4) a peptide containing the N-terminal 112-119 amino acid sequence in the amino acid sequence represented by SEQ ID NO: 7 and consisting of 8 to 54 amino acid residues.

[20] A hyperglycemic agent, comprising a metastin receptor or a salt thereof.

[21] A pancreatic glucagon secretagogue agent, comprising a metastin receptor or a salt thereof.

[22] An agent for promoting urine formation, comprising a metastin receptor or a salt thereof.

[23] An agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising a metastin receptor or a salt thereof.

[24] A hyperglycemic agent, comprising a DNA comprising a DNA encoding a metastin receptor.

[25] A pancreatic glucagon secretagogue agent, comprising a DNA comprising a DNA encoding a metastin receptor.

[26] An agent for promoting urine formation, comprising a DNA comprising a DNA encoding a metastin receptor.

[27] An agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising a DNA comprising a DNA encoding a metastin receptor.

[28] A diagnostic agent for obesity, hyperlipemia, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders, lipotoxicity, diabetes mellitus, impaired glucose tolerance, ketosis, acidosis, pollakiuria, nocturnal enuresis, sexual dysfunction, skin disorders, arthropathy, osteopenia, arteriosclerosis, thrombotic disorders, dyspepsia or deficits in memory and learning, comprising a DNA comprising a DNA encoding a metastin receptor.

[29] A hypoglycemic agent, comprising an antibody to the metastin receptor or a salt thereof.

[30] An agent for suppressing pancreatic glucagon secretion, comprising an antibody to a metastin receptor or a salt thereof.

[31] An agent for suppressing urine formation, comprising an antibody to a metastin receptor or a salt thereof.

[32] An agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, comprising an antibody to a metastin receptor or a salt thereof.

[33] An agent for preventing/treating obesity, hyperlipemia, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders, lipotoxicity, diabetes mellitus, impaired glucose tolerance, ketosis, acidosis, pollakiuria, nocturnal enuresis, sexual dysfunction, skin disorders, arthropathy, osteopenia, arteriosclerosis, thrombotic disorders, dyspepsia or deficits in memory and learning, comprising an antibody to a metastin receptor or a salt thereof.

[34] A hypoglycemic agent, comprising an antisense DNA to a DNA comprising a DNA encoding a metastin receptor.

[35] An agent for suppressing pancreatic glucagon secretion, comprising an antisense DNA to a DNA comprising a DNA encoding a metastin receptor.

[36] An agent for suppressing urine formation, comprising an antisense DNA to a DNA comprising a DNA encoding a metastin receptor.

[37] An agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, comprising an antisense DNA to a DNA comprising a DNA encoding a metastin receptor.

[38] The agent according to [1] through [22], wherein the metastin receptor is a protein comprising the same or substantially the same amino acid sequence as the amino acid sequence represented by SEQ ID NO: 9, SEQ ID NO: 11 or SEQ ID NO: 13.

[39] A method of screening a blood glucose regulating drug, a pancreatic glucagon regulating drug or a urine formation regulating drug, which comprises using metastin or a salt thereof and/or a metastin receptor, its partial peptide or a salt thereof.

[40] A kit for screening a blood glucose regulating drug, a pancreatic glucagon regulating drug or a urine formation regulating drug, comprising metastin or a salt thereof and/or a metastin receptor, its partial peptide or a salt thereof.

[41] A method of screening a blood glucose regulating drug, a pancreatic glucagon regulating drug or a urine formation regulating drug, which comprises using a DNA comprising a DNA encoding metastin and/or a DNA comprising a DNA encoding a metastin receptor or its partial peptide.

[42] A kit for screening a blood glucose regulating drug, a pancreatic glucagon regulating drug or a urine formation regulating drug, comprising a DNA comprising a DNA encoding metastin and/or a DNA comprising a DNA encoding a metastin receptor or its partial peptide.

[43] A hypoglycemic agent, comprising an antagonist to a metastin receptor.

[44] An agent for suppressing pancreatic glucagon secretion, comprising an antagonist to a metastin receptor.

[45] An agent for suppressing urine formation, comprising an antagonist to a metastin receptor.

[46] An agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, comprising an antagonist to a metastin receptor.

[47] A hyperglycemic agent, comprising a substance that promotes the expression of metastin.

[48] A pancreatic glucagon secretagogue agent, comprising a substance that promotes the expression of metastin.

[49] An agent for promoting urine formation, comprising a substance that promotes the expression of metastin.

[50] An agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising a substance that promotes the expression of metastin.

[51] A hypoglycemic agent, comprising a substance that suppresses the expression of metastin.

[52] An agent for suppressing pancreatic glucagon secretion, comprising a substance that suppresses the expression of metastin.

[53] An agent for suppressing urine formation, comprising a substance that suppresses the expression of metastin.

[54] An agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, comprising a substance that suppresses the expression of metastin.

[55] A hyperglycemic agent, comprising a substance that promotes the expression of a metastin receptor.

[56] A pancreatic glucagon secretagogue agent, comprising a substance that promotes the expression of a metastin receptor.

[57] An agent for promoting urine formation, comprising a substance that promotes the expression of a metastin receptor.

[58] An agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, comprising a substance that promotes the expression of a metastin receptor.

[59] A hypoglycemic agent, comprising a substance that suppresses the expression of a metastin receptor.

[60] An agent for suppressing pancreatic glucagon secretion, comprising a substance that suppresses the expression of a metastin receptor.

[61] An agent for suppressing urine formation, comprising a substance that suppresses the expression of a metastin receptor.

[62] An agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, comprising a substance that suppresses the expression of a metastin receptor.

[63] A method of increasing blood glucose, which comprises administering to a mammal an effective dose of:
(1) metastin or a salt thereof,
(2) a DNA comprising a DNA encoding metastin,
(3) a metastin receptor or a salt thereof,
(4) a DNA comprising a DNA encoding a metastin receptor,
(5) a substance that promotes the expression of metastin, or,
(6) a substance that promotes the expression of a metastin receptor.

[64] A method of promoting pancreatic glucagon secretion, which comprises administering to a mammal an effective dose of:
(1) metastin or a salt thereof,
(2) a DNA comprising a DNA encoding metastin,
(3) a metastin receptor or a salt thereof,
(4) a DNA comprising a DNA encoding a metastin receptor,
(5) a substance that promotes the expression of metastin, or,
(6) a substance that promotes the expression of a metastin receptor.

[65] A method of preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity, which comprises administering to a mammal an effective dose of:
(1) metastin or a salt thereof,
(2) a DNA comprising a DNA encoding metastin,
(3) a metastin receptor or a salt thereof,
(4) a DNA comprising a DNA encoding a metastin receptor,
(5) a substance that promotes the expression of metastin, or,
(6) a substance that promotes the expression of a metastin receptor.

[66] A method of lowering blood glucose, which comprises administering to a mammal an effective dose of:
(1) an antibody to metastin or a salt thereof,
(2) an antisense DNA to a DNA comprising a DNA encoding metastin,
(3) an antibody to a metastin receptor or a salt thereof,
(4) an antisense DNA to a DNA comprising a DNA encoding a metastin receptor,
(5) an antagonist to a metastin receptor,
(6) a substance that suppresses the expression of metastin, or,
(7) a substance that suppresses the expression of a metastin receptor.

[67] A method of suppressing pancreatic glucagon secretion, which comprises administering to a mammal an effective dose of:
(1) an antibody to metastin or a salt thereof,
(2) an antisense DNA to a DNA comprising a DNA encoding metastin,
(3) an antibody to a metastin receptor or a salt thereof, (4) an antisense DNA to a DNA comprising a DNA encoding a metastin receptor,
(5) an antagonist to a metastin receptor,
(6) a substance that suppresses the expression of metastin, or,
(7) a substance that suppresses the expression of a metastin receptor.

[68] A method of preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning, which comprises administering to a mammal an effective dose of:
(1) an antibody to metastin or a salt thereof,
(2) an antisense DNA to a DNA comprising a DNA encoding metastin,
(3) an antibody to a metastin receptor or a salt thereof,
(4) an antisense DNA to a DNA comprising a DNA encoding a metastin receptor,
(5) an antagonist to a metastin receptor,
(6) a substance that suppresses the expression of metastin, or,
(7) a substance that suppresses the expression of a metastin receptor.

[69] Use of:
(1) metastin or a salt thereof,
(2) a DNA comprising a DNA encoding metastin,
(3) a metastin receptor or a salt thereof,
(4) a DNA comprising a DNA encoding a metastin receptor,
(5) a substance that promotes the expression of metastin, or,
(6) a substance that promotes the expression of a metastin receptor,
to manufacture a hyperglycemic agent.

[70] Use of:
(1) metastin or a salt thereof,
(2) a DNA comprising a DNA encoding metastin,
(3) a metastin receptor or a salt thereof,
(4) a DNA comprising a DNA encoding a metastin receptor,
(5) a substance that promotes the expression of metastin, or,
(6) a substance that promotes the expression of a metastin receptor,
to manufacture a pancreatic glucagon secretagogue agent.

[71] Use of:
(1) metastin or a salt thereof,
(2) a DNA comprising a DNA encoding metastin,
(3) a metastin receptor or a salt thereof,
(4) a DNA comprising a DNA encoding a metastin receptor,
(5) a substance that promotes the expression of metastin, or,
(6) a substance that promotes the expression of a metastin receptor,
to manufacture an agent for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

[72] Use of:
(1) an antibody to metastin or a salt thereof,
(2) an antisense DNA to a DNA comprising a DNA encoding metastin,
(3) an antibody to a metastin receptor or a salt thereof,
(4) an antisense DNA to a DNA comprising a DNA encoding a metastin receptor,
(5) an antagonist to a metastin receptor,
(6) a substance that suppresses the expression of metastin, or,
(7) a substance that suppresses the expression of a metastin receptor,
to manufacture a hypoglycemic agent.

[73] Use of:
(1) an antibody to metastin or a salt thereof,
(2) an antisense DNA to a DNA comprising a DNA encoding metastin,
(3) an antibody to a metastin receptor or a salt thereof,
(4) an antisense DNA to a DNA comprising a DNA encoding a metastin receptor,
(5) an antagonist to a metastin receptor,
(6) a substance that suppresses the expression of metastin, or,
(7) a substance that suppresses the expression of a metastin receptor,
to manufacture an agent for suppressing pancreatic glucagon secretion.

[74] Use of:
(1) an antibody to metastin or a salt thereof,
(2) an antisense DNA to a DNA comprising a DNA encoding metastin,
(3) an antibody to a metastin receptor or a salt thereof,
(4) an antisense DNA to a DNA comprising a DNA encoding a metastin receptor,
(5) an antagonist to a metastin receptor,
(6) a substance that suppresses the expression of metastin, or,
(7) a substance that suppresses the expression of a metastin receptor,
to manufacture an agent for preventing/treating diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning.

[75] A method of screening a blood glucose regulating drug, a pancreatic glucagon regulating drug or a urine formation regulating drug, which comprises using (a) metastin and/or (b) a metastin receptor (hereinafter, including its partial peptide).

[76] A method of screening a blood glucose regulating drug, a pancreatic glucagon regulating drug or a urine formation regulating drug, which comprises using (a) a DNA comprising a DNA encoding metastin and/or (b) a DNA encoding a metastin receptor.

[77] A method of screening a substance that alters the binding property of metastin to a metastin receptor, which comprises assaying the binding amount of labeled metastin to a metastin receptor in the case wherein labeled metastin is brought in contact with the metastin receptor and in the case wherein labeled metastin and a test compound are brought in contact with the metastin receptor, and comparing the binding amount between these cases.

[78] A method of screening a substance that alters the binding property of metastin to a cell containing a metastin receptor or a membrane fraction of the cell, which comprises assaying the binding amount of labeled metastin to a cell containing a metastin receptor in the case wherein labeled metastin is brought in contact with the cell containing the metastin receptor or a membrane fraction of the cell and in the case wherein labeled metastin and a test compound are brought in contact with the cell or the membrane fraction, and comparing the binding amount between these cases.

[79] A method of screening a substance that alters the binding property of metastin to a metastin receptor, which comprises assaying the binding amount of labeled metastin to a metastin receptor, in the case wherein labeled metastin is brought in contact with a metastin receptor expressed on a cell membrane by culturing a transformant containing a DNA encoding the metastin receptor and in the case wherein labeled metastin and a test compound are brought in contact with the metastin receptor expressed on a cell membrane by culturing a transformant containing a DNA encoding the metastin receptor, and comparing the binding amount between the cases.

[80] A method of screening a substance that alters the binding property of metastin to a metastin receptor, which comprises assaying a cell stimulating activity mediated by a metastin receptor, in the case wherein a metastin receptor-activating compound (e.g., metastin, the metastin derivative (I) according to [1] or a salt thereof, or a prodrug thereof) is brought in contact with a cell (e.g., CHO cell, human colon cancer-derived cell line SW620) containing the metastin receptor and in the case wherein a metastin receptor-activating compound and a test compound are brought in contact with a cell containing the metastin receptor, and comparing the activity between the cases.

[81] A method of screening a substance that alters the binding property of metastin to a metastin receptor, which comprises assaying a cell stimulating activity mediated by a metastin receptor, in the case wherein a metastin receptor-activating compound (e.g., metastin, the metastin derivative (I) according to [1] or a salt thereof, or a prodrug thereof) is brought in contact with a metastin receptor expressed on a cell membrane by culturing a transformant containing a DNA encoding the metastin receptor and in the case wherein a metastin receptor-activating compound and a test compound are brought in contact with the metastin receptor expressed on a cell membrane by culturing a transformant containing a DNA encoding the metastin receptor, and comparing the activity between the cases.

[82] A method of screening an agonist for a metastin receptor, which comprises assaying and comparing a cell stimulating activity mediated by the metastin receptor when a test compound is brought in contact with a cell containing the metastin receptor.

[83] A method of screening an agonist for a metastin receptor, which comprises assaying and comparing a cell stimulating activity mediated by the metastin receptor when a test compound is brought in contact with the metastin receptor expressed on a cell membrane by culturing a transformant containing a DNA encoding the metastin receptor.

[84] The screening method according to [80] through [83], wherein the cell stimulating activity is an intracellular $Ca^{2+}$ release promoting activity, a cell growth inhibition activity, a chemotaxis inhibition activity, a tumor growth suppression activity, a hyperglycemic activity or a pancreatic glucagon secretagogue activity.

[85] A method of screening an agonist for a metastin receptor or an antagonist to a metastin receptor, which comprises using (a) the metastin derivative (I) according to

[1] or a salt thereof, or a prodrug thereof and/or (b) a metastin receptor.

In the formula described above, each of $Z^1$, $Z^3$, $Z^5$ and $Z^7$ represents hydrogen atom or a $C_{1-3}$ alkyl group; and each of $Z^2$, $Z^4$, $Z^6$ and $Z^8$ represents hydrogen atom, O or S.

The $C_{1-3}$ alkyl group used includes methyl group, ethyl group, propyl group and isopropyl group.

Preferred combinations of $Z^1$ through $Z^8$ further include the cases wherein $Z^1$ and $Z^3$ represent hydrogen atom, each of $Z^5$ and $Z^7$ represents hydrogen atom or a $C_{1-3}$ alkyl group and each of $Z^2$, $Z^4$, $Z^6$ and $Z^8$ represents O or S.

More preferably, the combinations of $Z^1$ through $Z^8$ include:

(a) the case wherein $Z^1$ is hydrogen atom, $Z^3$ is hydrogen atom, $Z^5$ is hydrogen atom, $Z^7$ is hydrogen atom, $Z^2$ is O, $Z^4$ is O, $Z^6$ is O and $Z^8$ is O;

(b) the case wherein $Z^1$ is hydrogen atom, $Z^3$ is hydrogen atom, $Z^5$ is hydrogen atom, $Z^7$ is hydrogen atom, $Z^2$ is O, $Z^4$ is O, $Z^6$ is O and $Z^8$ is S;

(c) the case wherein $Z^1$ and $Z^3$ are hydrogen atom, $Z^5$ is hydrogen atom, $Z^7$ is methyl group, $Z^2$ is O, $Z^4$ is O, $Z^6$ is 0 and $Z^8$ is O; etc. Among others, the cases (a) and (b) are preferred.

$R^1$ represents (1) hydrogen atom, (2) a $C_{1-8}$ alkyl group optionally substituted with a substituent selected from the group consisting of an optionally substituted carbamoyl group, an optionally substituted hydroxyl group and an optionally substituted aromatic cyclic group; among others, (1) hydrogen atom or (2) a $C_{1-8}$ alkyl group, which is substituted with a substituent selected from the group consisting of an optionally substituted carbamoyl group, an optionally substituted hydroxyl group and an optionally substituted aromatic cyclic group, is preferred.

The "$C_{1-8}$ alkyl group" used includes, for example, a linear $C_{1-8}$ alkyl group such as methyl, ethyl, propyl, isopropyl, butyl, isobutyl, sec-butyl, tert-butyl, pentyl, isopentyl, neopentyl, hexyl, heptyl, octyl, etc., and a cyclic $C_{3-8}$ alkyl group such as cyclopropyl, cyclobutyl, cyclopentyl, cyclohexyl, etc. Among others, $C_{1-3}$ alkyl groups such as methyl, ethyl, etc. are preferred.

The "optionally substituted carbamoyl group" used includes, for example, carbamoyl, a mono-$C_{1-6}$ alkylcarbamoyl group (e.g., methylcarbamoyl, ethylcarbamoyl, etc.), a di-$C_{1-6}$ alkylcarbamoyl group (e.g., dimethylcarbamoyl, diethylcarbamoyl, ethylmethylcarbamoyl, etc.), a mono- or di-$C_{6-14}$ arylcarbamoyl group (e.g., phenylcarbamoyl, 1-naphthylcarbamoyl, 2-naphthylcarbamoyl, etc.), a mono- or di-5- to 7-membered heterocyclic carbamoyl group containing 1 to 4 hetero atoms of 1 or 2 members selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.) and the like.

The "optionally substituted hydroxyl group" used includes, for example, hydroxy group, an optionally substituted $C_{1-6}$ alkoxy group, an optionally substituted $C_{6-14}$ aryloxy group, an optionally substituted $C_{7-16}$ aralkyloxy group, etc. The "optionally substituted $C_{1-6}$ alkoxy group," "optionally substituted $C_{6-14}$ aryloxy group" and "optionally substituted $C_{7-16}$ aralkyloxy group" used are the same as given for the "optionally substituted $C_{1-6}$ alkoxy group," "optionally substituted $C_{6-14}$ aryloxy group" and "optionally substituted $C_{7-16}$ aralkyloxy group" in Substituent group A, which will be later described.

The "aromatic cyclic group" in "optionally substituted aromatic cyclic group" includes, for example, an aromatic hydrocarbon group, an aromatic heterocyclic group, an aromatic fused-ring group, an aromatic fused heterocyclic group, etc.

The "aromatic hydrocarbon group" used includes, for example, a $C_{6-14}$ aryl group such as phenyl, 2-biphenylyl, 3-biphenylyl, 4-biphenylyl, cyclooctatetraenyl, etc.

The "aromatic heterocyclic group" used includes, for example, a 5- to 14-membered, preferably 5- to 10-membered, more preferably 5- or 6-membered aromatic heterocyclic group containing 1 to 4 hetero atoms of 1 or 2 members selected from nitrogen, sulfur and oxygen atoms in addition to carbon atoms. Specific examples are thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isooxazolyl (e.g., 3-isooxazolyl), etc.

The "aromatic fused-ring group" used includes a $C_{8-14}$ aromatic fused-ring group such as naphthyl (e.g., 1-naphthyl, 2-naphthyl), anthryl (e.g., 2-anthryl, 9-anthryl) and the like.

The "aromatic fused heterocyclic group" used includes, for example, a 5- to 14-membered (preferably 5- to 10-membered) bicyclic or tricyclic aromatic heterocyclic group containing 1 to 4 hetero atoms of 1 or 2 members selected from nitrogen, sulfur and oxygen atoms in addition to 3 to 11 carbon atoms, or a monovalent group formed by removing one optional hydrogen atom from a 7- to 10-membered aromatic bridged-hetero ring in a 5- to 14-membered (preferably 5- to 10-membered) ring containing 1 to 4 hetero atoms of 1 or 2 members selected from nitrogen, sulfur and oxygen atoms in addition to carbon atoms. Specific examples of these groups used are quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl (e.g., 2-benzo[b]thienyl, 3-benzo[b]thienyl), benzo[b]furanyl (e.g., 2-benzo[b]furanyl, 3-benzo[b]furanyl) and the like.

The "substituent" used for the "aromatic cyclic group" includes a substituent selected from the Substituent group A, which will be later described.

For $R^1$, there are used, for example, hydrogen atom, carbamoylmethyl, 2-carbamoylethyl, hydroxymethyl, 1-hydroxyethyl, benzyl, 4-hydroxybenzyl, 2-pyridylmethyl, 3-pyridylmethyl, 4-pyridylmethyl, 2-thienylmethyl, 3-thienylmethyl, 1-naphthylmethyl, 2-naphthylmethyl, 3-indolemethyl, methyl, ethyl, propyl, isopropyl, butyl, isobutyl, sec-butyl, tert-butyl, cyclohexylmethyl, etc.; among others, hydroxymethyl, 1-hydroxyethyl, benzyl, 4-hydroxybenzyl, 3-indolemethyl, methyl, isobutyl, etc. are preferably used, with particular preference of hydroxymethyl, 1-hydroxyethyl, etc.

$R^2$ represents (1) hydrogen atom, (2) a cyclic or linear $C_{1-10}$ alkyl group or (3) a $C_{1-10}$ alkyl group consisting of a cyclic alkyl group and a linear alkyl group.

The cyclic $C_{1-10}$ alkyl group used includes, for example, a $C_{3-8}$ cycloalkyl group such as cyclopropyl, cyclobutyl, cyclopentyl, cyclohexyl, etc.

The linear $C_{1-10}$ alkyl group includes, for example, methyl, ethyl, propyl, isopropyl, butyl, isobutyl, sec-butyl, tert-butyl, pentyl, isopentyl, neopentyl, hexyl, heptyl, octyl, nonanyl, decanyl, etc.

The $C_{1-10}$ alkyl group consisting of a cyclic alkyl group and a linear alkyl group used includes, for example, a $C_{3-7}$ cycloalkyl-$C_{1-3}$ alkyl group such as cyclopentylmethyl, cyclohexylmethyl, etc.

Preferably, $R^2$ is methyl, ethyl, propyl, isopropyl, butyl, isobutyl, sec-butyl, tert-butyl, cyclohexylmethyl, etc.; among others, methyl, ethyl, isopropyl, isobutyl, sec-butyl, tert-butyl, etc. are preferred, with particular preference of isopropyl, isobutyl, etc.

$R^3$ represents:
(1) a $C_{1-8}$ alkyl group having an optionally substituted basic group and further optionally having an additional substituent,
(2) an aralkyl group having an optionally substituted basic group and optionally having an additional substituent,
(3) a $C_{1-4}$ alkyl group having a non-aromatic cyclic hydrocarbon group of carbon atoms not greater than 7 having an optionally substituted basic group, and further optionally having an additional substituent, or,
(4) a $C_{1-4}$ alkyl group having a non-aromatic heterocyclic group of carbon atoms not greater than 7 having an optionally substituted basic group, and further optionally having an additional substituent.

The "optionally substituted basic group" used includes, for example, (1) a guanidino group optionally having 1 or 2 substituents from a $C_{1-6}$ alkyl, a $C_{1-6}$ acyl (e.g., methyl, ethyl, propyl, isopropyl, butyl, acetyl, propionyl, etc.), etc., (2) an amino group optionally having 1 to 3 substituents from a $C_{1-6}$ alkyl, a $C_{1-6}$ acyl (e.g., methyl, ethyl, propyl, isopropyl, butyl, acetyl, propionyl, etc.), etc., (3) a $C_{1-6}$ alkylcarbonyl-amino group (e.g., acetamido) optionally substituted with a guanidino group optionally having 1 or 2 substituents from a $C_{1-6}$ alkyl, a $C_{1-6}$ acyl (e.g., methyl, ethyl, propyl, isopropyl, butyl, acetyl, propionyl, etc.), etc., (4) a $C_{1-6}$ alkylcarbonyl-amino group (e.g., acetamido) optionally substituted with an amino group optionally having 1 to 3 substituents from a $C_{1-6}$ alkyl, a $C_{1-6}$ acyl (e.g., methyl, ethyl, propyl, isopropyl, butyl, acetyl, propionyl, etc.), etc. Among others, preferred are guanidino, N-methylguanidino, N,N-dimethylguanidino, N,N'-dimethylguanidino, N-ethylguanidino, N-acetylguanidino, amino, N-methylamino, N,N-dimethylamino, aminoacetamido, guanidinoacetamido, amidino, etc.

The "additional substituent" other than the "optionally substituted basic group" used includes a substituent selected from the Substituent group A later described.

The "$C_{1-8}$ alkyl group" used includes, for example, methyl, ethyl, propyl, isopropyl, butyl, isobutyl, sec-butyl, tert-butyl, pentyl, isopentyl, neopentyl, hexyl, heptyl, octyl, etc.

The "aralkyl group" used includes, for example, a $C_{7-16}$ aralkyl group such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl, etc.

The "non-aromatic cyclic hydrocarbon group of carbon atoms not greater than 7" used includes, for example, a $C_{3-7}$ cycloalkyl group such as cyclopropyl, cyclobutyl, cyclopentyl, cyclohexyl, etc.

The "non-aromatic heterocyclic group of carbon atoms not greater than 7" used includes, for example, a 5- to 10-membered non-aromatic heterocyclic group containing 1 to 4 hetero atoms of 1 or 2 members selected from nitrogen, sulfur and oxygen atoms in addition to 1 to 7 carbon atoms, etc. Specifically used are pyrrolidinyl (e.g., 1-pyrrolidinyl, 2-pyrrolidinyl, 3-pyrrolidinyl), an oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The "$C_{1-4}$ alkyl group" used includes, for example, methyl, ethyl, propyl, isopropyl, butyl, isobutyl, sec-butyl, tert-butyl, etc.

For $R^3$, there are used, for example, (1) 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, aminomethyl, aminoacetamidomethyl, guanidinoacetamidomethyl, 2-(guanidinocarbonyl)ethyl, (2) 4-guanidinobenzyl, 4-aminobenzyl, (3) 4-guanidinocyclohexylmethyl, 4-aminocyclohexylmethyl, (4) 1-amidinopiperidin-4-ylmethyl, etc.; among others, preferred are 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-propylguanidino)propyl, 3-(N-acetylguanidino)propyl, 4-guanidinobutyl, 4-(N-methylguanidino)butyl, 2-guanidinoethyl, 2-(N-methylguanidino)ethyl, 4-aminobutyl, 4-(N-methylamino)butyl, 4-(N,N-dimethylamino)butyl, 3-aminopropyl, 2-aminoethyl, 4-aminobenzyl, aminoacetamidomethyl, guanidinoacetamidomethyl, etc., and particularly preferred are 3-guanidinopropyl, 3-(N-methylguanidino)propyl, 3-(N,N-dimethylguanidino)propyl, 3-(N,N'-dimethylguanidino)propyl, 3-(N-ethylguanidino)propyl, 3-(N-acetylguanidino)propyl, 4-guanidinobutyl, 4-(N-methylguanidino)butyl, 2-guanidinoethyl, 4-aminobutyl, etc.

$R^4$ represents a $C_{1-4}$ alkyl group, which may optionally be substituted with a substituent selected from the group consisting of:

(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused-ring group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7, and
(6) an optionally substituted non-aromatic heterocyclic group having carbon atoms not greater than 7; among others, preferred are a $C_{1-4}$ alkyl group substituted with a substituent selected from the group consisting of:

(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused-ring group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7; and,
(6) an optionally substituted non-aromatic heterocyclic group having carbon atoms not greater than 7.

The "$C_{1-4}$ alkyl group" used includes, for example, methyl, ethyl, propyl, isopropyl, butyl, isobutyl, sec-butyl, tert-butyl, etc.

The "$C_{6-12}$ aromatic hydrocarbon group" used includes, for example, a monocyclic $C_{6-12}$ aromatic hydrocarbon group such as phenyl, cyclooctatetraenyl, etc.

The "5- to 14-membered aromatic heterocyclic group consisting of 1 to 7 carbon atoms and hetero atoms selected from the group consisting of nitrogen, oxygen and sulfur atoms" used includes, for example, a 5- to 14-membered, preferably 5- to 10-membered, more preferably 5- or 6-membered monocyclic aromatic heterocyclic group containing 1 to 4 hetero atoms of 1 or 2 members selected from nitrogen, sulfur and oxygen atoms in addition to 1 to 7 carbon atoms. Specific examples used are thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), etc.

The "$C_{8-14}$ aromatic fused-ring group" used includes, for example, naphthyl (e.g., 1-naphthyl, 2-naphthyl), anthryl (e.g., 2-anthryl, 9-anthryl), etc.

The "optionally substituted 5- to 14-membered aromatic fused heterocyclic group consisting of 3 to 11 carbon atoms and hetero atoms selected from the group consisting of nitrogen, oxygen and sulfur atoms" includes, for example, a 5- to 14-memberd (preferably 5- to 10-membered) bicyclic or tricyclic aromatic heterocyclic group containing 1 to 4 hetero atoms of 1 or 2 members selected from nitrogen, sulfur and oxygen atoms in addition to 3 to 11 carbon atoms, or a monovalent group formed by removing one optional hydrogen atom from a 7- to 10-membered aromatic bridged-hetero ring in a 5- to 14-membered (preferably 5- to 10-membered) ring containing 1 to 4 hetero atoms of 1 or 2 members selected from nitrogen, sulfur and oxygen atoms in addition to carbon atoms. Specific examples used are quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), indolyl (e.g., 1-indolyl, 2-indolyl, 3-indolyl), 2-benzothiazolyl, benzo[b]thienyl (e.g., 2-benzo[b]thienyl, 3-benzo[b]thienyl), benzo[b]furanyl (e.g., 2-benzo[b]furanyl, 3-benzo[b]furanyl), etc.

The "non-aromatic cyclic hydrocarbon group of carbon atoms not greater than 7" used includes, for example, a $C_{3-7}$ cycloalkyl group such as cyclopropyl, cyclobutyl, cyclopentyl, cyclohexyl, etc.

The "non-aromatic heterocyclic group of carbon atoms not greater than 7" used includes, for example, a 5- to 10-membered non-aromatic heterocyclic group containing 1 to 4 hetero atoms of 1 or 2 members selected from nitrogen, sulfur and oxygen atoms, in addition to 1 to 7 carbon atoms, such as pyrrolidinyl (e.g., 1-pyrrolidinyl, 2-pyrrolidinyl, 3-pyrrolidinyl), an oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The substituents used in these "$C_{6-12}$ aromatic hydrocarbon group," "5- to 14-membered aromatic heterocyclic group consisting of 1 to 7 carbon atoms and hetero atoms selected from the group consisting of nitrogen, oxygen and sulfur atoms," "$C_{8-14}$ aromatic fused-ring group," "5- to 14-membered aromatic fused heterocyclic group consisting of 3 to 11 carbon atoms and hetero atoms selected from the group consisting of nitrogen, oxygen and sulfur atoms," "non-aromatic cyclic hydrocarbon group of carbon atoms not greater than 7" and "non-aromatic heterocyclic group of carbon atoms not greater than 7" include, for example, substituents selected from oxo, a halogen atom (e.g., fluorine, chlorine, bromine, iodine, etc.), a $C_{1-3}$ alkylenedioxy (e.g., methylenedioxy, ethylenedioxy, etc.), nitro, cyano, an optionally substituted $C_{1-6}$ alkyl, an optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted $C_{7-16}$ aralkyl, an optionally substituted $C_{1-6}$ alkoxy, hydroxy, an optionally substituted $C_{6-14}$ aryloxy, an optionally substituted $C_{7-16}$ aralkyloxy, mercapto, an optionally substituted $C_{1-6}$ alkylthio, an optionally substituted $C_{6-14}$ arylthio, an optionally substituted $C_{7-16}$ aralkylthio, an optionally substituted amino [amino, an optionally substituted mono- or di-$C_{1-6}$ alkyl-amino (e.g., methylamino, dimethylamino, ethylamino, diethylamino, propylamino, isopropylamino, etc.), an optionally substituted mono- or di-$C_{2-6}$ alkenyl-amino (e.g., vinylamino, propenylamino, isopropenylamino), an optionally substituted $C_{2-6}$ alkynyl-amino (e.g., 2-butyn-1-yl-amino, 4-pentyn-1-yl-amino, 5-hexyn-1-yl-amino), an optionally substituted mono- or di-$C_{3-8}$ cycloalkyl-amino (e.g., cyclopropylamino, cyclohexylamino), an optionally substituted $C_{6-14}$ aryl-amino (e.g., phenylamino, diphenyl]amino, naphthylamino), an optionally substituted $C_{1-6}$ alkoxy-amino (e.g., methoxyamino, ethoxyamino, propoxyamino, isopropoxyamino), formylamino, an optionally substituted $C_{1-6}$ alkylcarbonyl-amino (e.g., acetylamino, propionylamino, pivaloylamino, etc.), an optionally substituted $C_{3-8}$ cycloalkyl-carbonylamino (e.g., cyclopropylcarbonylamino, cyclopentylcarbonylamino, cyclohexylcarbonylamino, etc.), an optionally substituted $C_{6-14}$ aryl-carbonylamino (e.g., benzoylamino, naphthoylamino, etc.), an optionally substituted $C_{1-6}$ alkoxy-carbonylamino (e.g., methoxycarbonylamino, ethoxycarbonylamino, propoxycarbonylamino, butoxycarbonylamino, etc.), an optionally substituted $C_{1-6}$ alkylsulfonylamino (e.g., methylsulfonylamino, ethylsulfonylamino, etc.), an optionally substituted $C_{6-14}$ arylsulfonylamino (e.g., phenylsulfonylamino, 2-naphthylsulfonylamino, 1-naphthylsulfonylamino, etc.)], formyl, carboxy, an optionally substituted $C_{1-6}$ alkylcarbonyl (e.g., acetyl, propionyl, pivaloyl, etc.), an optionally substituted $C_{3-8}$ cycloalkylcarbonyl (e.g., cyclopropylcarbonyl, cyclopentylcarbonyl, cyclohexylcarbonyl, 1-methylcyclohexylcarbonyl, etc.), an optionally substituted $C_{6-14}$ arylcarbonyl (e.g., benzoyl, 1-naphthoyl, 2-naphthoyl, etc.), an optionally substituted $C_{7-16}$ aralkylcarbonyl (e.g., phenylacetyl, 3-phenylpropionyl, etc.), an optionally substituted 5- to 7-membered heterocyclic carbonyl containing 1 to 4 hetero atoms of 1 or 2 members selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), an optionally esterified carboxyl, an optionally substituted carbamoyl group, an optionally substituted $C_{1-6}$ alkylsulfonyl (e.g., methylsulfonyl, ethylsulfonyl, etc.), an optionally substituted $C_{1-6}$ alkylsulfinyl (e.g., methylsulfinyl, ethylsulfinyl, etc.), an optionally substituted $C_{6-14}$ arylsulfonyl (e.g., phenylsulfonyl, 1-naphthylsulfonyl, 2-naphthylsulfonyl, etc.), an optionally substituted $C_{6-14}$ arylsulfinyl (e.g., phenylsulfinyl, 1-naphthylsulfinyl, 2-naphthylsulfinyl, etc.), an optionally substituted $C_{1-6}$ alkylcarbonyloxy (e.g., acetoxy, propionyloxy, etc.), an optionally substituted $C_{6-14}$ arylcarbonyloxy (e.g., benzoyloxy, naphthylcarbonyloxy, etc.), an optionally substituted $C_{1-6}$ alkoxycarbonyloxy (e.g., methoxycarbonyloxy, ethoxycarbonyloxy, propoxycarbonyloxy, butoxycarbonyloxy, etc.), an optionally substituted a mono-$C_{1-6}$ alkylcarbamoyloxy (e.g., methylcarbamoyloxy, ethylcarbamoyloxy, etc.), an optionally substituted di-$C_{1-6}$ alkylcarbamoyloxy (e.g., dimethylcarbamoyloxy, diethylcarbamoyloxy, etc.), an optionally substituted a mono- or di-$C_{6-14}$ arylcarbamoyloxy (e.g., phenylcarbamoyloxy, naphthylcarbamoyloxy, etc.), an optionally substituted heterocyclic group, sulfo, sulfamoyl, sulfinamoyl, sulfenamoyl, or a group of 2 or more (e.g., 2 or 3) of these substituents combined, and the like (Substituent group A). The number of the substituents is not particularly limited but these rings may have 1 to 5, preferably 1 to 3 substituents in substitutable positions; when there are two or more substituents, these substituents may be the same or different.

The "optionally esterified carboxyl group" in the Substituent group A includes, for example, an optionally substituted $C_{1-6}$ alkoxycarbonyl (e.g., methoxycarbonyl, ethoxycarbonyl, propoxycarbonyl, tert-butoxycarbonyl, etc.), an optionally substituted $C_{6-14}$ aryloxycarbonyl (e.g., phenoxycarbonyl, etc.), an optionally substituted $C_{7-16}$ aralkyloxycarbonyl (e.g., benzyloxycarbonyl, phenethyloxycarbonyl, etc.), and the like.

The "$C_{1-6}$ alkyl" in the "optionally substituted $C_{1-6}$ alkyl" in the Substituent group A includes, for example, methyl, ethyl, propyl, isopropyl, butyl, isobutyl, sec-butyl, tert-butyl, pentyl, isopentyl, neopentyl, hexyl, etc.

The "$C_{2-6}$ alkenyl" of the "optionally substituted $C_{2-6}$ alkenyl" in the Substituent group A includes, for example, vinyl, propenyl, isopropenyl, 2-buten-1-yl, 4-penten-1-yl, 5-hexen-1-yl, etc.

The "$C_{2-6}$ alkynyl" in the "optionally substituted $C_{2-6}$ alkynyl" in the Substituent group A includes, for example, 2-butyn-1-yl, 4-pentyn-1-yl, 5-hexyn-1-yl, etc.

The "$C_{3-8}$ cycloalkyl" in the "optionally substituted $C_{3-8}$ cycloalkyl" in the Substituent group A includes, for example, cyclopropyl, cyclobutyl, cyclopentyl, cyclohexyl, etc.

The $C_{6-14}$ aryl in the optionally substituted $C_{6-14}$ aryl in the Substituent group A includes, for example, phenyl, 1-naphthyl, 2-naphthyl, 2-biphenylyl, 3-biphenylyl, 4-biphenylyl, 2-anthryl, etc.

The "$C_{7-16}$ aralkyl" in the "optionally substituted $C_{7-16}$ aralkyl" in the Substituent group A includes, for example, benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl), etc.

The "$C_{1-6}$ alkoxy" in the "optionally substituted $C_{1-6}$ alkoxy" in the Substituent group A includes, for example, methoxy, ethoxy, propoxy, isopropoxy, butoxy, isobutoxy, sec-butoxy, pentyloxy, hexyloxy, etc.

The "$C_{6-14}$ aryloxy" in the "optionally substituted $C_{6-14}$ aryloxy" in the Substituent group A includes, for example, phenyloxy, 1-naphthyloxy, 2-naphthyloxy, etc.

The "$C_{7-16}$ aralkyloxy" in the "optionally substituted $C_{7-16}$ aralkyloxy" in the Substituent group A includes, for example, benzyloxy, phenethyloxy, etc.

The "$C_{1-6}$ alkylthio" in the "optionally substituted $C_{1-6}$ alkylthio" in the Substituent group A includes, for example, methylthio, ethylthio, propylthio, isopropylthio, butylthio, sec-butylthio, tert-butylthio, etc.

The "$C_{6-14}$ arylthio" in the "optionally substituted $C_{6-14}$ arylthio" in the Substituent group A includes, for example, phenylthio, 1-naphthylthio, 2-naphthylthio, etc.

The "$C_{7-16}$ aralkylthio" in the "optionally substituted $C_{7-16}$ aralkylthio" in the Substituent group A includes, for example, benzylthio, phenethylthio, etc.

The substituents in the Substituent group A for these "$C_{1-6}$ alkoxycarbonyl," "$C_{1-6}$ alkyl group," "$C_{2-6}$ alkenyl," "$C_{2-6}$ alkynyl," "$C_{1-6}$ alkoxy," "$C_{1-6}$ alkylthio," "$C_{1-6}$ alkylamino," $C_{2-6}$ alkenylamino," "$C_{2-6}$ alkynylamino," $C_{1-6}$ alkoxyamino," "$C_{1-6}$ alkylcarbonyl," "$C_{1-6}$ alkylsulfonyl," "$C_{1-6}$ alkylsulfinyl," "$C_{1-6}$ alkylcarbonylamino," "$C_{1-6}$ alkoxycarbonylamino," "$C_{1-6}$ alkylsulfonylamino," "$C_{1-6}$ alkylcarbonyloxy," "$C_{1-6}$ alkoxycarbonyloxy," "mono-$C_{1-6}$ alkylcarbamoyloxy" and "di-$C_{1-6}$ alkylcarbamoyloxy" include, for example, 1 to 5 substituents selected from a halogen atom (e.g., fluorine atom, chlorine atom, bromine atom, iodine atom), carboxy, hydroxy, amino, a mono- or di-$C_{1-6}$ alkylamino, a mono- or di-$C_{6-14}$ arylamino, a $C_{3-8}$ cycloalkyl, a $C_{1-6}$ alkoxy, a $C_{1-6}$ alkoxycarbonyl, a $C_{1-6}$ alkylthio, a $C_{1-6}$ alkylsulfinyl, a $C_{1-6}$ alkylsulfonyl, the optionally esterified carboxyl described above, carbamoyl, thiocarbamoyl, a mono-$C_{1-6}$ alkylcarbamoyl (e.g., methylcarbamoyl, ethylcarbamoyl, etc.), a di-$C_{1-6}$ alkylcarbamoyl (e.g., dimethylcarbamoyl, diethylcarbamoyl, ethylmethylcarbamoyl, etc.), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-membered heterocyclic carbamoyl containing 1 to 4 hetero atoms of 1 or 2 members selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.) and the like.

The substituents in the Substituent group A for the "$C_{6-14}$ aryloxycarbonyl," "$C_{7-16}$ aralkyloxycarbonyl," "$C_{3-8}$ cycloalkyl," "$C_{6-14}$ aryl," "$C_{7-16}$ aralkyl," "$C_{6-14}$ aryloxy," "$C_{7-16}$ aralkyloxy," "$C_{6-14}$ arylthio," "$C_{7-16}$ aralkylthio," $C_{3-8}$ cycloalkylamino, $C_{6-14}$ arylamino, "$C_{3-8}$ cycloalkylcarbonyl," "$C_{6-14}$ arylcarbonyl," "$C_{7-16}$ aralkylcarbonyl," "5- to 7-membered heterocyclic carbonyl containing 1 to 4 hetero atoms of 1 or 2 members selected from nitrogen, sulfur and oxygen atoms in addition to carbon atoms," "$C_{6-14}$ arylsulfonyl," "$C_{6-14}$ arylsulfinyl," "$C_{3-8}$ cycloalkylcarbonylamino," "$C_{6-14}$ arylcarbonylamino," "$C_{6-14}$ arylsulfonylamino," "$C_{6-14}$ arylcarbonyloxy" and "mono- or di-$C_{6-14}$ arylcarbamoyloxy" include, for example, 1 to 5 substituents selected from a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{1-6}$ alkoxy described above, the optionally substituted $C_{1-6}$ alkylthio described above, the optionally substituted $C_{1-6}$ alkylsulfinyl described above, the optionally substituted $C_{1-6}$ alkylsulfonyl described above, the optionally esterified carboxyl described above, carbamoyl, thiocarbamoyl, a mono-$C_{1-6}$ alkylcarbamoyl, a di-$C_{1-6}$ alkylcarbamoyl, a mono- or di-$C_{6-14}$ arylcarbamoyl, a mono- or di-5- to 7-membered heterocyclic carbamoyl containing 1 to 4 hetero atoms of 1 or 2 members selected from nitrogen, sulfur and oxygen atoms in addition to carbon atoms, and the like.

The "optionally substituted heterocyclic group" in the Substituent group A includes, for example, a 5- to 14-membered (monocyclic, bicyclic or tricyclic) heterocyclic group containing 1 to 4 hetero atoms of 1 or 2 members selected from nitrogen, sulfur and oxygen atoms in addition to carbon atoms, which may optionally be substituted with a halogen atom, hydroxy, carboxy, nitro, cyano, the optionally substituted $C_{1-6}$ alkyl described above, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above, the optionally substituted $C_{1-6}$ alkylthio described above, the optionally substituted $C_{6-14}$ arylthio described above, the optionally substituted $C_{7-16}$ aralkylthio described above, the optionally substituted $C_{1-6}$ alkylsulfinyl described above, the optionally substituted $C_{6-14}$ arylsulfinyl described above, the optionally substituted $C_{1-6}$ alkylsulfonyl described above, the optionally substituted $C_{6-14}$ arylsulfonyl described above, the optionally esterified carboxyl described above, carbamoyl, thiocarbamoyl, a mono-$C_{1-6}$ alkylcarbamoyl, a di-lower alkylcarbamoyl, a mono- or di-$C_{6-14}$ arylcarbamoyl, a mono- or di-5- to 7-membered heterocyclic carbamoyl containing 1 to 4 hetero atoms of 1 or 2 members selected from nitrogen, sulfur and oxygen atoms in addition to carbon atoms, or the like; preferably (i) a 5- to 14-membered (preferably, 5- to 10-membered) aromatic heterocyclic group, (ii) a 5- to 10-membered non-aromatic heterocyclic group or (iii) a monovalent group formed by removing one optional hydrogen atom from a 7- to 10-membered bridged-hetero ring, and more preferably, a 5-membered aromatic heterocyclic group. Specifically used are an aromatic heterocyclic group such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl), isoxazolyl (e.g., 3-isoxazolyl), indolyl (e.g., 1-indolyl, 2-indolyl, 3-indolyl), 2-benzothiazolyl, benzo[b]thienyl (e.g., 2-benzo[b]thienyl, 3-benzo[b]thienyl), benzo[b]furanyl (e.g., 3-benzo[b]furanyl), etc., a non-aromatic heterocyclic group such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The "optionally substituted carbamoyl group" in the Substituent group A includes a carbamoyl group, which may optionally be substituted with the optionally substituted $C_{1-6}$ alkyl described above, an optionally substituted $C_{2-6}$ alkenyl, an optionally substituted $C_{2-6}$ alkynyl, an optionally substituted $C_{3-8}$ cycloalkyl, an optionally substituted $C_{6-14}$ aryl, an optionally substituted heterocyclic group, etc. Specific examples are carbamoyl, thiocarbamoyl, a mono-$C_{1-6}$ alkylcarbamoyl (e.g., methylcarbamoyl, ethylcarbamoyl, etc.), a di-$C_{1-6}$ alkylcarbamoyl (e.g., dimethylcarbamoyl, diethylcarbamoyl, ethylmethylcarbamoyl, etc.), a $C_{1-6}$ alkyl ($C_{1-6}$ alkoxy)carbamoyl (e.g., methyl(methoxy)carbamoyl, ethyl (methoxy)carbamoyl), a mono- or di-$C_{6-14}$ arylcarbamoyl (e.g., phenylcarbamoyl, 1-naphthylcarbamoyl, 2-naphthylcarbamoyl, etc.), a mono- or di-5- to 7-membered heterocyclic carbamoyl containing 1 to 4 hetero atoms of 1 or 2 members selected from nitrogen, sulfur and oxygen atoms in addition to carbon atoms (e.g., 2-pyridylcarbamoyl, 3-pyridylcarbamoyl, 4-pyridylcarbamoyl, 2-thienylcarbamoyl, 3-thienylcarbamoyl, etc.), a 5- to 7-membered cyclic carbamoyl (e.g., 1-pyrrolidinylcarbonyl, 1-piperidinylcarbonyl, hexamethyleneiminocarbonyl), and the like.

The "optionally substituted amino" in the Substituent group A includes an amino, which may optionally be substituted with 1 or 2 groups selected from the optionally substituted $C_{1-6}$ alkyl, the optionally substituted $C_{2-6}$ alkenyl described above, the optionally substituted $C_{2-6}$ alkynyl described above, the optionally substituted $C_{3-8}$ cycloalkyl described above, the optionally substituted $C_{6-14}$ aryl described above, the optionally substituted $C_{1-6}$ alkoxy described above described above, formyl, the optionally substituted $C_{1-6}$ alkylcarbonyl described above, the optionally substituted $C_{3-8}$ cycloalkylcarbonyl described above, the optionally substituted $C_{6-14}$ arylcarbonyl described above, the optionally substituted $C_{1-6}$ alkoxycarbonyl described above, the optionally substituted $C_{1-6}$ alkylsulfonyl described above, an optionally substituted $C_{6-14}$ arylsulfonyl) and the like.

More preferably, the substituents for the "$C_{6-12}$ aromatic hydrocarbon group," "5- to 14-membered aromatic heterocyclic group consisting of 1 to 7 carbon atoms and hetero atoms selected from the group consisting of nitrogen, oxygen and sulfur atoms," "$C_{8-14}$ aromatic fused-ring group," "5- to 14-membered aromatic fused heterocyclic group consisting of 3 to 11 carbon atoms and hetero atoms selected from the group consisting of nitrogen, oxygen and sulfur atoms," "non-aromatic cyclic hydrocarbon group of carbon atoms not greater than 7" and "non-aromatic heterocyclic group of carbon atoms not greater than 7" include a halogen atom, hydroxy, a $C_{1-6}$ alkoxy, an optionally halogenated $C_{1-6}$ alkyl, an optionally halogenated $C_{1-6}$ alkoxy, amino, nitro, cyano, etc.

Examples of $R^4$ used include:

(1) "a $C_{1-4}$ alkyl group having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 3-trifluoromethylbenzyl, 4-aminobenzyl, 4-nitrobenzyl, 4-cyanobenzyl, phenethyl, etc.;

(2) "a $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms" such as 2-pyridylmethyl, 3-pyridylmethyl, 4-pyridylmethyl, 2-thienylmethyl, 3-thienylmethyl, 4-thiazolylmethyl, etc.;

(3) "a $C_{1-4}$ alkyl group having an optionally substituted $C_{8-14}$ aromatic fused-ring group" such as 1-naphthylmethyl, 2-naphthylmethyl, inden-2-ylmethyl, etc.;

(4) "a $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms" such as 3-indolemethyl, 1-formylindol-3-ylmethyl, 3-benzo[b]thienylmethyl, 2-quinolylmethyl, etc.;

(5) "a $C_{1-4}$ alkyl group having an optionally substituted non-aromatic cyclic hydrocarbon group having carbon atoms not greater than 7" such as cyclohexylmethyl, cyclopentylmethyl, indan-2-ylmethyl, etc.;

(6) "a $C_{1-4}$ alkyl group having an optionally substituted non-aromatic heterocyclic group having carbon atoms not greater than 7" such as 4-piperidinylmethyl, tetrahydrofurfuryl, tetrahydrofuran-2-yl, tetrahydropyran-3-yl, indolin-3-yl, etc.; among others, preferred are benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 1-formylindol-3-ylmethyl, 3-benzo[b]thienylmethyl, 2-quinolylmethyl, 1-naphthylmethyl, 2-naphthylmethyl, cyclohexylmethyl, phenethyl, etc., and more preferably, benzyl, 2-fluorobenzyl, 3-fluorobenzyl, 4-fluorobenzyl, 4-hydroxybenzyl, 4-aminobenzyl, 4-nitrobenzyl, 4-chlorobenzyl, 4-methoxybenzyl, 4-cyanobenzyl, 3-trifluoromethylbenzyl, 3,4-dichlorobenzyl, 3,4-difluorobenzyl, pentafluorobenzyl, 3-pyridylmethyl, 4-pyridylmethyl, 3-indolemethyl, 3-benzo[b]thienylmethyl, 1-naphthylmethyl, 2-naphthylmethyl, cyclohexylmethyl, etc.

X represents a group shown by formula:

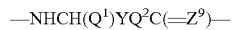

—NHCH($Q^1$)Y$Q^2$C(=$Z^9$)—

(wherein, each symbol has the same significance as described above).

$Q^1$ represents a $C_{1-4}$ alkyl group optionally substituted with a substituent selected from the group consisting of:

(1) an optionally substituted $C_{6-12}$ aromatic hydrocarbon group;

(2) an optionally substituted 5- to 14-membered aromatic heterocyclic group consisting of 1 to 7 carbon atoms and hetero atoms selected from the group consisting of nitrogen, oxygen and sulfur atoms;

(3) an optionally substituted $C_{8-14}$ aromatic fused-ring group;

(4) an optionally substituted 5- to 14-membered aromatic fused heterocyclic group consisting of 3 to 11 carbon atoms and hetero atoms selected from the group consisting of nitrogen, oxygen and sulfur atoms;

(5) an optionally substituted non-aromatic cyclic hydrocarbon group having carbon atoms not greater than 7; and (6) an optionally substituted non-aromatic heterocyclic group having carbon atoms not greater than 7; and the same substituents as in $R^4$ are used.

Examples of $Q^1$ include:

(1) "a $C_{1-4}$ alkyl group having an optionally substituted $C_{6-12}$ aromatic hydrocarbon group" such as benzyl, 2-fluorobenzyl, 3-fluorobenzyl, 4-fluorobenzyl, 4-chlorobenzyl, 3,4-difluorobenzyl, 3,4-dichlorobenzyl, pentafluorobenzyl, 4-hydroxybenzyl, 4-methoxybenzyl, 4-trifluoromethylbenzyl, 4-aminobenzyl, 4-nitrobenzyl, 4-cyanobenzyl, phenethyl, etc.;

(2) "a $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms" such as 2-pyridylmethyl, 3-pyridylmethyl, 4-pyridylmethyl, 2-thienylmethyl, 3-thienylmethyl, 4-thiazolylmethy, etc.;

(3) "a $C_{1-4}$ alkyl group having an optionally substituted $C_{8-14}$ aromatic fused-ring group" such as 1-naphthylmethyl, 2-naphthylmethyl, inden-2-ylmethyl, etc.

(4) "a $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms" such as 3-indolemethyl, 1-formylindol-3-ylmethyl, 3-benzo[b]thienylmethyl, 2-quinolylmethyl, etc.;

(5) "a $C_{1-4}$ alkyl group having an optionally substituted non-aromatic cyclic hydrocarbon group having carbon atoms not greater than 7" such as cyclohexylmethyl, cyclopentylmethyl, indan-2-ylmethyl, etc.;

(6) "a $C_{1-4}$ alkyl group having an optionally substituted non-aromatic heterocyclic group having carbon atoms not greater than 7" such as 4-piperidinylmethyl, tetrahydrofurfuryl, tetrahydrofuran-2-yl, tetrahydropyran-3-yl, indolin-3-yl, etc.; preferably, cyclohexylmethyl, benzyl, 4-fluorobenzyl, 4-hydroxybenzyl, pentafluorobenzyl, 2-pyridylmethyl, 4-pyridylmethyl, 1-naphthylmethyl, 2-naphthylmethyl, 3-indolemethyl, etc. and more preferably, benzyl, 4-fluorobenzyl, cyclohexylmethyl, etc.

$Q^2$ represents (1) $CH_2$, which may optionally be substituted with an optionally substituted $C_{1-4}$ alkyl group with a substituent selected from the group consisting of carbamoyl group and hydroxyl group, (2) NH, which may optionally be substituted with an optionally substituted $C_{1-4}$ alkyl group with a substituent selected from the group consisting of carbamoyl group and hydroxyl group, or (3) O.

The "$C_{1-4}$ alkyl group" used includes, for example, methyl, ethyl, propyl, isopropyl, butyl, isobutyl, sec-butyl, tert-butyl, etc.

Preferably, $Q^2$ is $CH_2$, $CH(CH_3)$, $CH(CH_2OH)$, NH, or the like.

Y represents a group shown by formula: —CONH—, —CSNH—, —$CH_2$NH—, —NHCO—, —$CH_2$O—, —CH$_2$S— or —CH$_2$CH$_2$—, which may optionally be substituted with a C$_{1-6}$ alkyl group.

The "C$_{1-6}$ alkyl group" used includes, for example, methyl, ethyl, propyl, isopropyl, butyl, isobutyl, sec-butyl, tert-butyl, pentyl, isopentyl, neopentyl, hexyl, etc.

Preferably, Y represents a group shown by formula: —CONH—, —CSNH—, —NHCO— or —CH$_2$NH—.

Z$^9$ represents hydrogen atom, O or S and, among others O and S are preferred.

P represents:
(1) hydrogen atom;
(2) an optional amino acid residue continuously or discontinuously bound from the C-terminal end of the 1-48 amino acid sequence in the amino acid sequence represented by SEQ ID NO: 1 (54 amino acid residues of human metastin);
(3) a group represented by formula: J$^1$-J$^2$-C(J$^3$)(Q$^3$)Y$^1$C(J$^4$)(Q$^4$)Y$^2$C(J$^5$)(Q$^5$)Y$^3$C(J$^6$)(Q$^6$)C(=Z$^{10}$)—
(wherein each symbol has the same significance as described above);
(4) a group represented by formula: -J$^1$-J$^2$-C(J$^7$)(Q$^7$)Y$^2$C(J$^8$)(Q$^8$)Y$^3$C(J$^9$)(Q$^9$)C(=Z$^{10}$)—
(wherein each symbol has the same significance as described above);
(5) a group represented by formula: J$^1$-J$^2$-C(J$^{10}$)(Q$^{10}$)Y$^3$C(J$^{11}$)(Q$^{11}$)C(=Z$^{10}$)—
(wherein each symbol has the same significance as described above);
(6) a group represented by formula: J$^1$-J$^2$-C(J$^{12}$)(Q$^{12}$)C(=Z$^{10}$)—
(wherein each symbol has the same significance as described above); or,
(7) a group represented by formula: J$^1$- (wherein J$^1$ has the same significance as described above).

Specific examples of the "optional amino acid residue continuously or discontinuously bound from the C-terminal end of the 1-48 amino acid sequence represented by SEQ ID NO: 1" used include:

(1) Asn- (2) Trp Asn-, (3) Asn Trp Asn-, (4) Tyr Asn Trp Asn-, (SEQ ID NO: 28)

(5) Asn Tyr Asn Trp Asn-, (SEQ ID NO: 29)

(6) Pro Asn Tyr Asn Trp Asn-, (SEQ ID NO: 30)

(7) Leu Pro Asn Tyr Asn Trp Asn-, (SEQ ID NO: 31)

(8) Asp Leu Pro Asn Tyr Asn Trp Asn-, (SEQ ID NO: 32)

(9) Lys Asp Leu Pro Asn Tyr Asn Trp Asn-, (SEQ ID NO: 33)

(10) Glu Lys Asp Leu Pro Asn Tyr Asn Trp Asn-, (SEQ ID NO: 34)

(11) Arg Glu Lys Asp Leu Pro Asn Tyr Asn Trp Asn-, (SEQ ID NO: 35)

(12) Gln Arg Glu Lys Asp Leu Pro Asn Tyr Asn Trp Asn-, (SEQ ID NO: 36)

(13) Val Gln Arg Glu Lys Asp Leu Pro Asn Tyr Asn Trp Asn-, (SEQ ID NO: 37)

(14) Leu Val Gln Arg Glu Lys Asp Leu Pro Asn Tyr Asn Trp Asn-, (SEQ ID NO: 38)

(15) Val Leu Val Gln Arg Glu Lys Asp Leu Pro Asn Tyr Asn Trp Asn-, (SEQ ID NO: 39)

(16) Ala Val Leu Val Gln Arg Glu Lys Asp Leu Pro Asn Tyr Asn Trp Asn-, (SEQ ID NO: 40)

(17) Gly Ala Val Leu Val Gln Arg Glu Lys Asp Leu Pro Asn Tyr Asn Trp Asn-, (SEQ ID NO: 41)

(18) Gln Gly Ala Val Leu Val Gln Arg Glu Lys Asp Leu Pro Asn Tyr Asn Trp Asn-, (SEQ ID NO: 42)

(19) Pro Gln Gly Ala Val Leu Val Gln Arg Glu Lys Asp Leu Pro Asn Tyr Asn Trp Asn-, (SEQ ID NO: 43)

(20) Ala Pro Gln Gly Ala Val Leu Val Gln Arg Glu Lys Asp Leu Pro Asn Tyr Asn Trp Asn-, (SEQ ID NO: 44)

(21) Pro Ala Pro Gln Gly Ala Val Leu Val Gln Arg Glu Lys Asp Leu Pro Asn Tyr Asn Trp Asn-, (SEQ ID NO: 45)

(22) Ile Pro Ala Pro Gln Gly Ala Val Leu Val Gln Arg Glu Lys Asp Leu Pro Asn Tyr Asn Trp Asn-, (SEQ ID NO: 46)

(23) Gln Ile Pro Ala Pro Gln Gly Ala Val Leu Val Gln Arg Glu Lys Asp Leu Pro Asn Tyr Asn Trp Asn-, (SEQ ID NO: 47)

(24) Arg Gln Ile Pro Ala Pro Gln Gly Ala Val Leu Val Gln Arg Glu Lys Asp Leu Pro Asn Tyr Asn Trp Asn-, (SEQ ID NO: 48)

(25) Ser Arg Gln Ile Pro Ala Pro Gln Gly Ala Val Leu Val Gln Arg Glu Lys Asp Leu Pro Asn Tyr Asn Trp Asn-, (SEQ ID NO: 49)

(26) His Ser Arg Gln Ile Pro Ala Pro Gln Gly Ala Val Leu Val Gln Arg Glu Lys Asp Leu Pro Asn Tyr Asn Trp Asn-, (SEQ ID NO: 50)

(SEQ ID NO: 51)
(27) Pro His Ser Arg Gln Ile Pro Ala Pro Gln
Gly Ala Val Leu Val Gln Arg Glu Lys Asp Leu
Pro Asn Tyr Asn Trp Asn-, (SEQ ID NO: 52)
(28) Ala Pro His Ser Arg Gln Ile Pro Ala Pro
Gln Gly Ala Val Leu Val Gln Arg Glu Lys Asp
Leu Pro Asn Tyr Asn Trp Asn-, (SEQ ID NO: 53)
(29) Ser Ala Pro His Ser Arg Gln Ile Pro Ala
Pro Gln Gly Ala Val Leu Val Gln Arg Glu
Lys Asp Leu Pro Asn Tyr Asn Trp Asn-, (SEQ ID NO: 54)
(30) Leu Ser Ala Pro His Ser Arg Gln Ile Pro
Ala Pro Gln Gly Ala Val Leu Val Gln Arg Glu
Lys Asp Leu Pro Asn Tyr Asn Trp Asn-, (SEQ ID NO: 55)
(31) Gly Leu Ser Ala Pro His Ser Arg Gln Ile
Pro Ala Pro Gln Gly Ala Val Leu Val Gln Arg
Glu Lys Asp Leu Pro Asn Tyr Asn Trp Asn-, (SEQ ID NO: 56)
(32) Pro Gly Leu Ser Ala Pro His Ser Arg Gln
Ile Pro Ala Pro Gln Gly Ala Val Leu Val Gln
Arg Glu Lys Asp Leu Pro Asn Tyr Asn Trp Asn-, (SEQ ID NO: 57)
(33) Gln Pro Gly Leu Ser Ala Pro His Ser Arg
Gln Ile Pro Ala Pro Gln Gly Ala Val Leu Val Gln
Arg Glu Lys Asp Leu Pro Asn Tyr Asn Trp Asn-, (SEQ ID NO: 58)
(34) Gln Gln Pro Gly Leu Ser Ala Pro His Ser Arg
Gln Ile Pro Ala Pro Gln Gly Ala Val Leu Val Gln
Arg Glu Lys Asp Leu Pro Asn Tyr Asn Trp Asn-, (SEQ ID NO: 59)
(35) Arg Gln Gln Pro Gly Leu Ser Ala Pro His Ser
Arg Gln Ile Pro Ala Pro Gln Gly Ala Val Leu Val
Gln Arg Glu Lys Asp Leu Pro Asn Tyr Asn Trp Asn-, (SEQ ID NO: 60)
(36) Ser Arg Gln Gln Pro Gly Leu Ser Ala Pro His
Ser Arg Gln Ile Pro Ala Pro Gln Gly Ala Val Leu
Val Gln Arg Glu Lys Asp Leu Pro Asn Tyr Asn Trp
Asn-, (SEQ ID NO: 61)
(37) Gly Ser Arg Gln Gln Pro Gly Leu Ser Ala Pro
His Ser Arg Gln Ile Pro Ala Pro Gln Gly Ala Val
Leu Val Gln Arg Glu Lys Asp Leu Pro Asn Tyr
Asn Trp Asn-, (SEQ ID NO: 62)
(38) Ser Gly Ser Arg Gln Gln Pro Gly Leu Ser Ala
Pro His Ser Arg Gln Ile Pro Ala Pro Gln Gly Ala
Val Leu Val Gln Arg Glu Lys Asp Leu Pro Asn Tyr
Asn Trp Asn-, (SEQ ID NO: 63)
(39) Ser Ser Gly Ser Arg Gln Gln Pro Gly Leu
Ser Ala Pro His Ser Arg Gln Ile Pro Ala Pro Gln
Gly Ala Val Leu Val Gln Arg Glu Lys Asp Leu
Pro Asn Tyr Asn Trp Asn-, (SEQ ID NO: 64)
(40) Glu Ser Ser Gly Ser Arg Gln Gln Pro Gly
Leu Ser Ala Pro His Ser Arg Gln Ile Pro Ala Pro
Gln Gly Ala Val Leu Val Gln Arg Glu Lys Asp
Leu Pro Asn Tyr Asn Trp Asn-, (SEQ ID NO: 65)
(41) Pro Glu Ser Ser Gly Ser Arg Gln Gln Pro
Gly Leu Ser Ala Pro His Ser Arg Gln Ile Pro Ala
Pro Gln Gly Ala Val Leu Val Gln Arg Glu Lys
Asp Leu Pro Asn Tyr Asn Trp Asn-, (SEQ ID NO: 66)
(42) Pro Pro Glu Ser Ser Gly Ser Arg Gln Gln
Pro Gly Leu Ser Ala Pro His Ser Arg Gln Ile Pro
Ala Pro Gln Gly Ala Val Leu Val Gln Arg Glu Lys
Asp Leu Pro Asn Tyr Asn Trp Asn-, (SEQ ID NO: 67)
(43) Pro Pro Pro Glu Ser Ser Gly Ser Arg Gln
Gln Pro Gly Leu Ser Ala Pro His Ser Arg Gln Ile
Pro Ala Pro Gln Gly Ala Val Leu Val Gln Arg Glu
Lys Asp Leu Pro Asn Tyr Asn Trp Asn-, (SEQ ID NO: 68)
(44) Ser Pro Pro Pro Glu Ser Ser Gly Ser Arg
Gln Gln Pro Gly Leu Ser Ala Pro His Ser Arg Gln
Ile Pro Ala Pro Gln Gly Ala Val Leu Val Gln Arg
Glu Lys Asp Leu Pro Asn Tyr Asn Trp Asn-, (SEQ ID NO: 69)
(45) Leu Ser Pro Pro Pro Glu Ser Ser Gly Ser
Arg Gln Gln Pro Gly Leu Ser Ala Pro His Ser Arg
Gln Ile Pro Ala Pro Gln Gly Ala Val Leu Val Gln
Arg Glu Lys Asp Leu Pro Asn Tyr Asn Trp Asn-, (SEQ ID NO: 70)
(46) Ser Leu Ser Pro Pro Pro Glu Ser Ser Gly
Ser Arg Gln Gln Pro Gly Leu Ser Ala Pro His Ser
Arg Gln Ile Pro Ala Pro Gln Gly Ala Val Leu Val
Gln Arg Glu Lys Asp Leu Pro Asn Tyr Asn Trp Asn-,

-continued

(47) Thr Ser Leu Ser Pro Pro Pro Glu Ser Ser Gly  (SEQ ID NO: 71)

Ser Arg Gln Gln Pro Gly Leu Ser Ala Pro His Ser

Arg Gln Ile Pro Ala Pro Gln Gly Ala Val Leu Val

Gln Arg Glu Lys Asp Leu Pro Asn Tyr Asn Trp Asn-,

(48) Gly Thr Ser Leu Ser Pro Pro Pro Glu Ser  (SEQ ID NO: 72)

Ser Gly Ser Arg Gln Gln Pro Gly Leu Ser Ala Pro

His Ser Arg Gln Ile Pro Ala Pro Gln Gly Ala Val

Leu Val Gln Arg Glu Lys Asp Leu Pro Asn Tyr

Asn Trp Asn-, and the like.

$J^1$ represents (a) hydrogen atom or (b) (i) a $C_{1-15}$ acyl group, (ii) a $C_{1-15}$ alkyl group, (iii) a $C_{6-14}$ aryl group, (iv) a carbamoyl group, (v) a carboxyl group, (vi) a sulfino group, (vii) an amidino group or (viii) a glyoxyloyl group, which groups may optionally be substituted with a substituent containing an optionally substituted cyclic group.

The "cyclic group" used includes, for example, "an optionally substituted aromatic hydrocarbon group," "an optionally substituted aromatic heterocyclic group," "an optionally substituted aromatic fused-ring group," "an optionally substituted aromatic fused heterocyclic group," "an optionally substituted non-aromatic cyclic hydrocarbon group," "an optionally substituted non-aromatic heterocyclic group", etc., and examples of the "aromatic hydrocarbon group," "aromatic heterocyclic group," "aromatic fused-ring group" and "aromatic fused heterocyclic group" used are the same as those given above.

The "non-aromatic cyclic hydrocarbon group" used includes a $C_{3-8}$ cycloalkyl group such as cyclopropyl, cyclobutyl, cyclopentyl, cyclohexyl, etc.

The "non-aromatic heterocyclic group" used includes a 5- to 10-membered non-aromatic heterocyclic group containing 1 to 4 hetero atoms of 1 or 2 members selected from nitrogen, sulfur and oxygen atoms in addition to 1 to 7 carbon atoms such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., 1-piperidinyl, 2-piperidinyl, 3-piperidinyl, 4-piperidinyl), piperazinyl (e.g., 1-piperazinyl, 2-piperazinyl), morpholino, thiomorpholino, etc.

The substituent optionally present on the "cyclic group" includes the same substituents as the Substituent group A described above.

The "$C_{1-15}$ acyl group" used includes, for example, formyl, a $C_{1-14}$ alkyl-carbonyl (e.g., a $C_{1-6}$ alkyl-carbonyl such as acetyl, propionyl, pivaloyl, etc.) and the like.

The "$C_{1-15}$ alkyl group" used include, for example, methyl, ethyl, propyl, isopropyl, butyl, isobutyl, sec-butyl, tert-butyl, pentyl, isopentyl, neopentyl, hexyl, heptyl, octyl, nonanyl, decanyl, etc.

The "$C_{6-14}$ aryl group" used includes, for example, phenyl, 1-naphthyl, 2-naphthyl, biphenyl, etc.

(1) The $C_{1-15}$ acyl group, which may optionally be substituted with a substituent containing a cyclic group, includes (i) formyl, (ii) a $C_{1-14}$ alkyl-carbonyl (e.g., a $C_{1-6}$ alkyl-carbonyl such as acetyl, propionyl, pivaloyl, etc.), (iii) a $C_{3-8}$ cycloalkyl-carbonyl (e.g., cyclopropylcarbonyl, cyclopentylcarbonyl, cyclohexylcarbonyl, 1-methylcyclohexylcarbonyl, etc.), (iv) a $C_{3-8}$ cycloalkyl-$C_{1-6}$ alkyl-carbonyl (e.g., cyclopropylacetyl, cyclopentylacetyl, cyclohexylacetyl, etc.), (v) a $C_{6-14}$ aryl-carbonyl (e.g., benzoyl, 1-naphthoyl, 2-naphthoyl, etc.), a $C_{6-14}$ aralkyl-carbonyl (e.g., phenylacetyl, 3-phenylpropionyl, etc.), (vi) a 5- to 7-membered monocyclic heterocyclic carbonyl containing 1 to 4 hetero atoms of 1 or 2 members selected from nitrogen, sulfur and oxygen atoms in addition to carbon atoms (e.g., nicotinoyl, isonicotinoyl, thenoyl, furoyl, morpholinocarbonyl, thiomorpholinocarbonyl, piperazin-1-ylcarbonyl, pyrrolidin-1-ylcarbonyl, etc.), (vii) a 5- to 7-membered monocyclic heterocyclic-$C_{1-6}$ alkylcarbonyl containing 1 to 4 hetero atoms of 1 or 2 members selected from nitrogen, sulfur and oxygen atoms in addition to carbon atoms (e.g., 3-pyridylacetyl, 4-pyridylacetyl, 2-thienylacetyl, 2-furylacetyl, morpholinoacetyl, thiomorpholinoacetyl, piperidin-2-acetyl, pyrrolidine-2-ylacetyl, etc.), (viii) a 5- to 14-membered (preferably, 5- to 10-membered) bicyclic or tricyclic aromatic heterocyclic carbonyl containing 1 to 4 hetero atoms of 1 or 2 members selected from nitrogen, sulfur and oxygen atoms in addition to 3 to 11 carbon atoms (e.g., 2-indolecarbonyl, 3-indolecarbonyl, 2-quinolylcarbonyl, 1-isoquinolylcarbonyl, 2-benzo[b]thienylcarbonyl, 2-benzo[b]furanylcarbonyl, etc.), (ix) a 5- to 14-membered (preferably 5- to 10-membered) bicyclic or tricyclic aromatic heterocyclic-$C_{1-6}$ alkylcarbonyl containing 1 to 4 hetero atoms of 1 or 2 members selected from nitrogen, sulfur and oxygen atoms in addition to 3 to 11 carbon atoms (e.g., 2-indoleacetyl, 3-indoleacetyl, 2-quinolylacetyl, 1-isoquinolylacetyl, 2-benzo[b]thienylacetyl, 2-benzo[b]furanylacetyl, etc.), etc., among others, preferably used are acetyl, 2-indolecarbonyl, 3-indolecarbonyl, 3-indoleacetyl, 3-indolepropionyl, 2-indolinecarbonyl, 3-phenylpropionyl, diphenylacetyl, 2-pyridinecarbonyl, 3-pyridinecarbonyl, 4-pyridinecarbonyl, 1-pyridinioacetyl, 2-pyridineacetyl, 3-pyridineacetyl, 4-pyridineacetyl, 3-(1-pyridinio)propionyl, 3-(pyridin-2-yl)propionyl, 3-(pyridin-3-yl)propionyl, 3-(pyridin-4-yl)propionyl, 4-imidazoleacetyl, cyclohexanecarbonyl, 1-piperidineacetyl, 1-methyl-1-piperidinioacetyl, 4-piperidinecarbonyl, 2-pyrimidinecarbonyl, 4-pyrimidinecarbonyl, 5-pyrimidinecarbonyl, 2-pyrimidineacetyl, 4-pyrimidineacetyl, 5-pyrimidineacetyl, 3-(pyrimidin-2-yl)propionyl, 3-(pyrimidin-4-yl)propionyl, 3-(pyrimidin-5-yl)propionyl, butanoyl, hexanoyl, octanoyl, D-glucuronyl, amino-(4-hydroxyphenyl)acetyl), etc.

(2) The $C_{1-15}$ alkyl group, which may optionally be substituted with a substituent containing a cyclic group, includes, for example, (i) a mono- or di-$C_{1-15}$ alkyl (e.g., methyl, ethyl, propyl, isopropyl, butyl, isobutyl, sec-butyl, tert-butyl, pentyl, isopentyl, neopentyl, hexyl, heptyl, octyl, nonanyl, decanyl), (ii) a mono- or di-$C_{3-8}$ cycloalkyl (e.g., cyclopropyl, cyclopentyl, etc.), (iii) a mono- or di-$C_{3-8}$ cycloalkyl-$C_{1-7}$ alkyl (e.g., cyclopropylmethyl, cyclopentylmethyl, cyclohexylethyl, etc.), (iv) a mono- or di-$C_{7-15}$ aralkyl (e.g., benzyl, phenethyl, etc.), (v) a mono- or di-5- to 7-membered monocyclic heterocyclic-$C_{1-6}$ alkyl group containing 1 to 4 hetero atoms of 1 or 2 members selected from nitrogen, sulfur and oxygen atoms in addition to carbon atoms (e.g., 3-pyridylmethyl, 4-pyridylmethyl, 2-thienylmethyl, furfuryl, etc.), (vi) a mono- or di-5- to 14-membered (preferably, 5- to 10-membered) bicyclic or tricyclic aromatic heterocyclic-$C_{1-6}$ alkyl group containing 1 to 4 hetero atoms of 1 or 2 members selected from nitrogen, sulfur and oxygen atoms in addition to 3 to 11 carbon atoms (e.g., 2-indolemethyl, 3-indolemethyl, 3-(indol-3-yl)propyl, 2-quinolylmethyl, 1-isoquinolylmethyl, 2-benzo[b]thienylmethyl, 2-benzo[b]furanylmethyl, etc.), etc.; among others, methyl, ethyl, benzyl, 3-(indol-3-yl) propyl, etc. are preferably used.

(3) The $C_{6-14}$ aryl group, which may optionally be substituted with a substituent containing a cyclic group, includes, for example, a $C_{6-14}$ aryl group (e.g., phenyl, naphthyl, biphenyl), which may optionally be substituted with (i) a $C_{6-14}$ carbocyclic group (e.g., cycloalkyl, phenyl, 1-naphthyl, 2-naphthyl, etc.), (ii) a 5- to 7-membered monocyclic heterocyclic group containing 1 to 4 hetero atoms of 1 or 2 members selected from nitrogen, sulfur and oxygen atoms in addition to carbon atoms (e.g., 3-pyridyl, 2-thienyl, etc.), (iii) a 5- to 14-membered (preferably, 5- to 10-membered) bicyclic or tricyclic aromatic heterocyclic group containing 1 to 4 hetero atoms of 1 or 2 members selected from nitrogen, sulfur and oxygen atoms in addition to 3 to 11 carbon atoms (e.g., 2-indolyl, 3-indolyl, 2-quinolyl, 1-isoquinolyl, 2-benzo[b]thienyl, 2-benzo[b]furanyl, etc.), etc.

(4) The optionally substituted carbamoyl group, which may optionally be substituted with a substituent containing a cyclic group, includes (i) carbamoyl, (ii) a mono- or di-$C_{1-15}$ alkylcarbamoyl group (e.g., methylcarbamoyl, ethylcarbamoyl), (iii) a mono- or di-$C_{3-8}$ cycloalkylcarbamoyl (e.g., cyclopropylcarbamoyl, cyclopentylcarbamoyl, cyclohexylcarbamoyl, etc.), (iv) a mono- or di-$C_{3-8}$ cycloalkyl-$C_{1-6}$ alkyl-carbamoyl (e.g., cyclopropylmethylcarbamoyl, cyclopentylmethylcarbamoyl, 2-cyclohexylethylcarbamoyl, etc.) (v) a mono- or di-$C_{6-14}$ aryl-carbamoyl (e.g., phenylcarbamoyl, etc.), a mono- or di-$C_{6-14}$ aralkyl-carbamoyl (e.g., benzylcarbamoyl, phenethylcarbamoyl, etc.), (vi) a mono- or di-5- to 7-membered monocyclic heterocyclic carbamoyl containing 1 to 4 hetero atoms of 1 or 2 members selected from nitrogen, sulfur and oxygen atoms in addition to carbon atoms (e.g., 3-pyridinecarbamoyl, 2-thiophenecarbamoyl, piperidin-3-ylcarbamoyl, etc.), (vii) a mono- or di-5- to 7-membered monocyclic heterocyclic-$C_{1-6}$ alkylcarbamoyl containing 1 to 4 hetero atoms of 1 or 2 members selected from nitrogen, sulfur and oxygen atoms in addition to carbon atoms (e.g., 3-pyridylmethylcarbamoyl, 2-(pyridin-2-yl)ethylcarbamoyl, 2-(piperidin-1-yl)ethylcarbamoyl, etc.), (viii) a mono- or di-5- to 14-membered (preferably, 5- to 10-membered) bicyclic or tricyclic aromatic heterocyclic carbamoyl containing 1 to 4 hetero atoms of 1 or 2 members selected from nitrogen, sulfur and oxygen atoms in addition to 3 to 11 carbon atoms (e.g., 4-indolecarbamoyl, 5-indolecarbamoyl, 3-quinolylcarbamoyl, 5-quinolylcarbamoyl, etc.), (ix) a mono- or di-5- to 14-membered (preferably, 5- to 10-membered) bicyclic or tricyclic aromatic heterocyclic-$C_{1-6}$ alkylcarbonyl containing 1 to 4 hetero atoms of 1 or 2 members selected from nitrogen, sulfur and oxygen atoms in addition to 3 to 11 carbon atoms (e.g., benzimidazol-2-ylmethylcarbamoyl, 2-(indol-3-yl)ethylcarbamoyl, etc.), (x) a 5- to 7-membered cyclic carbamoyl (e.g., 1-pyrrolidinylcarbonyl, 1-piperidinylcarbonyl, hexamethyleneiminocarbonyl, etc.), (xi) a $C_{1-15}$ acylcarbamoyl (the $C_{1-15}$ acyl herein has the same significance as the "$C_{1-15}$ acyl group" in the "$C_{1-15}$ acyl group, which may optionally be substituted with a substituent containing a cyclic group"), (xii) a $C_{1-15}$ alkylaminocarbamoyl (the $C_{1-15}$ alkyl herein has the same significance as the "$C_{1-15}$ alkyl group" in the "$C_{1-15}$ alkyl group, which may optionally be substituted with a substituent containing a cyclic group"), (xiii) a $C_{6-14}$ arylaminocarbamoyl (the $C_{6-14}$ aryl group herein has the same significance as the "$C_{6-14}$ aryl group, which may optionally be substituted with a substituent containing a cyclic group"), etc.; among others, 2-(indol-3-yl)ethylcarbamoyl, etc. are preferably used.

(5) The carboxyl group, which may optionally be substituted with a substituent containing a cyclic group, includes (i) a $C_{1-15}$ alkyloxycarbonyl (the $C_{1-15}$ alkyl herein has the same significance as the "$C_{1-15}$ alkyl group" in the "$C_{1-15}$ alkyl group, which may optionally be substituted with a substituent containing a cyclic group," e.g., tert-butyloxycarbonyl, benzyloxycarbonyl, 9-fluorenylmethoxycarbonyl), (ii) a $C_{6-14}$ aryloxycarbonyl (the $C_{6-14}$ aryl herein has the same significance as the "$C_{6-14}$ aryl group" in the "$C_{6-14}$ aryl group, which may optionally be substituted with a substituent containing a cyclic group," e.g., phenoxycarbonyl), etc.

(6) The sulfino group, which may optionally be substituted with a substituent containing a cyclic group, includes (i) a $C_{1-15}$ alkylsulfonyl (the $C_{1-15}$ alkyl herein has the same significance as the "$C_{1-15}$ alkyl group" in the "$C_{1-15}$ alkyl group, which may optionally be substituted with a substituent containing a cyclic group," e.g., benzylsulfonyl), (ii) a $C_{6-14}$ arylsulfonyl (the $C_{6-14}$ aryl herein has the same significance as the "$C_{6-14}$ aryl group" in the "$C_{6-14}$ aryl group, which may optionally be substituted with a substituent containing a cyclic group," e.g., tosyl), etc.

(7) The amidino group, which may optionally be substituted with a substituent containing a cyclic group, includes (i) amidino, (ii) a $C_{1-15}$ alkylamidino (the $C_{1-15}$ alkyl herein has the same significance as the "$C_{1-15}$ alkyl group" in the "$C_{1-15}$ alkyl group, which may optionally be substituted with a substituent containing a cyclic group," e.g., N-methylamidino), (iii) a $C_{1-15}$ acylamidino (the $C_{1-15}$ acyl herein has the same significance as the "$C_{1-15}$ acyl group" in the "$C_{1-15}$ acyl group, which may optionally be substituted with a substituent containing a cyclic group," e.g., N-acetylamidino), etc.

(8) The glyoxyloyl group, which may optionally be substituted with a substituent containing a cyclic group, includes (i) a $C_{1-15}$ alkyloxalyl (the $C_{1-15}$ alkyl herein has the same significance as the "$C_{1-15}$ alkyl group" in the "$C_{1-15}$ alkyl group, which may optionally be substituted with a substituent containing a cyclic group," e.g., ethyloxalyl), (ii) a $C_{6-14}$ aryloxalyl (the $C_{6-14}$ aryl herein has the same significance as the "$C_{6-14}$ aryl group" in the "$C_{6-14}$ aryl group, which may optionally be substituted with a substituent containing a cyclic group," e.g., phenyloxalyl), etc.

Among those described above, $J^1$ is preferably hydrogen atom, acetyl, 3-indolecarbonyl, 3-(indol-3-yl)propionyl, 3-phenylpropionyl, diphenylacetyl, 3-(pyridin-3-yl)propionyl, 4-imidazoleacetyl, cyclohexanecarbonyl, 1-piperidineacetyl, 1-methyl-1-piperidinioacetyl, 4-piperidinecarbonyl, hexanoyl, amino-(4-hydroxyphenyl)acetyl, D-glucuronyl, 2-(indol-3-yl)ethylcarbamoyl, tert-butyloxycarbonyl, 9-fluorenylmethoxycarbonyl, amidino, etc.; among others, preferred are hydrogen atom, acetyl, 3-indolecarbonyl, 3-(indol-3-yl)propionyl, 3-phenylpropionyl, 3-(pyridin-3-yl)propionyl, 4-imidazoleacetyl, cyclohexanecarbonyl, hexanoyl, amino-(4-hydroxyphenyl)acetyl, 2-(indol-3-yl)ethylcarbamoyl, 9-fluorenylmethoxycarbonyl, amidino, etc.

$J^2$ represents (1) NH optionally substituted with a $C_{1-6}$ alkyl group, (2) $CH_2$ optionally substituted with a $C_{1-6}$ alkyl group, (3) 0 or (4) S.

The "$C_{1-6}$ alkyl group" used includes methyl, ethyl, propyl, isopropyl, butyl, isobutyl, sec-butyl, tert-butyl, pentyl, isopentyl, neopentyl, hexyl, etc.

Preferably, $J^2$ is NH.

Each of $J^3$ through $J^{12}$ represents hydrogen atom or a $C_{1-3}$ alkyl group.

The "$C_{1-3}$ alkyl group" used includes methyl, ethyl, propyl, isopropyl, etc.

Preferably, $J^3$ is hydrogen atom.
Preferably, $J^4$ is hydrogen atom.
Preferably, $J^5$ is hydrogen atom.
Preferably, $J^6$ is hydrogen atom.
Preferably, $J^7$ is hydrogen atom.
Preferably, $J^8$ is hydrogen atom.

Preferably, $J^9$ is hydrogen atom.
Preferably, $J^{10}$ is hydrogen atom.
Preferably, $J^{11}$ is hydrogen atom.
Preferably, $J^{12}$ is hydrogen atom.

Each of $Q^3$ through $Q^{12}$ represents a $C_{1-4}$ alkyl group, which may optionally have a substituent selected from the group consisting of:
(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused-ring group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7;
(6) an optionally substituted non-aromatic heterocyclic group having carbon atoms not greater than 7;
(7) an optionally substituted amino group;
(8) an optionally substituted guanidino group;
(9) an optionally substituted hydroxyl group;
(10) an optionally substituted carboxyl group;
(11) an optionally substituted carbamoyl group; and,
(12) an optionally substituted sulfhydryl group.

Particularly preferred $Q^3$ to $Q^6$ are a $C_{1-4}$ alkyl group having a substituent selected from the group consisting of:
(1) an optionally substituted $C_{6-12}$ aromatic hydrocarbon group;
(2) an optionally substituted 5- to 14-membered aromatic heterocyclic group consisting of 1 to 7 carbon atoms and hetero atoms selected from the group consisting of nitrogen, oxygen and sulfur atoms;
(3) an optionally substituted $C_{8-14}$ aromatic fused-ring group;
(4) an optionally substituted 5- to 14-membered aromatic fused heterocyclic group consisting of 3 to 11 carbon atoms and hetero atoms selected from the group consisting of nitrogen, oxygen and sulfur atoms;
(5) an optionally substituted non-aromatic cyclic hydrocarbon group having carbon atoms not greater than 7;
(6) an optionally substituted non-aromatic heterocyclic group having carbon atoms not greater than 7;
(7) an optionally substituted amino group;
(8) an optionally substituted guanidino group;
(9) an optionally substituted hydroxyl group;
(10) an optionally substituted carboxyl group;
(11) an optionally substituted carbamoyl group; and,
(12) an optionally substituted sulfhydryl group.

The "optionally substituted $C_{6-12}$ aromatic hydrocarbon group," "optionally substituted 5- to 14-membered aromatic heterocyclic group consisting of 1 to 7 carbon atoms and hetero atoms selected from the group consisting of nitrogen, oxygen and sulfur atoms," "optionally substituted $C_{8-14}$ aromatic fused-ring group," "optionally substituted 5- to 14-membered aromatic fused heterocyclic group consisting of 3 to 11 carbon atoms and hetero atoms selected from the group consisting of nitrogen, oxygen and sulfur atoms," "optionally substituted non-aromatic cyclic hydrocarbon group having carbon atoms not greater than 7" and "optionally substituted non-aromatic heterocyclic group having carbon atoms not greater than 7" used are the same as those given above.

(1) As the $C_{1-4}$ alkyl group having an optionally substituted $C_{6-12}$ aromatic hydrocarbon group, there are used, for example, benzyl, 4-hydroxybenzyl, 2-chlorobenzyl, 3-chlorobenzyl, 4-chlorobenzyl, 4-aminobenzyl, etc.

(2) As the $C_{1-4}$ alkyl group having an optionally substituted 5- to 14-membered aromatic heterocyclic group consisting of 1 to 7 carbon atoms and hetero atoms selected from the group consisting of nitrogen, oxygen and sulfur atoms, there are used, for example, 2-pyridylmethyl, 3-pyridylmethyl, 4-pyridylmethyl, 4-imidazolemethyl, etc.

(3) As the $C_{1-4}$ alkyl group having an optionally substituted $C_{8-14}$ aromatic fused-ring group, there are used, for example, 1-naphthylmethyl, 2-naphthylmethyl, etc.

(4) As the $C_{1-4}$ alkyl group having an optionally substituted 5- to 14-membered aromatic fused heterocyclic group consisting of 3 to 11 carbon atoms and hetero atoms selected from the group consisting of nitrogen, oxygen and sulfur atoms, there are used, for example, 3-indolemethyl, 1-formylindol-3-ylmethyl, 2-quinolylmethyl, etc.

(5) As the $C_{1-4}$ alkyl group having an optionally substituted non-aromatic cyclic hydrocarbon group having carbon atoms not greater than 7, there are used, for example, cyclohexylmethyl, etc.

(6) As the $C_{1-4}$ alkyl group having an optionally substituted non-aromatic heterocyclic group having carbon atoms not greater than 7, there are used, for example, piperidin-1-ylmethyl, etc.

(7) As the $C_{1-4}$ alkyl group having an optionally substituted amino group, there are used, for example, 2-aminoethyl, 3-aminopropyl, 4-aminobutyl, 4-acetamidobutyl, etc.

(8) As the $C_{1-4}$ alkyl group having an optionally substituted guanidino group, there are used, for example, 3-guanidinopropyl, 3-(N-tosyl)guanidinopropyl, etc.

(9) As the $C_{1-4}$ alkyl group having an optionally substituted hydroxyl group, there are used, for example, hydroxymethyl, 1-hydroxyethyl, benzyloxymethyl, etc.

(10) As the $C_{1-4}$ alkyl group having an optionally substituted carboxyl group, there are used, for example, carboxylmethyl, 2-carboxylethyl, benzyloxycarbonylmethyl, etc.

(11) As the $C_{1-4}$ alkyl group having an optionally substituted carbamoyl group, there are used, for example, carbamoylmethyl, 2-carbamoylethyl, xanthylcarbamoyl, etc.

(12) As the $C_{1-4}$ alkyl group having an optionally substituted sulfhydryl group, there are used, for example, sulfhydrylmethyl, 2-(methylsulfhydryl)ethyl, etc.

(13) As the unsubstituted $C_{1-4}$ alkyl group, there are used, for example, methyl, ethyl, propyl, isopropyl, butyl, isobutyl, sec-butyl, tert-butyl, etc.

Examples of $Q^3$, which is preferably used, include 4-hydroxybenzyl, 3-pyridylmethyl, 4-pyridylmethyl, methyl, isobutyl, hydroxymethyl, carboxymethyl, 4-aminobutyl, etc., and more preferably, 4-hydroxybenzyl, 3-pyridylmethyl, 4-pyridylmethyl, etc.

Examples of $Q^4$, which is preferably used, include carbamoylmethyl, 2-carbamoylethyl, 4-hydroxybenzyl, 4-imidazolemethyl, isobutyl, hydroxymethyl, 1-hydroxyethyl, carboxymethyl, 4-aminobutyl, etc., and more preferably, carbamoylmethyl, 2-carbamoylethyl, 4-hydroxybenzyl, etc.

Examples of $Q^5$, which is preferably used, include benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 1-formylindol-3-ylmethyl, 2-quinolylmethyl, cyclohexylmethyl, hydroxymethyl, 1-hydroxyethyl, methyl, isopropyl, isobutyl, sec-butyl, carboxymethyl, 4-aminobutyl, etc., and more preferably, benzyl, 2-chlorobenzyl, 3-chlorobenzyl, 4-chlorobenzyl, 4-aminobenzyl, 2-pyridylmethyl, 3-pyridylmethyl, 4-pyridylmethyl, 1-naphthylmethyl, 2-naphthylmethyl, 3-indolemethyl, 2-quinolylmethyl, cyclohexylmethyl, 1-hydroxyethyl, isopropyl, isobutyl, sec-butyl, etc.

$Q^6$ is particularly preferable methyl, hydroxymethyl, 1-hydroxyethyl, carbamoylmethyl, 2-carbamoylethyl, etc., and more preferably, carbamoylmethyl, etc.

$Q^7$ is particularly preferably 4-hydroxybenzyl, carbamoylmethyl, 3-pyridylmethyl, etc., and more preferably, 4-hydroxybenzyl, etc.

$Q^8$ is particularly preferably benzyl, 4-pyridylmethyl, 2-naphthylmethyl, 3-indolemethyl, hydroxymethyl, cyclohexylmethyl, sec-butyl, 1-hydroxyethyl, etc., and more preferably, 4-pyridylmethyl, 3-indolemethyl, sec-butyl, etc.

$Q^9$ is particularly preferably carbamoylmethyl, etc.

$Q^{10}$ is particularly preferably 4-hydroxbenzyl, 3-indolemethyl, methyl, 1-hydroxyethyl, 3-guanidinopropyl, etc., and more preferably, 3-indolemethyl, etc.

$Q^{11}$ is particularly preferably carbamoylmethyl, etc.

$Q^{12}$ is particularly preferably carbamoylmethyl, etc.

Each of $Y^1$ through $Y^3$ represents a group shown by formula: —CON($J^{13}$)-, —CSN($J^{13}$)-, —C($J^{14}$)N($J^{13}$)- or —N($J^{13}$)CO— (wherein each of $J^{13}$ and $J^{14}$ represents hydrogen atom or a $C_{1-3}$ alkyl group).

As the $C_{1-3}$ alkyl group shown by $J^{13}$ and $J^{14}$, methyl, ethyl, propyl or isopropyl is used.

$J^{13}$ is preferably hydrogen atom. $J^{14}$ is preferably hydrogen atom.

$Y^1$ is preferably a group shown by formula: —CONH— or —CH$_2$NH—, etc.

$Y^2$ is preferably a group shown by formula: —CONH— or —CH$_2$NH—, etc.

$Y^3$ is preferably a group shown by formula: —CONH—, etc.

$J^3$ and $Q^3$, $J^4$ and $Q^4$, $J^5$ and $Q^5$, $J^6$ and $Q^6$, $J^7$ and $Q^7$, $J^8$ and $Q^8$, $J^9$ and $Q^9$, $J^{10}$ and $Q^{10}$, $J^{17}$ and $Q^{11}$, and $J^{12}$ and $Q^{12}$ may be combined together to form a ring. In this case, C($J^3$)($Q^3$), C($J^4$)($Q^4$), C($J^5$)($Q^5$), C($J^6$)($Q^6$), C($J^7$)($Q^7$), C($J^8$)($Q^8$), C($J^9$)($Q^9$), C($J^{10}$)($Q^{10}$), C($J^{11}$)($Q^{11}$) or C($J^{12}$)($Q^{12}$) may form, for example, cyclopentane, cyclohexane, piperidine, etc.

$J^2$ and $Q^3$, $Y^1$ and $Q^4$, $Y^2$ and $Q^5$, $Y^3$ and $Q^6$, $J^2$ and $Q^7$, $Y^2$ and $Q^8$, $Y^3$ and $Q^9$, $J^2$ and $Q^{10}$, $Y^3$ and $Q^{11}$, and $J^2$ and $Q^{12}$ may be combined together to form a ring.

In the case where $J^2$ and $Q^3$, $J^2$ and $Q^7$, $J^2$ and $Q^{10}$, or $J^2$ and $Q^{12}$ are combined together to form a ring, $J^2$-C($J^3$)($Q^3$), $J^2$-C($J^7$)($Q^7$), $J^2$-C($J^{10}$)($Q^{10}$), or $J^2$-C($J^{12}$)($Q^{12}$) may form, for example, pyrrolidine, piperidine, thiazolidine.

In the case where $Y^1$ and $Q^4$, $Y^2$ and $Q^5$, $Y^3$ and $Q^6$, $Y^2$ and $Q^8$, $Y^3$ and $Q^9$, and $Y^3$ and $Q^{11}$ are combined together to form a ring, $Y^1$C($J^4$)($Q^4$)$Y^2$C($J^5$)($Q^5$), $Y^3$C($J^6$)($Q^6$), $Y^2$C($J^8$)($Q^8$), $Y^3$C($J^9$)($Q^9$), or $Y^3$C($J^{11}$)($Q^{11}$) may form, for example, pyrrolidine-2-carbonyl, piperidine-2-carbonyl or thiazolidine-4-carbonyl.

Preferred examples of the group shown by formula: $J^1$-$J^2$-C($J^3$)($Q^3$)$Y^1$C($J^4$)($Q^4$)$Y^2$C($J^5$)($Q^5$)$Y^3$C($J^6$)($Q^6$)C(=$Z^{10}$)— include:

| | |
|---|---|
| Tyr Asn Trp Asn-, | (SEQ ID NO: 28) |
| Tyr Asn Trp D-Asn-, | |
| Tyr Asn D-Trp Asn-, | |
| Tyr D-Asn Trp Asn-, | |
| D-Tyr Asn Trp Asn-, | |
| Tyr Lys Trp Asn-, | (SEQ ID NO: 73) |
| Tyr Asp Trp Asn-, | (SEQ ID NO: 74) |
| Tyr Tyr Trp Asn-, | (SEQ ID NO: 75) |
| Tyr Leu Trp Asn-, | (SEQ ID NO: 76) |
| Tyr Asn Ala Asn-, | (SEQ ID NO: 77) |
| Tyr Asn Leu Asn-, | (SEQ ID NO: 78) |
| Tyr Asn Ser Asn-, | (SEQ ID NO: 79) |
| Tyr Asn Asp Asn-, | (SEQ ID NO: 80) |
| Tyr Asn Lys Asn-, | (SEQ ID NO: 81) |
| Ala Asn Trp Asn-, | (SEQ ID NO: 82) |
| Leu Asn Trp Asn-, | (SEQ ID NO: 83) |
| Ser Asn Trp Asn-, | (SEQ ID NO: 84) |
| Asp Asn Trp Asn-, | (SEQ ID NO: 85) |
| Lys Asn Trp Asn-, | (SEQ ID NO: 86) |
| Tyr Asn Trp(For) Asn-, | (SEQ ID NO: 87) |
| D-Tyr Asn D-Trp Asn-, | |
| D-Tyr Asn Ala Asn-, | |
| D-Tyr Asn Ser Asn-, | |
| D-Tyr Asn Cha Asn-, | |
| D-Tyr Asn Thr Asn-, | |
| D-Tyr Asn Ile Asn-, | |
| D-Tyr Gln Trp Asn-, | |
| D-Tyr Thr Trp Asn-, | |
| D-Tyr Asn Val Asn-, | |
| D-Tyr D-Asn Trp Asn-, | |
| D-Tyr D-Asn D-Trp Asn-, | |
| D-Tyr Asn Phe Asn-, | |
| D-Tyr Asn Nal(1) Asn-, | |
| D-Tyr Asn Nal(2) Asn-, | |
| D-Tyr Asn Phe(2Cl) Asn-, | |
| D-Tyr Asn Phe(3Cl) Asn-, | |
| D-Tyr Asn Phe(4Cl) Asn-, | |
| D-Tyr Asn Phe(4NH$_2$) Asn-, | |
| D-Tyr Asn Pya(3) Asn-, | |
| D-Tyr D-Asn Phe Asn-, | |
| D-Tyr D-Asn Cha Asn-, | |
| D-Tyr D-Asn Thr Asn-, | |
| D-Tyr Asn Pya(2) Asn-, | |
| D-Tyr Asn Pya(4) Asn-, | |
| D-Tyr D-Ser Trp Asn-, | |
| D-Tyr D-His Trp Asn-, | |
| D-Pya(3) D-Asn Cha Asn-, | |
| D-Pya(3) D-Tyr Cha Asn-, | |

```
TyrΨ(CH₂NH)Asn Trp Asn-,      (SEQ ID NO: 88)

D-Tyr AsnΨ(CH₂NH) Trp Asn-,

TyrΨ(CH₂NH)Asn D-Trp Asn-,

D-Tyr Asn Ala(2-Qui) Asn-,

D-Tyr Asn D-Pya(4) Asn-,

D-Tyr D-Asn Pya(4) Asn-,

Tyr D-Asn Cha Asn-,

D-Tyr D-Asn Thr Asn-,

D-Tyr D-Asn Pya(4) Asn-, etc.
```

Preferred examples of the group shown by formula: $J^1$-$J^2$C $(J^7)(Y^2C(J^8)(Y^3C(J^9)(Q^9)C(=Z^{10})$— include:
Fmoc Asn Trp Asn-,
D-Asn Trp Asn-,
D-Tyr Trp Asn-,
D-Tyr D-Trp Asn-,
D-Tyr Ser Asn-,
d-Tyr Thr Asn-,
D-Tyr Ile Asn-,
D-Tyr Phe Asn-,
D-Tyr Nal(2) Asn-,
D-Pya(3) Phe Asn-,
D-Pya(3) Trp Asn-,
D-Tyr D-Pya(4) Asn-,
D-Asn Cha Asn-, etc.

Preferred examples of the group shown by formula: $J^1$-$J^2$C $(J^{10})(Q^{10})Y^3C(J^{11})(Q^{11})C(Z^{10})$— include:
Fmoc Trp Asn-,
Boc Tyr Asn-,
Tyr Asn-,
D-Trp Asn-,
Ac Trp Asn-,
Amidino Trp Asn-,
Ac Ala Asn-,
Ac Arg Asn-,
Ac Thr Asn-, etc.

Preferred examples of the group shown by formula: $J^1$-$J^2$- $C(J^{12})(Q^{12})C(=Z^{10})$— include:
Fmoc Asn-,
3-(Indol-3-yl)propionyl Asn-,
3-Indolecarbonyl Asn-,
3-Indoleacetyl Asn-,
4-(Indol-3-yl)butyryl Asn-,
Diphenylacetyl Asn-,
Hexanoyl Asn-,
Cyclohexanecabonyl Asn-,
2-(Indol-3-yl)ethylcabamoyl Asn-,
3-Pyridylpropionyl Asn-,
4-Imidzoleacetyl Asn-,
Piperidinecarbonyl Asn-,
1-Piperidineacetyl Asn-,
1-Methyl-1-piperidinioacetyl Asn-,
1-Pyridinioacetyl Asn-,
D-Glucuronyl Asn-, etc.

Preferred examples of the group shown by formula: $J^1$- include hydrogen atom, etc.

In the metastin derivatives (I) of the present invention, all compounds in which the groups shown by the respective symbols are optionally combined are preferably used. Among others, the compounds shown by Compound Numbers below (Tables 1 through 11) are preferred.

```
                                                              (SEQ ID NO: 89)
         MS10: Tyr-Asn-Trp-Asn-Ser-Phe-Gly-Leu-Arg-Phe-NH₂
                1   2   3   4   5   6   7   8   9   10

Compound No. 17: [Pya(4)10]MS10
                                                              (SEQ ID NO: 90)
Tyr-Asn-Trp-Asn-Ser-Phe-Gly-Leu-Arg-Pya(4)-NH₂

Compound No. 18: [Tyr(Me)10]MS10
                                                              (SEQ ID NO: 91)
Tyr-Asn-Trp-Asn-Ser-Phe-Gly-Leu-Arg-Tyr(Me)-NH₂

Compound No. 19: [Phe(2F)10]MS10
                                                              (SEQ ID NO: 92)
Tyr-Asn-Trp-Asn-Ser-Phe-Gly-Leu-Arg-Phe(2F)-NH₂

Compound No. 23: [Tyr5]MS10
                                                              (SEQ ID NO: 93)
Tyr-Asn-Trp-Asn-Tyr-Phe-Gly-Leu-Arg-Phe-NH₂

Compound No. 24: [Leu5]MS10
                                                              (SEQ ID NO: 94)
Tyr-Asn-Trp-Asn-Leu-Phe-Gly-Leu-Arg-Phe-NH₂

Compound No. 30: Acetyl-MS10
                                                              (SEQ ID NO: 95)
Acetyl-Tyr-Asn-Trp-Asn-Ser-Phe-Gly-Leu-Arg-Phe-NH₂

Compound No. 31: Fmoc-MS10
                                                              (SEQ ID NO: 96)
Fmoc-Tyr-Asn-Trp-Asn-Ser-Phe-Gly-Leu-Arg-Phe-NH₂

Compound No. 38: [D-Ser5]MS10
Tyr-Asn-Trp-Asn-D-Ser-Phe-Gly-Leu-Arg-Phe-NH₂

Compound No. 39: [D-Asn4]MS10
Tyr-Asn-Trp-D-Asn-Ser-Phe-Gly-Leu-Arg-Phe-NH₂
```

-continued

Compound No. 40: [D-Trp3]MS10
Tyr-Asn-D-Trp-Asn-Ser-Phe-Gly-Leu-Arg-Phe-NH$_2$

Compound No. 41: [D-Asn2]MS10
Tyr-D-Asn-Trp-Asn-Ser-Phe-Gly-Leu-Arg-Phe-NH$_2$

Compound No. 42: [D-Tyr1]MS10
D-Tyr-Asn-Trp-Asn-Ser-Phe-Gly-Leu-Arg-Phe-NH$_2$

Compound No. 44: [Lys9]MS10  (SEQ ID NO: 97)
Tyr-Asn-Trp-Asn-Ser-Phe-Gly-Leu-Lys-Phe-NH$_2$ Compound No. 45: [Ala8]MS10  (SEQ ID NO: 98)
Tyr-Asn-Trp-Asn-Ser-Phe-Gly-Ala-Arg-Phe-NH$_2$ Compound No. 50: [Ala7]MS10  (SEQ ID NO: 99)
Tyr-Asn-Trp-Asn-Ser-Phe-Ala-Leu-Arg-Phe-NH$_2$ Compound No. 51: [NMePhe10]MS10  (SEQ ID NO: 100)
Tyr-Asn-Trp-Asn-Ser-Phe-Gly-Leu-Arg-NMePhe-NH$_2$ Compound No. 53: des(1-3)-Fmoc-MS10  (SEQ ID NO: 101)
Fmoc-Asn-Ser-Phe-Gly-Leu-Arg-Phe-NH$_2$ Compound No. 54: des(1-2)-Fmoc-MS10  (SEQ ID NO: 102)
Fmoc-Trp-Asn-Ser-Phe-Gly-Leu-Arg-Phe-NH$_2$ Compound No. 55: des(1)-Fmoc-MS10  (SEQ ID NO: 103)
Fmoc-Asn-Trp-Asn-Ser-Phe-Gly-Leu-Arg-Phe-NH$_2$ Compound No. 56: [Lys2]MS10  (SEQ ID NO: 104)
Tyr-Lys-Trp-Asn-Ser-Phe-Gly-Leu-Arg-Phe-NH$_2$ Compound No. 57: [Asp2]MS10  (SEQ ID NO: 105)
Tyr-Asp-Trp-Asn-Ser-Phe-Gly-Leu-Arg-Phe-NH$_2$ Compound No. 58: [Tyr2]MS10  (SEQ ID NO: 106)
Tyr-Tyr-Trp-Asn-Ser-Phe-Gly-Leu-Arg-Phe-NH$_2$ Compound No. 59: [Leu2]MS10  (SEQ ID NO: 107)
Tyr-Leu-Trp-Asn-Ser-Phe-Gly-Leu-Arg-Phe-NH$_2$ Compound No. 60: [Pya(3)10]MS10  (SEQ ID NO: 108)
Tyr-Asn-Trp-Asn-Ser-Phe-Gly-Leu-Arg-Pya(3)-NH$_2$ Compound No. 61: [Phe(4F)10]MS10  (SEQ ID NO: 109)
Tyr-Asn-Trp-Asn-Ser-Phe-Gly-Leu-Arg-Phe(4F)-NH$_2$ Compound No. 67: [Ala3]MS10  (SEQ ID NO: 110)
Tyr-Asn-Ala-Asn-Ser-Phe-Gly-Leu-Arg-Phe-NH$_2$ Compound No. 68: [Leu3]MS10  (SEQ ID NO: 111)
Tyr-Asn-Leu-Asn-Ser-Phe-Gly-Leu-Arg-Phe-NH$_2$ Compound No. 69: [Ser3]MS10  (SEQ ID NO: 112)
Tyr-Asn-Ser-Asn-Ser-Phe-Gly-Leu-Arg-Phe-NH$_2$ Compound No. 70: [Asp3]MS10  (SEQ ID NO: 113)
Tyr-Asn-Asp-Asn-Ser-Phe-Gly-Leu-Arg-Phe-NH$_2$ Compound No. 71: [Lys3]MS10  (SEQ ID NO: 114)
Tyr-Asn-Lys-Asn-Ser-Phe-Gly-Leu-Arg-Phe-NH$_2$ -continued Compound No. 72: [Ala1]MS10

Ala-Asn-Trp-Asn-Ser-Phe-Gly-Leu-Arg-Phe-NH$_2$ (SEQ ID NO: 115)

Compound No. 73: [Leu1]MS10

Leu-Asn-Trp-Asn-Ser-Phe-Gly-Leu-Arg-Phe-NH$_2$ (SEQ ID NO: 116)

Compound No. 74: [Ser1]MS10

Ser-Asn-Trp-Asn-Ser-Phe-Gly-Leu-Arg-Phe-NH$_2$ (SEQ ID NO: 117)

Compound No. 75: [Asp1]MS10

Asp-Asn-Trp-Asn-Ser-Phe-Gly-Leu-Arg-Phe-NH$_2$ (SEQ ID NO: 118)

Compound No. 76: [Lys1]MS10

Lys-Asn-Trp-Asn-Ser-Phe-Gly-Leu-Arg-Phe-NH$_2$ (SEQ ID NO: 119)

Compound No. 77: [Phe(4CN)10]MS10

Tyr-Asn-Trp-Asn-Ser-Phe-Gly-Leu-Arg-Phe(4CN)-NH$_2$ (SEQ ID NO: 120)

Compound No. 78: [Trp(For) 3, Phe(4CN)10]MS10

Tyr-Asn-Trp(For)-Asn-Ser-Phe-Gly-Leu-Arg-Phe(4CN)-NH$_2$ (SEQ ID NO: 121)

Compound No. 79: [Hph10]MS10

Tyr-Asn-Trp-Asn-Ser-Phe-Gly-Leu-Arg-Hph-NH$_2$ (SEQ ID NO: 122)

Compound No. 81: [NMeArg9]MS10

Tyr-Asn-Trp-Asn-Ser-Phe-Gly-Leu-NMeArg-Phe-NH$_2$ (SEQ ID NO: 123)

Compound No. 82: [Arg(Me)9]MS10

Tyr-Asn-Trp-Asn-Ser-Phe-Gly-Leu-Arg(Me)-Phe-NH$_2$ (SEQ ID NO: 124)

Compound No. 83: [Arg(asy Me$_2$)9]MS10

Tyr-Asn-Trp-Asn-Ser-Phe-Gly-Leu-Arg(asy Me$_2$)-Phe-NH$_2$ (SEQ ID NO: 125)

Compound No. 87: des(4-5)-Boc-MS10

Boc-Tyr-Asn-Trp-Phe-Gly-Leu-Arg-Phe-NH$_2$ (SEQ ID NO: 126)

Compound No. 88: des(4-5)-MS10

Tyr-Asn-Trp-Phe-Gly-Leu-Arg-Phe-NH$_2$ (SEQ ID NO: 127)

Compound No. 90: [9Ψ10, CH$_2$NH]MS10

Tyr-Asn-Trp-Asn-Ser-Phe-Gly-Leu-ArgΨ(CH$_2$NH)Phe-NH$_2$ (SEQ ID NO: 128)

Compound No. 91: [8Ψ9, CH$_2$NH]MS10

Tyr-Asn-Trp-Asn-Ser-Phe-Gly-LeuΨ(CH$_2$NH)Arg-Phe-NH$_2$ (SEQ ID NO: 129)

Compound No. 97: [Har9]MS10

Tyr-Asn-Trp-Asn-Ser-Phe-Gly-Leu-Har-Phe-NH$_2$ (SEQ ID NO: 130)

Compound No. 98: [Lys(Me$_2$)9]MS10

Tyr-Asn-Trp-Asn-Ser-Phe-Gly-Leu-Lys(Me$_2$)-Phe-NH$_2$ (SEQ ID NO: 131)

Compound No. 101: [Ser7]MS10

Tyr-Asn-Trp-Asn-Ser-Phe-Ser-Leu-Arg-Phe-NH$_2$ (SEQ ID NO: 132)

Compound No. 105: [Nle8]MS10

Tyr-Asn-Trp-Asn-Ser-Phe-Gly-Nle-Arg-Phe-NH$_2$ (SEQ ID NO: 133)

Compound No. 107: [Val8]MS10

Tyr-Asn-Trp-Asn-Ser-Phe-Gly-Val-Arg-Phe-NH$_2$ (SEQ ID NO: 134)

-continued

Compound No. 109: [Tyr10]MS10  (SEQ ID NO: 135)
Tyr-Asn-Trp-Asn-Ser-Phe-Gly-Leu-Arg-Tyr-NH$_2$ Compound No. 110: [Nal(2)10]MS10  (SEQ ID NO: 136)
Tyr-Asn-Trp-Asn-Ser-Phe-Gly-Leu-Arg-Nal(2)-NH$_2$ Compound No. 111: [Phe(F$_5$)10]MS10  (SEQ ID NO: 137)
Tyr-Asn-Trp-Asn-Ser-Phe-Gly-Leu-Arg-Phe(F$_5$)-NH$_2$ Compound No. 112: [Cha10]MS10  (SEQ ID NO: 138)
Tyr-Asn-Trp-Asn-Ser-Phe-Gly-Leu-Arg-Cha-NH$_2$ Compound No. 114: des(1-3)-3-(3-Indolyl)propionyl-MS10  (SEQ ID NO: 139)
3-(3-Indolyl)propionyl-Asn-Ser-Phe-Gly-Leu-Arg-Phe-NH$_2$ Compound No. 121: des(1-4)-[Trp5]MS10  (SEQ ID NO: 140)
Trp-Phe-Gly-Leu-Arg-Phe-NH$_2$ Compound No. 123: [NMeLeu8]MS10  (SEQ ID NO: 141)
Tyr-Asn-Trp-Asn-Ser-Phe-Gly-NMeLeu-Arg-Phe-NH$_2$ Compound No. 126: [NMeSer5]MS10  (SEQ ID NO: 142)
Tyr-Asn-Trp-Asn-NMeSer-Phe-Gly-Leu-Arg-Phe-NH$_2$ Compound No. 127: [D-Asn4,NMePhe6]MS10
Tyr-Asn-Trp-D-Asn-Ser-NMePhe-Gly-Leu-Arg-Phe-NH$_2$ Compound No. 128: [10Ψ,CSNH]MS10  (SEQ ID NO: 143)
Tyr-Asn-Trp-Asn-Ser-Phe-Gly-Leu-Arg-PheΨ(CSNH)NH$_2$ Compound No. 129: [Arg(symMe$_2$)9]MS10  (SEQ ID NO: 144)
Tyr-Asn-Trp-Asn-Ser-Phe-Gly-Leu-Arg(symMe$_2$)-Phe-NH$_2$ Compound No. 130: [Phe(4Cl)10]MS10  (SEQ ID NO: 145)
Tyr-Asn-Trp-Asn-Ser-Phe-Gly-Leu-Arg-Phe(4Cl)-NH$_2$ Compound No. 131: [Phe(4NH$_2$)10]MS10  (SEQ ID NO: 146)
Tyr-Asn-Trp-Asn-Ser-Phe-Gly-Leu-Arg-Phe(4NH$_2$)-NH$_2$ Compound No. 132: [Phe(4NO$_2$)10]MS10  (SEQ ID NO: 147)
Tyr-Asn-Trp-Asn-Ser-Phe-Gly-Leu-Arg-Phe(4NO$_2$)-NH$_2$ Compound No. 133: [Nal(1)10]MS10  (SEQ ID NO: 148)
Tyr-Asn-Trp-Asn-Ser-Phe-Gly-Leu-Arg-Nal(1)-NH$_2$ Compound No. 134: [Trp10]MS10  (SEQ ID NO: 149)
Tyr-Asn-Trp-Asn-Ser-Phe-Gly-Leu-Arg-Trp-NH$_2$ Compound No. 137: [Nle9]MS10  (SEQ ID NO: 150)
Tyr-Asn-Trp-Asn-Ser-Phe-Gly-Leu-Nle-Phe-NH$_2$ Compound No. 138: [Cit9]MS10  (SEQ ID NO: 151)
Tyr-Asn-Trp-Asn-Ser-Phe-Gly-Leu-Cit-Phe-NH$_2$ Compound No. 140: [Arg(Me)9,NMePhe10]MS10  (SEQ ID NO: 152)
Tyr-Asn-Trp-Asn-Ser-Phe-Gly-Leu-Arg(Me)-NMePhe-NH$_2$ Compound No. 141: [D-Tyr1,Arg(Me)9]MS10
D-Tyr-Asn-Trp-Asn-Ser-Phe-Gly-Leu-Arg(Me)-Phe-NH$_2$ Compound No. 142: [D-Tyr1,D-Trp3,Arg(Me)9]MS10
D-Tyr-Asn-D-Trp-Asn-Ser-Phe-Gly-Leu-Arg(Me)-Phe-NH$_2$ -continued Compound No. 143: [D-Trp3,Arg(Me)9]MS10
Tyr-Asn-D-Trp-Asn-Ser-Phe-Gly-Leu-Arg(Me)-Phe-NH$_2$ Compound No. 144: des(1-3)-Fmoc-[Arg(Me)9]MS10
Fmoc-Asn-Ser-Phe-Gly-Leu-Arg(Me)-Phe-NH$_2$       (SEQ ID NO: 153)

Compound No. 145: des(1-2)-Fmoc-[Arg(Me)9]MS10
Fmoc-Trp-Asn-Ser-Phe-Gly-Leu-Arg(Me)-Phe-NH$_2$      (SEQ ID NO: 154)

Compound No. 146: [10Ψ,CSNH,D-Tyr1]MS10
D-Tyr-Asn-Trp-Asn-Ser-Phe-Gly-Leu-Arg-PheΨ(CSNH)NH$_2$ Compound No. 150: [Tyr6]MS10                          (SEQ ID NO: 155)
Tyr-Asn-Trp-Asn-Ser-Tyr-Gly-Leu-Arg-Phe-NH$_2$ Compound No. 151: [Nal(1)6]MS10                       (SEQ ID NO: 156)
Tyr-Asn-Trp-Asn-Ser-Nal(1)-Gly-Leu-Arg-Phe-NH$_2$ Compound No. 152: [Nal(2)6]MS10                       (SEQ ID NO: 157)
Tyr-Asn-Trp-Asn-Ser-Nal(2)-Gly-Leu-Arg-Phe-NH$_2$ Compound No. 153: [Phe(F$_5$)6]MS10                   (SEQ ID NO: 158)
Tyr-Asn-Trp-Asn-Ser-Phe(F$_5$)-Gly-Leu-Arg-Phe-NH$_2$ Compound No. 154: [Phe(4F)6]MS10                      (SEQ ID NO: 159)
Tyr-Asn-Trp-Asn-Ser-Phe(4F)-Gly-Leu-Arg-Phe-NH$_2$ Compound No. 156: [Cha6]MS10                          (SEQ ID NO: 160)
Tyr-Asn-Trp-Asn-Ser-Cha-Gly-Leu-Arg-Phe-NH$_2$ Compound No. 163: [6Ψ7, CH$_2$NH]MS10                 (SEQ ID NO: 161)
Tyr-Asn-Trp-Asn-Ser-PheΨ(CH$_2$NH)Gly-Leu-Arg-Phe-NH$_2$ Compound No. 165: [Dap(Gly)9]-MS10                    (SEQ ID NO: 162)
Tyr-Asn-Trp-Asn-Ser-Phe-Gly-Leu-Dap(Gly)-Phe-NH$_2$ Compound No. 166: [6Ψ7,CSNH]MS10                      (SEQ ID NO: 163)
Tyr-Asn-Trp-Asn-Ser-Phe Ψ(CSNH)Gly-Leu-Arg-Phe-NH$_2$ Compound No. 169: [D-Tyr1,Ala3,Arg(Me)9]MS10
D-Tyr-Asn-Ala-Asn-Ser-Phe-Gly-Leu-Arg(Me)-Phe-NH$_2$ Compound No. 170: [D-Tyr1,Ser3,Arg(Me)9]MS10
D-Tyr-Asn-Ser-Asn-Ser-Phe-Gly-Leu-Arg(Me)-Phe-NH$_2$ Compound No. 171: [D-Tyr1,Cha3,Arg(Me)9]MS10
D-Tyr-Asn-Cha-Asn-Ser-Phe-Gly-Leu-Arg(Me)-Phe-NH$_2$ Compound No. 172: [D-Tyr1,Cha6,Arg(Me)9]MS10
D-Tyr-Asn-Trp-Asn-Ser-Cha-Gly-Leu-Arg(Me)-Phe-NH$_2$ Compound No. 173: [D-Tyr1,Ala7,Arg(Me)9]MS10
D-Tyr-Asn-Trp-Asn-Ser-Phe-Ala-Leu-Arg(Me)-Phe-NH$_2$ Compound No. 174: [D-Tyr1,Arg(Me)9,Trp10]MS10
D-Tyr-Asn-Trp-Asn-Ser-Phe-Gly-Leu-Arg(Me)-Trp-NH$_2$ Compound No. 176: [AzaGly7]MS10                       (SEQ ID NO: 164)
Tyr-Asn-Trp-Asn-Ser-Phe-AzaGly-Leu-Arg-Phe-NH$_2$ Compound No. 181: [D-Tyr1,Cha3,6,Arg(Me)9]MS10
D-Tyr-Asn-Cha-Asn-Ser-Cha-Gly-Leu-Arg(Me)-Phe-NH$_2$ Compound No. 182: [D-Tyr1,Cha3,6,Arg(Me)9,Trp10]MS10
D-Tyr-Asn-Cha-Asn-Ser-Cha-Gly-Leu-Arg(Me)-Trp-NH$_2$ -continued Compound No. 183: [Phe(4NH₂)9]MS10 (SEQ ID NO: 165)
Tyr-Asn-Trp-Asn-Ser-Phe-Gly-Leu-Phe(4NH₂)-Phe-NH₂

Compound No. 184: [Phe(4-Guanidino)9]MS10 (SEQ ID NO: 166)
Tyr-Asn-Trp-Asn-Ser-Phe-Gly-Leu-Phe(4-Guanidino)-Phe-NH₂

Compound No. 185: [Dap(GnGly)9]MS10 (SEQ ID NO: 167)
Tyr-Asn-Trp-Asn-Ser-Phe-Gly-Leu-Dap(GnGly)-Phe-NH₂

Compound No. 186: [Trp(For)10]MS10 (SEQ ID NO: 168)
Tyr-Asn-Trp-Asn-Ser-Phe-Gly-Leu-Arg-Trp(For)-NH₂

Compound No. 187: [Abu8]MS10 (SEQ ID NO: 169)
Tyr-Asn-Trp-Asn-Ser-Phe-Gly-Abu-Arg-Phe-NH₂

Compound No. 189: [Ala(3-Bzt)10]MS10 (SEQ ID NO: 170)
Tyr-Asn-Trp-Asn-Ser-Phe-Gly-Leu-Arg-Ala(3-Bzt)-NH₂

Compound No. 190: [D-Tyr1,Cha3,AzaGly7,Arg(Me)9]MS10
D-Tyr-Asn-Cha-Asn-Ser-Phe-AzaGly-Leu-Arg(Me)-Phe-NH₂

Compound No. 191: [D-Tyr1,Ser3,AzaGly7,Arg(Me)9]MS10
D-Tyr-Asn-Ser-Asn-Ser-Phe-AzaGly-Leu-Arg(Me)-Phe-NH₂

Compound No. 192: [D-Tyr1,Arg(Et)9]MS10
D-Tyr-Asn-Trp-Asn-Ser-Phe-Gly-Leu-Arg(Et)-Phe-NH₂

Compound No. 193: [D-Tyr1,Arg(n-Pr)9]MS10
D-Tyr-Asn-Trp-Asn-Ser-Phe-Gly-Leu-Arg(n-Pr)-Phe-NH₂

Compound No. 194: [D-Tyr1,Arg(Ac)9]MS10
D-Tyr-Asn-Trp-Asn-Ser-Phe-Gly-Leu-Arg(Ac)-Phe-NH₂

Compound No. 197: [Phe(3F)10]MS10 (SEQ ID NO: 171)
Tyr-Asn-Trp-Asn-Ser-Phe-Gly-Leu-Arg-Phe(3F)-NH₂

Compound No. 198: [Phe(3,4F₂)10]MS10 (SEQ ID NO: 172)
Tyr-Asn-Trp-Asn-Ser-Phe-Gly-Leu-Arg-Phe(3,4F₂)-NH₂

Compound No. 199: [Phe(3,4Cl₂)10]MS10 (SEQ ID NO: 173)
Tyr-Asn-Trp-Asn-Ser-Phe-Gly-Leu-Arg-Phe(3,4Cl₂)-NH₂

Compound No. 200: [Phe(3CF₃)10]MS10 (SEQ ID NO: 174)
Tyr-Asn-Trp-Asn-Ser-Phe-Gly-Leu-Arg-Phe(3CF₃)-NH₂

Compound No. 201: [Ala(2-Qui)10]MS10 (SEQ ID NO: 175)
Tyr-Asn-Trp-Asn-Ser-Phe-Gly-Leu-Arg-Ala(2-Qui)-NH₂

Compound No. 203: [D-Tyr1,Cha6,Arg(Me)9]MS10
D-Tyr-Asn-Trp-Asn-Ser-Cha-Gly-Leu-Arg(Me)-Phe-NH₂

Compound No. 204: [D-Tyr1, Ala7, Arg(Me)9]MS10
D-Tyr-Asn-Trp-Asn-Ser-Phe-Ala-Leu-Arg(Me)-Phe-NH₂

Compound No. 205: [D-Tyr1,Thr3,Arg(Me)9]MS10
D-Tyr-Asn-Thr-Asn-Ser-Phe-Gly-Leu-Arg(Me)-Phe-NH₂

Compound No. 206: [D-Tyr1,Ile3,Arg(Me)9]MS10
D-Tyr-Asn-Ile-Asn-Ser-Phe-Gly-Leu-Arg(Me)-Phe-NH₂

Compound No. 207: [D-Tyr1,Ser4,Arg(Me)9]MS10
D-Tyr-Asn-Trp-Ser-Ser-Phe-Gly-Leu-Arg(Me)-Phe-NH₂

Compound No. 208: [D-Tyr1,Thr4,Arg(Me)9]MS10
D-Tyr-Asn-Trp-Thr-Ser-Phe-Gly-Leu-Arg(Me)-Phe-NH₂

Compound No. 209: [D-Tyr1,Gln4,Arg(Me)9]MS10
D-Tyr-Asn-Trp-Gln-Ser-Phe-Gly-Leu-Arg(Me)-Phe-NH₂

-continued

Compound No. 210: [D-Tyr1,Ala4,Arg(Me)9]MS10
D-Tyr-Asn-Trp-Ala-Ser-Phe-Gly-Leu-Arg(Me)-Phe-NH$_2$ Compound No. 211: [D-Tyr1,Thr5,Arg(Me)9]MS10
D-Tyr-Asn-Trp-Asn-Thr-Phe-Gly-Leu-Arg(Me)-Phe-NH$_2$ Compound No. 212: [D-Tyr1,Ala5,Arg(Me)9]MS10
D-Tyr-Asn-Trp-Asn-Ala-Phe-Gly-Leu-Arg(Me)-Phe-NH$_2$ Compound No. 213: [D-Tyr1,Val8,Arg(Me)9]MS10
D-Tyr-Asn-Trp-Asn-Ser-Phe-Gly-Val-Arg(Me)-Phe-NH$_2$ Compound No. 214: [D-Tyr1,Gln2,Arg(Me)9]MS10
D-Tyr-Gln-Trp-Asn-Ser-Phe-Gly-Leu-Arg(Me)-Phe-NH$_2$ Compound No. 215: [D-Tyr1,Thr2,Arg(Me)9]MS10
D-Tyr-Thr-Trp-Asn-Ser-Phe-Gly-Leu-Arg(Me)-Phe-NH$_2$ Compound No. 216: des(1)-[D-Asn2,Arg(Me)9]MS10
D-Asn-Trp-Asn-Ser-Phe-Gly-Leu-Arg(Me)-Phe-NH$_2$ Compound No. 217: des(1)-[D-Tyr2,Arg(Me)9]MS10
D-Tyr-Trp-Asn-Ser-Phe-Gly-Leu-Arg(Me)-Phe-NH$_2$ Compound No. 218: [N((CH$_2$) 3Gn)]Gly9]MS10

Tyr-Asn-Trp-Asn-Ser-Phe-Gly-Leu-N((CH$_2$) 3Gn)Gly-Phe-NH$_2$ (SEQ ID NO: 176)

Compound No. 220: [Arg(Et)9]MS10

(SEQ ID NO: 177)

Tyr-Asn-Trp-Asn-Ser-Phe-Gly-Leu-Arg(Et)-Phe-NH$_2$

Compound No. 221: [D-Tyr1,Thr3,AzaGly7,Arg(Me)9]MS10
D-Tyr-Asn-Thr-Asn-Ser-Phe-AzaGly-Leu-Arg(Me)-Phe-NH$_2$ Compound No. 222: des(1)-[D-Tyr2,AzaGly7,Arg(Me)9]MS10
D-Tyr-Trp-Asn-Ser-Phe-AzaGly-Leu-Arg(Me)-Phe-NH$_2$ Compound No. 223: des(1-2)-[D-Trp3,Arg(Me)9]MS10
D-Trp-Asn-Ser-Phe-Gly-Leu-Arg(Me)-Phe-NH$_2$ Compound No. 224: des(1)-[D-Tyr2,D-Trp3,Arg(Me)9]MS10
D-Tyr-D-Trp-Asn-Ser-Phe-Gly-Leu-Arg(Me)-Phe-NH$_2$ Compound No. 225: des(1)-[D-Asn2,D-Trp3,Arg(Me)9]MS10
D-Asn-D-Trp-Asn-Ser-Phe-Gly-Leu-Arg(Me)-Phe-NH$_2$ Compound No. 226: des(1)-[D-Tyr2,Ser3,Arg(Me)9]MS10
D-Tyr-Ser-Asn-Ser-Phe-Gly-Leu-Arg(Me)-Phe-NH$_2$ Compound No. 227: des(1)-[D-Tyr2,Thr3,Arg(Me)9]MS10
D-Tyr-Thr-Asn-Ser-Phe-Gly-Leu-Arg(Me)-Phe-NH$_2$ Compound No. 228: des(1)-[D-Tyr2,Ile3,Arg(Me)9]MS10
D-Tyr-Ile-Asn-Ser-Phe-Gly-Leu-Arg(Me)-Phe-NH$_2$ Compound No. 229: [D-Tyr1,Val3,Arg(Me)9]MS10
D-Tyr-Asn-Val-Asn-Ser-Phe-Gly-Leu-Arg(Me)-Phe-NH$_2$ Compound No. 230: [D-Tyr1,D-Asn2,Arg(Me)9]MS10
D-Tyr-D-Asn-Trp-Asn-Ser-Phe-Gly-Leu-Arg(Me)-Phe-NH$_2$ Compound No. 231: [D-Tyr1,D-Asn2,D-Trp3,Arg(Me)9]MS10
D-Tyr-D-Asn-D-Trp-Asn-Ser-Phe-Gly-Leu-Arg(Me)-Phe-NH$_2$ Compound No. 232: [D-Tyr1,AzaGly7,Arg(Me)9]MS10
D-Tyr-Asn-Trp-Asn-Ser-Phe-AzaGly-Leu-Arg(Me)-Phe-NH$_2$ Compound No. 233: [D-Tyr1,Ile3,AzaGly7,Arg(Me)9]MS10
D-Tyr-Asn-Ile-Asn-Ser-Phe-AzaGly-Leu-Arg(Me)-Phe-NH$_2$ Compound No. 234: [D-Tyr1,Val3,AzaGly7,Arg(Me)9]MS10
D-Tyr-Asn-Val-Asn-Ser-Phe-AzaGly-Leu-Arg(Me)-Phe-NH$_2$ Compound No. 235: [D-Tyr1,Ala3,AzaGly7,Arg(Me)9]MS10
D-Tyr-Asn-Ala-Asn-Ser-Phe-AzaGly-Leu-Arg(Me)-Phe-NH$_2$ Compound No. 236: [D-Tyr1,D-Trp3,AzaGly7,Arg(Me)9]MS10
D-Tyr-Asn-D-Trp-Asn-Ser-Phe-AzaGly-Leu-Arg(Me)-Phe-NH$_2$ -continued Compound No. 237: [D-Tyr1,D-Asn2,AzaGly7,Arg(Me)9]MS10
D-Tyr-D-Asn-Trp-Asn-Ser-Phe-AzaGly-Leu-Arg(Me)-Phe-NH$_2$ Compound No. 238: [D-Tyr1,D-Asn2,D-Trp3,AzaGly7,Arg(Me)9]MS10
D-Tyr-D-Asn-D-Trp-Asn-Ser-Phe-AzaGly-Leu-Arg(Me)-Phe-NH$_2$ Compound No. 239: des(1)-[D-Tyr2,Ser3,AzaGly7,Arg(Me)9]MS10
D-Tyr-Ser-Asn-Ser-Phe-AzaGly-Leu-Arg(Me)-Phe-NH$_2$ Compound No. 240: des(1)-[D-Tyr2,Ile3,AzaGly7,Arg(Me)9]MS10
D-Tyr-Ile-Asn-Ser-Phe-AzaGly-Leu-Arg(Me)-Phe-NH$_2$ Compound No. 241: des(1)-[D-Tyr2,Thr3,AzaGly7,Arg(Me)9]MS10
D-Tyr-Thr-Asn-Ser-Phe-AzaGly-Leu-Arg(Me)-Phe-NH$_2$ Compound No. 242: des(1)-[D-Tyr2,D-Trp3,AzaGly7,Arg(Me)9]MS10
D-Tyr-D-Trp-Asn-Ser-Phe-AzaGly-Leu-Arg(Me)-Phe-NH$_2$ Compound No. 244: [D-Tyr1,Phe3,AzaGly7,Arg(Me)9]MS10
D-Tyr-Asn-Phe-Asn-Ser-Phe-AzaGly-Leu-Arg(Me)-Phe-NH$_2$ Compound No. 245: [D-Tyr1,Nal(1) 3,AzaGly7,Arg(Me)9]MS10
D-Tyr-Asn-Nal(1)-Asn-Ser-Phe-AzaGly-Leu-Arg(Me)-Phe-NH$_2$ Compound No. 246: [D-Tyr1,Nal(2) 3,AzaGly7,Arg(Me)9]MS10
D-Tyr-Asn-Nal(2)-Asn-Ser-Phe-AzaGly-Leu-Arg(Me)-Phe-NH$_2$ Compound No. 247: [D-Tyr1,Phe(2Cl) 3,AzaGly7,Arg(Me)9]MS10
D-Tyr-Asn-Phe(2Cl)-Asn-Ser-Phe-AzaGly-Leu-Arg(Me)-Phe-NH$_2$ Compound No. 248: [D-Tyr1,Phe(3Cl) 3,AzaGly7,Arg(Me)9]MS10
D-Tyr-Asn-Phe(3Cl)-Asn-Ser-Phe-AzaGly-Leu-Arg(Me)-Phe-NH$_2$ Compound No. 249: [D-Tyr1,Phe(4Cl) 3,AzaGly7,Arg(Me)9]MS10
D-Tyr-Asn-Phe(4Cl)-Asn-Ser-Phe-AzaGly-Leu-Arg(Me)-Phe-NH$_2$ Compound No. 250: [D-Tyr1,Phe(4NH$_2$) 3,AzaGly7,Arg(Me)9]MS10
D-Tyr-Asn-Phe(4NH$_2$)-Asn-Ser-Phe-AzaGly-Leu-Arg(Me)-Phe-NH$_2$ Compound No. 251: [D-Tyr1,Pya(3) 3,AzaGly7,Arg(Me)9]MS10
D-Tyr-Asn-Pya(3)-Asn-Ser-Phe-AzaGly-Leu-Arg(Me)-Phe-NH$_2$ Compound No. 252: [D-Tyr1,D-Ala3,AzaGly7,Arg(Me)9]MS10
D-Tyr-Asn-D-Ala-Asn-Ser-Phe-AzaGly-Leu-Arg(Me)-Phe-NH$_2$ Compound No. 253: [D-Tyr1,Pro3,AzaGly7,Arg(Me)9]MS10
D-Tyr-Asn-Pro-Asn-Ser-Phe-AzaGly-Leu-Arg(Me)-Phe-NH$_2$ Compound No. 254: des(1)-[D-Tyr2,Phe3,AzaGly7,Arg(Me)9]MS10
D-Tyr-Phe-Asn-Ser-Phe-AzaGly-Leu-Arg(Me)-Phe-NH$_2$ Compound No. 255: des(1)-[D-Tyr2,Nal(2) 3,AzaGly7,Arg(Me)9]MS10
D-Tyr-Nal(2)-Asn-Ser-Phe-AzaGly-Leu-Arg(Me)-Phe-NH$_2$ Compound No. 256: des(1)-[D-Pya(3) 2,Phe3,AzaGly7,Arg(Me)9]MS10
D-Pya(3)-Phe-Asn-Ser-Phe-AzaGly-Leu-Arg(Me)-Phe-NH$_2$ Compound No. 257: [D-Tyr1,D-Asn2,Phe3,AzaGly7,Arg(Me)9]MS10
D-Tyr-D-Asn-Phe-Asn-Ser-Phe-AzaGly-Leu-Arg(Me)-Phe-NH$_2$ Compound No. 258: [D-Pya(3)1,AzaGly7,Arg(Me)9]MS10
D-Pya(3)-Asn-Trp-Asn-Ser-Phe-AzaGly-Leu-Arg(Me)-Phe-NH$_2$ Compound No. 259: [D-Ala1,AzaGly7,Arg(Me)9]MS10
D-Ala-Asn-Trp-Asn-Ser-Phe-AzaGly-Leu-Arg(Me)-Phe-NH$_2$ Compound No. 260: des(1-3)-3-(3-Indolyl)propionyl-[AzaGly7,Arg(Me)9]MS10
(SEQ ID NO: 178)
3-(3-Indolyl)propionyl-Asn-Ser-Phe-AzaGly-Leu-Arg(Me)-Phe-NH$_2$ Compound No. 261: [7Ψ8, CH$_2$NH]MS10
(SEQ ID NO: 179)
Tyr-Asn-Trp-Asn-Ser-Phe-GlyΨ(CH$_2$NH)Leu-Arg-Phe-NH$_2$ Compound No. 265: des(1-3)-Indole-3-carbonyl-[AzaGly7,Arg(Me)9]MS10
(SEQ ID NO: 180)
Indole-3-carbonyl-Asn-Ser-Phe-AzaGly-Leu-Arg(Me)-Phe-NH$_2$ -continued

```
Compound No. 266: des(1-3)-Indole-3-acetyl-[AzaGly7,Arg(Me)9]MS10
                                                              (SEQ ID NO: 181)
Indol-3-acetyl-Asn-Ser-Phe-AzaGly-Leu-Arg(Me)-Phe-NH₂

Compound No. 267: des(1-3)-4-(3-Indolyl)butyryl-[AzaGly7,Arg(Me)9]MS10
                                                              (SEQ ID NO: 182)
4-(3-Indolyl)butyryl-Asn-Ser-Phe-AzaGly-Leu-Arg(Me)-Phe-NH₂

Compound No. 268: des(1-3)-Diphenylacetyl-[AzaGly7,Arg(Me)9]MS10
                                                              (SEQ ID NO: 183)
Diphenylacetyl-Asn-Ser-Phe-AzaGly-Leu-Arg(Me)-Phe-NH₂

Compound No. 269: des(1-3)-3-Phenylpropionyl-[AzaGly7,Arg(Me)9]MS10
                                                              (SEQ ID NO: 184)
3-Phenylpropionyl-Asn-Ser-Phe-AzaGly-Leu-Arg(Me)-Phe-NH₂

Compound No. 270: [D-Tyr1,Phe3,Ser-Phe5,AzaGly7,Arg(Me)9]MS10
D-Tyr-Asn-Phe-Asn-Ser-Phe-Phe-AzaGly-Leu-Arg(Me)-Phe-NH₂

Compound No. 271: des(1-2)-[AzaGly7,Arg(Me)9]MS10
                                                              (SEQ ID NO: 185)
Trp-Asn-Ser-Phe-AzaGly-Leu-Arg(Me)-Phe-NH₂

Compound No. 272: des(1-2)-Acetyl-[AzaGly7,Arg(Me)9]MS10
                                                              (SEQ ID NO: 186)
Acetyl-Trp-Asn-Ser-Phe-AzaGly-Leu-Arg(Me)-Phe-NH₂

Compound No. 273: des(1-2)-Amidino-[AzaGly7,Arg(Me)9]MS10
                                                              (SEQ ID NO: 187)
Amidino-Trp-Asn-Ser-Phe-AzaGly-Leu-Arg(Me)-Phe-NH₂

Compound No. 274: des(1-2)-Acetyl-[Ala3,AzaGly7,Arg(Me)9]MS10
                                                              (SEQ ID NO: 188)
Acetyl-Ala-Asn-Ser-Phe-AzaGly-Leu-Arg(Me)-Phe-NH₂

Compound No. 275: des(1-2)-Acetyl-[Arg3,AzaGly7,Arg(Me)9]MS10
                                                              (SEQ ID NO: 189)
Acetyl-Arg-Asn-Ser-Phe-AzaGly-Leu-Arg(Me)-Phe-NH₂

Compound No. 276: des(1-2)-Acetyl-[Thr3,AzaGly7,Arg(Me)9]MS10
                                                              (SEQ ID NO: 190)
Acetyl-Thr-Asn-Ser-Phe-AzaGly-Leu-Arg(Me)-Phe-NH₂

Compound No. 277: des(1-3)-n-Hexanoyl-[AzaGly7,Arg(Me)9]MS10
                                                              (SEQ ID NO: 191)
n-Hexanoyl-Asn-Ser-Phe-AzaGly-Leu-Arg(Me)-Phe-NH₂

Compound No. 278: des(1-3)-Cyclohexanecarbonyl-[AzaGly7, Arg(Me)9]MS10
                                                              (SEQ ID NO: 192)
Cyclohexanecarbonyl-Asn-Ser-Phe-AzaGly-Leu-Arg(Me)-Phe-NH₂

Compound No. 279:
                                                              (SEQ ID NO: 193)
des(1-3)-2-(Indol-3-yl)ethylcarbamoyl-[AzaGly7,Arg(Me)9]MS10
2-(indol-3-yl)ethylcarbamoyl-Asn-Ser-Phe-AzaGly-Leu-Arg(Me)-Phe-NH₂

Compound No. 281: [D-Tyr1,Pya(2)6,Arg(Me)9]MS10
D-Tyr-Asn-Trp-Asn-Ser-Pya(2)-Gly-Leu-Arg(Me)-Phe-NH₂

Compound No. 282: [D-Tyr1,Pya(4)6,Arg(Me)9]MS10
D-Tyr-Asn-Trp-Asn-Ser-Pya(4)-Gly-Leu-Arg(Me)-Phe-NH₂

Compound No. 283: [D-Tyr1,D-Asn2,Cha3,AzaGly7,Arg(Me)9]MS10
D-Tyr-D-Asn-Cha-Asn-Ser-Phe-AzaGly-Leu-Arg(Me)-Phe-NH₂

Compound No. 284: [D-Tyr1,D-Asn2,Thr3,AzaGly7,Arg(Me)9]MS10
D-Tyr-D-Asn-Thr-Asn-Ser-Phe-AzaGly-Leu-Arg(Me)-Phe-NH₂

Compound No. 285: [D-Tyr1,Pya(2) 3,AzaGly7,Arg(Me)9]MS10
D-Tyr-Asn-Pya(2)-Asn-Ser-Phe-AzaGly-Leu-Arg(Me)-Phe-NH₂

Compound No. 286: [D-Tyr1,Pya(4) 3,AzaGly7,Arg(Me)9]MS10
D-Tyr-Asn-Pya(4)-Asn-Ser-Phe-AzaGly-Leu-Arg(Me)-Phe-NH₂

Compound No. 287: [D-Tyr1,D-Ser2,AzaGly7,Arg(Me)9]MS10
D-Tyr-D-Ser-Trp-Asn-Ser-Phe-AzaGly-Leu-Arg(Me)-Phe-NH₂

Compound No. 288: [D-Tyr1,D-His2,AzaGly7,Arg(Me)9]MS10
D-Tyr-D-His-Trp-Asn-Ser-Phe-AzaGly-Leu-Arg(Me)-Phe-NH₂
```

-continued

Compound No. 289: des(1)-[D-Pya(3) 2,AzaGly7,Arg(Me)9]MS10
D-Pya(3)-Trp-Asn-Ser-Phe-AzaGly-Leu-Arg(Me)-Phe-NH$_2$ Compound No. 290: [D-Pya(3)1,D-Asn2,Cha3,AzaGly7,Arg(Me)9]MS10
D-Pya(3)-D-Asn-Cha-Asn-Ser-Phe-AzaGly-Leu-Arg(Me)-Phe-NH$_2$ Compound No. 291: [D-Pya(3)1,D-Tyr2,Cha3,AzaGly7,Arg(Me)9]MS10
D-Pya(3)-D-Tyr-Cha-Asn-Ser-Phe-AzaGly-Leu-Arg(Me)-Phe-NH$_2$ Compound No. 293: [4Ψ5, CH$_2$NH]MS10
(SEQ ID NO: 194)
Tyr-Asn-Trp-AsnΨ(CH$_2$NH)Ser-Phe-Gly-Leu-Arg-Phe-NH$_2$ Compound No. 294: [1Ψ2, CH$_2$NH]MS10
(SEQ ID NO: 195)
TyrΨ(CH$_2$NH)Asn-Trp-Asn-Ser-Phe-Gly-Leu-Arg-Phe-NH$_2$ Compound No. 295: [2Ψ3, CH$_2$NH]MS10
(SEQ ID NO: 196)
Tyr-AsnΨ(CH$_2$NH) Trp-Asn-Ser-Phe-Gly-Leu-Arg-Phe-NH$_2$ Compound No. 296: [6Ψ7, CSNH, D-Tyr1, Arg(Me)9]MS10
D-Tyr-Asn-Trp-Asn-Ser-PheΨ(CSNH)Gly-Leu-Arg(Me)-Phe-NH$_2$ Compound No. 297: [D-Tyr1, Thr5, AzaGly7, Arg(Me)9]MS10
D-Tyr-Asn-Trp-Asn-Thr-Phe-AzaGly-Leu-Arg(Me)-Phe-NH$_2$ Compound No. 298: [D-Tyr1, D-Asn2, Thr5, AzaGly7, Arg(Me)9]MS10
D-Tyr-D-Asn-Trp-Asn-Thr-Phe-AzaGly-Leu-Arg(Me)-Phe-NH$_2$ Compound No. 299: [1Ψ2, CH$_2$NH, AzaGly7, Arg(Me)9]-MS10
(SEQ ID NO: 197)
TyrΨ(CH$_2$NH)Asn-Trp-Asn-Ser-Phe-AzaGly-Leu-Arg(Me)-Phe-NH$_2$ Compound No. 300: [1Ψ2, CH$_2$NH, D-Trp3, AzaGly7, Arg(Me)9]-MS10
TyrΨ(CH$_2$NH)Asn-D-Trp-Asn-Ser-Phe-AzaGly-Leu-Arg(Me)-Phe-NH$_2$ Compound No. 301: [D-Tyr1,Ala(2-Qui) 3,AzaGly7,Arg(Me)9]MS10
D-Tyr-Asn-Ala(2-Qui)-Asn-Ser-Phe-AzaGly-Leu-Arg(Me)-Phe-NH$_2$ Compound No. 302: [D-Tyr1,D-Pya(4) 3,AzaGly7,Arg(Me)9]MS10
D-Tyr-Asn-D-Pya(4)-Asn-Ser-Phe-AzaGly-Leu-Arg(Me)-Phe-NH$_2$ Compound No. 303: [D-Tyr1,D-Asn2,Pya(4) 3,AzaGly7,Arg(Me)9]MS10
D-Tyr-D-Asn-Pya(4)-Asn-Ser-Phe-AzaGly-Leu-Arg(Me)-Phe-NH$_2$ Compound No. 304: [D-Asn2,Pya(4) 3,AzaGly7,Arg(Me)9]MS10
Tyr-D-Asn-Pya(4)-Asn-Ser-Phe-AzaGly-Leu-Arg(Me)-Phe-NH$_2$ Compound No. 305: des(1)-[D-Tyr2,D-Pya(4) 3,AzaGly7,Arg(Me)9]MS10
D-Tyr-D-Pya(4)-Asn-Ser-Phe-AzaGly-Leu-Arg(Me)-Phe-NH$_2$ Compound No. 306: [D-Pya(4)1,D-Asn2,Cha3,AzaGly7,Arg(Me)9]MS10
D-Pya(4)-D-Asn-Cha-Asn-Ser-Phe-AzaGly-Leu-Arg(Me)-Phe-NH$_2$ Compound No. 307: [7Ψ8,CH$_2$NH,D-Tyr1,Arg(Me)9]MS10
D-Tyr-Asn-Trp-Asn-Ser-Phe-GlyΨ(CH$_2$NH)Leu-Arg(Me)-Phe-NH$_2$ Compound No. 308: [6Ψ7, CH$_2$NH,D-Tyr1,Arg(Me)9]MS10
D-Tyr-Asn-Trp-Asn-Ser-PheΨ(CH$_2$NH)Gly-Leu-Arg(Me)-Phe-NH$_2$ Compound No. 310: [Nar9]MS10
(SEQ ID NO: 198)
Tyr-Asn-Trp-Asn-Ser-Phe-Gly-Leu-Nar-Phe-NH$_2$ Compound No. 311: [Nar(Me)9]MS10
(SEQ ID NO: 199)
Tyr-Asn-Trp-Asn-Ser-Phe-Gly-Leu-Nar(Me)-Phe-NH$_2$ Compound No. 312: [Har(Me)9]MS10
(SEQ ID NO: 200)
Tyr-Asn-Trp-Asn-Ser-Phe-Gly-Leu-Har(Me)-Phe-NH$_2$ Compound No. 313: [Dab9]MS10
(SEQ ID NO: 201)
Tyr-Asn-Trp-Asn-Ser-Phe-Gly-Leu-Dab-Phe-NH$_2$ Compound No. 314: [Orn9]MS10
(SEQ ID NO: 202)
Tyr-Asn-Trp-Asn-Ser-Phe-Gly-Leu-Orn-Phe-NH$_2$ -continued Compound No. 315: des(1)-[D-Asn2,Cha3,AzaGly7,Arg(Me)9]MS10
D-Asn-Cha-Asn-Ser-Phe-AzaGly-Leu-Arg(Me)-Phe-NH$_2$ Compound No. 316: [D-Tyr1,D-Asn2,Thr3,AzaGly7,Arg(Me)9,Phe(4F)10]MS10
D-Tyr-D-Asn-Thr-Asn-Ser-Phe-AzaGly-Leu-Arg(Me)-Phe(4F)-NH$_2$ Compound No. 317: [D-Tyr1,D-Asn2,Pya(4) 3,AzaGly7,Arg(Me)9,Phe(4F)10]MS10
D-Tyr-D-Asn-Pya(4)-Asn-Ser-Phe-AzaGly-Leu-Arg(Me)-Phe(4F)-NH$_2$ Compound No. 318: [D-Tyr1,AzaGly7,Arg(Me)9,Phe(4F)10]MS10
D-Tyr-Asn-Trp-Asn-Ser-Phe-AzaGly-Leu-Arg(Me)-Phe(4F)-NH$_2$ Compound No. 319: [6Ψ7,NHCO,D-Tyr1,Arg(Me)9]MS10
D-Tyr-Asn-Trp-Asn-Ser-PheΨ(NHCO)Gly-Leu-Arg(Me)-Phe-NH$_2$ Compound No. 322: des(1-3)-3-Pyridylpropionyl-[AzaGly7,Arg(Me)9]MS10
(SEQ ID NO: 203)
3-Pyridylpropionyl-Asn-Ser-Phe-AzaGly-Leu-Arg(Me)-Phe-NH$_2$ Compound No. 323: des(1-3)-4-Imidazoleacetyl-[AzaGly7,Arg(Me)9]MS10
(SEQ ID NO: 204)
4-Imidazoleacetyl-Asn-Ser-Phe-AzaGly-Leu-Arg(Me)-Phe-NH$_2$ Compound No. 324: des(1-3)-4-Piperidinecarbonyl-[AzaGly7,Arg(Me)9]MS10
(SEQ ID NO: 205)
Piperidinecarbonyl-Asn-Ser-Phe-AzaGly-Leu-Arg(Me)-Phe-NH$_2$ Compound No. 325: des(1-3)-1-Piperidineacetyl-[AzaGly7,Arg(Me)9]MS10
(SEQ ID NO: 206)
Piperidineacetyl-Asn-Ser-Phe-AzaGly-Leu-Arg(Me)-Phe-NH$_2$ Compound No. 326: des(1-3)-1-Methylpiperidinio-1-acetyl-[AzaGly7,Arg(Me)9]
MS10
(SEQ ID NO: 207)
Methylpiperidino-1-acetyl-Asn-Ser-Phe-AzaGly-Leu-Arg(Me)-Phe-NH$_2$ Compound No. 327: des(1-3)-1-Pyridinioacetyl-[AzaGly7,Arg(Me)9]MS10
(SEQ ID NO: 208)
1-Pyridinoacetyl-Asn-Ser-Phe-AzaGly-Leu-Arg(Me)-Phe-NH$_2$ Compound No. 328: des(1-3)-D-Glucuronyl-[AzaGly7,Arg(Me)9]MS10
(SEQ ID NO: 209)
D-Glucuronyl-Asn-Ser-Phe-AzaGly-Leu-Arg(Me)-Phe-NH$_2$ Compound No. 375: 2-Aminoethyl-Gly-[D-Tyr1,Arg(Me)9]MS10
2-Aminoethyl-Gly-D-Tyr-Asn-Trp-Asn-Ser-Phe-Gly-Leu-Arg(Me)-Phe-NH$_2$ Compound No. 385: des(1)-[D-Tyr2,D-Pya(4) 3,AzaGly7,Arg(Me)9,Trp10]MS10
D-Tyr-D-Pya(4)-Asn-Ser-Phe-AzaGly-Leu-Arg(Me)-Trp-NH$_2$ Compound No. 386: des(1-3)-3-Pyridylpropionyl-[AzaGly7,Arg(Me)9,Trp10]MS10
(SEQ ID NO: 210)
3-Pyridylpropionyl-Asn-Ser-Phe-AzaGly-Leu-Arg(Me)-Trp-NH$_2$ Compound No. 387: Dap-[D-Tyr1,Arg(Me)9]MS10
Dap-D-Tyr-Asn-Trp-Asn-Ser-Phe-Gly-Leu-Arg(Me)-Phe-NH$_2$ Compound No. 397: Methylthiocarbamoyl-Sar-[D-Tyr1,Arg(Me)9]MS10
Methylthiocarbamoyl-Sar-D-Tyr-Asn-Trp-Asn-Ser-Phe-Gly-Leu-Arg(Me)-Phe-NH$_2$ Compound No. 400:
(S)-1-(Quinolin-8-yl-carbamoyl)-4-thiapentylcarbamoyl-[D-Tyr1,Arg(Me)9]MS10
(S)-1-(Quinolin-8-yl-carbamoyl)-4-thiapentylcarbamoyl-D-Tyr-Asn-Trp-Asn-Ser-Phe-
Gly-Leu-Arg(Me)-Phe-NH$_2$ However, the metastin derivatives (I) of the present invention exclude the peptide consisting of the amino acid sequence of 1-54 (Compound No. 1), 2-54, 3-54, 4-54, 5-54, 6-54, 7-54, 8-54, 9-54, 10-54, 11-54, 12-54, 13-54, 14-54, 15-54, 16-54, 17-54, 18-54, 19-54, 20-54, 21-54, 22-54, 23-54, 24-54, 25-54, 26-54, 27-54, 28-54, 29-54, 30-54, 31-54, 32-54, 33-54, 34-54, 35-54, 36-54, 37-54, 38-54, 39-54, 40-54 (Compound No. 2), 41-54, 42-54 (Compound No. 32), 43-54, 44-54, 45-54 (Compound No. 3), 46-54 (Compound No. 4), 47-54, 48-54 or 49-54 in the amino acid sequence represented by SEQ ID NO: 1 (native human metastin or its partial peptides).

The ordinate denotes a relative activity when the chemotactic activity in the presence of FBS is made 100%.

Figure 2:
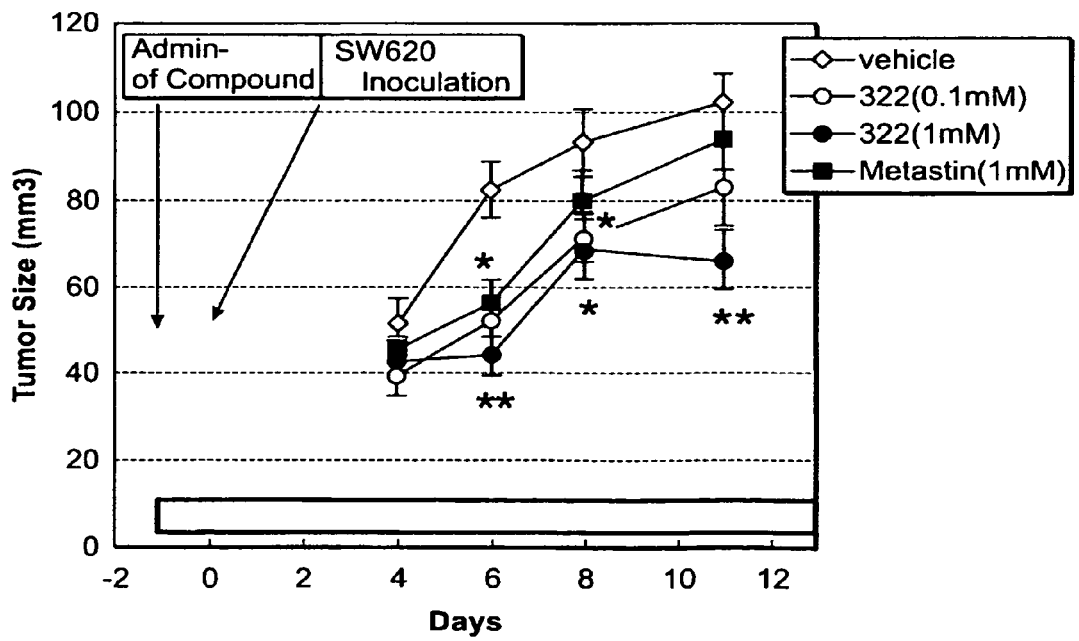

FIG. 2 shows evaluation of the tumor growth inhibition activity of Compound No. 322 and Metastin (1-54) using tumor-bearing mice with human colon cancer-derived cell line SW620, wherein the value indicates (mean)±(standard error). The symbols, open diamond, open circle, closed circle and closed square designate the results obtained when Vehicle (distilled water), Compound No. 322 (0.1 mM), Compound No. 322 (1 mM), and Metastin (Metastin 1-54) were added, respectively. The abscissa denotes the number of days after injection. The bar on the abscissa designates a dosing period. The ordinate denotes a tumor size ($mm^3$).

Figure 3:
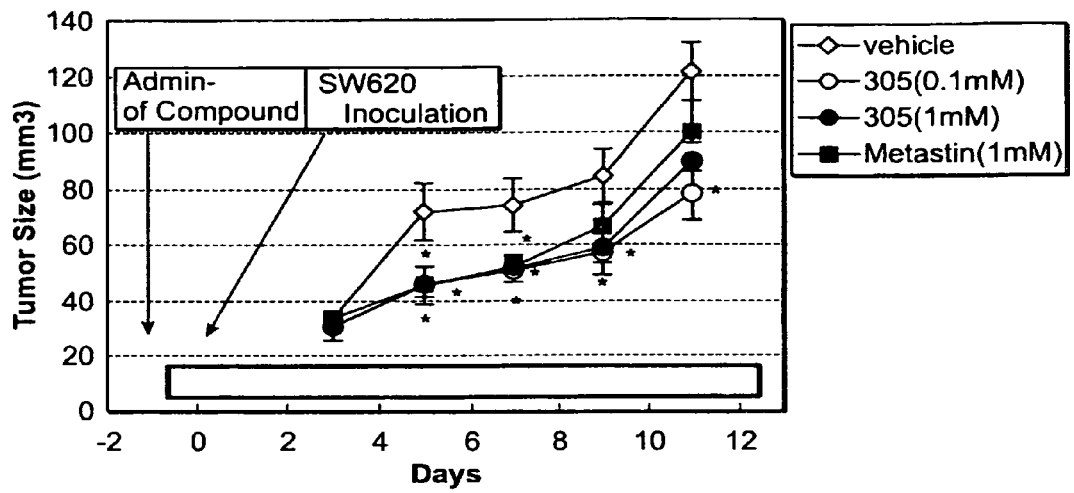

FIG. 3 shows evaluation of the tumor growth inhibition activity of Compound No. 305 and Metastin (1-54) using tumor-bearing mice with human colon tumor-derived cell line SW620, wherein the value indicates (mean)±(standard error). The symbols, open diamond, open circle, closed circle and closed square designate the results obtained when Vehicle (distilled water), Compound No. 305 (0.1 mM), Compound No. 305 (1 mM), and Metastin (Metastin 1-54) were added, respectively. The abscissa denotes the number of days after injection. The bar on the abscissa designates a dosing period. The ordinate denotes a tumor size ($mm^3$).

Figure 4:
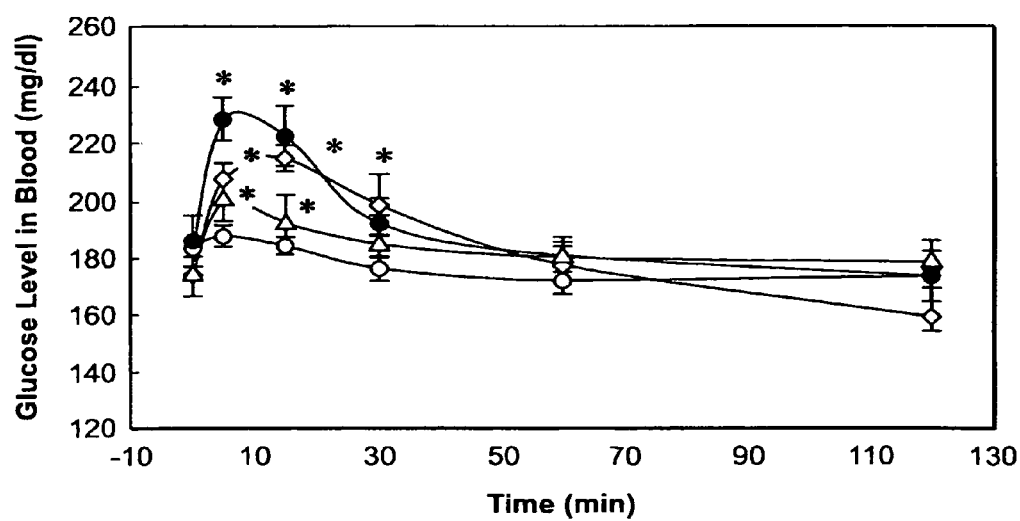

FIG. 4 shows the results obtained by monitoring changes in blood glucose level when metastin was intravenously injected into rats under no anesthesia. In the figure, the symbols, open circle, closed triangle, closed circle and closed diamond designate the blood glucose level in the saline group, the group receiving 17 nmol/kg metastin, the group receiving 80 nmol/kg metastin and the group receiving 170 nmol/kg metastin, respectively. The value indicates (mean±SE) (n=5). The symbol * designates that the P-value is 0.05 or less, when compared to the saline group and the symbol ** designates that the P-value is 0.01 or less, when compared to the saline group.

Figure 5:
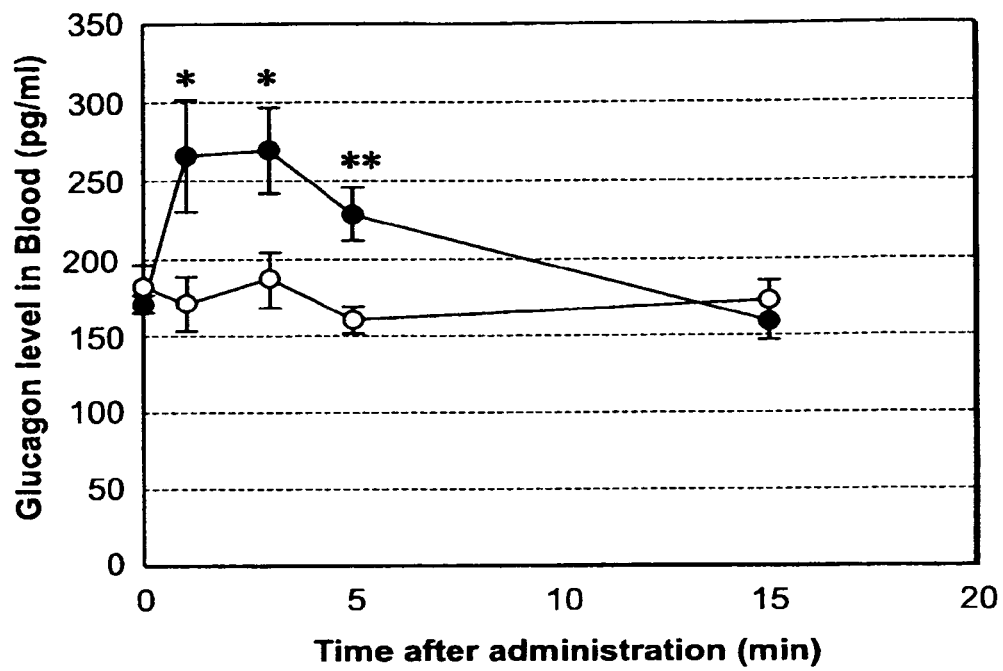

FIG. 5 shows the results obtained by monitoring changes in the blood glucagon level when metastin was intravenously injected into rats under no anesthesia. In the figure, the symbols, open circle and closed circle designate the blood glucagon level in the saline group and the group receiving 80 nmol/kg metastin, respectively. The value indicates (mean±SE) (n=6-9). The symbol * designates that the P-value is 0.05 or less, when compared to the saline group and the symbol ** designates that the P-value is 0.01 or less, when compared to the saline group.

Figure 6:
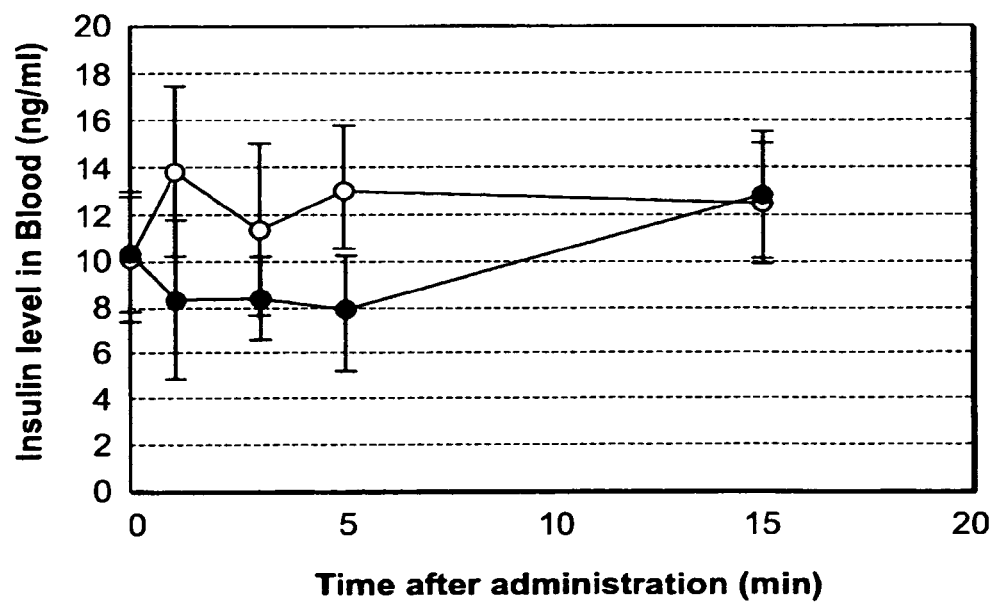

FIG. 6 shows the results obtained by monitoring changes in the blood insulin level when metastin was intravenously injected into rats under no anesthesia. In the figure, the symbols, open circle and closed circle designate the blood insulin level in the saline group and the group receiving 80 nmol/kg metastin, respectively. The value indicates (mean±SE) (n=6-9).

Figure 7:
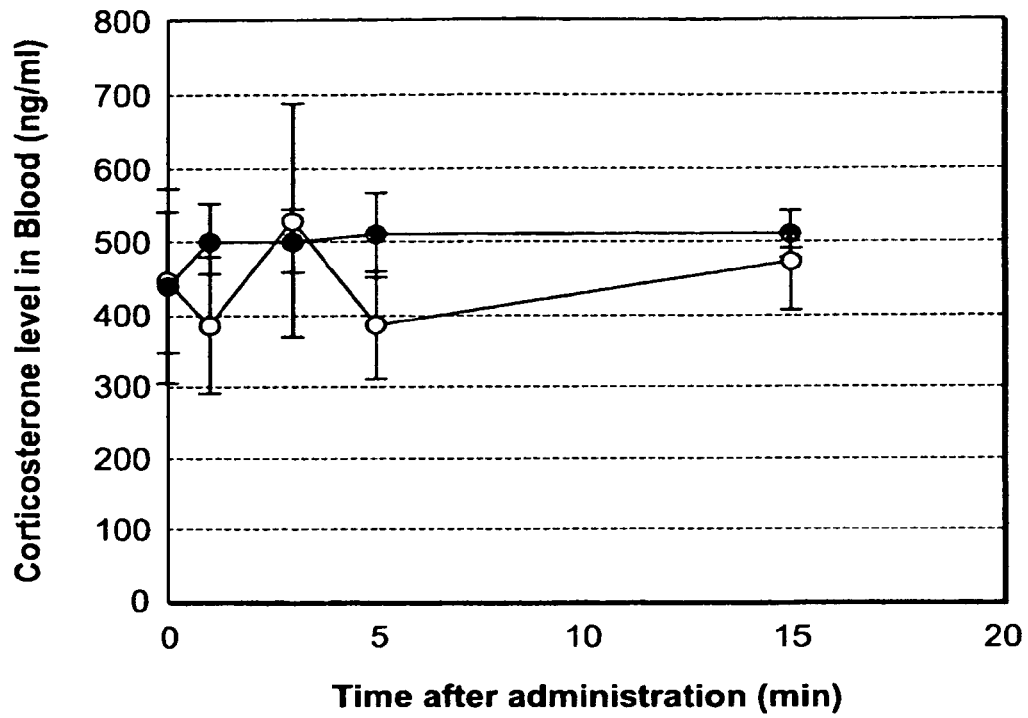

FIG. 7 shows the results obtained by monitoring changes in the blood corticosterone level when metastin was intravenously injected into rats under no anesthesia. In the figure, the symbols, open circle and closed circle designate the blood corticosterone level in the saline group and the group receiving 80 nmol/kg metastin, respectively. The value indicates (mean±SE) (n=4-5).

Figure 8:
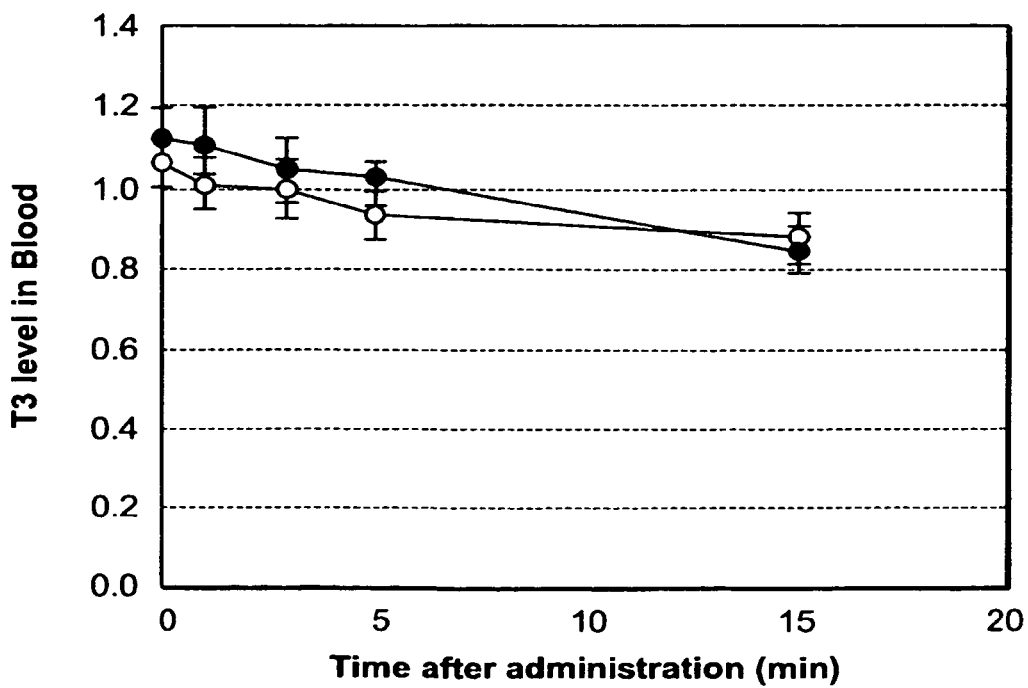

FIG. 8 shows the results obtained by monitoring changes in the thyroid hormone (T3) level in blood when metastin was intravenously injected into rats under no anesthesia. In the figure, the symbols, open circle and closed circle designate the thyroid hormone (T3) level in blood in the saline group and the group receiving 80 nmol/kg metastin, respectively. The value indicates (mean±SE) (n=4-5).

Figure 9:
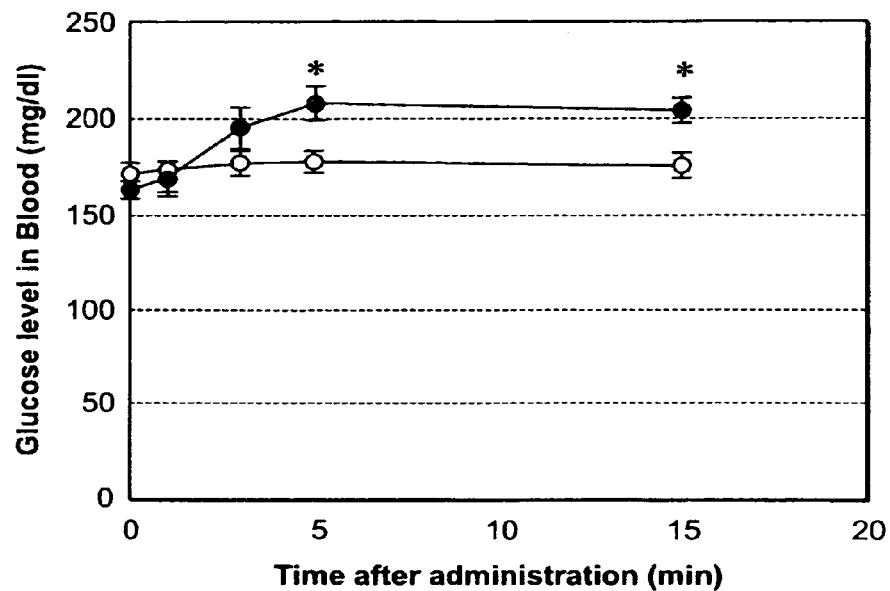
Figure 10:
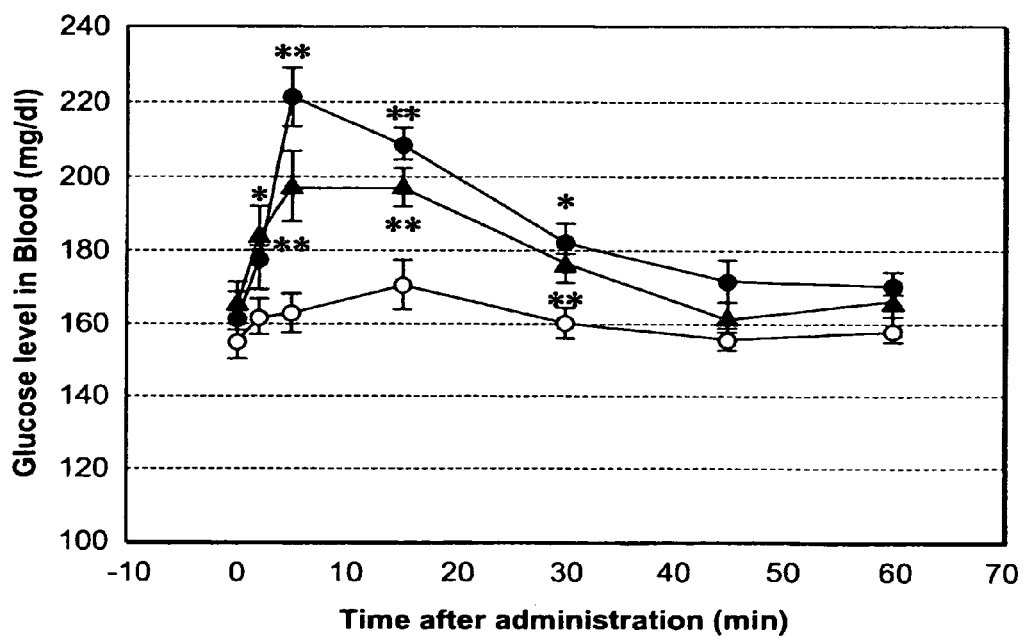

FIG. 9 shows the results obtained by monitoring changes in the blood glucose level when metastin was intravenously injected into rats under no anesthesia. In the figure, the symbols, open circle and closed circle designate the blood glucose level in the saline group and the group receiving 80 nmol/kg metastin, respectively. The value indicates (mean±SE) (n=6-9). The symbol * designates that the P-value is 0.05 or less, when compared to the saline group FIG. 10 shows the results obtained by monitoring changes in the blood glucose level when a metastin derivative was intravenously injected into rats under no anesthesia. In the figure, the symbols, open circle, closed circle and closed triangle designate the blood glucose level in the saline group, the group receiving 80 nmol/kg KiSS1-305 and the group receiving 80 nmol/kg metastin, respectively. The value indicates (mean±SE) (n=5). The symbol * designates that the P-value is 0.05 or less, when compared to the saline group and the symbol ** designates that the P-value is 0.01 or less, when compared to the saline group.

Figure 11:
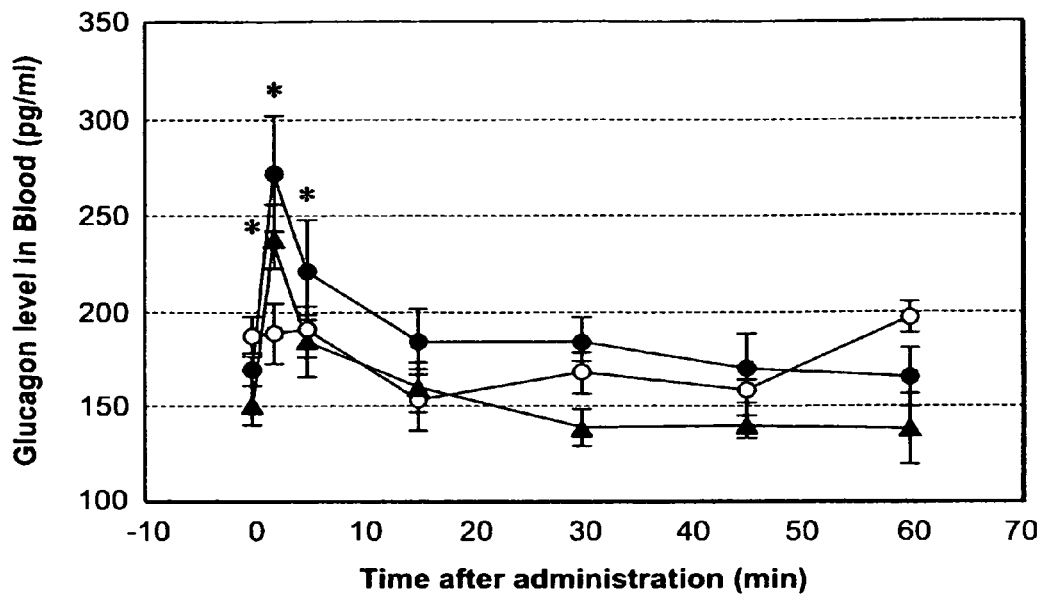

FIG. 11 shows the results obtained by monitoring changes in the blood glucagon level when metastin was intravenously injected into rats under no anesthesia. In the figure, the symbols, open circle, closed circle and closed triangledesignate the blood glucagon level in the saline group and the group receiving 80 nmol/kg KiSS1-305 (Compound No. 305), the group receiving 80 nmol/kg KiSS1-322 (Compound No. 322), respectively. The value indicates (mean±SE) (n=5). The symbol * designates that the P-value is 0.05 or less, when compared to the saline group.

Figure 12:
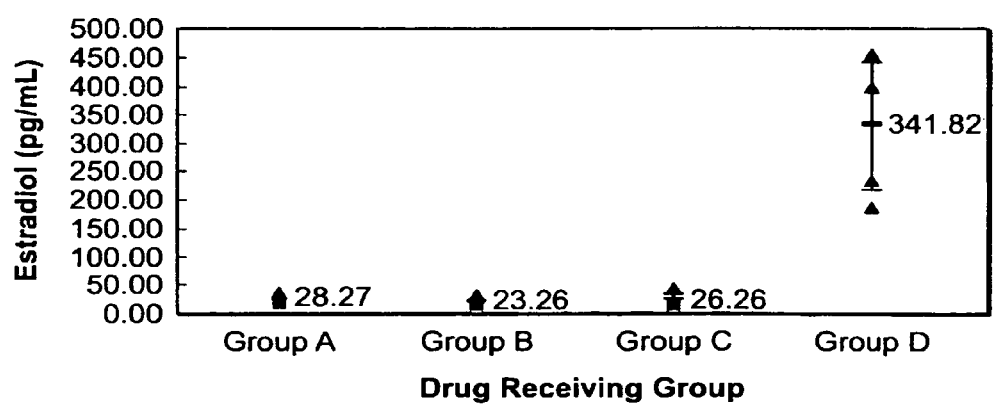

FIG. 12 shows the level of estradiol contained in the rat plasma. In the figure, the ordinate and the abscissa denote the estradiol level and the dosing groups, respectively.

Figure 13:
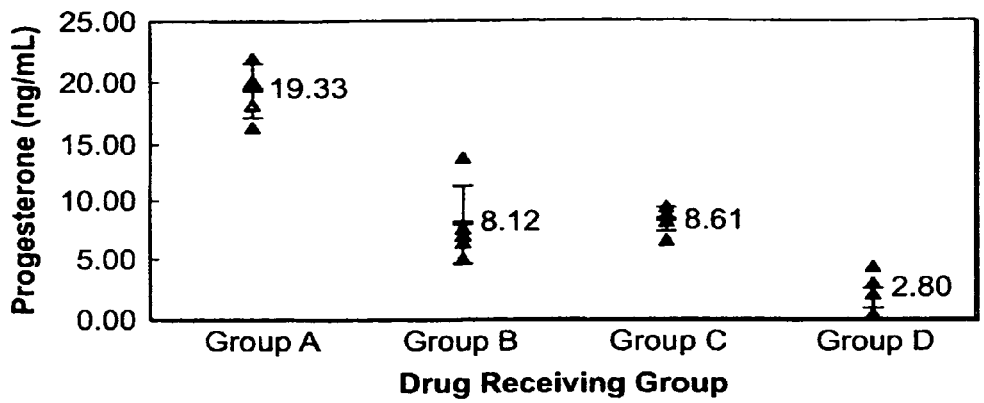

FIG. 13 shows the level of progesterone contained in the rat plasma. In the figure, the ordinate and the abscissa denote the estradiol level and the dosing groups, respectively.

Figure 14:
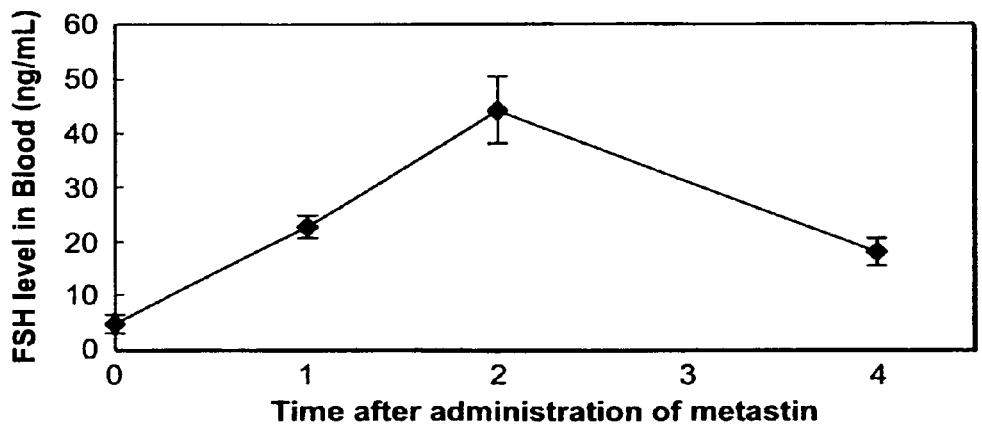

FIG. 14 shows changes in the blood level of FSH in immature rat by metastin injection.

Figure 15:
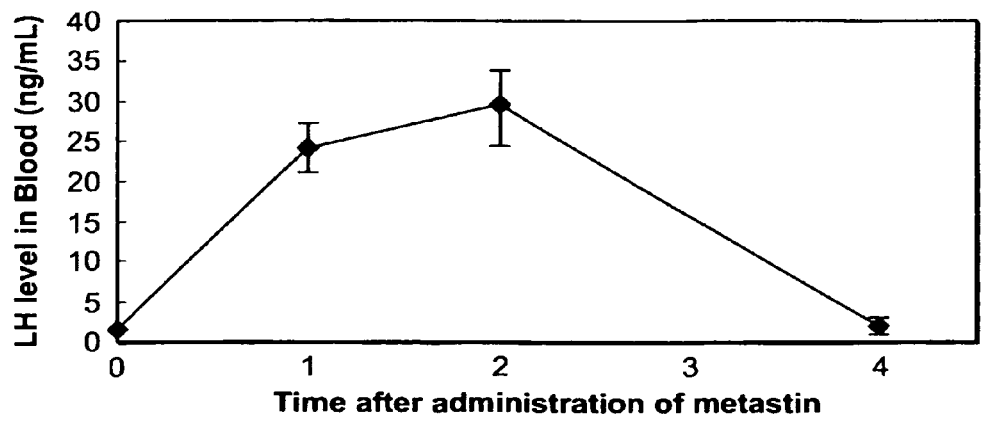

FIG. 15 shows changes in the blood level of LH in immature rat by metastin injection.

Figure 16:
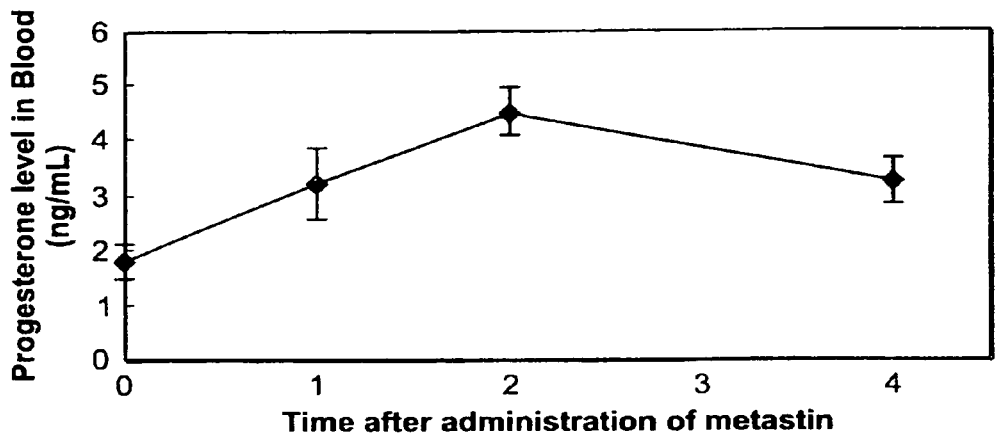

FIG. 16 shows changes in the blood level of progesterone in immature rat by metastin injection.

Figure 17:
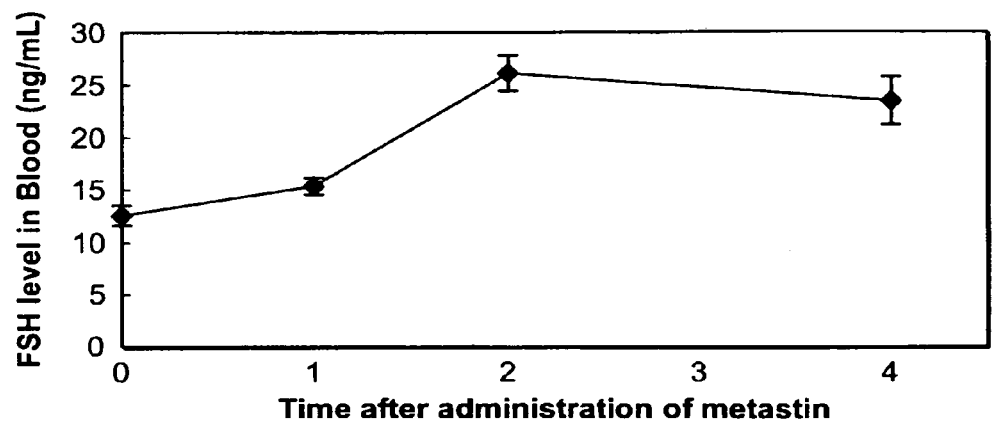

FIG. 17 shows changes in the blood level of FSH in rat by metastin injection.

Figure 18:
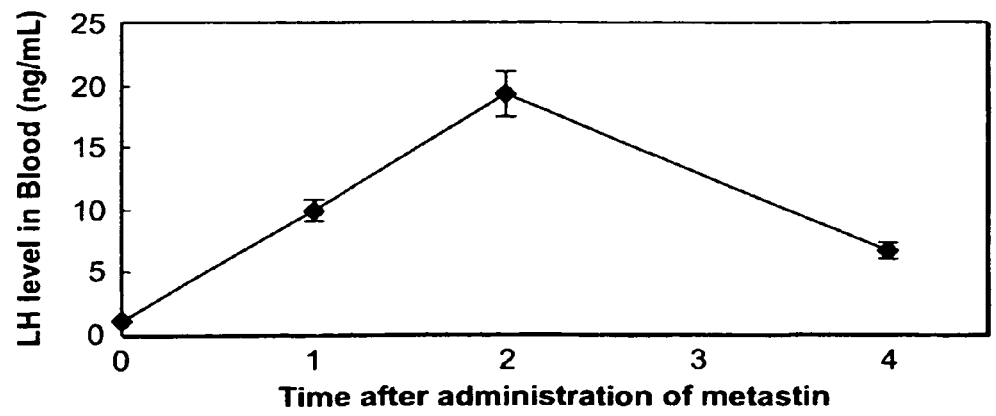

FIG. 18 shows changes in the blood level of LH in rat by metastin injection.

Figure 19:
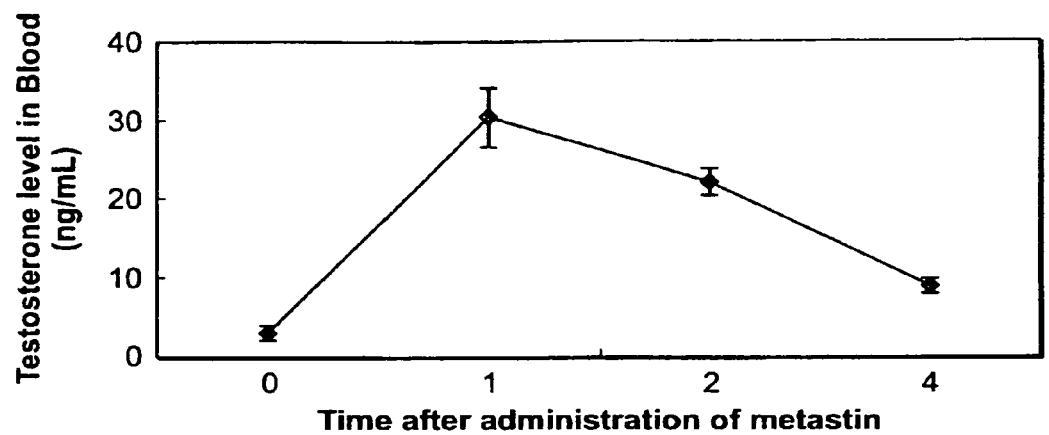

FIG. 19 shows changes in the blood level of testosterone in rat by metastin injection.

Figure 20:
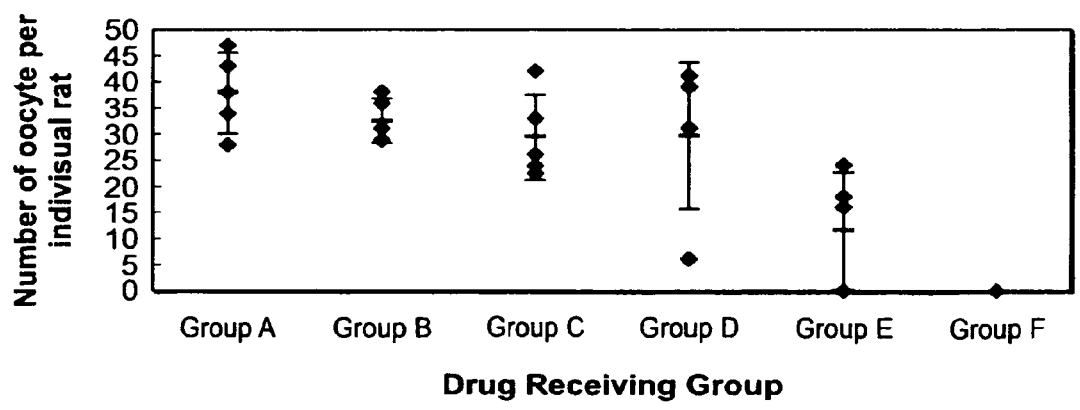

FIG. 20 shows the number of oocytes per rat in each dosing group measured in TEST EXAMPLE 13. In the figure, the symbol, closed diamond designates the data for each rat and the symbol - (solid bar) designates the mean value in each group.

Figure 21:
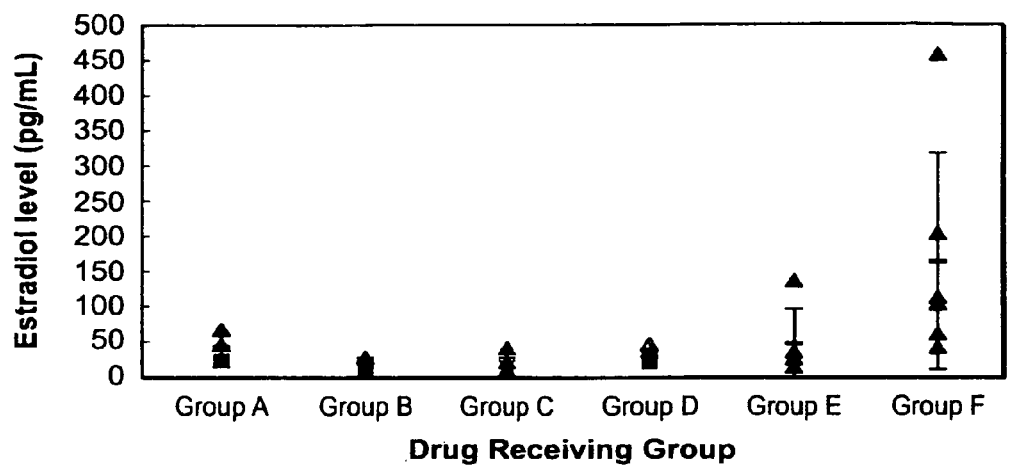

FIG. 21 shows the blood levels of estradiol in the dosing groups measured in TEST EXAMPLE 13. In the figure, the symbol, closed triangle designates the data for each rat and the symbol - (solid bar) designates the mean value in each group.

Figure 22:
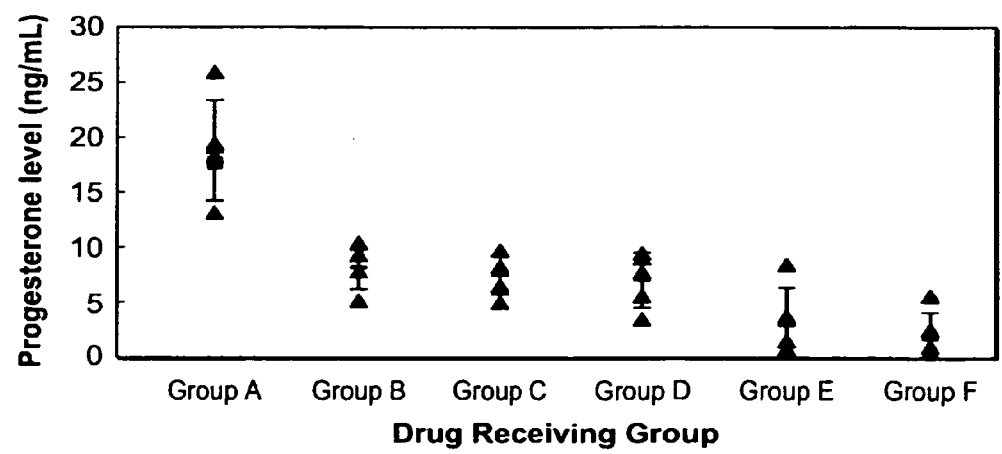

FIG. 22 shows the blood levels of progesterone in the dosing groups measured in TEST EXAMPLE 13. In the figure, the symbol, closed triangle designates the data for each rat and the symbol - (solid bar) designates the mean value in each group.

SEQUENCE LISTING FREE TEXT

SEQ ID NO: 15 The C-terminal amino acid residue is amidated.

SEQ ID NO: 16 The C-terminal amino acid residue is amidated.

SEQ ID NO: 17 The C-terminal amino acid residue is amidated.

SEQ ID NO: 18 The C-terminal amino acid residue is amidated.

BEST MODE FOR CARRYING OUT THE INVENTION

The metastin derivatives (I) of the present invention can be prepared by publicly known methods for peptide synthesis. As the methods for peptide synthesis, for example, either solid phase synthesis or liquid phase synthesis may be used. That is, the partial peptide or amino acids that can constitute the peptide of the present invention are condensed with the remaining part to give the product having a desired sequence. Where the product has protecting groups, these protecting groups are removed to give the desired peptide. Publicly known methods for condensation and removal of the protecting groups are described in (1) to (5) below.

(1) M. Bodanszky & M. A. Ondetti: Peptide Synthesis, Interscience Publishers, New York (1966)
(2) Schroeder & Luebke: The Peptide, Academic Press, New York (1965)
(3) Nobuo Izumiya, et al.: *Peptide Gosei-no-Kiso to Jikken* (Basics and experiments of peptide synthesis), published by Maruzen Co. (1975)
(4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)
(5) Haruaki Yajima, ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the peptide of the present invention. When the peptide obtained by the above methods is in a free form, the peptide can be converted into an appropriate salt by a publicly known method; when the protein is obtained in a salt form, it can be converted into its free form by publicly known methods.

For condensation of the protected amino acids or peptides, a variety of activation reagents for peptide synthesis may be used, but trisphosphonium salts, tetramethyluronium salts, carbodiimides, etc. are particularly preferred. Examples of trisphosphonium salts include benzotriazol-1-yloxytris(pyrrolidino)phosphonium hexafluorophosphate (PyBOP), bromotris(pyrrolidino) phosphonium hexafluorophosphate (PyBroP) and 7-azabenzotriazol-1-yloxytris(pyrrolidino)-phosphonium hexafluorophosphate (PyAOP), examples of tetramethyluronium salts include 2-(1H-benzotriazol-1-yl)-1,1,3,3-hexafluorophosphate (HBTU), 2-(7-azabenzotriazol-1-yl)-1,1,3,3-hexafluorophosphate (HATU), 2-(1H-benzotriazol-1-yl)-1,1,3,3-tetramethyluronium tetrafluoroborate (TBTU), 2-(5-norbornene-2,3-dicarboxyimido)-1,1,3,3-tetramethyluronium tetrafluoroborate (TNTU) and O—(N-succimidyl)-1,1,3,3-tetramethyluronium tetrafluoroborate (TSTU); examples of carbodiimides include DCC, N,N'-diisopropylcarbodiimide (DIPCDI) and N-ethyl-N'-(3-dimethylaminopropyl) carbodiimide hydrochloride (EDCI.HCl); etc. For condensation using these reagents, the addition of racemization inhibitors (e.g., HONB, HOBt, HOAt, HOOBt, etc.) is preferred. Solvents used in condensation may be appropriately chosen from solvents that are known to be usable for condensation. For example, acid amides such as anhydrous or hydrous N,N-dimethylformamide, N,N-dimethylacetamide, N-methylpyrrolidone, etc., halogenated hydrocarbons such as methylene chloride, chloroform, etc., alcohols such as trifluoroethanol, phenol, etc., sulfoxides such as dimethyl sulfoxide, etc., tertiary amines such as pyridine, etc., ethers such as dioxan, tetrahydrofuran, etc., nitriles such as acetonitrile, propionitrile, etc., esters such as methyl acetate, ethyl acetate, etc., or suitable mixtures thereof, etc. are used. The reaction temperature is appropriately chosen from the range known to be applicable to peptide binding reactions and is normally suitably chosen from the range of about $-20°$ C. to $50°$ C. The activated amino acid derivatives are used generally in 1.5 to 6 times excess. In the case of solid phase synthesis, the condensation is examined using the ninhydrin reaction; when the condensation is insufficient, the condensation can be completed by repeating the condensation reaction without removal of the protecting groups. When the condensation is yet insufficient even after repeating the reaction, the unreacted amino acids are acylated with acetic anhydride or acetylimidazole to cancel any adverse effect on the subsequent reaction.

Examples of the protecting groups used to protect amino groups in the starting amino acids include Z, Boc, tert-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulphenyl, diphenylphosphinothioyl, Fmoc, etc. Examples of protecting groups for a carboxyl group include, in addition to the $C_{1-6}$ alkyl group, $C_{3-8}$ cycloalkyl group and $C_{7-14}$ aralkyl group for R described above, allyl, 2-adamantyl, 4-nitrobenzyl, 4-methoxybenzyl, 4-chlorobenzyl, phenacyl group, benzyloxycarbonylhydrazide, tert-butoxycarbonylhydrazide, tritylhydrazide, etc.

The hydroxyl group of serine and threonine can be protected, for example, by esterification or etherification. Examples of groups suitable for this esterification include a lower $(C_{2-4})$ alkanoyl group such as acetyl group, an aroyl group such as benzoyl group, etc. and a group derived from organic acid. Examples of a group suitable for the etherification include benzyl group, tetrahydropyranyl group, tert-butyl group, trytyl group (Trt), etc.

Examples of groups for protecting the phenolic hydroxyl group of tyrosine include Bzl, 2,6-dichlorobenzyl, 2-nitrobenzyl, Br—Z, tert-butyl, etc.

Examples of groups used to protect the imidazole moiety of histidine include Tos, 4-methoxy-2,3,6-trimethylbenzenesulfonyl (Mtr), DNP, Bom, Bum, Boc, Trt, Fmoc, etc.

Examples of the protecting groups for a guanidino group of arginine include Tos, Z, 4-methoxy-2,3,6-trimethylbenzenesulfonyl (Mtr), p-methoxybenzenesulfonyl (MBS), 2,2,5,7,8-pentamethylchroman-6-sulfonyl (Pmc), mesitylene-2-sulfonyl (Mts), 2,2,4,6,7-pentamethyldihydrobenzofuran-5-sulfonyl (Pbf), Boc, Z, $NO_2$, etc.

Examples of the protecting groups for side chain amino group of lysine include Z, Cl-Z, trifluoroacetyl, Boc, Fmoc, Trt, Mtr, 4,4-dimethyl-2,6-dioxocyclo-hexylideneyl (Dde), etc.

Examples of protecting groups for indolyl of tryptophan include formyl (For), Z, Boc, Mts, Mtr, etc.

The protecting groups for asparagine and glutamine include Trt, xanthyl (Xan), 4,4'-dimethoxybenzhydryl (Mbh), 2,4,6-trimethoxybenzyl (Tmob), etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, 1-hydroxybenzotriazole (HOBt) or 1-hydroxy-7-azabenzotriazole (HOAt)], etc. As the amino acids in which the amino groups in the starting material are activated, the corresponding phosphorous amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, trimethylsilane bromide (TMSBr), trimethylsilyl trifluoromethanesulfonate, tetrafluoroboric acid, tris(trifluoro)boron, boron tribromide or a mixed solution thereof, a base treatment with diisopropylethylamine, triethylamine, piperidine, piperazine, etc., and reduction with sodium in liquid ammonia. The elimination of protecting groups by the acid treatment described above is carried out generally at a temperature of approximately −20° C. to 40° C. In the acid treatment, it is efficient to add a cation scavenger such as anisole, phenol, thioanisole, m-cresol, p-cresol, etc., dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is removed by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of the functional groups that should not be involved in the reaction of the starting materials, protecting groups, removal of the protecting groups and activation of functional groups involved in the reaction may be appropriately chosen from publicly known groups and publicly known means.

In a method for obtaining the amides of the peptide, for example, the amidated form is synthesized on the solid phase using the resin for amidation, or the α-carboxyl group of the carboxy terminal amino acid is first protected by amidation; the peptide chain is then extended from the amino group side to a desired length. Thereafter, a peptide in which only the protecting group of the N-terminal α-amino group in the peptide chain has been removed and a peptide (or an amino acid) in which only the protecting group of the C-terminal carboxyl group has been eliminated are prepared. The two peptides are condensed in a mixture of the solvents described above. The details of the condensation reaction are the same as described above. After the protected peptide obtained by the condensation is purified, all the protecting groups are removed by the method described above to give the desired crude polypeptide. This crude peptide is purified by various known purification means. Lyophilization of the major fraction gives the amide of the desired peptide.

When the metastin derivatives (I) of the present invention are present as a configurational isomer, a diastereomer, a conformer or the like, each can be isolated by the separating and purifying means described above, if desired. In addition, when the compound of the present invention is racemic, it can be separated into an S isomer and an R isomer by the conventional optical resolving means.

When the metastin derivatives (I) of the present invention have steric isomers, the present invention includes both of these isomers alone and the isomers present as a mixture thereof.

In addition, the metastin derivatives (I) of the present invention may be hydrated or non-hydrated.

The metastin derivatives (I) of the present invention may be labeled with an isotope (e.g., $^{3}H$, $^{14}C$, $^{35}S$), etc.

Throughout the present specification, the peptides are represented in accordance with the conventional way of describing peptides, that is, the N-terminus (amino terminus) at the left hand and the C-terminus (carboxyl terminus) at the right hand. In the peptides, the C-terminus is usually in the form of an amide (—$CONH_2$), a carboxyl group (—COOH), a carboxylate (—$COO^-$), an alkylamide (—CONHR) or an ester (—COOR) and the amide (—$CONH_2$) is particularly preferred. Examples of the ester or alkylamide as R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl group such as a phenyl-$C_{1-2}$-alkyl group, e.g., benzyl, phenethyl, etc., or an α-naphthyl-$C_{1-2}$-alkyl group such as α-naphthylmethyl, etc.; pivaloyloxymethyl group, which are widely used as an ester for oral use, and the like.

Examples of a salt of the metastin derivative (I) of the present invention include a metal salt, a salt with ammonium, a salt with an organic base, a salt with inorganic acid, a salt with organic acid, a salt with basic or acidic amino acid, and the like. Preferred examples of the metal salt include alkali metal salts such as sodium salts, potassium salts, etc.; alkaline earth metal salts such as calcium salts, magnesium salts, barium salts, etc.; aluminum salts; and the like. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of salts with basic amino acids include salts with arginine, lysine, ornithine, etc., and preferred examples of salts with acidic amino acids include salts with aspartic, glutamic acid, etc.

Among them, pharmaceutically acceptable salts are preferable. For example, when the compound has an acidic functional group, inorganic salts such as alkali metal salts (e.g., sodium salt, potassium salt, etc.), alkaline earth metal salts (e.g., calcium salt, magnesium salt, barium salt, etc.), ammonium salts, etc. are preferable. When the compound has a basic functional group, salts with inorganic acids with hydrochloric acid, hydrobromic acid, nitric acid, sulfuric acid, phosphoric acid, etc., and salts with organic acids such as acetic acid, phthalic acid, fumaric acid, oxalic acid, tartaric acid, maleic acid, citric acid, succinic acid, methanesulfonic acid, p-toluenesulfonic acid, etc. are preferable.

A prodrug of the metastin derivative (I) or a salt thereof (hereinafter sometimes briefly referred to as the metastin derivative (I) of the present invention) means a metastin derivative that is converted into the metastin derivative (I) of the present invention under physiological conditions or with a reaction due to an enzyme, a gastric acid, etc., in the living body. That is, the prodrug of the present invention is a metastin derivative that undergoes enzymatic oxidation, reduction, hydrolysis, etc. to be converted into the metastin derivative (I) of the present invention, or a metastin derivative that undergoes hydrolysis, etc. by gastric acid, etc. to be converted into the metastin derivative (I) of the present invention.

Examples of the prodrugs of the metastin derivatives (I) of the present invention include metastin derivatives wherein an amino group of the metastin derivative (I) of the present invention is acylated, alkylated, phosphorylated, etc. (e.g., metastin derivatives wherein an amino group of the metastin derivative (I) of the present invention is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated, etc); metastin derivatives wherein a hydroxy group of the metastin derivative (I) of the present invention is acylated, alkylated, phosphorylated, borated, etc. (e.g., metastin derivatives wherein an hydroxy group of the metastin derivative (I) of the present invention is acetylated, palmitoylated, propanoylated, pivaloylated, succinylated, fumarylated, alanylated, dimethylaminomethylcarbonylated, etc.); and metastin derivatives wherein a carboxyl group of the metastin derivative (I) of the present invention is esterified, amidated, etc. (e.g., metastin derivatives wherein a carboxyl group of the metastin derivative (I) of the present invention is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, methylamidated, etc); and the like. These metastin derivatives can be produced from the metastin derivative (I) of the present invention by per se publicly known methods.

The prodrugs of the metastin derivative (I) of the present invention may be those that are converted into the metastin derivative (I) of the present invention under the physiological conditions as described in "Pharmaceutical Research and Development", Vol. 7 (Drug Design), pages 163-198, published 1990 by Hirokawa Publishing Co.

The metastin derivatives (I) of the present invention or their salts or prodrugs (hereinafter sometimes simply referred to as the compound of the present invention) possess a cancer metastasis suppressing activity or a cancer growth suppressing activity. Thus, the metastin derivatives are useful for pharmaceuticals such as agents for preventing or treating all cancers (e.g., lung cancer, gastric cancer, liver cancer, pancreatic cancer, colorectal cancer, rectal cancer, colonic cancer, prostate cancer, ovarian cancer, cervical cancer, breast cancer, etc.).

The compounds of the present invention also possess the effect of regulating a function of the pancreas and are thus useful as agents for treating/preventing various pancreatic diseases (e.g., acute or chronic pancreatitis, pancreatic cancer, etc.) as agents for regulating a function of the pancreas.

The compounds of the present invention also possess the effect of regulating a function of the placenta and are thus useful as pharmaceuticals for preventing or treating choriocarcinoma, hydatid mole, invasive mole, miscarriage, fetal hypoplasia, abnormal glucose metabolism, abnormal lipid metabolism or labor induction, as agents for regulating a function of the placenta.

Furthermore, since the compounds of the present invention possess the effects of increasing blood glucose level, promoting pancreatic glucagon secretion and promoting urine formation, the compounds are useful as pharmaceuticals such as hyperglycemic agents, pancreatic glucagon secretagogue agents or agents for promoting urine formation, which are useful for preventing or treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

In addition, the compounds of the present invention possess the effects of promoting gonadotropic hormone (e.g., FSH, LH, etc.) secretion, promoting sex hormone [e.g., androgens (e.g., testosterone, androstenedione, etc.), estrogens (e.g., estradiol, estrone, etc.), progesterones, etc.] secretion, improving gonadal function and inducing or stimulating ovulation, as well as a sexual maturation effect, etc. Therefore, the compounds can be used as agents for improving gonadal function, agents for inducing or stimulating ovulation, gonadotropic hormone secretagogue agents or sex hormone secretagogue agents, or agents for preventing/treating hormone-dependent cancers [e.g., prostate cancer, breast cancer, etc.], infertility [e.g., irregular menstruation, dysmenorrhea, amenorrhea, weight loss-induced amenorrhea, secondary amenorrhea, anovulation, hypoovarianism, hypogonadism, spermatogenetic failure, hypogonadism (e.g., impotence, etc.), genital atrophy, testicular atrophy, testicular function disorders, azoospermia, hypoandrogenemia, etc.], endometriosis, myoma of the uterus, etc.

Furthermore, the metastin derivative of the present invention or salts thereof or their prodrugs are useful as agents for preventing/treating Alzheimer's disease, mild cognitive impairment, etc.

Moreover, the compounds of the present invention have excellent blood stability, as compared to native metastin such as metastin 54 (1-54) or metastin 10 (45-54).

The pharmaceutical compositions comprising the compounds of the present invention are low toxic and hence, the compounds of the present invention can be safely administered orally or parenterally (e.g., topically, rectally, intravenously, etc.) either directly as they are or in the form of pharmaceutical preparations such as tablets (including dragees and film-coated tablets), powdery dosage forms, granules, capsules (including soft capsules), liquid dosage forms, injections, suppositories, sustained release dosage forms, etc.

The compound of the present invention is contained in the pharmaceutical preparation of the present invention in about 0.01 to about 100 wt %, based on the total weight of the preparation.

A dose of the compound of the present invention may vary depending upon subject to be administered, target organ, conditions, route of administration, etc., and in oral administration, the compound is generally administered to the patient with cancer (as 60 kg body weight) in a daily dose of about 0.1 to about 100 mg, preferably about 1.0 to about 50 mg and more preferably about 1.0 to about 20 mg. In parenteral administration, a single dose of the compound may vary depending upon subject to be administered, target organ, conditions, route of administration, etc., and in the form of injectable preparation, it is advantageous to administer the compound intravenously to the patient with cancer (as 60 kg body weight) generally in a daily dose of about 0.01 to about 30 mg, preferably about 0.1 to about 20 mg, and more preferably about 0.1 to about 10 mg. For other animal species, the corresponding dose as converted per 60 kg weight can be administered.

Pharmacologically acceptable carriers, which may be used in manufacturing the pharmaceutical preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary.

Examples of excipients include, e.g., lactose, saccharose, D-mannitol, starch, cornstarch, crystalline cellulose, light anhydrous silicic acid, etc.

Examples of lubricants include, e.g., magnesium stearate, calcium stearate, talc, colloidal silica, etc.

Examples of binders include, e.g., crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include, e.g., starch, carboxymethylcellulose, carboxymethylcellulose calcium, sodium carboxymethyl starch, L-hydroxypropylcellulose, etc.

Examples of solvents include, e.g., water for injection, alcohol, propylene glycol, Macrogol, sesame oil, corn oil, olive oil, etc.

Examples of dissolution aids include, e.g., polyethylene glycol, propylene glycol, D-mannitol, benzyl benzoate, ethanol, trisaminomethane, cholesterol, triethanolamine, sodium carbonate, sodium citrate, etc.

Examples of suspending agents include, e.g., surfactants such as stearyltriethanolamine, sodium laurylsulfate, lauryl aminopropionate, lecithin, benzalkonium chloride, benzethonium chloride, glycerine monostearate, etc.; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, etc.

Examples of isotonizing agents include, e.g., glucose, D-sorbitol, sodium chloride, glycerine, D-mannitol, etc.

Examples of buffers include, e.g., buffering solutions of a phosphate, acetate, carbonate, citrate, etc.

Examples of soothing agents include, e.g., benzyl alcohol, etc.

Examples of preservatives include, e.g., p-hydroxybenzoates, chlorobutanol, benzyl alcohol, phenethyl alcohol, dehydroacetic acid, sorbic acid, etc.

Examples of antioxidants include, e.g., a sulfite, ascorbic acid, α-tocopherol, etc.

Furthermore, the compound of the present invention can be used in combination with drugs other than the compound of the present invention.

Examples of the drugs, which can be used in combination with the compound of the present invention include agents for treating cancer such as chemotherapeutic agents, hormone therapeutic agents, immunotherapeutic agents, etc. (hereinafter referred to as a concomitant drug).

Examples of "chemotherapeutic agents" include, e.g., alkylating agents, antimetabolites, anticancer antibiotics, plant-derived anticancer agents, etc.

Examples of "alkylating agents" include, e.g., nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, rnelphalan, dacarbazine, ranimustine, estramustine sodium phosphate, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, carboquone, adozelesin, cystemustine, bizelesin, etc.

Examples of "antimetabolites" include, e.g., mercaptopurine, 6-mercaptopurine riboside, thioinosine, methotrexate, enocitabine, cytarabine, cytarabine ocfosfate, ancitabine hydrochloride, 5-FU drugs (e.g., fluorouracil, tegafur, UFT, doxifluridine, carmofur, gallocitabine, emmitefur, etc.), aminopterin, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, thiazophrine, ambamustine, etc.

Examples of "anticancer antibiotics" include, e.g., actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, etc.

Examples of "plant-derived anticancer agents" include, e.g., etoposide, etoposide phosphate, vinblastine sulfate, vincristine sulfate, vindesine sulfate, teniposide, paclitaxel, docetaxel, vinorelbine, etc.

Examples of "hormone therapeutic agents" include, e.g., fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogens (e.g., tamoxifen citrate, toremifene citrate, etc.), pill dosage forms, mepitiostane, testrolactone, aminoglutethimide, LH-RH agonists (e.g., goserelin acetate, buserelin, Leuprorelin, etc.), droloxifene, epitiostanol, ethinylestradiol sulfonate, aromatase inhibitors (e.g., fadrozole hydrochloride, anastrozole, retrozole, exemestane, vorozole, formestane, etc.), anti-androgens (e.g., flutamide, bicartamide, nilutamide, etc.), 5α-reductase inhibitors (e.g., finasteride, epristeride, etc.), adrenocorticohormone drugs (e.g., dexamethasone, prednisolone, betamethasone, triamcinolone, etc.), androgen synthesis inhibitors (e.g., abiraterone, etc.), retinoid and drugs that retard retinoid metabolism (e.g., liarozole, etc.), and among them, LH-RH agonists (e.g., goserelin acetate, buserelin, Leuprorelin, etc.) are preferable.

Examples of "immunotherapeutic agents (BRM)" include, e.g., picibanil, krestin, sizofuran, lentinan, ubenimex, interferons, interleukins, macrophage colony-stimulating factor, granulocyte colony-stimulating factor, erythropoietin, lymphotoxin, BCG vaccine, Corynebacterium parvum, levamisole, polysaccharide K, procodazole, etc.

The combined use of the compound of the present invention and a concomitant drug results in, for example, the following excellent effects.

(1) The dose of the compound of the present invention can be reduced when compared with the dose when administered alone.

(2) A concomitant drug with the compound of the present invention can be chosen depending on the condition (mild, severe, etc.) of a patient.

(3) A concomitant drug, whose functional mechanism is different from that of the compound of the present invention, can be chosen so that a treatment period can be set longer.

(4) A concomitant drug, whose functional mechanism is different from that of the compound of the present invention, can be chosen so that sustained therapeutic effects can be achieved.

(5) A synergistic effect can be obtained by the combined use of the compound of the present invention and a concomitant drug.

Hereinafter, the combined use of the compound (I) of the present invention and a concomitant drug is referred to as "the combined preparation of the present invention."

When the combined preparation of the present invention is used, a dosing period of the compound of the present invention and the combination is not restricted; the compound of the present invention or its pharmaceutical composition and a concomitant drug or its pharmaceutical composition may be administered to the subject to be administered either simultaneously or at certain time intervals. The dose of a concomitant drug may be modified according to the dose used clinically and may be appropriately chosen depending upon subject to be administered, route for administration, disease, combination, etc.

A mode for administration of the combined preparation of the present invention is not particularly limited, but it is sufficient that the compound of the present invention is used in combination with a concomitant drug at the time of administration. For such mode of administration, there are, for example, (1) administration of a bolus dosage form obtained by mixing the compound of the present invention and a concomitant drug together at the same time, (2) simultaneous administration of two dosage forms prepared separately from the compound of the present invention and a concomitant drug through the same route for administration, (3) administration of two dosage forms prepared separately from the compound of the present invention and a concomitant drug at certain time intervals through the same route for administration, (4) simultaneous administration of two dosage forms prepared separately from the compound of the present invention and a concomitant drug through different routes for administration, (5) administration of two dosage forms prepared separately from the compound of the present invention and a concomitant drug at certain time intervals (e.g., administration of the compound of the present invention and a concomitant drug in this order, or administration in a reversed order) through different routes for administration, etc.

The combined preparation of the present invention is low toxic and can be safely administered orally or parenterally (e.g., topically, rectally, intravascularly, etc.) either directly as they are or in the form of pharmaceutical preparations such as tablets (including dragees and film-coated tablets), powdery dosage forms, granules, capsules (including soft capsules), liquid dosage forms, injections, suppositories, sustained release dosage forms, etc., which are obtained by mixing the compound of the present invention or (and) a concomitant drug described above with pharmacologically acceptable carriers. Injectable dosage forms can be administered intravenously, intramuscularly or subcutaneously, into the organ, or directly at the focus.

Pharmacologically acceptable carriers, which may be used to manufacture the combined preparation of the present invention, include various organic or inorganic carrier substances conventionally used as materials for pharmaceutical preparations. These substances include, e.g., an excipient, a lubricant, a binder and a disintegrating agent in a solid dosage form, and a solvent, a dissolution aid, a suspending agent, an isotonizing agent, a buffer, a soothing agent, etc. in a liquid dosage form. In addition, conventional additives such as a preservative, an antioxidant, a colorant, a sweetener, an adsorbent, a wetting agent, etc. can be appropriately used in suitable amounts, if necessary.

Examples of excipients include, e.g., lactose, saccharose, D-mannitol, starch, cornstarch, crystalline cellulose, light anhydrous silicic acid, etc.

Examples of useful lubricants include, e.g., magnesium stearate, calcium stearate, talc, colloidal silica, etc.

Examples of binders include, e.g., crystalline cellulose, saccharose, D-mannitol, dextrin, hydroxypropylcellulose, hydroxypropylmethylcellulose, polyvinylpyrrolidone, starch, sucrose, gelatin, methylcellulose, sodium carboxymethylcellulose, etc.

Examples of disintegrating agents include, e.g., starch, carboxymethylcellulose, carboxymethylcellulose calcium, sodium carboxymethyl starch, L-hydroxypropylcellulose, etc.

Examples of solvents include, e.g., water for injection, alcohol, propylene glycol, Macrogol, sesame oil, corn oil, olive oil, etc.

Examples of dissolution aids include, e.g., polyethylene glycol, propylene glycol, D-mannitol, benzyl benzoate, ethanol, trisaminomethane, cholesterol, triethanolamine, sodium carbonate, sodium citrate, etc.

Examples of suspending agents include, e.g., surfactants such as stearyltriethanolamine, sodium laurylsulfate, lauryl aminopropionate, lecithin, benzalkonium chloride, benzethonium chloride, glycerine monostearate, etc.;

hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose, etc.

Examples of isotonizing agents include, e.g., glucose, D-sorbitol, sodium chloride, glycerine, D-mannitol, etc.

Examples of buffers include, e.g., buffering solutions of a phosphate, acetate, carbonate, citrate, etc.

Examples of soothing agents include, e.g., benzyl alcohol, etc. Examples of preservatives include, e.g., p-hydroxybenzoates, chlorobutanol, benzyl alcohol, phenethyl alcohol, dehydroacetic acid, sorbic acid, etc.

Examples of antioxidants include, e.g., a sulfite, ascorbic acid, α-tocopherol, etc.

In the combined preparation of the present invention, a ratio of the compound of the present invention to a concomitant drug may be appropriately chosen depending upon subject to be administered, route for administration, disease, combination, etc.

For example, the amount of the compound of the present invention contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of a concomitant drug contained in the combined preparation of the present invention varies depending on the dosage form of the preparation, but is usually about 0.01 to 100% by weight, preferably about 0.1 to 50% by weight, and more preferably about 0.5 to 20% by weight, based on the total weight of the preparation.

The amount of additives such as a carrier, etc. contained in the combined preparation of the present invention varies depending on the dosage form of the preparation, and is usually about 1 to 99.99% by weight, preferably about 10 to 90% by weight, based on the total weight of the preparation.

These amounts may be the same, also when the compound of the present invention and a concomitant drug are separately prepared, respectively.

These preparations can be manufactured by methods per se publicly known generally used conventionally.

For example, an injectable dosage form can be prepared by dissolving, suspending or emulsifying the compound of the present invention or a concomitant drug in a dispersing agent (e.g., Tween 80 (manufactured by Atlas Powder Company, USA), HCO 60 (manufactured by Nikko Chemicals Co., Ltd.), polyethylene glycol, carboxymethyl cellulose, sodium alginate, etc.), a stabilizer (e.g., ascorbic acid, sodium pyrosulfite), a surfactant (e.g., polysorbate 80, macrogol, etc.), a solubilizing agent (e.g., glycerin, ethanol, etc.), a buffering agent (e.g., phosphoric acid or its alkali metal salt, citric acid or its alkali metal salt, etc.), an isotonizing agent (e.g., sodium chloride, potassium chloride, mannitol, sorbitol, glucose, etc.), a pH adjusting agent (e.g., hydrochloric acid, sodium hydroxide, etc.), a preservative (e.g., ethyl p-oxybenzoate, benzoic acid, methylparabene, propylparabene, benzyl alcohol, etc.), a solubilizer (e.g., concentrated glycerin, meglumine, etc.), a dissolution aid (e.g., propylene glycol, sucrose, etc.), a soothing agent (e.g., glucose, benzyl alcohol, etc.), a vegetable oil such as olive oil, sesame oil, cottonseed oil, corn oil, etc., a dissolution aid such as propylene glycol or the like to prepare into an oily injection.

An oral dosage form can be produced in a conventional manner by adding to the compound of the present invention or a concomitant drug, for example, an excipient (e.g., lactose, sucrose, starch, etc.), a disintegrating agent (e.g., starch, calcium carbonate, etc.), a binder (e.g., starch, gum arabic, carboxymethyl cellulose, polyvinylpyrrolidone, hydroxypropyl cellulose, etc.), a lubricant (e.g., talc, magnesium stearate, polyethylene glycol 6000, etc.) and other additives, compressing the resulting mixture and, if necessary, coating the compressed product for the purpose of taste masking, enteric degradation or sustained release by techniques per se publicly known. Coating agents for this purpose include, for example, hydroxypropylmethyl cellulose, ethyl cellulose, hydroxymethyl cellulose, hydroxypropyl cellulose, polyoxyethylene glycol, Tween 80, Prulonic F68, cellulose acetate phthalate, hydroxypropylmethyl cellulose phthalate, hydroxymethyl cellulose acetate succinate, Eudragit (manufactured by Rohm Company, Germany, methacrylic acid/acrylic acid copolymer) and dyes (e.g., iron oxide, titanium dioxide). The oral dosage form may be either a rapid release dosage form or a sustained release dosage form.

For example, in a suppository, the compound of the present invention or a concomitant drug is prepared into an oily or aqueous solid, semi-solid or liquid composition by techniques per se publicly known. Oily bases used for the composition described above include glycerides of higher fatty acids [e.g., cacao butter, uitepsols (manufactured by Dynamite Nobel Company, Germany), etc.], moderate fatty acids [e.g., miglyols (manufactured by Dynamite Nobel Company, Germany), etc.], vegetable oils (e.g., sesame oil, soybean oil, cottonseed oil, etc.), and the like. Aqueous bases include, for example, polyethylene glycols and propylene glycol. Bases for aqueous gels include, for example, natural rubbers, cellulose derivatives, vinyl polymers, acrylic polymers, etc.

Examples of the sustained release dosage form above include sustained release microcapsules, and the like.

Sustained release microcapsules can be obtained by per se publicly known methods, and are preferably prepared in the form of, e.g., a sustained release dosage form by the method [2] shown below and administered.

Preferably, the compound of the present invention is prepared into a dosage form for oral administration such as a solid dosage form (e.g., powdery dosage form, granules, tablets, capsules) or into a dosage form for rectal administration such as a suppository, etc. A dosage form for oral administration is particularly preferred.

A concomitant drug can be prepared into the dosage form described above, depending on the kind of drug.

Hereinafter, [1] an injectable preparation of the compound of the present invention or a concomitant drug and its production, [2] a sustained release or immediate release preparation of the compound of the present invention or a concomitant drug and its production and [3] a sublingual, buccal or rapid oral disintegrating preparations of the compound of the present invention or a concomitant drug and its production will be specifically described.

[1] Injectable Preparation and its Production

An injectable preparation obtained by dissolving the compound of the present invention or a concomitant drug in water is preferred. The injectable preparation may contain a benzoate and/or a salicylate.

The injectable preparation is obtained by dissolving the compound of the present invention or a concomitant drug and optionally a benzoate and/or a salicylate in water.

Examples of the benzoate and/or salicylate described above include an alkali metal salt such as sodium and potassium salts, etc., an alkaline earth metal salt such as calcium and magnesium salts, etc., an ammonium salt, a meglumine salt, a salt of an organic acid such as trometamol, and the like.

The concentration of the compound of the present invention or a concomitant drug in the injectable preparation is about 0.5 to 50 w/v %, preferably about 3 to 20 w/v %. The concentration of the benzoate and/or salicylate is 0.5 to 50 w/v %, preferably 3 to 20 w/v %.

Furthermore, additives generally used in an injectable preparation such as a stabilizer (ascorbic acid, sodium pyrosulfite, etc.), a surfactant (polysorbate 80, macrogol, etc.), a solubilizing agent (glycerin, ethanol, etc.), a buffering agent (phosphoric acid and its alkali metal salt, citric acid and its alkali metal salt, etc.), an isotonizing agent (sodium chloride, potassium chloride, etc.), a dispersing agent (hydroxypropylmethyl cellulose, dextrin), a pH adjusting agent (hydrochloric acid, sodium hydroxide, etc.), a preservative (ethyl p-oxybenzoate, benzoic acid, etc.), a solubilizer (concentrated glycerin, meglumine, etc.), a dissolution aid (propylene glycol, saccharose, etc.), a soothing agent (glucose, benzyl alcohol, etc.) are appropriately added to the preparation. Any of these additives is added in an amount generally used in an injectable preparation.

The injectable preparation is adjusted to pH of 2 to 12, preferably 2.5 to 8.0 by adding a pH adjusting agent.

The injectable preparation is obtained by dissolving both the compound of the present invention or a concomitant drug and optionally a benzoate and/or salicylate, and, if necessary, the above additives in water. These components may be dissolved in any order according to the same manner as in a conventional injectable preparation.

An aqueous solution for injection is preferably warmed, and used as an injectable preparation after filtration sterilization by filtration or autoclaved as in a conventional injectable preparation to provide for an injectable preparation.

An aqueous injectable preparation is preferably autoclaved, e.g., at 100 to 121° C. for 5 to 30 minutes.

Moreover, the preparation may be in a solution form to which antibacterial activity is imparted to be usable as a multiple dosage form in divided dosing.

[2] Sustained Release or Immediate Release Preparation and Its Production

A preferred sustained release preparation comprises a core comprising the compound of the present invention or a concomitant drug, which is optionally coated with a water-insoluble material or a swelling polymer. For example, a sustained release preparation for oral administration of a once-daily dosage form is preferred.

Examples of the water-insoluble material used for the coating agent include cellulose ethers such as ethyl cellulose, butyl cellulose, etc., cellulose esters such as cellulose acetate, cellulose propionate, etc., polyvinyl esters such as polyvinyl acetate, polyvinyl butyrate, etc., acrylic acid polymers such as an acrylic acid/methacrylic acid copolymer, a methyl methacrylate copolymer, an ethoxyethyl methacrylate/cinnamoethyl methacrylate/aminoalkyl methacrylate copolymer, a polyacrylic acid, a polymethacrylic acid, a methacrylic acid alkylamide copolymer, a poly(methyl methacrylate), a polymethacrylate, an aminoalkyl methacrylate copolymer, a poly (methacrylic anhydride), a glycidyl methacrylate copolymer, in particular, a series of Eudragits (Rohm & Pharma) such as Eudragit RS-100, RL-100, RS-30D, RL-30D, RL-PO, RS-PO (ethyl acrylate/methyl methacrylate/chlorotrimethyl methacrylate/ethyl ammonium copolymer) and Eudragit NE-30D (methyl methacrylate/ethyl acrylate copolymer), etc., hydrogenated oils such as hydrogenated castor oil (e.g., LUBRI WAX (Freund Industrial Co., Ltd.), etc.), waxes such as carnauba wax, a fatty acid glycerin ester, paraffin, etc., polyglycerin fatty acid esters, etc.

The swelling polymer is preferably a polymer having an acidic dissociated radical and exhibiting pH-dependent swelling, and a polymer having an acidic dissociated radical, which undergoes a less swelling at an acidic pH such as in the stomach but is swollen extensively at a neutral pH region such as in the small and large intestines, is preferred.

Examples of such a polymer having an acidic dissociated radical and exhibiting pH-dependent swelling include a crosslinked polyacrylic acid polymer such as Carbomers 934P, 940, 941, 974P, 980, 1342, etc., polycarbophil and calcium polycarbophil (all manufactured by BF Goodrich Chemicals), Hivis Wakos 103, 104, 105 and 304 (all manufactured by Wako Pure Chemical Industries, Ltd.), etc.

The coating agent used in the sustained release preparation may further contain a hydrophilic material.

Examples of the hydrophilic material include a polysaccharide which may have a sulfate group, such as pullulan, dextrin, alkali metal alginates, etc., a polysaccharide having a hydroxyalkyl group or a carboxyalkyl group such as hydroxypropyl cellulose, hydroxypropylmethyl cellulose, sodium carboxymethylcellulose, etc., methyl cellulose, polyvinylpyrrolidone, polyvinyl alcohol, polyethylene glycol, etc.

The amount of the water-insoluble material contained in the coating agent of the sustained release preparation is about 30 to about 90% (w/w), preferably about 35 to about 80% (w/w), more preferably about 40 to about 75% (w/w), and the swelling polymer content is about 3 to about 30% (w/w), preferably about 3 to about 15% (w/w). The coating agent may further contain a hydrophilic material, and the amount of the hydrophilic material contained in the coating agent is about 50% (w/w) or less, preferably about 5 to about 40% (w/w), more preferably about 5 to about 35% (w/w). As used herein, the % (w/w) above is used to mean a % by weight based on the coating agent composition, which is the remainder of the coating agent solution after removing any solvent (e.g., water, a lower alcohol such as methanol, ethanol, etc.).

The sustained release preparation is manufactured by preparing a core containing a drug as illustrated below, followed by coating the resulting core with a coating agent solution obtained by heat-melting a water-insoluble material or a swelling polymer or by dissolving or dispersing such a material in a solvent.

I. Preparation of Drug-Containing Core

The shape of a core containing a drug to be coated with a coating agent (hereinafter sometimes simply referred to as a core) is not specifically limited but preferably prepared into a particulate shape such as granules, fine granules, or the like.

When the core is granules or fine granules, they have a mean particle size of preferably about 150 to about 2,000 µm, more preferably about 500 to about 1,400 µm.

The core can be prepared in a conventional manner. For example, a drug is mixed with a suitable excipient, binder, disintegrating agent, lubricant, stabilizer, etc., and then subjected to wet extrusion granulation, fluidized bed granulation, or the like.

The drug content in the core is about 0.5 to about 95% (w/w), preferably about 5.0 to about 80% (w/w), more preferably about 30 to about 70% (w/w).

Examples of the excipient contained in the core include a saccharide such as saccharose, lactose, mannitol, glucose, etc., starch, crystalline cellulose, calcium phosphate, cornstarch, etc. Among others, crystalline cellulose and cornstarch are preferred.

Examples of the binder used include polyvinyl alcohol, hydroxypropyl cellulose, polyethylene glycol, polyvinylpyrrolidone, Pluronic F68, gum arabic, gelatin, starch, etc. Examples of the disintegrating agent include calcium carboxymethyl cellulose (ECG505), sodium croscarmellose (Ac-Di-Sol), crosslinked polyvinylpyrrolidone (crospovidone), low substituted hydroxypropyl cellulose (L-HPC), etc. Among them, hydroxypropyl cellulose, polyvinylpyrrolidone and low substituted hydroxypropyl cellulose are preferred. Examples of the lubricant and the anticoagulant include talc, magnesium stearate and its inorganic salts, and examples of the lubricant include polyethylene glycol, etc. Examples of the stabilizer include an acid such as tartaric acid, citric acid, succinic acid, fumaric acid, maleic acid, etc.

In addition to the technique described above, the core can be prepared by using other techniques such as an tumbling granulation technique, a pan coating technique, a fluidized bed coating technique and a melt granulation technique, wherein a drug or a mixture of the drug with an excipient, a lubricant, etc. is portionwise added to inert carrier particles as seeds for the core with spraying a binder dissolved in a suitable solvent such as water, a lower alcohol (e.g., methanol, ethanol, etc.) or the like. Examples of the inert carrier particles include those prepared from sucrose, lactose, starch, crystalline cellulose and waxes, and, preferably, these carriers have a mean particle size of about 100 µm to about 1,500 µm.

In order to separate the drug contained in the core from a coating agent, the surface of the core may be covered with a protective material. Examples of the protective material include the hydrophilic material described above and water-insoluble material. The preferred protective material is polyethylene glycol or a polysaccharide having a hydroxyalkyl group or a carboxyalkyl group, more preferably, hydroxypropylmethyl cellulose and hydroxypropyl cellulose. The protective material may contain, as a stabilizer, an acid such as tartaric acid, citric acid, succinic acid, fumaric acid, maleic acid, etc., and a lubricant such as talc. When the protective material is used, the amount thereof to be coated is about 1 to about 15% (w/w), preferably about 1 to about 10% (w/w), more preferably about 2 to about 8% (w/w) based on the core.

The protective material can be coated by a conventional coating method and specifically, the core is spray-coated with the protective material by a fluidized bed coating technique, a pan coating technique, etc.

II. Coating of Core with Coating Agent

The core obtained in I above is coated with a coating agent solution prepared by melt-heating the water-insoluble material and pH-dependent swelling polymer described above and a hydrophilic material or by dissolving or dispersing them in a solvent to obtain a sustained release preparation.

As a coating method of the core with the coating agent solution, there are, for example, spray-coating, etc.

The composition ratio of the water-insoluble material, swelling polymer and hydrophilic material in the coating agent solution can be appropriately chosen to be within the amounts of the respective components contained in the coating.

The amount of the coating agent is about 1 to about 90% (w/w), preferably about 5 to about 50% (w/w), more preferably about 5 to about 35% (w/w) based on the core (excluding the protective material coating).

As the solvent for the coating agent solution, water and an organic solvent can be used alone or as a mixture thereof. When a mixture is used, the ratio of water and the organic solvent (water/organic solvent: a weight ratio) may vary with the range of 1 to 100%, and is preferably 1 to about 30%. The organic solvent is not particularly limited so far as it can dissolve the water-insoluble material, and examples of the solvent include a lower alcohol such as methyl alcohol, ethyl alcohol, isopropyl alcohol, n-butyl alcohol, etc., a lower alkanone such as acetone, acetonitrile, chloroform, methylene chloride, etc. Among them, a lower alcohol is preferred, with ethyl alcohol and isopropyl alcohol being more preferred. Water and a mixture of water and an organic solvent are used preferably as solvents for the coating agent solution. In this case, an acid such as tartaric acid, citric acid, succinic acid, fumaric acid, maleic acid, etc. may be added to the coating agent solution, if necessary, for the purpose of stabilizing the coating agent solution.

Where the coating is performed by spray coating, the coating can be carried out using a conventional coating technique. Specifically, the core is sprayed with a coating agent solution by a fluidized bed coating technique, a pan coating technique, or the like. At this time, a lubricant such as talc, titanium oxide, magnesium stearate, calcium stearate, light silicic anhydride, etc., and a plasticizer such as glycerin fatty ester, hardened castor oil, triethyl citrate, cetyl alcohol, stearyl alcohol, etc. may also be added.

After coating with a coating agent, an antistatic agent such as talc may also be admixed, if necessary.

The immediate release preparation may be a liquid (solution, suspension, emulsion, etc.) or a solid (particles, pills, tablets, etc.). An oral preparation and a parenteral preparation such as an injectable preparation may be used, and an oral preparation is preferred.

The immediate release preparation may usually contain a carrier, additives and an excipient (hereinafter sometimes abbreviated as excipients) which are conventionally used in the pharmaceutical field, in addition to a drug which is an active ingredient. The pharmaceutical excipients are not specifically limited so long as they are excipients conventionally used in the pharmaceutical field. Examples of the excipient for an oral solid preparation include lactose, starch, cornstarch, crystalline cellulose (Avicel PH101, manufactured by Asahi Kasei Corporation, etc.), powdered sugar, granulated sugar, mannitol, light silicic anhydride, magnesium carbonate, calcium carbonate, L-cysteine, etc., with cornstarch and mannitol being preferred. Any of these excipients may be employed alone or in combination with each other. The amounts of the excipients are, for example, about 4.5 to about 99.4 w/w %, preferably about 20 to about 98.5 w/w %, more preferably about 30 to about 97 w/w %, based on the total weight of the immediate release preparation.

The amount of the drug contained in the immediate release preparation is appropriately chosen from the range of about 0.5 to about 95%, preferably about 1 to about 60%, based on the total amount of the immediate release preparation.

When the immediate release preparation is an oral solid preparation, the preparation contains a disintegrating agent in addition to the components described above. Examples of the disintegrating agent include calcium carboxymethylcellulose (ECG-505 manufactured by GOTOKU CHEMICAL Co., Ltd.), sodium croscarmellose (for example, Ac-Di-Sol manufactured by Asahi Kasei Corporation), crospovidone (for example, COLIDON CL manufactured by BASF), low-substituted hydroxypropyl cellulose (Shin-Etsu Chemical Co., Ltd.), carboxymethyl starch (MATSUTANI CHEMICAL INDUSTRY Co., Ltd.), sodium carboxymethyl starch (EXORITAB manufactured by KIMURA SANGYO), partial a starch (PCS manufactured by Asahi Kasei Corporation), etc. For example, the disintegrating agent that disintegrates granules by water absorption or swelling upon contact with water, or forming a channel between the active component comprising the core and an excipient can be used. Any of these disintegrating agents can be used alone or in combination with each other. The amount of the disintegrating agent used may be appropriately chosen depending upon the type and the amount of the drug used or a particular preparation design for the intended release performance. For example, the amount is about 0.05 to about 30 w/w %, preferably about 0.5 to about 15 w/w % based on the total weight of the immediate release preparation.

When the immediate release preparation is an oral solid preparation, the preparation may optionally contain additives conventionally used in a solid preparation, in addition to the components described above. Examples of the additives include binders (for example, sucrose, gelatin, powdery gum arabic, methyl cellulose, hydroxypropyl cellulose, hydroxypropylmethyl cellulose, carboxymethylcellulose, polyvinylpyrrolidone, pullran, dextrin, etc.), lubricants (polyethylene glycol, magnesium stearate, talc, light silicic anhydride (for example, aerosil (NIPPON AEROSIL)), surfactants (for example, anionic surfactants such as sodium alkylsulfate, nonionic surfactants such as polyoxyethylene fatty ester, polyoxyethylene sorbitan fatty ester, polyoxyethylene castor oil derivatives, etc.), colorants (for example, tar colorants, caramel, colcothar, titanium oxide, riboflavins), if necessary, corrigents (for example, sweeteners, flavors, etc.), adsorbents, preservatives, wetting agents, antistatic agents, etc. Furthermore, an organic acid such as tartaric acid, citric acid, succinic acid, fumaric acid or the like can also be added as a stabilizer.

As the binder above, hydroxypropyl cellulose, polyethylene glycol and polyvinylpyrrolidone, etc. are preferably used.

The immediate release preparation can be prepared by mixing the components described above and kneading the mixture, if necessary, and then molding according to a conventional technique for making pharmaceutical preparations. The mixing above can be carried out in a conventional manner, e.g., by mixing, kneading, etc. Specifically, where the immediate release preparation is in the form of particles, the preparation can be prepared by mixing components with a vertical granulator, a multi-purpose kneader (HATA IRON WORKS CO., LTD), a fluidized bed granulator FD-5S(POWREX CORPORATION) or thee like, and then granulating the resulting by wet extrusion granulation or fluidized bed granulation by a technique similar to that for preparing the core of the sustained release preparation described above.

The immediate release preparation and the sustained release preparation thus obtained can be compounded, as they are, or, together with appropriate pharmaceutical excipients, in pharmaceutical preparations separately in a conventional manner to prepare respective preparations for administering in combination with each other simultaneously or at certain time intervals. Alternatively, both preparations may be compounded in a single dosage form for oral administration (e.g., granules, fine granules, tablets, capsules) as they are, or, together with appropriate pharmaceutical excipients. Both preparations in the form of granules or fine granules may also be filled in a single capsule for oral administration.

[3] Sublingual, Buccal or Rapid Oral Disintegrating Preparation and Its Production A sublingual, buccal or rapid oral disintegrating preparation may be in the form of a solid preparation such as a tablet, or may be in the form of an oral mucosal patch (film).

The sublingual, buccal or rapid oral disintegrating preparation is preferably a preparation containing the compound of the present invention or a concomitant drug and an excipient. The preparation may also contain auxiliary agents such as a lubricant, an isotonizing agent, a hydrophilic carrier, a water-dispersible polymer, a stabilizer, etc. Further for the purpose of promoting the absorption and enhancing the bioavailability, the preparation may also contain β-cyclodextrin or β-cyclodextrin derivatives (e.g., hydroxypropyl-β-cyclodextrin, etc.), or the like.

Examples of the above excipient include lactose, saccharose, D-mannitol, starch, crystalline cellulose, light silicic anhydride, etc. Examples of the lubricant include magnesium stearate, calcium stearate, talc, colloidal silica, etc., with magnesium stearate and colloidal silica being preferred. Examples of the isotonizing agent include sodium chloride, glucose, fructose, mannitol, sorbitol, lactose, saccharose, glycerin and urea, with mannitol being particularly preferred. As the hydrophilic carrier, there are, for example, a swelling hydrophilic carrier such as crystalline cellulose, ethyl cellulose, crosslinked polyvinylpyrrolidone, light silicic anhydride, silicic acid, dicalcium phosphate, calcium carbonate, etc., with crystalline cellulose (e.g., microcrystalline cellulose, etc.) being preferred. As the water-dispersible polymer, there are, for example, a gum (e.g., tragacanth gum, acacia gum, guar gum), alginate (e.g., sodium alginate), cellulose derivatives (e.g., methyl cellulose, carboxymethylcellulose, hydroxymethyl cellulose, hydroxypropyl cellulose, hydroxypropylmethyl cellulose), gelatin, water-soluble starch, polyacrylic acid (e.g., carbomer), polymethacrylic acid, polyvinyl alcohol, polyethylene glycol, polyvinylpyrrolidone, polycarbophil, ascorbate palmitate salt, etc., with hydroxypropylmethyl cellulose, polyacrylic acid, alginate, gelatin, carboxymethylcellulose, polyvinylpyrrolidone and polyethylene glycol being preferred. Hydroxypropylmethyl cellulose is particularly preferred. As the stabilizer, there are, for example, cysteine, thiosorbitol, tartatic acid, citric acid, sodium carbonate, ascrobic acid, glycine, sodium sulfite, etc., with citric acid and ascorbic acid being particularly preferred.

The sublingual, buccal or rapid oral disintegrating preparation can be prepared by mixing the compound of the present invention or a concomitant drug and an excipient by a method per se known. Furthermore, if desired, the auxiliary agents described above, such as the lubricant, isotonizing agent, hydrophilic carrier, water-dispersible polymer, stabilizer, colorant, sweetener, preservative, etc. may also be admixed. After mixing the components described above simultaneously or at certain time intervals, the mixture is compressed into tablets to obtain the sublingual, buccal or oral quick disintegration tablet. In order to obtain a suitable hardness, a solvent such as water, an alcohol, etc. can be used to moisturize or wet the components before or after tabletting, followed by drying.

In preparing the oral mucosal patch (film), the compound of the present invention or a concomitant drug and the water-dispersible polymer (preferably, hydroxypropyl cellulose, hydroxypropylmethyl cellulose), excipient, etc. described above are dissolved in a solvent such as water, etc. and then the resulting solution is cast into a film. In addition, additives such as a plasticizer, a stabilizer, an antioxidant, a preservative, a colorant, a buffering agent, a sweeteners, etc. may be added to the preparation. A glycol such as polyethylene glycol, propylene glycol, etc. may be added to impart an appropriate elasticity to a film, and a bioadhesive polymer (e.g., polycarbophile, carbopol) may also be added to enhance the adhesion of the film to the oral mucosal lining. The casting can be carried out by pouring a solution onto a non-adhesive surface, spreading the solution using a coater such as a doctor blade in a uniform thickness (preferably, approximately 10 to 1000 microns), and then drying the solution to form a film. The film thus formed is dried at room temperature or while warming, and then cut into pieces each having a desired surface area.

A preferred rapid oral disintegrating preparation is, for example, a rapid diffusion preparation in a solid network form, which comprises the compound of the present invention or a concomitant drug and a water-soluble or water-diffusible carrier inert to the compound of the present invention or the concomitant drug. The network is formed by sublimating a solvent from a solid composition comprising a solution of the compound of the present invention or a concomitant drug in a suitable solvent.

In addition to the compound of the present invention or a concomitant drug, the composition of the rapid oral disintegrating preparation may preferably contain a matrix-forming agent and a secondary component.

Examples of the matrix-forming agent include gelatins, dextrins and animal or vegetable proteins from soybean, wheat, psyllium seed proteins, etc.; gummy materials such as gum arabic, guar gum, agar, xanthane gum, etc.; polysaccharides; alginates; carboxymethylcelluloses; carrageenans; dextrans; pectins; synthetic polymers such as polyvinylpyrrolidones; materials derived from gelatin-gum arabic complexes, etc. The matrix-forming agent further includes saccharides such as mannitol, dextrose, lactose, galactose, trehalose, etc.; cyclic saccharides such as cyclodextrins, etc.; inorganic salts such as sodium phosphate, sodium chloride, aluminum silicate, etc.; amino acids having 2 to 12 carbon atoms such as glycine, L-alanine, L-aspartic acid, L-glutamic acid, L-hydroxyproline, L-isoleucine, L-leucine, L-phenylalanine, etc.

One or more matrix-forming agents can be incorporated into a solution or suspension before solidification. The matrix-forming agents may be present in addition to a surfactant, or may be present in the absence of a surfactant. The matrix-forming agents serve not only to form a matrix itself, but also assist to maintain diffusion of the compound of the present invention or a concomitant drug in the solution or suspension.

The composition may contain a secondary component such as a preservative, an antioxidant, a surfactant, a thickening agent, a colorant, pH adjusting agent, a flavor, a sweetener, a taste masking agent, etc. As the suitable colorant, there are, for example, iron oxide red, black and yellow, FD & C dyes available from ERIS & EVERALD such as FD & C Blue No. 2 and FD & C Red No. 40, etc. Examples of the suitable flavor include mint, raspberry, licorice, orange, lemon, grapefruit, caramel, vanilla, cherry, grape flavor and a combination thereof.

Examples of the suitable pH adjusting agent include citric acid, tartaric acid, phosphoric acid, hydrochloric acid and maleic acid. Examples of the suitable sweetener include aspartame, acesulfame K and thaumatine. Examples of the suitable taste masking agent include sodium bicarbonate, ion exchange resins, cyclodextrin inclusion compounds, adsorbents and microencapsulated apomorphine.

The preparation generally contains the compound of the present invention or a concomitant drug in an amount of about 0.1 to about 50% by weight, preferably about 0.1 to about 30% by weight and, preferably, the preparation (the sublingual tablet, buccal, etc. described above) allows 90% or more of the compound of the present invention or a concomitant drug to be dissolved (in water) within a time period of about 1 to about 60 minutes, preferably about 1 minute to about 15 minutes, more preferably about 2 minutes to about 5 minutes, or is a rapid oral disintegrating preparation which disintegrates within about 1 to about 60 seconds, preferably about 1 to about 30 seconds, more preferably about 1 to about 10 seconds, after being placed in the oral cavity.

The amount of the above excipient is about 10 to about 99% by weight, preferably about 30 to about 90% by weight based on the total weight of the preparation. The amount of β-cyclodextrin or β-cyclodextrin derivative is about 0 to about 30% by weight based on the total weight of the preparation. The amount of the lubricant is about 0.01 to about 10% by weight, preferably about 1 to about 5% by weight based on the total weight of the preparation. The amount of the isotonizing agent is about 0.1 to about 90% by weight, preferably about 10 to about 70% by weight based on the total weight of the preparation. The amount of the hydrophilic carrier is about 0.1 to about 50% by weight, preferably about 10 to about 30% by weight based on the total weight of the preparation. The amount of the water-dispersible polymer is about 0.1 to about 30% by weight, preferably about 10 to about 25% by weight based on the total weight of the preparation. The amount of the stabilizer is about 0.1 to about 10% by weight, preferably about 1 to about 5% by weight based on the total weight of the preparation. If necessary, the preparation described above may further contain additives such as a colorant, a sweetener, a preservative, etc.

A dose of the combined preparations of the present invention varies depending upon kind of the compound of the present invention, age, body weight, conditions, dosage form, route for administration, dosing period, etc.

A dose of the compound of the present invention may vary depending upon subject to be administered, target organ, conditions, route of administration, etc., and in oral administration, the compound is generally administered to the patient with cancer (as 60 kg body weight) in a daily dose of about 0.1 to about 100 mg, preferably about 1.0 to about 50 mg and more preferably about 1.0 to about 20 mg. In parenteral administration, a single dose of the compound may vary depending upon subject to be administered, target organ, conditions, route of administration, etc., and in the form of injectable preparation, it is advantageous to administer the compound intravenously to the patient with cancer (as 60 kg body weight) generally in a daily dose of about 0.01 to about 30 mg, preferably about 0.1 to about 20 mg, and more preferably about 0.1 to about 10 mg. For other animal species, the corresponding dose as converted per 60 kg weight can be administered. Of course, the dose may vary depending on individual conditions as described above; in such a case, a dose less than the dose given above may be sufficient, or may be higher than the range above.

It is possible to set any range of a dose for the concomitant drug, so long as it causes no adverse side effects. A daily dose of the concomitant drug may vary depending on the severity of disease, subject's age, sex, body weight and susceptibility, the dosing period and intervals, the characteristics, formulation, type and active components of the pharmaceutical preparation, etc. and is not particularly limited. For example, in oral administration, the dose is about 0.001 to 2000 mg, preferably about 0.01 to 500 mg, and more preferably about 0.1 to 100 mg in terms of a drug; usually, this dose is administered by dividing 1 to 4 times per day.

When the pharmaceutical preparations of the present invention are administered, the compound and a concomitant drug may be administered at the same time. Alternatively, a concomitant drug is first administered and then the compound of the present invention is administered, or the compound of the present invention is first administered and then a concomitant drug is administered. When they are administered at certain time intervals, the intervals vary depending on the active component to be administered, dosage form and route of administration; when a concomitant drug is first administered, the compound of the present invention may be administered within 1 minute to 3 days, preferably 10 minutes to 1 day, more preferably 15 minutes to 1 hour after the administration of the concomitant drug. When the compound of the present invention is first administered, a concomitant drug may be administered within 1 minute to 1 day, preferably 10 minutes to 6 hours, more preferably 15 minutes to 1 hour after the administration of the compound of the present invention.

As a preferred method of administration, for example, about 0.001 to 200 mg/kg of a concomitant drug in the form of an oral dosage preparation is administered orally and, after about 15 minutes, about 0.005 to 0.5 mg/kg of the compound of the present invention in the form of a parenteral preparation is administered parenterally as a daily dose.

As the metastins, there are used, for example, human metastin described in WO 00/24890, mouse or rat metastin described in WO 01/75104, etc.

Specific examples of human metastin include a peptide containing the N-terminal 47-54 amino acid sequence in the amino acid sequence represented by SEQ ID NO: 1 and consisting of 8 to 54 amino acid residues, and the like.

The "peptide containing the N-terminal 47-54 amino acid sequence in the amino acid sequence represented by SEQ ID NO: 1 and consisting of 8 to 54 amino acid residues" may be any peptide, as far as it is a peptide containing the N-terminal 47-54 amino acid sequence in the amino acid sequence represented by SEQ ID NO: 1 and consisting of 8 to 54 amino acid residues, but means that these peptides have substantially the same physiological activity (e.g., a receptor binding activity, a signal transduction activity, a glucose level increasing activity, a pancreatic glucagon secretagogue activity, a urine formation promoting activity, etc.). Specifically, there are used (i) a peptide having the amino acid sequence represented by SEQ ID NO: 1, (ii) a peptide having the N-terminal 47-54 amino acid sequence at the C terminus in the amino acid sequence represented by SEQ ID NO: 1 and consisting of 8 to 15 amino acid residues, etc.

More specifically, human metastin used includes (i) a peptide consisting of the amino acid sequence represented by SEQ ID NO: 1 (human metastin 54 (1-54)), (ii) a peptide consisting of the N-terminal 40-54 amino acid sequence in the amino acid sequence represented by SEQ ID NO: 1 (human metastin 15 (40-54); SEQ ID NO: 15), (iii) a peptide consisting of the N-terminal 45-54 amino acid sequence in the amino acid sequence represented by SEQ ID NO: 1 (human metastin 10 (45-54); SEQ ID NO: 16), (iv) a peptide consisting of the N-terminal 46-54 amino acid sequence in the amino acid sequence represented by SEQ ID NO: 1 (human metastin 9 (46-54); SEQ ID NO: 17), (v) a peptide consisting of the N-terminal 47-54 amino acid sequence in the amino acid sequence represented by (human metastin 8 (47-54); SEQ ID NO: 18), etc.

As mouse metastin (A), there are used, for example, a peptide containing the N-terminal 134-141 amino acid sequence in the amino acid sequence represented by SEQ ID NO: 3 and consisting of 8 to 52 amino acid residues. Specific examples of mouse metastin (A) used include (i) a peptide consisting of the N-terminal 90-141 amino acid sequence in the amino acid sequence represented by SEQ ID NO: 3, (ii) a peptide consisting of the N-terminal 132-141 amino acid sequence in the amino acid sequence represented by SEQ ID NO: 3, (iii) a peptide consisting of the N-terminal 127-141 amino acid sequence in the amino acid sequence represented by SEQ ID NO: 3, and the like.

As mouse metastin (B), there are used, for example, a peptide containing the N-terminal 138-145 amino acid sequence in the amino acid sequence represented by SEQ ID NO: 5 and consisting of 8 to 52 amino acid residues. Specific examples of mouse metastin (B) used include a peptide consisting of the N-terminal 94-145 amino acid sequence in the amino acid sequence represented by SEQ ID NO: 5, and the like.

As rat metastin, there are used, for example, a peptide containing the N-terminal 112-119 amino acid sequence in the amino acid sequence represented by SEQ ID NO: 7 and consisting of 8 to 52 amino acid residues. Specific examples of rat metastin used include (i) a peptide consisting of the N-terminal 68-119 amino acid sequence in the amino acid sequence represented by SEQ ID NO: 7, (ii) a peptide consisting of the N-terminal 110-119 amino acid sequence in the amino acid sequence represented by SEQ ID NO: 7, (iii) a peptide consisting of the N-terminal 105-119 amino acid sequence in the amino acid sequence represented by SEQ ID NO: 7, and the like.

Throughout the specification, the metastins are represented in accordance with the conventional way of describing peptides, that is, the N-terminus (amino terminus) at the left hand and the C-terminus (carboxyl terminus) at the right hand. In the peptide represented by SEQ ID NO: 1, the C-terminus may be in any form of a carboxyl group (—COOH), a carboxylate (—COO—), an amide (—CONH$_2$) and an ester (—COOR). Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl group, which are widely used as an ester for oral use, and the like.

Furthermore, the metastins include peptides, wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, —COOH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated peptides such as glycopeptides bound to sugar chains.

For salts of the metastins of the present invention, preferred are salts with physiologically acceptable acids (e.g., inorganic acids or organic acids) or bases (e.g., alkali metal salts), etc., especially physiologically acceptable acid addition salts. Examples of such salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNA encoding the metastin, there are used, for example, DNA encoding human metastin described in WO 00/24890, DNA encoding mouse or rat metastin described in WO 01/75104, etc.

The DNA encoding the metastin may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

The DNA encoding human metastin, mouse metastin precursor (A), mouse metastin precursor (B) or rat metastin precursor may be any DNA, so long as each is a DNA containing a base sequence represented by SEQ ID NO: 2, SEQ ID NO: 4, SEQ ID NO: 6 or SEQ ID NO: 8, or a DNA having a base sequence hybridizable to the base sequence represented by any base sequence represented by SEQ ID NO: 2, SEQ ID NO: 4, SEQ ID NO: 6 or SEQ ID NO: 8 under highly stringent conditions and encoding the human metastin, mouse metastin (A), mouse metastin (B) or rat metastin described above.

Specific examples of the DNA hybridizable to the base sequence represented by any of SEQ ID NO: 2, SEQ ID NO: 4, SEQ ID NO: 6 or SEQ ID NO: 8 under highly stringent conditions include DNAs containing a base sequence having at least about 70% homology, preferably at least about 80% homology, more preferably at least about 90% homology and the most preferably at least about 95% homology, to the base sequence represented by any of SEQ ID NO: 2, SEQ ID NO: 4, SEQ ID NO: 6 or SEQ ID NO: 8.

Homology in the base sequence can be measured under the following conditions (an expectation value=10; gaps are allowed; filtering =ON; match score=1; mismatch score=−3) using the homology scoring algorithm NCBI BLAST (National Center for Biotechnology Information Basic Local Alignment Search Tool).

The hybridization can be carried out by per se publicly known methods or by modifications of these methods, for example, according to the method described in Molecular Cloning, 2nd (J. Sambrook et al., Cold Spring Harbor Lab. Press, 1989). A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

Specifically, as the DNA encoding the human metastin consisting of the amino acid sequence represented by SEQ ID NO: 1, the DNA consisting of the base sequence represented by SEQ ID NO: 2 is used. Accordingly, for the base sequence encoding the human metastin consisting of the various amino acid sequences described above, a base sequence corresponding to each of the partial amino acid sequences in the amino acid sequence represented by SEQ ID NO: 1 may be chosen from the base sequence represented by SEQ ID NO: 2.

As the DNA encoding the mouse metastin precursor (A) comprising the amino acid sequence represented by SEQ ID NO: 3, there are employed a DNA consisting of the base sequence represented by SEQ ID NO: 4, and the like. Accordingly, for the base sequence encoding the mouse metastin precursor (A) consisting of the various amino acid sequences described above, a base sequence corresponding to each of the partial amino acid sequences in the amino acid sequence represented by SEQ ID NO: 3 may be chosen from the base sequence represented by SEQ ID NO: 4.

As the DNA encoding the mouse metastin precursor (B) comprising the amino acid sequence represented by SEQ ID NO: 5, there are employed a DNA consisting of the base sequence represented by SEQ ID NO: 6, and the like. Accordingly, for the base sequence encoding the mouse metastin precursor (B) consisting of the various amino acid sequences described above, a base sequence corresponding to each of the partial amino acid sequences in the amino acid sequence represented by SEQ ID NO: 5 may be chosen from the base sequence represented by SEQ ID NO: 6.

As the DNA encoding the rat metastin comprising the amino acid sequence represented by SEQ ID NO: 7, there are employed a DNA consisting of the base sequence represented by SEQ ID NO: 8, and the like. Accordingly, for the base sequence encoding the rat metastin consisting of the various amino acid sequences described above, a base sequence corresponding to each of the partial amino acid sequences in the amino acid sequence represented by SEQ ID NO: 7 may be chosen from the base sequence represented by SEQ ID NO: 8.

More specifically, for the peptide consisting of the amino acid sequence represented by SEQ ID NO: 1 (human metastin 54 (1-54)), a DNA containing the base sequence represented by SEQ ID NO: 2, etc. is used.

For the peptide consisting of the N-terminal 40-54 amino acid sequence in the amino acid sequence represented by SEQ ID NO: 1 (human metastin 15 (40-54); SEQ ID NO: 15), a DNA containing the base sequence represented by SEQ ID NO: 19, etc. is used.

For the peptide consisting of the N-terminal 45-54 amino acid sequence in the amino acid sequence represented by SEQ ID NO: 1 (human metastin 10 (45-54); represented by SEQ ID NO: 16), a DNA containing the base sequence represented by SEQ ID NO: 20, etc. is used.

For the peptide consisting of the N-terminal 46-54 amino acid sequence in the amino acid sequence represented by SEQ ID NO: 1 (human metastin 9 (46-54); represented by SEQ ID NO: 17), a DNA containing the base sequence represented by SEQ ID NO: 21, etc. is used.

For the peptide consisting of the N-terminal 47-54 amino acid sequence in the amino acid sequence represented by SEQ ID NO: 1 (human metastin 8 (47-54); represented by SEQ ID NO: 18), a DNA containing the base sequence represented by SEQ ID NO: 22, etc. is used.

As the metastin receptor, its partial peptides or salts thereof, there are used, for example, a human metastin receptor, its partial peptides or salts thereof described in WO 00/24890, a mouse or rat human metastin receptor, its partial peptides or salts thereof described in WO 01/75104, etc.

Specifically, the metastin receptor includes a protein containing the same or substantially the same amino acid sequence as the amino acid sequence represented by SEQ ID NO: 9, SEQ ID NO: 11 or SEQ ID NO: 13, etc.

The amino acid sequence which has substantially the same amino acid sequence as the amino acid sequence represented by SEQ ID NO: 9, SEQ ID NO: 11 or SEQ ID NO: 13 includes, for example, an amino acid sequence having at least about 70% homology, preferably at least about 80% homology, more preferably at least about 90% homology, and most preferably at least about 95% homology, to the amino acid sequence represented by SEQ ID NO: 9, SEQ ID NO: 11 or SEQ ID NO: 13.

Homology of the amino acid sequences can be determined under the following conditions (an expectation value=10; gaps are allowed; matrix=BLOSUM62; filtering=OFF) using a homology scoring algorithm NCBI BLAST (National Center for Biotechnology Information Basic Local Alignment Search Tool).

As the protein comprising substantially the same amino acid sequence as the amino acid sequence represented by SEQ ID NO: 9, SEQ ID NO: 11 or SEQ ID NO: 13, preferred is a protein having substantially the same amino acid sequence as the amino acid sequence represented by SEQ ID NO: 9, SEQ ID NO: 11 or SEQ ID NO: 13 and having the activity of the same nature as that of a protein consisting of the amino acid sequence represented by SEQ ID NO: 9, SEQ ID NO: 11 or SEQ ID NO: 13, etc.

As the activity of substantially the same nature, there are, for example, a ligand binding activity, a signal transduction activity, and the like. The "substantially the same nature" is used to mean that the nature of these activities is equivalent in terms of quality. Thus, the activities such as a ligand binding activity, a signal transduction activity, etc. are preferably equivalent (e.g., about 0.01 to 100 times, preferably about 0.5 to 20 times, more preferably 0.5 to 2 times), but differences in degree such as a level of these activities, quantitative factors such as a molecular weight of the protein may be present and allowable.

The activities such as a ligand binding activity, a signal transduction activity, etc. can be assayed by per se publicly known method with modifications and may be determined according to methods of determining a ligand or screening methods described in, e.g., WO 00/24890 or WO 01/75104.

Examples of the metastin receptor used include proteins comprising (i) the amino acid sequence represented by SEQ ID NO: 9, SEQ ID NO: 11 or SEQ ID NO: 13, of which at least 1 or 2 (preferably about 1 to about 30, more preferably about 1 to about 10 and most preferably several (1 or 2)) amino acids are deleted; (ii) the amino acid sequence represented by SEQ ID NO: 9, SEQ ID NO: 11 or SEQ ID NO: 13, to which at least 1 or 2 (preferably about 1 to about 30, more preferably about 1 to about 10 and most preferably several (1 or 2)) amino acids are added; (iii) the amino acid sequence represented by SEQ ID NO: 9, SEQ ID NO: 11 or SEQ ID NO: 13, in which at least 1 or 2 (preferably about 1 to about 30, more preferably about 1 to about 10 and most preferably several (1 or 2)) amino acids are substituted by other amino acids; or (iv) a combination of these amino acid sequences; and the like.

Throughout the specification, the metastin receptors are represented in accordance with the conventional way of describing peptides, that is, the N-terminus (amino terminus) at the left hand and the C-terminus (carboxyl terminus) at the right hand. In the metastin receptors including the metastin receptor represented by SEQ ID NO: 9, SEQ ID NO: 11 or SEQ ID NO: 13, the C-terminus may be in any form of a carboxyl group (—COOH), a carboxylate (—COO—), an amide (—CONH$_2$) and an ester (—COOR). Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and pivaloyloxymethyl group, which are widely used as an ester for oral use, and the like.

Where the metastin receptors contain a carboxyl group (or a carboxylate) at a position other than the C-terminus, the carboxyl group may be amidated or esterified and such amides or esters are also included within the receptor protein of the present invention. In this case, the ester group used may be the same group as the C-terminal esters described above.

Furthermore, the metastin receptors include those wherein the amino group at the N-terminal methionine residue is protected with a protecting group (e.g., a $C_{1-6}$ acyl group such as a $C_{2-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, —COOH, amino group, imidazole group, indole group, guanidino group, etc.) on the side chain of an amino acid in the molecule is protected with a suitable protecting group (e.g., a $C_{1-6}$ acyl group such as a $C_{2-6}$ alkanoyl group, e.g., formyl group, acetyl group, etc.), or conjugated proteins such as glycoproteins bound to sugar chains.

Specific examples of the metastin receptors include human metastin receptor consisting of the amino acid sequence represented by SEQ ID NO: 9, rat metastin receptor consisting of the amino acid sequence represented by SEQ ID NO: 11, mouse metastin receptor consisting of the amino acid sequence represented by SEQ ID NO: 13, etc.

The partial peptides of the metastin receptor (hereinafter sometimes simply referred to as the partial peptide) may be any peptide, so long as they are partial peptides of the metastin receptor described above; there are used those such as protein molecules of the metastin receptor, which are the sites exposed outside the cell membrane, and having a ligand binding activity.

Specifically, the partial peptide of the metastin receptor consisting of the amino acid sequence represented by SEQ ID NO: 9, SEQ ID NO: 11 or SEQ ID NO: 13 is a peptide containing the parts analyzed to be extracellular domains (hydrophilic domains) in the hydrophobic plotting analysis. A peptide containing a hydrophobic domain in part can be used as well. In addition, the peptide may contain each domain separately or a plurality of domains together.

In the metastin receptor, preferred partial peptides are those having the number of amino acids of at least 20, preferably at least 50, and more preferably at least 100, in the amino acid sequence described above, which constitutes the metastin receptor.

The partial peptide may be a peptide having the amino acid sequence described above, of which at least 1 or 2 (preferably about 1 to about 10 and more preferably several (1 or 2)) amino acids are deleted; to which at least 1 or 2 (preferably about 1 to about 20, more preferably about 1 to about 10 and most preferably several (1 or 2)) amino acids are added; or, in which at least 1 or 2 (preferably about 1 to about 10 and more preferably several (1 or 2)) amino acids are substituted by other amino acids.

In the partial peptide, the C terminus may be any form of a carboxyl group (—COOH), a carboxylate (—COO—), an amide (—CONH$_2$) and an ester (—COOR), as in the metastin receptor described above.

Furthermore, the partial peptides include peptides, wherein the amino group at the N-terminal methionine residue is protected with a protecting group; those wherein the N-terminal region is cleaved in vivo and the Gln thus formed is pyroglutaminated; those wherein a substituent on the side chain of an amino acid in the molecule is protected with a suitable protecting group, or conjugated peptides such as glycopeptides bound to sugar chains, as in the metastin receptors described above.

For salts of the metastin receptor or the partial peptide, preferred are salts with physiologically acceptable acids, especially physiologically acceptable acid addition salts. Examples of the salts include salts with, for example, inorganic acids (e.g., hydrochloric acid, phosphoric acid, hydrobromic acid, sulfuric acid); salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

As the DNA encoding the metastin receptor or its partial peptides, there are used, for example, a DNA encoding the human metastin receptor or its partial peptides described in WO 00/24890, a DNA encoding the mouse or rat metastin receptor or its partial peptides described in WO 01/75104, etc.

The DNA encoding the metastin receptor or its partial peptides may be any of genomic DNA, genomic DNA library, cDNA derived from the cells and tissues described above, cDNA library derived from the cells and tissues described above and synthetic DNA. The vector to be used for the library may be any of bacteriophage, plasmid, cosmid and phagemid. The DNA may also be directly amplified by reverse transcriptase polymerase chain reaction (hereinafter abbreviated as RT-PCR) using the total RNA or mRNA fraction prepared from the cells and tissues described above.

Specifically, the DNA encoding human metastin receptor, mouse metastin receptor or rat metastin receptor may be any DNA, so long as it is a DNA containing each base sequence represented by SEQ ID NO: 10, SEQ ID NO: 12 or SEQ ID NO: 14, or a DNA containing a base sequence hybridizable to the base sequence represented by SEQ ID NO: 10, SEQ ID NO: 12 or SEQ ID NO: 14 under highly stringent conditions and encoding a receptor having the activity of substantially the same nature (e.g., a ligand binding activity, a signal transduction activity, etc.) as that of the human metastin receptor, mouse metastin receptor or rat metastin receptor consisting of the amino acid sequence represented by SEQ ID NO: 10, SEQ ID NO: 12 or SEQ ID NO: 14.

Examples of the DNA hybridizable to the base sequence represented by any of SEQ ID NO: 10, SEQ ID NO: 12 or SEQ ID NO: 14 include DNAs containing a base sequence having at least about 70% homology, preferably at least about 80% homology, more preferably at least about 90% homology and the most preferably at least about 95% homology, to the base sequence represented by any of SEQ ID NO: 10, SEQ ID NO: 12 or SEQ ID NO: 14.

Homology in the base sequence can be measured under the following conditions (an expectation value=10; gaps are allowed; filtering =ON; match score=1; mismatch score=−3) using the homology scoring algorithm NCBI BLAST (National Center for Biotechnology Information Basic Local Alignment Search Tool).

The hybridization can be carried out by publicly known methods or by modifications of these methods, for example, according to the method described in Molecular Cloning, 2nd (J. Sambrook et al., Cold Spring Harbor Lab. Press, 1989), etc. A commercially available library may also be used according to the instructions of the attached manufacturer's protocol. Preferably, the hybridization can be carried out under highly stringent conditions.

The highly stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration of about 19 mM at a temperature of about 65° C. are most preferred.

More specifically, as the DNA encoding the human metastin receptor consisting of the amino acid sequence represented by SEQ ID NO: 9, the DNA consisting of the base sequence represented by SEQ ID NO: 10 is used.

As the DNA encoding the rat metastin receptor consisting of the amino acid sequence represented by SEQ ID NO: 11, the DNA consisting of the base sequence represented by SEQ ID NO: 12 is used.

As the DNA encoding the mouse metastin receptor consisting of the amino acid sequence represented by SEQ ID NO: 13, the DNA consisting of the base sequence represented by SEQ ID NO: 14 is used.

The metastin receptors, their partial peptides or salts thereof and the DNAs encoding the metastin receptors or their partial peptides can be obtained or manufactured by the methods described in WO 00/24890 or WO 01/75104.

As the antibodies to human metastin or its salts or human metastin receptors, their partial peptides or salts thereof, there may be used those described in WO 00/24890.

As the antibodies to mouse or rat metastin or its salts, or mouse or rat metastin receptors, their partial peptides or salts thereof, there may be used those described in WO 01/75104.

The antisense polynucleotide to the DNA encoding the metastin or metastin receptor is a polynucleotide containing a part of the base sequence of a DNA encoding the metastin or metastin receptor or a part of the complementary base sequence to the DNA. The antisense polynucleotide is used to embrace not only the DNA encoding the metastin or metastin receptor but also RNA.

The antisense polynucleotide (nucleic acid) capable of inhibiting the replication or expression of a gene for metastin or a gene for metastin receptor can be designed and synthesized based on the base sequence information of cloned or identified metastin-encoding DNA. Such a polynucleotide (nucleic acid) is hybridizable to RNA of a gene for metastin or a gene for the metastin receptor to inhibit the synthesis or function of said RNA or is capable of regulating/controlling the expression of a gene for metastin or a gene for metastin receptor via interaction with RNA associated with the metastin or metastin receptor.

Polynucleotides complementary to the selected sequences of metastin-related RNA or metastin receptor-related RNA and polynucleotides specifically hybridizable to the metastin-related RNA or metastin receptor-related RNA are useful in regulating/controlling the expression of a gene for metastin or a gene for metastin receptor in vivo and in vitro. These polynucleotides are also useful for the treatment or diagnosis of diseases, etc. The term "corresponding" is used to mean homologous to or complementary to a particular sequence of the nucleotide including the gene, base sequence or nucleic acid. The term "corresponding" between nucleotides, base sequences or nucleic acids and peptides (proteins) usually refers to amino acids of a peptide (protein) under the order derived from the sequence of nucleotides (nucleic acids) or their complements.

In the gene for metastin or gene for the metastin receptor, the 5' end hairpin loop, 5' end 6-base-pair repeats, 5' end untranslated region, peptide translation initiation codon, protein coding region, ORF translation termination codon, 3' end untranslated region, 3' end palindrome region, and 3' end hairpin loop, may be selected as preferred target regions, though any other region may be selected as a target in the gene for metastin or gene for the metastin receptor.

The relationship between the targeted nucleic acids and the complementary polynucleotides at least to a part of the target, specifically the relationship between the target and the polynucleotides hybridizable to the target, can be denoted to be "antisense". Examples of the antisense polynucleotides include polydeoxyribonucleotides containing 2-deoxy-D-ribose, polyribonucleotides containing D-ribose, any other type of polynucleotides which are N-glycosides of a purine or pyrimidine base, or other polymers containing non-nucleotide backbones (e.g., protein, nucleic acids and synthetic sequence-specific nucleic acid polymers commercially available) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive metals, boron, oxidative metals, etc.), those containing alkylating agents, those with modified linkages (e.g., a anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense nucleotide (nucleic acid) is RNA, DNA, or a modified nucleic acid (RNA or DNA). Specific examples of the modified nucleic acid include, but are not limited to, a sulfur derivative of a nucleic acid, a thiophosphate derivative of a nucleic acid, and a degradation-resistant polynucleoside amide or oligonucleoside amide. The antisense nucleic acid of the present invention may preferably be designed based on the following principles. That is, the antisense nucleic acid should be more stable in cells; the cell permeability of the antisense nucleic acid should be more enhanced; the affinity for a target sense strand should be higher; and if the antisense nucleic acid has any toxicity, such toxicity should be minimized.

Many modification techniques for such purposes are known in the art, for example, the techniques are disclosed in J. Kawakami et al., Pharm Tech Japan, Vol. 8, pp. 247, 1992; Vol. 8, pp. 395, 1992; S. T. Crooke et al., ed. Antisense Research and Applications, CRC Press, 1993; etc.

The antisense nucleic acid of the present invention may contain altered or modified sugars, bases or linkages. The antisense nucleic acid may also be provided in a special form such as liposomes, microspheres, or may be applied to gene therapy, or may be provided in an added form. Examples of such an added form include polycations such as polylysine that serves to neutralize the charge of a phosphate backbone, or hydrophobic materials such as lipids (e.g., phospholipids, cholesterols, etc.) that enhance the interaction with cell membranes or increase uptake of the nucleic acid. Examples of the preferred lipids to be added are cholesterols or derivatives thereof (e.g., cholesteryl chloroformate, cholic acid, etc.). These materials may be added to the 3' or 5' end of the nucleic acid or may be added through a base, a sugar, or an intramolecular nucleoside linkage. Another moiety may include a group for capping that is specifically placed at the 3' or 5' end of the nucleic acid to prevent degradation by a nuclease such as exonuclease and RNase. Examples of the group for capping include, but are not limited to, hydroxyl-protecting groups known in the art field such as glycols, e.g., polyethylene glycol and tetraethylene glycol.

The inhibiting activity of the antisense nucleic acid can be examined using a transformant transformed by the transformant vector containing the DNA encoding the metastin or metastin receptor described above, an in vivo or in vitro expression system for the metastin or metastin receptor, or an in vivo or in vitro translation system for the metastin or metastin receptor. The nucleic acid itself may be applied to cells by a variety of per se publicly known methods.

Hereinafter, the metastin or salts thereof (hereinafter briefly referred to as metastin), the DNA encoding metastin, the antibody to metastin, the anti DNA to the DNA encoding metastin, the metastin receptor, its partial peptides or salts thereof (hereinafter briefly referred to as the metastin receptor), the DNA encoding the metastin receptor, the antibody to the metastin receptor, the anti DNA to the DNA encoding the metastin receptor, etc. are described specifically in terms of their applications.

(1) Pharmaceutical Comprising Metastin, DNA Encoding Metastin, Metastin Receptor or DNA Encoding Metastin Receptor Metastin has the effects of increasing glucose level, promoting pancreatic glucagon secretion and promoting urine formation. Therefore, metastin, the DNA encoding metastin, the metastin receptor or the DNA encoding the metastin receptor is useful, for example, as a hyperglycemic agent, a pancreatic glucagon secretagogue agent or a urine formation promoting agent.

Moreover, metastin, the DNA encoding metastin, the metastin receptor or the DNA encoding the metastin receptor is useful as an agent for preventing/treating, e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

Metastin, the DNA encoding metastin, the metastin receptor or the DNA encoding the metastin receptor can be used as the pharmaceutical described above in a conventional manner. These metastin, etc. can be used orally, for example, in the form of tablets which may be sugar coated if necessary, capsules, elixirs, microcapsules etc., or parenterally in the form of injectable preparations such as a sterile solution or suspension in water or other pharmaceutically acceptable liquid. These preparations can be manufactured by mixing metastin or the like with a physiologically acceptable carrier, a flavoring agent, an excipient, a vehicle, an antiseptic agent, a stabilizer, a binder, etc. in a unit dosage form required in a generally accepted manner that is applied to making pharmaceutical preparations. The active ingredient in these preparations is controlled in such a dose that an appropriate dose is obtained within the specified range given.

The DNA encoding the metastin or the DNA encoding the metastin receptor is expressed (a) by administering the DNA encoding the metastin or the DNA encoding the metastin receptor directly to the patient; or the DNA encoding the metastin or the DNA encoding the metastin receptor can increase the amount of the metastin or metastin receptor in the patient (b) by inserting the DNA encoding the metastin or the DNA encoding the metastin receptor into a cell, etc. and then transplanting the cell to the patient. Thus, the activity of metastin can be sufficiently exhibited.

Where the DNA encoding the metastin or the DNA encoding the metastin receptor is used, the DNA itself is administered; alternatively, the DNA is inserted into an appropriate vector such as retrovirus vector, adenovirus vector, adenovirus-associated virus vector, etc. and then administered in a conventional manner.

Additives miscible with tablets, capsules, etc. include a binder such as gelatin, cornstarch, tragacanth and gum arabic, an excipient such as crystalline cellulose, a swelling agent such as cornstarch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol.

The preparation may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule. Since the thus obtained pharmaceutical preparation is safe and low toxic, the preparation can be administered to human or other mammals (e.g., mice, rats, guinea pigs, rabbits, fowl, sheep, swine, bovine, cats, dogs, monkeys, hamadryad baboons, chimpanzees, etc.).

The dose of metastin, the DNA encoding metastin, the metastin receptor or the DNA encoding the metastin receptor varies depending on conditions, etc.; in oral administration for the treatment of, e.g., obesity, the dose is normally about 0.1 mg to about 100 mg, preferably about 1.0 to about 50 mg, and more preferably about 1.0 to about 20 mg per day for the adult patient with obesity (as 60 kg body weight). In parenteral administration, the single dose varies depending on subject to be administered, target disease, conditions, method of administration, etc. but it is advantageous to administer the active ingredient intravenously to the adult patient with obesity (as 60 kg body weight) intravenously at a daily dose of about 0.01 to about 30 mg, preferably about 0.1 to about 20 mg, and more preferably about 0.1 to about 10 mg for. For other animal species, the corresponding dose as converted per 60 kg body weight can be administered.

(2) Pharmaceutical Comprising the Antibody to the Metastin or Metastin Receptor

The antibody to neutralize the activity of the metastin or metastin receptor can suppress the effects of increasing glucose level, promoting pancreatic glucagon secretion and promoting urine formation, and is thus useful as a hypoglycemic agent, a pancreatic glucagon secretion suppressing agent or a urine formation suppressing agent.

Furthermore, the antibody having the effect of neutralizing the activity of the metastin or metastin receptor can be used as an agent for preventing/treating, e.g., diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning. Diabetes mellitus includes insulin-dependent (type I) diabetes, insulin-independent type II diabetes, etc.

The agent for treating/preventing the diseases described above comprising the antibody to the metastin or metastin receptor (hereinafter briefly referred to as the antibody of the present invention) can be administered to human or mammal (e.g., rat, rabbit, sheep, swine, bovine, cat, dog, monkey, etc.) orally or parenterally directly as a liquid preparation, or as a pharmaceutical composition of suitable dosage form. The dose may vary depending upon subject to be administered, target disease, conditions, route of administration, etc. For example, when the agent is used for adult, it is advantageous to intravenously administer the antibody of the present invention in a single dose of about 0.01 to about 20 mg/kg body weight, preferably about 0.1 to about 10 mg/kg body weight and more preferably about 0.1 to about 5 mg/kg body weight in approximately 1 to 5 times a day, preferably in approximately 1 to 3 times a day. In other parenteral administration and oral administration, the agent can be administered in a dose corresponding to the dose given above. When the condition is especially severe, the dose may be increased according to the condition.

The antibody of the present invention may be administered in itself or in the form of an appropriate pharmaceutical composition. The pharmaceutical composition used for the administration may contain a pharmacologically acceptable carrier with the aforesaid antibody or its salts, a diluent or excipient. Such a composition is provided in the form of pharmaceutical preparations suitable for oral or parenteral administration.

For example, the composition for oral administration includes solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, etc. The injectable preparations include intravenous injections, subcutaneous injections, intracutaneous injections, intramuscular injections, drip infusions, etc. These injectable preparations may be prepared by methods publicly known. For example, the injectable preparations may be prepared by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is usually filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into pharmaceutical preparations in a unit dose suitable for a dose of the active ingredients. Such unit dose preparations include, for example, tablets, pills, capsules, injections (ampoules), suppositories, etc. The amount of the aforesaid antibody contained is generally about 5 to 500 mg per dosage unit form; especially in the form of injection, it is preferred that the aforesaid antibody is contained in about 5 to 100 mg and in about 10 to 250 mg for the other forms.

Each composition described above may further contain other active components unless they cause any adverse interaction with the antibody described above.

(3) Diagnostic Agent Comprising the Antibody of the Present Invention

The antibody of the present invention is capable of specifically recognizing the metastin receptor and therefore can be used for quantitative determination of the metastin receptor in a fluid to be tested, in particular, for quantitative determination by the sandwich immunoassay. The quantitative determination using the antibody of the present invention can be performed by the method described in WO 00/24890 or WO 01/75104.

Accordingly, the antibody of the present invention can detect blood glucose abnormalities, abnormalities in pancreatic glucagon secretion, and abnormalities in urine formation, accompanied by abnormal expression (overexpression or decreased expression) of the metastin or metastin receptor. Specifically, the antibody of the present invention can be used as a diagnostic agent for obesity, hyperlipemia, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders, lipotoxicity, diabetes mellitus, impaired glucose tolerance, ketosis, acidosis, pollakiuria, nocturnal enuresis, sexual dysfunction, skin disorders, arthropathy, osteopenia, arteriosclerosis, thrombotic disorders, dyspepsia, deficits in memory and learning, etc., which may be caused by blood glucose abnormalities, abnormalities in pancreatic glucagon secretion, and abnormalities in urine formation, accompanied by abnormal expression of the metastin or metastin receptor in human or mammals (e.g., rats, rabbits, sheep, swine, bovine, cats, dogs, monkeys, etc.).

More specifically, when a decreased level of the metastin or metastin receptor is detected by quantifying the level of the metastin or metastin receptor using the antibody of the present invention, it can be diagnosed that one suffers from diseases associated with dysfunction of the metastin or metastin receptor; or it is highly likely to suffer from these disease in the future.

Moreover, when a increased level of the metastin or metastin receptor is detected, it can be diagnosed that one suffers from diseases caused by over-expression of the metastin or metastin receptor; or it is highly likely to suffer from these disease in the future.

The diseases associated with dysfunction of the metastin or metastin receptor include, e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

The diseases associated with overexpression of the metastin or metastin receptor include, e.g., diabetes mellitus, impaired glucose tolerance, ketosis, acidosis, diabetic neuropathy, diabetic nephropathy, diabetic retinopathy, pollakiuria, nocturnal enuresis, sexual dysfunction, skin disorders, arthropathy, osteopenia, arteriosclerosis, thrombotic disorders, dyspepsia, deficits in memory and learning, etc. Diabetes mellitus includes insulin-dependent (type I) diabetes, insulin-independent type II diabetes, etc.

(4) Gene Diagnostic Agent

By using the DNA encoding the metastin or metastin receptor or the antisense polynucleotide to the DNA, e.g., as a probe, abnormality (gene abnormality) of the DNA or mRNA encoding the metastin or metastin receptor in human or other mammal (e.g., rat, mouse, guinea pig, rabbit, fowl, sheep, swine, bovine, horse, cat, dog, monkey, etc.) can be detected. Thus, the DNA or the antisense polynucleotide is useful as a gene diagnostic agent for the damage to the DNA or mRNA, mutation, a decreased expression, or an increased expression or overexpression of the DNA or mRNA.

The gene diagnosis described above using the DNA encoding the metastin or metastin receptor can be made, e.g., by the publicly known Northern hybridization assay or the PCR-SSCP assay (Genomics, 5, 874-879 (1989); Proceedings of the National Academy of Sciences of the United States of America, 86, 2766-2770 (1989)), etc.

Specifically, the DNA encoding the metastin or metastin receptor or the antisense polynucleotide to the DNA can be used as a diagnostic agent for obesity, hyperlipemia, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders, lipotoxicity, diabetes mellitus, impaired glucose tolerance, ketosis, acidosis, pollakiuria, nocturnal enuresis, sexual dysfunction, skin disorders, arthropathy, osteopenia, arteriosclerosis, thrombotic disorders, dyspepsia, deficits in memory and learning, etc., which may be caused by glucose abnormalities, abnormalities in pancreatic glucagon secretion, and abnormalities in urine formation, accompanied by abnormal expression of the metastin or metastin receptor in human or mammals.

When a decreased expression of the metastin or metastin receptor is detected, e.g., by Northern hybridization, it can be diagnosed that one is likely to suffer from diseases associated with dysfunction of the metastin or metastin receptor, or it is highly likely for one to suffer from diseases in the future.

When overexpression of the metastin or metastin receptor is detected by Northern hybridization, it can be diagnosed that one is likely to suffer from diseases caused by overexpression of the metastin or metastin receptor, or it is highly likely for one to suffer from these diseases in the future.

The diseases associated with dysfunction of the metastin or metastin receptor include, e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders, lipotoxicity, etc.

The diseases associated with overexpression of the metastin or metastin receptor include, e.g., diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia, deficits in memory and learning, etc. Diabetes mellitus includes insulin-dependent (type I) diabetes, insulin-independent type II diabetes, etc.

(5) Pharmaceutical Comprising Antisense DNA

The antisense DNA to the DNA encoding the metastin or metastin receptor can suppress the effects of increasing glucose level, promoting pancreatic glucagon secretion or promoting urine formation, and is thus useful as a hypoglycemic agent, a pancreatic glucagon secretion suppressing agent or a urine formation suppressing agent.

Furthermore, the antisense DNA to the DNA encoding the metastin or metastin receptor can be used as an agent for preventing/treating, e.g., diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning. Diabetes mellitus includes insulin-dependent (type I) diabetes, insulin-independent type II diabetes, etc.

Where the antisense DNA described above is used as the aforesaid agent for the treatment/prevention, the antisense DNA is prepared into pharmaceutical preparations as in the DNA encoding the metastin.

Since the pharmaceutical composition thus obtained is low toxic, it can be administered to human or mammals (e.g., rats, rabbits, sheep, swine, bovine, cats, dogs, monkeys, etc.) orally or parenterally.

The antisense DNA may also be administered as an intact DNA, or prepared into pharmaceutical preparations together with a physiologically acceptable carrier such as an auxiliary agent to assist its uptake and administered by gene gun or through a catheter such as a catheter with a hydrogel.

A dose of the antisense DNA may vary depending on target disease, subject to be administered, route for administration, etc. For example, where the antisense DNA is locally administered to the organ (e.g., liver, lung, heart, kidney, etc.) for the purpose of treating diabetes mellitus, the antisense DNA is generally administered to adult (60 kg body weight) in a daily dose of about 0.1 to 100 mg.

In addition, the double-stranded RNA (RNAi; RNA interference) comprising a part of RNA encoding the metastin or metastin receptor, the ribozyme comprising a part of RNA encoding the metastin or metastin receptor, etc. can suppress the expression of the DNA encoding the metastin or metastin receptor as in the antisense DNA described above, and can suppress the function of the metastin or metastin receptor or the DNA encoding the metastin or metastin receptor in vivo.

Therefore, the double-stranded RNA or ribozyme can suppress the effects of increasing glucose level, promoting pancreatic glucagon secretion or promoting urine formation, and is thus useful as a hypoglycemic agent, a pancreatic glucagon secretion suppressing agent or a urine formation suppressing agent. Moreover, the double-stranded RNA or ribozyme can be used as an agent for preventing/treating diabetes mellitus, impaired glucose tolerance, ketosis, acidosis, diabetic neuropathy, diabetic nephropathy, diabetic retinopathy, pollakiuria, nocturnal enuresis, sexual dysfunction, skin disorders, arthropathy, osteopenia, arteriosclerosis, thrombotic disorders, dyspepsia or deficits in memory and learning. Diabetes mellitus includes insulin-dependent (type I) diabetes, insulin-independent type II diabetes, etc.

The double-stranded RNA can be designed based on a sequence of the DNA of the present invention and manufactured by modifications of publicly known methods (e.g., Nature, 411, 494, 2001).

The ribozyme can be designed based on a sequence of the DNA of the metastin or metastin receptor and manufactured by modifications of publicly known methods (e.g., TRENDS in Molecular Medicine, 7, 221, 2001). For example, the ribozyme can be manufactured by ligating a publicly known ribozyme to a part of the RNA encoding the metastin or metastin receptor. A part of the RNA encoding the metastin or metastin receptor includes a portion proximal to a cleavage site on the RNA of the metastin or metastin receptor, which may be cleaved with a publicly known ribozyme (RNA fragment).

Where the double-stranded RNA or ribozyme described above is used as the prophylactic/therapeutic agent described above, the double-stranded RNA or the ribozyme is prepared into pharmaceutical preparations as in the antisense DNA, and the preparations can be provided for administration.

(6) Screening Method

The screening method of the present invention includes: (6-1) a method of screening a blood glucose regulating agent, a pancreatic glucagon regulating agent or a urine formation regulating agent, which comprises using (a) metastin and/or (b) a metastin receptor (hereinafter including its partial peptide), and, (6-2) a method of screening a blood glucose regulating agent, a pancreatic glucagon regulating agent or a urine formation regulating agent, which comprises using (a) a DNA comprising a DNA encoding metastin and/or (b) a DNA encoding a metastin receptor.

The blood glucose regulating agent, pancreatic glucagon regulating agent or urine formation regulating agent includes:
(a) a substance that alters the binding property of metastin to a metastin receptor, or,
(b) a substance that regulates the expression of metastin and/or a metastin receptor, etc.

First, the screening method is described on the substance that alters the binding property of metastin to a metastin receptor.

By using the metastin receptor, or by constructing the expression system of the recombinant metastin receptor and using the receptor-binding assay system via the expression system, the substance that alters the binding property of metastin to the metastin receptor can be screened.

Such a substance includes a substance having the cell-stimulating activity mediated by the metastin receptor (i.e., a metastin receptor agonist), a substance having no cell-stimulating activity (i.e., a metastin receptor antagonist), etc. The term "alters the binding property of metastin to the metastin receptor" is used to include both cases where binding of metastin to the metastin receptor is inhibited and binding of metastin to the metastin receptor is promoted.

The cell-stimulating activity includes, e.g., the activities that promote or suppress arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, etc., the cell proliferation inhibiting activity, chemotaxis inhibiting activity, tumor growth suppressing activity, hyperglycemic activity, pancreatic glucagon secretion promoting activity, etc. Among others, the activities of promoting intracellular $Ca^{2+}$ release, inhibiting cell proliferation, inhibiting chemotaxis, suppressing tumor growth, increasing blood glucose and promoting pancreatic glucagon secretion are preferred.

That is, the present invention provides a method of screening a substance that alters the binding property of metastin to the metastin receptor, which comprises assaying the binding amount of a labeled form of the metastin to metastin receptor, (i) in the case wherein metastin is brought in contact with a metastin receptor and (ii) in the case wherein metastin and a test compound are brought in contact with the metastin receptor, and comparing (i) and (ii);

According to the screening method of the present invention, the method comprises assaying, for example, the binding amount of metastin to the metastin receptor, the cell-stimulating activity, etc. (i) in the case wherein metastin is brought in contact with the metastin receptor and (ii) in the case wherein the peptide of the present invention and a test compound are brought in contact with the metastin receptor, and comparing (i) and (ii).

Specifically, the screening method of the present invention includes:

(i) a method of screening a substance that alters the binding property of metastin to the metastin receptor, which comprises assaying the binding amount of labeled metastin to the metastin receptor, in the case wherein labeled metastin is brought in contact with the metastin receptor and in the case wherein labeled metastin and a test compound are brought in contact with the metastin receptor, and comparing the binding amount between the cases;

(ii) a method of screening a substance that alters the binding property of metastin to the metastin receptor, which comprises assaying the binding amount of labeled metastin to a cell containing the metastin receptor or a membrane fraction of the cell, in the case wherein labeled metastin is brought in contact with the cell containing the metastin receptor or its membrane fraction and in the case wherein labeled metastin and a test compound are brought in contact with the cell containing metastin receptor or its membrane fraction, and comparing the binding amount between the cases;

(iii) a method of screening a substance that alters the binding property of metastin to the metastin receptor, which comprises assaying the binding amount of labeled metastin to the metastin receptor, in the case wherein labeled metastin is brought in contact with the metastin receptor expressed on a cell membrane by culturing a transformant containing a DNA encoding the metastin receptor and in the case wherein labeled metastin and a test compound are brought in contact with the metastin receptor expressed on a cell membrane by culturing a transformant containing a DNA encoding the metastin receptor, and comparing the binding amount between the cases;

(iv) a method of screening a substance that alters the binding property of metastin to the metastin receptor, which comprises assaying the cell-stimulating activity mediated by the metastin receptor, in the case wherein a compound that activates the metastin receptor (e.g., metastin, the metastin derivative of the present invention) is brought in contact with a cell containing the metastin receptor and in the case wherein the compound that activates the metastin receptor and a test compound are brought in contact with a cell containing the metastin receptor, and comparing the activity;

(v) a method of screening a substance that alters the binding property of metastin to the metastin receptor, which comprises assaying the cell-stimulating activity mediated by the metastin receptor, in the case wherein a compound that activates the metastin receptor (e.g., metastin or the metastin derivative of the present invention) is brought in contact with the metastin receptor expressed on a cell membrane by culturing a transformant containing a DNA encoding the metastin receptor and in the case wherein the compound that activates the metastin receptor and a test compound are brought in contact with the metastin receptor expressed on a cell membrane by culturing a transformant containing a DNA encoding the metastin receptor, and comparing the activity; etc.

(vi) a method of screening the metastin receptor, which comprises assaying the cell-stimulating activity mediated by the metastin receptor when a test compound is brought in contact with a cell containing the metastin receptor and comparing the activity;

(vii) a method of screening an agonist for the metastin receptor, which comprises assaying the cell-stimulating activity mediated by the metastin receptor when a test compound is brought in contact with the metastin receptor expressed on a cell membrane by culturing a transformant containing a DNA encoding the metastin receptor and comparing the activity; and the like.

In the screening method of the present invention, a compound (e.g., a low molecular synthetic compound, preferably a low molecular synthetic agonist) or its salt that alters the binding property of metastin to the metastin receptor can also be used as a ligand, instead of using metastin. The compound or its salt that alters the binding property of metastin to the metastin receptor can be obtained by performing the screening method of the present invention, using, e.g., metastin as a ligand. Specifically, the metastin derivative of the present invention or its salts described above can be used.

The screening method of the present invention will be described below more specifically.

First, the metastin receptor, which is used for the screening method of the present invention, may be any receptor, so long as it comprises the metastin receptor described above, and membrane fractions from human or other warm-blooded animal organs are preferably employed. Since it is very difficult to obtain human-derived organs especially, however, the metastin receptor expressed abundantly by use of recombinants are suitable for use in the screening.

Where the cell containing the metastin receptor or its cell membrane fraction is used in the screening method of the present invention, the procedures later described may apply.

When the cell containing metastin receptor is used, the cell may be fixed with glutaraldehyde, formalin, etc. The fixation may be carried out by a publicly known method.

The cell containing metastin receptor refers to a host cell expressing the metastin receptor. Examples of such a host cell include *Escherichia coli, Bacillus subtilis*, yeast, insect cells, animal cells, etc.

The membrane fraction refers to a fraction that abundantly contains cell membranes prepared by publicly known methods after disrupting cells. Examples of the cell disruption include cell squashing using a Potter-Elvehjem homogenizer, disruption using a Waring blender or Polytron (manufactured by Kinematica Inc.), disruption by ultrasonication, disruption by cell spraying via a thin nozzle under increasing pressure using a French press, etc., and the like. Cell membranes are fractionated mainly by fractionation using a centrifugal force such as for fractionation centrifugation, density gradient centrifugation, etc. For example, cell disruption fluid is centrifuged at a low rate (500 rpm to 3,000 rpm) for a short period of time (normally about 1 minute to about 10 minutes), the resulting supernatant is then centrifuged at a higher rate (15,000 rpm to 30,000 rpm) normally for 30 minutes to 2 hours.

The precipitate thus obtained is used as the membrane fraction. The membrane fraction is rich in the metastin receptor expressed and membrane components such as cell-derived phospholipids, membrane proteins, or the like.

The amount of the metastin receptor contained in the cells containing the metastin receptor or in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the aforesaid methods (i) through (iii) for screening the substance that alters the binding property of metastin to the metastin receptor, an appropriate fraction of the metastin receptor and labeled metastin, etc. are used. The fraction of the metastin receptor is preferably a fraction of a naturally occurring type metastin receptor or a fraction of a recombinant type metastin receptor having an equivalent activity. Herein, the term equivalent activity is intended to mean the ligand binding activity, etc. that is equivalent.

As the labeled metastin, there may be used a labeled ligand, a labeled ligand analog compound, etc. For example, metastin labeled with $[^3H]$, $[^{125}I]$, $[^{14}C]$, $[^{35}S]$, etc. can be utilized.

Specifically, the substance that alters the binding property of metastin to the metastin receptor is screened by the following procedures. First, a receptor preparation is prepared by suspending a cell containing the metastin receptor or a membrane fraction of the cell in a buffer appropriate for use in the screening method. Any buffer can be used so long as it does not interfere the metastin-metastin receptor binding, including a phosphate buffer or a Tris-HCl buffer, having pH of 4 to 10 (preferably pH of 6 to 8), etc. For the purpose of minimizing non-specific binding, a surfactant such as CHAPS, TWEEN-80™ (Kao-Atlas Inc.), digitonin, deoxycholate, etc., may optionally be added to the buffer. Further for the purpose of suppressing the degradation of the metastin receptor or metastin with a protease, a protease inhibitor such as PMSF, leupeptin, E-64 (manufactured by Peptide Institute, Inc.), pepstatin, etc. may also be added. A given amount (5,000 cpm to 500,000 cpm) of the labeled metastin is added to 0.01 ml to 10 ml of the receptor solution, in which $10^{-4}$ M to $10^{-1}$ M of a test compound is co-present. To determine the amount of non-specific binding (NSB), a reaction tube charged with unlabeled metastin in large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count (B0) where any antagonizing substance is absent and the resulting count (B0 minus NSB) is made 100%, the test compound showing the specific binding amount (B minus NSB) of, e.g., 50% or less may be selected as a candidate substance.

The methods (iv) to (vii) described above for screening the substance that alters the binding property of metastin to the metastin receptor can be carried out as follows. For example, the cell stimulating activity mediated by the metastin receptor may be determined by a publicly known method, or using an assay kit commercially available. Specifically, the cells containing the metastin receptor are first cultured on a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., $Ca^{2+}$ arachidonic acid, cAMP etc.) due to a degrading enzyme contained in the cells, an inhibitor against such as a degrading enzyme may be added prior to the assay. For detecting the activity such as the cAMP production suppression, the baseline production in the cells is increased by forskolin or the like and the suppressing effect on the increased baseline production can be detected.

For screening through the assay of the cell stimulating activity, appropriate cells, in which an appropriate metastin receptor is expressed, are required. The cells, in which the metastin receptor of the present invention is expressed, are preferably the aforesaid cell line in which the recombinant type metastin receptor is expressed, etc.

Examples of the test compounds include peptides, proteins, non-peptide compounds, synthetic compounds, fermentation products, cell extracts, plant extracts, animal tissue extracts, seminal plasma, etc. These compounds may be novel compounds or publicly known compounds.

The test compound may be in the form of salts. As salts of the test compound, there may be used salts with physiologically acceptable acids (e.g., inorganic acids, etc.) or bases (e.g., organic acids, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The test compound, which is preferably used is a compound designed to bind to the ligand-binding pocket, based on the atomic coordinate and the position of the ligand-binding pocket in the active site of metastin receptor. The atomic coordinate and the position of the ligand-binding pocket in the active site of metastin receptor can be determined by publicly known methods or modifications thereof.

The kit for screening a substance that alters the binding property of metastin to the metastin receptor comprises the metastin receptor, cells containing the metastin receptor or a membrane fraction of the cells, and/or metastin.

Examples of the screening kit of the present invention are given below:
1. Reagent for Screening
(1) Assay Buffer and Wash Buffer Hanks' Balanced Salt Solution (manufactured by Gibco Co.) supplemented with 0.05% bovine serum albumin (Sigma Co.).

The solution is sterilized by filtration through a 0.45 µm filter and stored at 4° C.; alternatively, the solution may be prepared at use.
(2) Metastin Receptor Preparation CHO cells on which the metastin receptor has been expressed are subcultured in a 12-well plate at the rate of $5 \times 10^5$ cells/well and then cultured at 37° C. under 5% $CO_2$ and 95% air for 2 days.
(3) Labeled Ligand Metastin labeled with commercially available [$^3$H], [$^{125}$I], [$^{14}$C], [$^{35}$S], etc. is dissolved in a suitable solvent or buffer. The solution is stored at 4° C. or −20° C., which is diluted to 1 µM with an assay buffer at use.

(4) Standard Ligand Solution

Metastin is dissolved in PBS supplemented with 0.1% bovine serum albumin (manufactured by Sigma, Inc.) in a concentration of 1 mM, and the solution is stored at −20° C.
2. Assay Method
(1) Cells are cultured in a 12-well tissue culture plate to express the metastin receptor. After washing the cells twice with 1 ml of the assay buffer, 490 µl of the assay buffer is added to each well.

(2) After 5 µl of a test compound solution of $10^{-3}$ to $10^{-10}$ M is added, 5 µl of labeled metastin is added to the system followed by reacting at room temperature for an hour. To determine the amount of the non-specific binding, the ligand of $10^{-3}$ M is added in an amount of 5 µl, instead of the test compound.

(3) The reaction mixture is removed and washed 3 times with 1 ml each of the wash buffer. The labeled metastin bound to the cells is dissolved in 0.2N NaOH-1% SDS and mixed with 4 ml of a liquid scintillator A (manufactured by Wako Pure Chemical Industries, Ltd.).

(4) Radioactivity is measured using a liquid scintillation counter (manufactured by Beckmann) and PMB (percent of the maximum binding) is calculated in accordance with the following equation 1:

$$PMB = [(B - NSB)/(B0 - NSB)] \times 100$$

wherein:
PMB: percent of the maximum binding
B: value when a sample is added
NSB: non-specific binding
B0: maximum binding The substance obtained by the screening method or the screening kit of the present invention is the substance that alters the binding property of metastin to the metastin receptor (promotes or inhibits the binding). Specifically, it is the substance having the cell stimulating activity mediated by the metastin receptor (a so-called agonist for the metastin receptor), or the compound having no such cell stimulating activity (a so-called antagonist to the metastin receptor).

The substance is a compound selected from the test compounds described above. These compounds may be novel or publicly known compounds.

In order to evaluate whether the compound is either an agonist or an antagonist of the metastin receptor, it is determined by (1) or (2) below.

(1) According to the screening methods (i) to (iii), the binding assay is carried out to obtain a substance that alters the binding property of metastin and the metastin receptor (especially, a substance that inhibits the binding). It is then determined if the substance has the above cell-stimulating activity mediated by the metastin receptor. The substance having the cell-stimulating activity is an agonist for the metastin receptor, whereas the substance having no such an activity is an antagonist to the metastin receptor.

(2) (a) A test compound is brought in contact with a cell containing the metastin receptor, whereby the aforesaid cell-stimulating activity mediated by the metastin receptor is assayed. The substance having the cell-stimulating activity is an agonist for the metastin receptor.

(b) The cell-stimulating activity mediated by the metastin receptor is assayed in the case where a compound that activates the metastin receptor (e.g., metastin, etc.) is brought in contact with cells containing the metastin receptor and in the case where a compound that activates the metastin receptor and a test compound are brought in contact with cells containing the metastin receptor, and comparison is made therebetween. The substance that can reduce the cell-stimulating activity induced by the compound that activates the metastin receptor is an antagonist to the metastin receptor.

Preferably, the cell-stimulating activity as an indicator includes, for example, the activities of promoting intracellular $Ca^{2+}$ release, inhibiting cell proliferation, inhibiting chemotaxis, suppressing tumor growth, increasing blood glucose and promoting pancreatic glucagon secretion.

As the metastin receptor agonists, there are used, e.g., prodrugs of the metastin derivative (I) of the present invention or its salts, etc.

The metastin receptor agonists have similar activities to the physiological activities metastin has, and are useful as safe and low-toxic pharmaceuticals as in metastin.

On the contrary, the metastin receptor antagonists can suppress the physiological activity that metastin has, and are useful as safe and low-toxic pharmaceuticals for suppressing the activity of metastin.

Accordingly, the metastin receptor agonists are useful as, e.g., hyperglycemic agents, pancreatic glucagon secretagogue agents or urine formation promoting agents. In addition, the metastin receptor agonists are useful as agents for preventing/treating, e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

Meanwhile, the metastin receptor antagonists are useful as, e.g., hypoglycemic agents, pancreatic glucagon secretion suppressing agents or urine formation suppressing agents. In addition, the metastin receptor antagonists can be used as agents for preventing/treating, e.g., diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning.

Moreover, substances derived from the substance, which can be obtained by using the screening method or screening kit described above, can be used similarly.

The substance obtained by the screening method above may be in the form of salts. As such salts, there may be used salts with physiologically acceptable acids (e.g., inorganic acids, organic acids, etc.) or bases (e.g., alkali metal salts, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

When the substance obtained using the screening method of the present invention is used as the therapeutic/preventive agent described above, the substance can be prepared into pharmaceutical preparations in a conventional manner. For example, the substance may be prepared in the form of tablets, capsules, elixir, microcapsules, a sterile solution, a suspension, etc., as in the aforesaid pharmaceutical composition comprising metastin.

Since the pharmaceutical preparation thus obtained is safe and low toxic, it can be administered to human or warm-blooded animal (e.g., mice, rats, rabbits, sheep, swine, bovine, horses, fowl, cats, dogs, monkeys, chimpanzees, etc.).

The dose of the substance may vary depending upon its action, target disease, subject to be administered, route of administration, etc. For example, where an agonist for the metastin receptor is orally administered, the compound is administered to adult (as 60 kg body weight) generally in a dose of about 0.1 to 100 mg, preferably about 1.0 to 50 mg and more preferably about 1.0 to 20 mg. In parenteral administration, a single dose of the substance may vary depending upon subject to be administered, target disease, etc. When an agonist for the metastin receptor is administered to adult (as 60 kg body weight) in the form of injectable preparation, it is advantageous to administer the compound intravenously in a single dose of about 0.01 to about 30 mg, preferably about 0.1 to about 20 mg and more preferably about 0.1 to about 10 mg a day. For other animal species, the corresponding dose as converted per 60 kg weight can be administered.

Next, the method of screening the substance that regulates the expression of metastin and/or the metastin receptor is described.

Specifically, the screening method of the present invention includes:

(1) (i) a method of screening a substance that promotes or suppresses the expression of metastin, which comprises assaying the expression level of metastin or the amount of mRNA encoding metastin, in the case wherein a cell or tissue capable of expressing metastin is cultured in the presence or absence of a test compound, and comparing the expression level in the cases; and, (2) (i) a method of screening a substance that promotes or suppresses the expression of the metastin receptor, which comprises assaying the expression level of the metastin receptor or the amount of mRNA encoding metastin, in the case wherein a cell or tissue capable of expressing the metastin receptor is cultured in the presence or absence of a test compound, and comparing the expression level in the cases.

As the cells or tissues capable of expressing metastin or the metastin receptor, there may be used cells of human and other warm-blooded animals (e.g., guinea pigs, rats, mice, fowl, rabbits, swine, sheep, bovine, monkeys, etc.) (e.g., nerve cell, endocrine cell, neuroendocrine cell, glial cell, β cell of pancreas, bone marrow cell, hepatocyte, splenocyte, mesangial cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte, dendritic cell), megakaryocyte, synovial cell, chondrocyte, bone cell, osteoblast, osteoclast, mammary gland cell, or interstitial cell, or the corresponding precursor cell, stem cell, cancer cell, etc.), or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, pituitary, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc. In this case, the cell line and the primary culture system may be used. A transformant transformed with recombinant vector having the DNA encoding the metastin or metastin receptor described above may also be used.

The cells capable of expressing the metastin or metastin receptor can be incubated in a manner similar to the method for incubation of transformants described above.

As the test compound, a DNA library may also be used, in addition to the test compounds described above.

The expression level of the metastin or metastin receptor can be determined by publicly known methods such as immunochemical methods, etc., using an antibody, etc. Alternatively, mRNA encoding metastin can be determined by publicly known methods including Northern hybridization, RT-PCR or TaqMan PCR.

Comparison of the expression level of mRNA can be made by publicly known methods or a modification thereof, for example, according to the method described in Molecular Cloning, 2nd (J. Sambrook et al., Cold Spring Harbor Lab. Press, 1989), etc.

Specifically, the level of mRNA encoding the metastin or metastin receptor is determined by contacting RNA extracted from cells according to publicly known methods with the DNA encoding the metastin or metastin receptor or a part thereof or the antisense polynucleotide of the present invention, and assaying the level of mRNA bound to the DNA encoding the metastin or metastin receptor or a part thereof or the antisense polynucleotide of the present invention. The level of mRNA bound to the DNA encoding the metastin or metastin receptor or a part thereof or the antisense polynucleotide of the present invention can be readily assayed by labeling the DNA encoding the metastin or metastin receptor or a part thereof or the antisense polynucleotide of the present invention with, e.g., a radioisotope, a dye, etc. Examples of the radioisotope are $^{32}P$, $^{3}H$, etc. Examples of the dye used are fluorescent dyes such as fluorescein, FAM (manufactured by Biosystems, Inc.), JOE (manufactured by PE Biosystems, Inc.), TAMRA (manufactured by PE Biosystems, Inc.), ROX (manufactured by PE Biosystems, Inc.), Cy5 (manufactured by Amersham), Cy3 (manufactured by Amersham), etc.

The level of mRNA can also be determined by converting RNA extracted from cells into cDNA by a reverse transcriptase, amplifying the cDNA by PCR using the DNA encoding the metastin or metastin receptor or a part thereof or antisense polynucleotide of the present invention as a primer, and assaying the level of the cDNA amplified.

As described above, the test compound that increases the level of mRNA encoding the metastin or metastin receptor can be selected as a substance having the activity of promoting the expression of the metastin or metastin receptor. Also, the test compound that lowers the level of mRNA encoding the metastin or metastin receptor can be selected as a substance having the activity of suppressing the expression of the metastin or metastin receptor.

The present invention further provides:

(ii) a method of screening a substance that promotes or inhibits a promoter activity, which comprises assaying the reporter activity in the case wherein a transformant transformed by a recombinant DNA ligated with a reporter gene downstream the promoter region or enhancer region of a gene encoding the metastin or metastin receptor is cultured in the presence or absence of a test compound, and comparing the activity in each case.

As the reporter gene, there may be employed, e.g., lacZ (β-galactosidase gene), chloramphenicol acetyltransferase (CAT), luciferase, growth factor, β-glcuronidase, alkaline phosphatase, green fluorescent protein (GFP), β-lactamase, etc.

By determining the level of the reporter gene product (e.g., mRNA, protein) using publicly known methods, the test compound that increases the level of the reporter gene product can be selected as the compound having the activity of regulating (especially promoting) the promoter or enhancer activity of the peptide of the present invention, i.e., the substance having the activity of promoting the expression of the metastin or metastin receptor. To the contrary, the test compound that decreases the level of the reporter gene product can be selected as the compound having the activity of regulating (especially suppressing) the promoter or enhancer activity of the metastin or metastin receptor, i.e., the substance having the activity of suppressing the expression of the metastin or metastin receptor.

As the test compounds, those described above are employed.

The transformants can be incubated as given for the transformants described above.

Construction of vectors for the reporter genes and assay can be performed according to publicly known techniques (e.g., Molecular Biotechnology, 13, 29-43, 1999).

The substance having the activity of promoting the expression of the metastin or metastin receptor has an effect of promoting the physiological activity that metastin has, and is thus useful as safe and low-toxic pharmaceuticals similarly to metastin.

To the contrary, the substance having the activity of suppressing the expression of the metastin or metastin receptor can suppress the physiological activity that metastin has, and is thus useful as safe and low-toxic pharmaceuticals, which suppress the activity of metastin.

Therefore, the substance that promotes the expression of the metastin or metastin receptor is useful as, e.g., a hyperglycemic agent, a pancreatic glucagon secretagogue agent or a urine formation promoting agent. In addition, the substance that promotes the expression of the metastin or metastin receptor is useful as an agent for preventing/treating, e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

On the other hand, the substance that suppresses the expression of the metastin or metastin receptor is useful as, e.g., a hypoglycemic agent, a pancreatic glucagon secretion suppressing agent or a urine formation suppressing agent. In addition, the substance that suppresses the expression of the metastin or metastin receptor is useful as an agent for preventing/treating, e.g., diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning.

The substances obtained by the screening method of the present invention include peptides, proteins, non-peptide compounds, synthetic compounds, fermentation products, cell extracts, plant extracts, animal tissue extracts, plasma, etc. The salts of said compounds are the same as the salts of metastin described above.

Moreover, substances derived from the substance obtained by using the screening method or screening kit described above can be used similarly.

When the substance obtained using the screening method of the present invention is used as the therapeutic/preventive agent described above, the substance can be prepared into pharmaceutical preparations in a conventional manner. For example, the substance may be prepared in the form of tablets, capsules, elixir, microcapsules, a sterile solution, a suspension, etc., as in the pharmaceutical composition comprising metastin described above.

Since the pharmaceutical preparation thus obtained is safe and low toxic, it can be administered to human or warm-blood animal (e.g., mouse, rat, rabbit, sheep, swine, bovine, horse, fowl, cat, dog, monkey, chimpanzee, etc.).

A dose of the substance may vary depending on its action, target disease, subject to be administered, route for administration, etc.; when a substance that promotes the expression of metastin is orally administered, the substance is administered to adult (as 60 kg body weight) normally in a daily dose of about 0.1 to 100 mg, preferably about 1.0 to 50 mg and more preferably about 1.0 to 20 mg. In parenteral administration, a single dose of the compound varies depending on subject to be administered, target disease, etc. but when a substance that promotes the expression of metastin is administered to adult (as 60 kg body weight) in the form of injectable preparation, it is advantageous to administer the substance intravenously in a daily dose of about 0.01 to about 30 mg, preferably about 0.1 to about 20 mg and more preferably about 0.1 to about 10 mg. For other animal species, the corresponding dose as converted per 60 kg weight can be administered.

(7) Dna Transgenic Animal

The present invention provides a non-human mammal bearing DNA encoding the metastin or metastin receptor, which is exogenous (hereinafter abbreviated as the exogenous DNA of the present invention) or its variant DNA (sometimes briefly referred to as the exogenous variant DNA of the present invention).

That is, the present invention provides:

(i) A non-human mammal bearing the exogenous DNA of the present invention or its variant DNA;

(ii) The mammal according to (i), wherein the non-human mammal is a rodent;

(iii) The mammal according to (ii), wherein the rodent is mouse or rat; and, (iv) A recombinant vector containing the exogenous DNA of the present invention or its variant DNA and capable of expressing in a mammal; etc.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the DNA transgenic animal of the present invention.

Examples of the non-human mammal that can be used include bovine, swine, sheep, goat, rabbits, dogs, cats, guinea pigs, hamsters, mice, rats, etc. Above all, preferred are rodents, especially mice (e.g., C57B1/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, SD, etc.) or the like, since they are relatively short in ontogeny and life cycle from a standpoint of creating model animals for human disease.

"Mammals" in a recombinant vector that can be expressed in the mammals include the aforesaid non-human mammals, human, etc.

The exogenous DNA of the present invention refers to the DNA of the present invention that is once isolated/extracted from mammals, not the metastin or metastin receptor (hereinafter briefly referred to as the DNA of the present invention) inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean the DNA that expresses the metastin or metastin receptor which is abnormal and exemplified by a DNA, etc. that expresses a peptide for suppressing the function of the metastin or metastin receptor which is normal.

The exogenous DNA of the present invention may be any one of those derived from a mammal of the same species as, or a different species from, the mammal as the target animal. In transfecting the DNA of the present invention into the target animal, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the metastin or metastin receptor, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression described above include promoters for DNA derived from viruses (e.g., simian virus, cytomegalovirus, Moloney leukemia virus, JC virus, breast cancer virus, poliovirus, etc.), and promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), protein chain elongation factor 1α (EF-1α), βactin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human peptide elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus and the like are preferably used.

In addition, for the purpose of enhancing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal metastin or metastin receptor can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of normal peptide obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by crossing.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygotic animals having the transfected DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the metastin or metastin receptor by accelerating the function of endogenous normal DNA. Therefore, the animal can be utilized as a pathologic model animal for such a disease. For example, using the normal DNA transgenic animal of the present invention, it is possible to elucidate the mechanism of hyperfunction in the function of the metastin or metastin receptor and the pathological mechanism of the disease associated with the metastin or metastin receptor and to investigate how to treat these diseases.

Furthermore, a mammal transfected with the exogenous normal DNA of the present invention exhibits a symptom of increasing the metastin or metastin receptor liberated. Thus, the animal is usable for screening test of prophylactic/therapeutic agents for diseases associated with the metastin or metastin receptor.

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material by inserting the DNA into the plasmid described above. The DNA construct with a promoter can be prepared by conventional DNA engineering techniques. The transfection of the abnormal DNA of the present invention at the fertilized egg cell stage is preserved to be present in all of the germinal and somatic cells of the target mammal. The fact that the abnormal DNA of the present invention is present in the germinal cells of the animal after DNA transfection means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to metastin or metastin receptor by inhibiting the functions of endogenous normal DNA. Therefore, the animal can be utilized as a pathologic model animal for such a disease. For example, using the abnormal DNA transgenic animal of the present invention, it is possible to elucidate the mechanism of the function inactive type inadaptability to the peptide of the present invention and the pathological mechanism and to investigate how to treat the disease.

More specifically, the transgenic animal of the present invention expressing the abnormal DNA of the present invention at a high level is expected to serve as an experimental model to elucidate the mechanism of the functional inhibition (dominant negative effect) of normal metastin or normal metastin receptor by the abnormal metastin or abnormal metastin receptor in the function inactive type inadaptability of the AEORIN or metastin receptor.

Since a mammal bearing the abnormal exogenous DNA of the present invention shows a symptom of increasing the metastin or metastin receptor of the present invention which is liberated, the animal can be utilized also in the screening test of agents for treating the function inactive type inadaptability of the metastin or metastin receptor (e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity).

Other potential applications of two kinds of the DNA transgenic animals of the present invention described above further include:

(1) Use as a cell source for tissue culture;

(2) Elucidation of the relation to a peptide that is specifically expressed or activated by the metastin or metastin receptor, by direct analysis of DNA or RNA in tissues of the DNA transgenic animal of the present invention or by analysis of the peptide tissues expressed by the DNA;

(3) Research on the function of cells derived from tissues that are usually cultured only with difficulty, using cells in tissues bearing the DNA cultured by a standard tissue culture technique;

(4) Screening a drug that enhances the functions of cells using the cells described in (1) above; and, (5) Isolation and purification of the variant peptide of the present invention and preparation of an antibody thereto; etc.

Furthermore, clinical conditions of a disease associated with the metastin or metastin receptor, including the function inactive type inadaptability to the metastin or metastin receptor can be determined by using the DNA transgenic animal of the present invention. Also, pathological findings on each organ in a disease model associated with the metastin or metastin receptor can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve to identify cells capable of producing the metastin or metastin receptor, and to study in association with apoptosis, differentiation or propagation or on the mechanism of signal transduction in these properties to inspect any abnormality therein. Accordingly, the DNA transgenic animal can provide an effective research material for the metastin or metastin receptor and for investigation of the function and effect thereof.

To develop a drug for the treatment of diseases associated with the metastin or metastin receptor, including the function inactive type inadaptability to the metastin or metastin receptor, using the DNA transgenic animal of the present invention, an effective and rapid method for screening can be provided by using the method for inspection and the method for quantification, etc. described above. It is also possible to investigate and develop a method for DNA therapy for the treatment of diseases associated with the metastin or metastin receptor, using the DNA transgenic animal of the present invention or a vector capable of expressing the exogenous DNA of the present invention.

(8) Knockout Animal

The present invention provides a non-human mammal embryonic stem cell bearing the DNA encoding the metastin or metastin receptor (hereinafter briefly referred to as the DNA of the present invention) inactivated and a non-human mammal deficient in expressing the DNA of the present invention.

Thus, the present invention provides:

(i) A non-human mammal embryonic stem cell in which the DNA of the present invention is inactivated;

(ii) The embryonic stem cell according to (i), wherein the DNA is inactivated by introducing a reporter gene (e.g., β-galactosidase gene derived from *Escherichia coli*);

(iii) The embryonic stem cell according to (i), which is resistant to neomycin;

(iv) The embryonic stem cell according to (i), wherein the non-human mammal is a rodent;

(v) The embryonic stem cell according to (iv), wherein the rodent is mouse;

(vi) A non-human mammal deficient in expressing the DNA of the present invention, wherein the DNA is inactivated;

(vii) The non-human mammal according to (vi), wherein the DNA is inactivated by inserting a reporter gene (e.g., β-galactosidase derived from *Escherichia coli*) therein and the reporter gene is capable of being expressed under control of a promoter for the DNA of the present invention;

(viii) The non-human mammal according to (vi), which is a rodent;

(ix) The non-human mammal according to (viii), wherein the rodent is mouse; and, (x) A method of screening a compound that promotes or inhibits (preferably inhibits) the promoter activity to the DNA of the present invention, which comprises administering a test compound to the mammal of (vii) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the peptide of the present invention (hereinafter sometimes referred to as the knockout DNA of the present invention) by substantially inactivating the activities of the peptide of the present invention encoded by the DNA (hereinafter briefly referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter simply referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. Embryos are preferably collected at the 8-cell stage, after culturing until the blastocyte stage; the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking incubation time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of incubation.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for cytological study of the peptide of the present invention or the receptor protein of the present invention in vitro.

The non-human mammal deficient in expression of the DNA of the present invention can be identified from a normal animal by measuring the mRNA level in the subject animal by a publicly known method, and indirectly comparing the degrees of expression.

As the non-human mammal, the same examples given above apply.

With respect to the non-human mammal deficient in expression of the DNA of the present invention, the DNA of the present invention can be knockout by transfecting a targeting vector, prepared as described above, to mouse embryonic stem cells or mouse oocytes, and conducting homologous recombination in which a targeting vector DNA sequence, wherein the DNA of the present invention is inactivated by the transfection, is replaced with the DNA of the present invention on a chromosome of a mouse embryonic stem cell or mouse embryo.

The knockout cells with the disrupted DNA of the present invention can be identified by the southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the peptide of the present invention. The individuals deficient in homozygous expression of the peptide of the present invention can be obtained from offspring of the intercross between those deficient in heterozygous expression of the peptide of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the peptide of the present invention, such an animal can be a disease model suspected of inactivated biological activities of the peptide of the present invention and thus, offers an effective study to investigate the causes for and therapy for these diseases.

(8a) Method of Screening the Substance Having Therapeutic/Prophylactic Effects on Diseases Caused by Deficiency, Damages, Etc. of the DNA of the Present Invention The non-human mammal deficient in expression of the DNA of the present invention can be employed for screening the compound having therapeutic/prophylactic effects on diseases caused by deficiency, damages, etc. of the DNA of the present invention (e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity).

That is, the present invention provides a method of screening the substance having therapeutic/prophylactic effects on diseases caused by deficiency, damages, etc. of the DNA of the present invention, which comprises administering a test compound to a non-human mammal deficient in expression of the DNA of the present invention and observing/measuring a change occurred on the animal.

As the non-human mammal deficient in expression of the DNA of the present invention, which can be employed for the screening method, the same examples as described above apply.

The same examples of the test compound apply to specific compounds described above.

Specifically, the non-human mammal deficient in expression of the DNA of the present invention is treated with a test compound, comparison is made with an intact animal for control and a change in each organ, tissue, disease conditions, etc. of the animal is used as an indicator to assess the therapeutic/prophylactic effects of the test compound.

For treating an animal to be tested with a test compound, for example, oral administration, intravenous injection, etc. are applied, and the treatment can be appropriately selected depending on conditions of the test animal, properties of the test compound, etc. Furthermore, a dose of the test compound to be administered can be appropriately chosen depending on the administration route, property of the test compound, etc.

In the screening method, when a test compound is administered to animal under test and disease conditions of the animal are improved by at least about 10%, preferably at least about 30% and more preferably at least about 50%, the test compound can be selected as a substance having therapeutic/prophylactic effects on the diseases described above.

Specifically, the test compound can be used as, e.g., a hyperglycemic agent, a pancreatic glucagon secretagogue agent or a urine formation promoting agent, and further as an agent for preventing/treating, e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

In addition, the test compound is applicable also as a test agent to examine the function of increasing blood glucose, promoting pancreatic glucagon secretion or promoting urine formation.

The substance obtained using the above screening method is a substance selected from the test compounds described above and exhibits therapeutic/prophylactic effects on diseases caused by deficiencies, damages, etc. of the metastin or metastin receptor. Therefore, the substance can be employed as a safe and low toxic pharmaceutical such as a prophylactic/therapeutic agent for these diseases.

Furthermore, substances derived from the substance obtained by the screening described above may be used as well.

The substance obtained by the screening method above may form salts, and may be used in the form of salts with physiologically acceptable acids (e.g., inorganic acids, organic acids, etc.) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical comprising the substance obtained by the above screening method or salts thereof can be manufactured in a manner similar to the method for preparing the pharmaceutical comprising metastin described above.

Since the pharmaceutical preparation thus obtained is safe and low toxic, it can be administered to human or mammal (e.g., rat, mouse, guinea pig, rabbit, sheep, swine, bovine, horse, cat, dog, monkey, etc.).

A dose of the substance may vary depending upon target disease, subject to be administered, route of administration, etc. For example, where the substance is orally administered, the compound is generally administered to an adult patient (as 60 kg body weight) in a daily dose of about 0.1 to about 100 mg, preferably about 1.0 to about 50 mg and more preferably about 1.0 to about 20 mg. In parenteral administration, a single dose of the substance may vary depending upon subject to be administered, target disease, etc.; for example, where the substance is administered to an adult patient (as 60 kg body weight) in the form of injectable preparation, it is advantageous to administer the substance intravenously generally in a daily dose of about 0.01 to about 30 mg, preferably about 0.1 to about 20 mg, and more preferably about 0.1 to about 10 mg. For other animal species, the corresponding dose as converted per 60 kg weight can be administered.

(8b) Method of Screening a Compound that Promotes or Inhibits the Activity of a Promoter for the DNA of the Present Invention The present invention provides a method of screening a substance that promote or inhibit the activity of a promoter for the DNA of the present invention, which comprises administering a test compound to a non-human mammal deficient in expression of the DNA of the present invention and detecting the expression of a reporter gene.

In the screening method described above, an animal in which the DNA of the present invention is inactivated by introducing a reporter gene and the reporter gene is expressed under control of a promoter for the DNA of the present invention is used as the non-human mammal deficient in expression of the DNA of the present invention, which is selected from the aforesaid non-human mammals deficient in expression of the DNA of the present invention.

The same examples of the test compound apply to specific compounds described above.

As the reporter gene, the same specific examples apply to this screening method. Preferably, there are used β-galactosidase (lacZ), soluble alkaline phosphatase gene, luciferase gene and the like.

Since the reporter gene is present under control of a promoter for the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the peptide of the present invention is substituted with, e.g., β-galactosidase gene (lacZ) derived from *Escherichia coli*, β-galactosidase is expressed in a tissue where the peptide of the present invention should originally be expressed, instead of the peptide of the present invention. Thus, the state of expression of the peptide of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the peptide of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The substance obtained using the screening method described above is a substance that is selected from the test compounds described above and that promotes or inhibits the activity of a promoter for the DNA of the present invention.

The substance obtained by the screening method above may form salts, and may be used in the form of salts with physiologically acceptable acids (e.g., inorganic acids, etc.) or bases (e.g., organic acids, etc.) or the like, especially in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The substance promoting the activity of a promoter for the DNA of the present invention can promote the expression of the metastin or metastin receptor and can promote the function of metastin. Thus, the substance is useful as a hyperglycemic agent, a pancreatic glucagon secretagogue agent or a urine formation promoting agent.

In addition, the substance that promotes the activity of a promoter for the DNA of the present invention is useful as an agent for preventing/treating, e.g., obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

On the other hand, the substance that inhibits the activity of a promoter for the DNA of the present invention inhibits the expression of the metastin or metastin receptor, and is thus useful as, e.g., a hypoglycemic agent, a pancreatic glucagon secretion suppressing agent or a urine formation suppressing agent.

Furthermore, the substance that inhibits the activity of a promoter for the DNA of the present invention can be used as an agent for preventing/treating, e.g., diabetes mellitus, impaired glucose tolerance, ketosis, acidosis, diabetic neuropathy, diabetic nephropathy, diabetic retinopathy, pollakiuria, nocturnal enuresis, hyperlipemia, sexual dysfunction, skin disorders, arthropathy, osteopenia, arteriosclerosis, thrombotic disorders, dyspepsia or deficits in memory and learning.

Moreover, substances derived from the substance obtained by the screening described above may be used as well.

A pharmaceutical comprising the substance obtained by the above screening method or salts thereof can be manufactured in a manner similar to the method for preparing the pharmaceutical comprising metastin described above.

Since the pharmaceutical preparation thus obtained is safe and low toxic, it can be administered to human or mammal (e.g., rat, mouse, guinea pig, rabbit, sheep, swine, bovine, horse, cat, dog, monkey, etc.).

A dose of the substance may vary depending upon target disease, subject to be administered, route of administration, etc. For example, where a substance that promotes or inhibits the activity of a promoter for the DNA of the present invention is orally administered, the substance is administered to an adult patient (as 60 kg body weight) generally in a daily dose of about 0.1 to about 100 mg, preferably about 1.0 to about 50 mg and more preferably about 1.0 to about 20 mg. In parenteral administration, a single dose of the substance may vary depending upon subject to be administered, target disease, etc. For example, where a substance that promotes or inhibits the activity of a promoter for the DNA of the present invention is administered in the form of injectable preparation, it is advantageous to administer the substance intravenously to an adult patient (as 60 kg body weight) generally in a daily dose of about 0.01 to about 30 mg, preferably about 0.1 to about 20 mg, and more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt that promotes or inhibits the promoter activity to the DNA of the present invention and, can greatly contribute to elucidation of causes for various diseases suspected of deficiency in expression of the DNA of the present invention and for the development of prophylactic/therapeutic agents for these diseases.

In addition, a so-called transgenic animal (gene transferred animal) can be prepared by using a DNA containing the promoter region of the peptide of the present invention, ligating genes encoding various proteins at the downstream and injecting the same into oocyte of an animal. It is thus possible to synthesize the peptide therein specifically and study its activity in vivo. When an appropriate reporter gene is ligated to the promoter site described above and a cell line that expresses the gene is established, the resulting system can be utilized as the search system for a low molecular compound having the action of specifically promoting or inhibiting the in vivo productivity of the peptide itself of the present invention.

The present invention will be further described in detail with reference to the following EXAMPLES, PREPARATION EXAMPLES and TEST EXAMPLES but these examples are given by way of illustration, not by way of limitation, and may be varied without departing from the scope of the present invention.

In the following EXAMPLES, the "room temperature" usually denotes from about 10° C. to about 35° C., % denotes mol/mol % in the case of a yield, denotes volume % in the case of a solvent used in chromatography, and denotes weight % in other cases. In the proton NMR spectrum, protons such as OH and NH protons, etc., which can not be confirmed because they are broad, are not shown in the data.

The other abbreviations used in the specification mean as follows.

| Abbreviation | Description |
|---|---|
| 10Ψ,CSNH: | The C-terminal $CONH_2$ at the 10-position is substituted with —$CSNH_2$. |
| 1Ψ2,$CH_2$NH: | The —CONH— bond between the 1- and 2-positions is substituted with the —$CH_2$NH— bond. |
| 2Ψ3,$CH_2$NH: | The —CONH— bond between the 2- and 3-positions is substituted with the —$CH_2$NH— bond. |
| 3Ψ4,$CH_2$NH: | The —CONH— bond between the 3- and 4-positions is substituted with the —$CH_2$NH— bond. |
| 4Ψ5,$CH_2$NH: | The —CONH— bond between the 4- and 5-positions is substituted with the —$CH_2$NH— bond. |
| 6Ψ7,CSNH: | The —CONH— bond between the 6- and 7-positions is substituted with the —CSNH— bond. |
| 6Ψ7,NHCO: | The —CONH— bond between the 6- and 7-positions is substituted with the —NHCO— bond. |
| 6Ψ7,$CH_2$NH: | The —CONH— bond between the 6- and 7-positions is substituted with the —$CH_2$NH— bond. |
| 7Ψ8,$CH_2$NH: | The —CONH— bond between the 7- and 8-positions is substituted with the —$CH_2$NH— bond. |
| 8Ψ9,$CH_2$NH: | The —CONH— bond between the 8- and 9-positions is substituted with the —$CH_2$NH— bond. |
| 9Ψ10,$CH_2$NH: | The —CONH— bond between the 9- and 10-positions is substituted with the —$CH_2$NH— bond. |
| Abu: | 2-aminobutanic acid |
| Ac: | acetyl |
| AcOEt: | ethyl acetate |
| AcOH: | acetic acid |
| Ala(2-Qui): | 2-quinolylalanine |
| Ala(3-Bzt): | 3-benzothienylalanine |
| Arg(Ac): | $N^{\omega}$-acetylarginine |
| Arg($Boc_2$,Me): | $N^{\omega,\omega'}$-bis-tert-butoxycarbonyl-$N^{\omega}$-methylarginine |
| Arg(Et): | $N^{\omega}$-ethylarginine |
| Arg(Me): | $N^{\omega}$-methylarginine |
| Arg(asy$Me_2$): | asymmetric-$N^{\omega,\omega'}$-dimethylarginine |
| Arg(sym$Me_2$): | symmetric-$N^{\omega,\omega'}$-dimethylarginine |
| Arg(n-Pr): | $N^{\omega}$-propylarginine |
| AzaGly: | azaglycine |
| β-Ala: | β-alanine |
| Boc: | tert-butoxycarbonyl |
| Br-Z: | 2-bromobenzyloxycarbonyl |
| $Bu^t$: | tert-butyl |
| Bzl: | benzyl |
| CDI: | 1,1'-carbonyldiimidazole |
| Cha: | cyclohexylalanine |
| CIP: | 2-chloro-1,3-dimethylimidazolium tetrafluoroborate |
| Cit: | citrulline |
| Clt resin: | 2-chlorotrytyl resin |
| Cl-Z: | 2-chlorobenzyloxycarbonyl |
| Dab: | 1,4-diaminobutanoic acid |
| Dap: | 1,3-diaminopropionic acid |
| Dap(Gly): | $N^{\beta}$-glycyldiaminopropionic acid |
| Dap(GnGly): | $N^{\beta}$-(N-guanidinoglycyl)diaminopropionic acid |
| DCM: | dichloromethane |
| DEA: | diethylamine |
| DIEA: | N,N-diisopropylethylamine |
| DMF: | N,N-dimethylformamide |
| EDT: | ethanedithiol |
| Fmoc: | 9-fluorenylmethoxycarbonyl |
| Gn: | guanidino |
| Har: | homoarginine |
| Har(Me): | $N^{\omega}$-methylhomoarginine |
| HOAt: | 1-hydroxy-7-azabenzotriazole |
| HOBt: | 1-hydroxybenzotriazole |

| Abbreviation | Description |
| --- | --- |
| HONB: | N-hydroxy-5-norbornene-2,3-dicarboxamide |
| Hph: | homophenylalanine |
| IndPr: | 3-(indol-3-yl)propionyl |
| Lys(Me$_2$): | N$^{\epsilon,\epsilon}$-dimethyllysine |
| MBHA: | p-methylbenzhydrylamine |
| MeOH | methanol |
| N((CH$_2$)$_3$Gn)Gly: | N-(3-guanidinopropyl)glycine |
| Nal(1): | 1-naphthylalanine |
| Nal(2): | 2-naphthylalanine |
| Nar: | norarginine |
| Nar(Me): | N$^\omega$-methylnorarginine |
| Nle: | norleucine |
| NMeArg: | N$^\alpha$-methylarginine |
| NMeLeu: | N$^\alpha$-methylleucine |
| NMePhe: | N$^\alpha$-methylphenylalanine |
| NMeSer: | N$^\alpha$-methylserine |
| Orn: | ornithine |
| Orn(Mtt): | N$^\delta$-(4-methyltrytyl)ornithine |
| PAL: | 5-(4-(9-fluorenylmethoxycarbonyl)aminomethyl3,5-dimethoxy-phenoxy)valeric acid |
| Pbf: | 2,2,4,6,7-pentamethyldihydrobenzofuran-5-sulfonyl |
| Phe(2Cl): | 2-chlorophenylalanine |
| Phe(2F): | 2-fluorophenylalanine |
| Phe(3,4Cl$_2$): | 3,4-dichlorophenylalanine |
| Phe(3,4F$_2$): | 3,4-difluorophenylalanine |
| Phe(3CF$_3$): | 3-trifluoromethylphenylalanine |
| Phe(3Cl): | 3-chlorophenylalanine |
| Phe(3F): | 3-fluorophenylalanine |
| Phe(4Cl): | 4-chlorophenylalanine |
| Phe(4CN): | 4-cyanophenylalanine |
| Phe(4F): | 4-fluorophenylalanine |
| Phe(4Gn): | 4-guanidinophenylalanine |
| Phe(4NH$_2$): | 4-aminophenylalanine |
| Phe(4NO$_2$): | 4-nitrophenylalanine |
| Phe(4CN): | 4-cyanophenylalanine |
| Phe(F$_5$): | pentafluorophenylalanine |
| PheΨ(CSNH)—NH$_2$: | The C-terminal phenylalanylamide is substituted with the phenylalanylthioamide. |
| Phg: | phenylglycine |
| PhOH: | phenol |
| PhSMe: | thioanisole |
| Pro: | proline |
| Pya(2): | 2-pyridylalanine |
| Pya(3): | 3-pyridylalanine |
| Pya(4): | 4-pyridylalanine |
| PyAOP: | (7-azabenzotriazole-l-yloxy)-tris(pyrrolidino)phosphonium hexafluorophosphate |
| PyBOP: | (benzotriazole-1-yloxy)-tris(pyrrolidino)phosphonium hexafluorophosphate |
| PyBrop: | bromo-tris(pyrrolidino)phosphonium hexafluorophosphate |
| Sar: | N-methylglycine |
| Tle: | tert-leucine |
| Trp(For): | N$^{in}$-formyltryptophan |
| Tyr(Me): | O-methyltyrosine |
| TyrΨ(CH$_2$NH)Asn: | The —CONH— bond between Tyr and Asn is substituted with the —CH$_2$NH— bond. |
| TFA: | trifluoroacetic acid |
| TFE: | trifluoroethanol |

When bases, amino acids, etc. are indicated by abbreviations in the specification and drawings, the abbreviations are denoted in accordance with the IUPAC-IUB Commission on Biochemical Nomenclature or by the common abbreviations in the art, examples of which are shown below. When the amino acids may have the optical isomer, L form is presented unless otherwise indicated.

DNA: deoxyribonucleic acid
cDNA: complementary deoxyribonucleic acid
A: adenine
T: thymine
G: guanine
C: cytosine
Y: thymine or cytosine
N: thymine, cytosine, adenine or guanine
R: adenine or guanine
M: cytosine or adenine
W: thymine or adenine
S: cytosine or guanine
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
TFA: trifluoroacetic acid
EIA: enzyme immunoassay Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
H is or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid The sequence identification numbers in the sequence listing of the specification indicates the following sequence, respectively.

SEQ ID NO: 1
This shows the amino acid sequence of human-derived metastin.
SEQ ID NO: 2
This shows the base sequence of DNA encoding human metastin.
SEQ ID NO: 3
This shows the amino acid sequence of mouse metastin precursor (A).
SEQ ID NO: 4
This shows the base sequence of DNA encoding mouse metastin precursor (A), which is the base sequence contained in plasmid pCMV-mKiSS-1 harbored on transformant *Escherichia coli* DH10B/pCMV-mKiSS-1.
SEQ ID NO: 5
This shows the amino acid sequence of mouse metastin precursor (B).
SEQ ID NO: 6
This shows the base sequence of DNA encoding mouse metastin precursor (B), which is the base sequence contained in plasmid pCR2.1-mKiSS-1.4A harbored on transformant *Escherichia coli* DH5αc/pCR2.1-mKiSS-1.4A.
SEQ ID NO: 7
This shows the amino acid sequence of rat-derived metastin precursor.
SEQ ID NO: 8
This shows the base sequence of DNA encoding rat metastin precursor.
SEQ ID NO: 9
This shows the amino acid sequence of human OT7T175 (metastin receptor).
SEQ ID NO: 10
This shows the base sequence of DNA encoding human OT7T175 (metastin receptor).
SEQ ID NO: 11
This shows the amino acid sequence of rat OT7T175 (metastin receptor).
SEQ ID NO: 12
This shows the base sequence of DNA encoding rat OT7T175 (metastin receptor).
SEQ ID NO: 13
This shows the amino acid sequence of mouse OT7T175 (metastin receptor).
SEQ ID NO: 14
This shows the base sequence of DNA encoding mouse OT7T175 (metastin receptor).
SEQ ID NO: 15
This shows the amino acid sequence of human metastin 15 (40-54).
SEQ ID NO: 16
This shows the amino acid sequence of human metastin 10 (45-54) (MS10).
SEQ ID NO: 17
This shows the amino acid sequence of human metastin 9 (46-54).
SEQ ID NO: 18
This shows the amino acid sequence of human metastin 8 (47-54).
SEQ ID NO: 19
This shows the base sequence of DNA encoding human metastin 15 (40-54).
SEQ ID NO: 20
This shows the base sequence of DNA encoding human metastin 10 (45-54).
SEQ ID NO: 21
This shows the base sequence of DNA encoding human metastin 9 (46-54).
SEQ ID NO: 22
This shows the base sequence of DNA encoding human metastin 8 (47-54).

The transformant *Escherichia coli* DH10B/pCMV-mKiSS-1 has been on deposit since Jan. 24, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan as the Accession Number FERM BP-7003 and since Dec. 16, 1999 with Institute for Fermentation (IFO), located at 2-17-85 Juso-honmachi, Yodogawa-ku, Osaka-shi, Osaka, Japan, as the Accession Number IFO 16348.

The transformant *Escherichia coli* DH5α/pCR2.1-mKiSS-1.4A has been on deposit since Mar. 6, 2000 with International Patent Organisms Depository, National Institute of Advanced Industrial Science and Technology (the former Ministry of International Trade and Industry, Agency of Industrial Science and Technology, National Institute of Bioscience and Human Technology (NIBH)), located at Central 6, 1-1-1 Higashi, Tsukuba, Ibaraki (postal code 305-8566), Japan as the Accession Number FERM BP-7073 and since Feb. 16, 2000 with Institute for Fermentation (IFO) as the Accession Number IFO 16360.

In the present invention, Tyr-Asn-Trp-Asn-Ser-Phe-Gly-Leu-Arg-Phe-NH$_2$ (SEQ ID NO: 16) is referred to as Metastin 10, namely, MS10.

In EXAMPLES later described, the N-terminal Tyr and the C-terminal Phe in MS10 are counted as the 1- and 10-positions, respectively.

(SEQ ID NO: 16)
Tyr-Asn-Trp-Asn-Ser-Phe-Gly-Leu-Arg-Phe-NH$_2$
1   2   3   4   5   6   7   8   9   10

For example, [Hph10]MS10 of Compound No. 79 (EXAMPLE 1) means a peptide wherein the C-terminal Phe (10-position) of MS10 is substituted with Hph.

For example, des(1)-MS10 of Compound No. 4 means a peptide wherein the N-terminal Tyr (1-position) is deleted.

For example, des(1-3)-Fmoc-MS10 of Compound No. 53 means a peptide wherein the N-terminal Tyr-Asn-Trp (1 to 3-positions) is deleted and the amino group of Asn at the 4-position is modified with Fmoc.

EXAMPLES

Example 1

(Synthesis Process A): Preparation of [Hph10]MS10 (Compound No. 79)

Using 51 mg of Fmoc-Hph-PAL resin (sub. 0.39 mmol/g), which was prepared by introducing Fmoc-Hph into PAL resin commercially available, the peptide chain was extended on a multiple peptide synthesizer ACT-396 to give Tyr(Bu$^t$)Asn(Trt)Trp(Boc)Asn(Trt)Ser(Bu$^t$)PheGlyLeuArg(Pbf)Hph-PAL resin (SEQ ID NO: 211). To 18.2 mg of the resin, 200 µL of TFA/PhSMe/m-cresol/TIS/EDT (85/5/5/2.5/2.5) was added and the mixture was shaken for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B: 73/27-63/37 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 2.6 mg of white powders.

Mass spectrum (M+H)$^+$ 1316.5 (Calcd. 1316.7)
Elution time on HPLC: 20.6 mins.
Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.).
Flow rate: 1.0 ml/min.

Example 2

(Synthesis Process B): Preparation of [Trp(For)10]MS10 (Compound No. 186)

Using 379 mg of Fmoc-Arg(Pbf)-O-Clt resin (sub. 0.33 mmol/g), which was prepared by introducing Fmoc-Arg(Pbf)-OH into 2-chlorotritylchloride resin (Clt resin, 1.33 mmol/g) commercially available, the peptide chain was extended on ABI 433A to give 540 mg of Boc-Tyr(Bu$^t$)Asn(Trt)Trp(Boc)Asn(Trt)Ser(Bu$^t$)PheGlyLeuArg(PbO-O-Clt resin (SEQ ID NO: 212). To 270 mg of the peptide, 10 mL of AcOH/TFE/DCM (1/1/8) was added the mixture was shaken for 30 minutes. After the resin was removed by filtration, the solvent was concentrated and the residue was dissolved in AcOEt. The solution was then washed with satd. NaCl aq. solution. After drying over Na$_2$SO$_4$, the solvent was concentrated and diethyl ether-petroleum ether was added to the residue to give 68 mg of Boc-Tyr(Bu$^t$)Asn(Trt)Trp(Boc)Asn(Trt)Ser(Bu$^t$)PheGlyLeuArg(Phe-OH (SEQ ID NO: 213) as precipitates. To 22 mg of the peptide, 4 mg of HCl H-Trp(For)-NH$_2$ (prepared by treating Boc-Trp(For)-NH$_2$ with 9.7 N HCl/dioxan at 0° C. for 30 minutes), 10 mg of PyAOP, 5 mg of HOAt and 11 µL of DIEA were added. The mixture was stirred for 15 hours. After the solvent was concentrated, chloroform-diethyl ether was added to the residue to give Boc-Tyr(Bu$^t$)Asn(Trt)Trp(Boc)Asn(Trt)Ser(Bu$^t$)PheGlyLeuArg(Pbf)Trp(For)-NH$_2$ (SEQ ID NO: 214) as precipitates. To the peptide, 1 mL of TFA/PhSMe/m-cresol/TIS/EDT (85/5/5/2.5/2.5) was added and the mixture was stirred for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B:73/27-63/37 using eluant A: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 2.0 mg of white powders.

Mass spectrum (M+H)$^+$ 1369.3 (Calcd. 1369.6)
Elution time on HPLC: 19.6 mins.
Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.)
Flow rate: 1.0 ml/min.

Example 3

(Synthesis Process C): Preparation of [10Ψ,CSNH]MS10 (Compound No. 128)

After 264 mg of Boc-Phe-NH$_2$ was dissolved in 20 mL of THF, 1.62 g of Lawesson's reagent was added to the solution, followed by stirring for 24 hours. Insoluble matters were removed by filtration, the solvent was concentrated and the concentrate was dissolved in AcOEt. The solution was washed with satd. NaHCO$_3$ aq. solution and then satd. NaCl aq. solution. After drying over Na$_2$SO$_4$, the solvent was concentrated and the concentrate was purified by flush column chromatography. Diethyl ether-petroleum ether was added to give 275 mg (yield 98%) of (S)-2-tert-Butoxycarbonylamino-3-phenylpropanethioamide (Boc-PheΨ(CSNH)—NH$_2$) as precipitates. After 42 mg of the peptide was treated at 0° C. with 9.7 N HCl to remove Boc, the removal of Fmoc with 10% DEA/DMF treatment followed by condensation by the PyBOP/HOBt method were repeated to give 66 mg of Fmoc-LeuArg(Pbf)PheΨ(CSNH)—NH$_2$ (yield 93%). To 17 mg of Boc-Tyr(Bu$^t$)Asn(Trt)Trp(Boc)Asn(Trt)Ser(Bu$^t$)PheGly-OH (SEQ ID NO: 215) prepared as in EXAMPLE 2, H-LeuArg(Pbf)PheΨ(CSNH)—NH$_2$ (prepared by treating 14 mg of Fmoc-LeuArg(Pbf)PheΨ(CSNH)—NH$_2$ with 10% DEA/DMF), 9 mg of PyBrop, 3 mg of HOAt and 7 mL of DIEA were added and the mixture was stirred for 15 hours. After the solvent was concentrated, chloroform-diethyl ether was added thereto for precipitation. To 10 mg of the product, 100 µL of TFA/PhSMe/m-cresol/TIS/EDT (85/5/5/2.5/2.5) was added and the mixture was stirred for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B:72/28-62/38 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 1.0 mg of white powders.

Mass spectrum (M+H)$^+$ 1318.4 (Calcd. 1318.6)
Elution time on HPLC: 21.8 mins.

Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.)
Flow rate: 1.0 ml/min.

Example 4

(Synthesis Process D): Preparation of [6Ψ7,CH$_2$NH]MS10 (Compound No. 163)

Using 321 mg of Fmoc-Phe-PAL resin, which was prepared by introducing Fmoc-Phe into PAL resin commercially available, the peptide chain was extended on ABI 433A to give Fmoc-LeuArg(Pbf)Phe-PAL resin. To a half volume of the peptide, Fmoc-Gly was condensed to give 190 mg of Fmoc-GlyLeuArg(Pbf)Phe-PAL resin (SEQ ID NO: 216). After 76 mg of the product was subjected to Fmoc deprotection, 2 mL of DMF, 50 μl of AcOH, 46 mg of Fmoc-Phe-H and 8 mg of NaBH$_3$CN were added thereto, followed by shaking an hour. After washing the resin, 2 mL of DMF, 22 μL of DIEA and 18 μL of Z—Cl were added thereto and the mixture was shaken for 3 hours. After washing the resin, the peptide chain was extended on ABI 433A to give Boc-Tyr(Bu$^t$)Asn(Trt)Trp(Boc)Asn(Trt)Ser(Bu$^t$)PheΨ(CH$_2$NH)GlyLeuArg(PbF)Phe-PAL resin (SEQ ID NO: 217). Under ice cooling, 46 μL of TMS-Br, 42 μL of PhSMe, 38 μL of m-cresol, 18 μL of EDT and 227 μL of TFA were added to 15 mg of the peptide an the mixture was stirred for 2 hours. After the solvent was removed by distillation, diethyl ether was added to the residue, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B:72/28-62/38 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 2.0 mg of white powders.
Mass spectrum (M+H)$^+$ 1288.7 (Calcd. 1288.7)
Elution time on HPLC: 18.2 mins.
Elution conditions:
Column: Wakosil-II 5C18 HG (4.6×100 mm)
Eluant: linear density gradient elution with eluants A/B=100/0-0/70, using 0.1% TFA in water as eluant A and 0.1% TFA-containing acetonitrile (35 mins.)
Flow rate: 1.0 ml/min.

Example 5

(Synthesis Process E): Preparation of [Arg(Me)9]MS10 (Compound No. 82)

In 20 mL of dry DMF, 360 mg of 60% NaH in oil was dissolved and 10 mL of dry DMF solution of 2793 mg of N,N'-Bis-Boc-1-guanylpyrazole was added to the solution at 0° C. The mixture was stirred for 10 minutes. Then, 748 μL of methyl iodide was added to the mixture, followed by stirring at room temperature for 24 hours. After the solvent was removed by distillation, the residue was dissolved in AcOEt, and washed with satd. NaHCO$_3$ aq. solution and then with satd. NaCl aq. solution After drying over Na$_2$SO$_4$, the solvent was concentrated. Purification by flash column chromatography gave 2.96 g of N-methyl-N,N'-bis-Boc-1-guanylpyrazole (yield 91%). Using 480 mg of Fmoc-Phe-Rink Amide MBHA resin, which was prepared by introducing Fmoc-Phe into Rink Amide MBHA resin commercially available, the peptide chain was extended on ABI 433A to give 1080 mg of Boc-Tyr(Bu$^t$)Asn(Trt)Trp(Boc)Asn(Trt)Ser(Bu$^t$)PheGlyLeuOrn(Mtt)Phe-Rink Amide MBHA resin (SEQ ID NO: 218). To 540 mg of the peptide, 10 mL of TFA/TIS/DCM (1/5/94) was added and the mixture was shaken for 50 minutes. The resin was washed and then dried. After 2 mL of DMF, 49 mg of N-methyl-N,N'-bis-Boc-1-guanylpyrazole prepared in REFERENCE EXAMPLE 1 and 87 μL of DIEA were added to 2/5 volume of the resin, the mixture was shaken for 15 hours to give 220 mg of Boc-Tyr(Bu$^t$)Asn(Trt)Trp(Boc)Asn(Trt)Ser(Bu$^t$)PheGlyLeuArg(Boc$_2$,Me)Phe-Rink Amide MBHA resin (SEQ ID NO: 219). To 50 mg of the peptide, 1 mL of TFA/PhSMe/m-cresol/TIS/EDT (85/5/5/2.5/2.5) was added and the mixture was stirred for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (30 minutes) was performed with eluants A/B:74/26-64/36 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 10.5 mg of white powders.
Mass spectrum (M+H)$^+$ 1316.5 (Calcd. 1316.7)
Elution time on HPLC: 20.1 mins.
Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.)
Flow rate: 1.0 ml/min.

Example 6

(Synthesis Process F): Preparation of [6Ψ7,CSNH]MS10 (Compound No. 166)

After 503 mg of HCl H-Gly-OBu$^t$ was dissolved in 10 mL of DMF, 1162 mg of Fmoc-Phe, 608 mg of HOBt, 1874 mg of PyBOP and 784 μL of DIEA were added to the solution at 0° C. The mixture was stirred for 4 hours. The solvent was then removed by distillation. The residue was dissolved in AcOEt and the solution was washed with 1N HCl aq. solution, satd. NaHCO$_3$ aq. solution and then satd. NaCl aq. solution. After drying over Na$_2$SO$_4$, the solvent was concentrated and diethyl ether-petroleum ether was added to give 1.48 g of Fmoc-PheGly-OBu$^t$ as precipitates (yield 99%). After 250 mg of the product was dissolved in 10 mL of toluene, 404 mg of Lawesson's reagent was added to the solution, followed by stirring at 80° C. for 2 hours. The solvent was concentrated and the concentrate was dissolved in AcOEt. The solution was then washed with satd. NaHCO$_3$ aq. solution and then satd. NaCl aq. solution. After drying over Na$_2$SO$_4$, the solvent was concentrated and the concentrate was purified by flush column chromatography. Diethyl ether-petroleum ether was added to the eluate to give 207 mg of Fmoc-PheΨ(CSNH)Gly-OBu$^t$ as precipitates (yield 80%). To 103 mg of the product, TFA/H$_2$O (95/5) was added and the mixture was stirred for an hour. After the solvent was concentrated, diethyl ether was added to give 82.4 mg of Fmoc-PheΨ(CSNH)Gly-OH as precipitates (yield 90%). Using Fmoc-Phe-PAL resin, which was prepared by introducing Fmoc-Phe into PAL resin commercially available, the peptide chain was extended on ABI 433A and 80 mg of Fmoc-LeuArg(Pbf)Phe-PAL resin thus extended was subjected to Fmoc deprotection. Then, 35 mg of Fmoc-PheΨ(CSNH)Gly-OH, 47 mg of PyBrop, 14 mg of HOAt and 35 µL of DIEA were added to the resin, and the mixture was shaken for 15 hours. After washing the resin, the peptide chain was extended on ABI 433A to give Boc-Tyr(Bu$^r$)Asn(Trt)Trp(Boc)Asn(Trt)Ser(Bu$^r$)PheΨ(CSNH)GlyLeuArg(Pbf)Phe-PA L resin (SEQ ID NO: 220). To 15 mg of the product, 200 µL of TFA/PhSMe/m-cresol/TIS/EDT (85/5/5/2.5/2.5) was added, followed by stirring for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Then, linear density gradient elution (60 minutes) was performed with eluants A/B:77/23-57/43 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 1.0 mg of white powders.

Mass spectrum (M+H)$^+$ 1318.7 (Calcd. 1318.6)
Elution time on HPLC: 20.8 mins.
Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.)
Flow rate: 1.0 ml/min.

Example 7

(Synthesis Process G): Preparation of [AzaGly7]MS10 (Compound No. 176)

Using 321 mg of Fmoc-Phe-PAL resin, which was prepared by introducing Fmoc-Phe into PAL resin commercially available, the peptide chain was extended on ABI 433A and 80 mg of Fmoc-LeuArg(Pbf)Phe-PAL resin thus extended was subjected to Fmoc deprotection. After 2 mL of THF and 16 mg of CDI were added, the mixture was shaken for 2 hours. Then 6 µL of hydrazine monohydrate was added to the mixture. The mixture was shaken for an hour and the resin was then washed. After 39 mg of Fmoc-Phe, 93 mg of PyBrop, 27 mg of HOAt and 105 µL of DIEA were added to the mixture, followed by shaking for 2 hours. The resin was washed and the peptide chain was extended on ABI 433A to give Boc-Tyr(Bu$^r$)Asn(Trt)Trp(Boc)Asn(Trt)Ser(Bu$^r$)PheAzaGlyLeuArg(Pbf)Phe-PAL resin (SEQ ID NO: 221). To 25 mg of the product, 1 mL of TFA/PhSMe/m-cresol/TIS/EDT (85/5/5/2.5/2.5) was added, and the mixture was shaken for 2 hours. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Linear density gradient elution (30 minutes) was performed with eluants A/B:74/26-64/36 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 5.5 mg of white powders.

Mass spectrum (M+H)$^+$ 1303.3 (Calcd. 1303.6)
Elution time on HPLC: 18.9 mins.
Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.)
Flow rate: 1.0 ml/min.

Example 8

(Synthesis Process H): Preparation of [D-Tyr1,AzaGly7,Arg(Me)9]MS10 (Compound No. 232)

Fmoc-Phe and Fmoc-Orn(Mtt) were introduced into 4 g (0.55 mmol/g) of Rink Amide MBHA resin commercially available to prepare Fmoc-Orn(Mtt)-Phe-Rink Amide MBHA resin, and 50 mL of TFA/TIS/DCM (1/5/94) was added to the resin. The mixture was then shaken for 50 minutes. After washing the resin, 40 mL of DCM and 2.27 g of N-methyl-N,N'-bis-Boc-1-guanylpyrazole prepared in EXAMPLE 5 were added to the resin. DIEA was added to the mixture to adjust pH of the solution to 9. The mixture was shaken for 15 hours to give 4.74 g of Fmoc-Arg(Boc$_2$,Me)Phe-Rink Amide MBHA resin. Separately, 145 mg of Fmoc-NHNH$_2$HCl was suspended in 10 mL of THF. Under ice cooling, 89 mg of CDI and 87 mL of DIEA were added to the suspension, followed by stirring at room temperature for an hour. Under ice cooling, a solution of 224 mg of H-Leu-OBu$^t$ HCl in 5 mL of DMF was added to the mixture. While reverting to room temperature, the mixture was stirred for 18 hours. After the solvent was distilled off, the residue was dissolved in AcOEt and the solution was washed with 1N HCl aq. solution, satd. NaHCO$_3$ aq. solution and then satd. NaCl aq. solution. After drying over Na$_2$SO$_4$, the solvent was concentrated. Purification by flush column chromatography gave 230 mg of Fmoc-AzaGly-Leu-OBu$^t$ (yield 99%). To 187 mg of the product, 10 mL of TFA/H$_2$O (9/1) was added, followed by stirring for an hour. After the solvent was distilled off, the residue was dissolved in AcOEt and the solution was washed with satd. NaCl aq. solution. After drying over Na$_2$SO$_4$, the solvent was concentrated and diethyl ether was added to give 143 mg of Fmoc-AzaGly-Leu-OH as precipitates (yield 87%). To Trt-Phe-AzaGly-Leu-Arg(Boc$_2$,Me)Phe-Rink Amide MBHA resin (SEQ ID NO: 222) prepared by introducing the resulting Fmoc-AzaGly-Leu-OH and Trt-Phe into Fmoc-Arg(Boc$_2$,Me)Phe-Rink Amide MBHA resin, 50 mL of TFA/TIS/DCM (1/5/94) was added and the mixture was shaken for 50 minutes. After the resin was washed and neutralized, Fmoc-Ser(Bu$^r$) and then Fmoc-Asn(Trt) were introduced into the resin. Using 80.3 mg of the resulting Fmoc-Asn(Trt)Ser(Bu$^r$)Phe-AzaGly-LeuArg(Boc$_2$,Me)Phe-Rink Amide MBHA resin (SEQ ID NO: 223), the peptide chain was extended to give 97.2 mg of H-$_D$-Tyr(Bu$^r$)Asn(Trt)Trp(Boc)Asn(Trt)Ser(Bu$^r$)Phe-AzaGly-LeuArg(Boc$_2$,Me)Phe-Rink Amide MBHA resin. To the resin obtained, 1 mL of TFA/PhSMe/m-cresol/H$_2$O/TIS/EDT (80/5/5/5/2.5/2.5) was added, and the mixture was stirred for 90 minutes. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Linear density gradient elution (60 minutes) was then performed with eluants A/B:76/24-66/34 using: 0.1% TFA in water and eluant B: 0.1% TFA-containing acetonitrile on preparative HPLC using YMC SH-343-5 S-5, 120A column (20×250 mm). The fractions containing the product were collected and lyophilized to give 11.7 mg of white powders.

Mass spectrum (M+H)⁺ 1317.0 (Calcd. 1317.6)
Elution time on HPLC: 21.0 mins.
Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.)
Flow rate: 1.0 ml/min.

Example 9

(Synthesis Process I): Preparation of des(1-3)-3-pyridinepropionyl-[AzaGly7,Arg(Me)9]MS10 (Compound No. 322)

In Fmoc-Asn(Trt)Ser(Bu$^t$)Phe-AzaGly-LeuArg(Boc$_2$,Me)Phe-Rink Amide MBHA resin (SEQ ID NO: 224) prepared in EXAMPLE 8, 48.2 mg of the resin was subjected to Fmoc deprotection. The resin was treated with 15.2 mg of 3-(3-pyridyl)propionic acid commercially available, 15.9 µL of DIPCDI and 200 µL of 0.5M HOAt/DMF at room temperature for 90 minutes. After the resin obtained was washed and dried, 1 mL of TFA/PhSMe/m-cresol/H$_2$O/TIS/EDT (80/5/5/5/2.5/2.5) was added to the resin, and the mixture was stirred for 90 minutes. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Linear density gradient elution (60 minutes) was then performed with eluants A/B:80/20-60/40 using: 0.1% TFA in water and eluant B: 0.1% TFA-containing acetonitrile on preparative HPLC using YMC SH-343-5 S-5, 120A column (20×250 mm). The fractions containing the product were collected and lyophilized to give 6.0 mg of white powders.
Mass spectrum (M+H)⁺987.4 (Calcd. 987.5)
Elution time on HPLC: 8.1 mins.
Elution conditions:
Column: YMC-AM301 (4.6×100 mm)
Eluant: linear density gradient elution with eluants A/B=80/20-30/70, using 0.1% TFA in water as eluant A and 0.1% TFA-containing acetonitrile (25 mins.)
Flow rate: 1.0 ml/min.

Example 10

(Synthesis Process J): Preparation of des(1-2)-Amidino-[AzaGly7,Arg(Me)9]MS10 (Compound No. 273)

After Fmoc-Trp(Boc) was introduced into 48.2 mg of Fmoc-Asn(Trt)Ser(Bu$^t$)Phe-AzaGly-LeuArg(Boc$_2$,Me)Phe-Rink Amide MBHA resin (SEQ ID NO: 223) prepared in EXAMPLE 8, the resin was subjected to Fmoc deprotection to give H-Trp(Boc)Asn(Trt)Ser(Bu$^t$)Phe-AzaGly-LeuArg(Boc$_2$,Me)Phe-Rink Amide MBHA resin (SEQ ID NO: 225). The resin thus obtained was treated in DMF with 29.3 mg of N,N'-bis-Boc-1-guanylpyrazole and 34.8 µL of DIEA for 14 hours at room temperature for 14 hours to give Amidino-Trp(Boc)Asn(Trt)Ser(Bu$^t$)Phe-AzaGly-LeuArg(Boc$_2$,Me)Phe-Rink Amide MBHA resin (SEQ ID NO: 226). After washing and drying the resin, 1 mL of TFA/PhSMe/m-cresol/H$_2$O/TIS/EDT (80/5/5/5/2.5/2.5) was added to the resin, and the mixture was stirred for 90 minutes. Diethyl ether was added to the reaction solution, the resulting precipitate was centrifuged and the supernatant was removed. This procedure was repeated for washing. The residue was extracted with an aqueous acetic acid solution and the extract was filtered to remove the resin. Linear density gradient elution (60 minutes) was then performed with eluants A/B: 78/22-58/42 using: 0.1% TFA in water and eluant B: 0.1% TFA-containing acetonitrile on preparative HPLC using YMC SH-343-5 S-5, 120A column (20×250 mm). The fractions containing the product were collected and lyophilized to give 0.6 mg of white powders.
Mass spectrum (M+H)⁺1082.3 (Calcd. 1082.6)
Elution time on HPLC: 11.4 mins.
Elution conditions:
Column: YMC-AM301 (4.6×100 mm)
Eluant: linear density gradient elution with eluants A/B=80/20-30/70, using 0.1% TFA in water as eluant A and 0.1% TFA-containing acetonitrile (25 mins.)
Flow rate: 1.0 ml/min.

Example 11

(Synthesis Process K): Preparation of [6ω7,NHCO,D-Tyr1,Arg(Me)9]MS10 (Compound No. 319)

In 30 mL of MeCN, 5.99 g of Z-Phe was dissolved, and 3.94 g of HONB and 4.59 g of WSCD HCl were added to the solution at 0° C., followed by stirring at room temperature for 4 hours. While keeping at 0° C., 3.4 mL of 25% NH$_3$ aq. solution and 10 mL of DMF were added to the mixture, followed by stirring for 4 hours. After the solvent was distilled off, the residue was dissolved in AcOEt and the solution was washed with 1N HCl aq. solution, satd. NaHCO$_3$ aq. solution and then satd. NaCl aq. solution. After drying over Na$_2$SO$_4$, the solvent was concentrated and diethyl ether was added to give 1.48 g of Z-Phe-NH$_2$ as precipitates (yield 99%). After 1.94 g of [Bis(trifluoroacetoxy)iodo]benzene was dissolved in 20 mL of MeCN and 5 mL of H$_2$O, 890 mg of Z-Phe-NH$_2$ prepared above and 972 µL of pyridine were added to the precipitate at 0° C., and the mixture was stirred at room temperature for 15 hours. After the solvent was concentrated, the concentrate was subjected to liquid-liquid separation with diethyl ether-1N HCl aq. solution. The 1N HCl aq. solution layer was concentrated and then dried. A half volume of the concentrate was dissolved in 5 mL of DMF, and 486 µL of mono-tert-butyl malonate and 540 mg of HOBt were added to the solution. Then, 2.08 g of PyBOP and 1394 µL of DIEA were added to the mixture at 0° C., followed by stirring at room temperature for 15 hours. The solvent was distilled off, the residue was dissolved in AcOEt and the solution was washed with 1N HCl aq. solution, satd. NaHCO$_3$ aq. solution and then satd. NaCl aq. solution. After drying over Na$_2$SO$_4$, the solvent was concentrated and the concentrate was purified by flush column chromatography. Diethyl ether-petroleum ether was added to give 304 mg (yield 33%) of Z-PheΨ(NHCO)Gly-OBu$^t$ as precipitates. After 154 mg of the product was dissolved in 20 mL of MeOH, 10% Pd—C was added to the solution, followed by catalytic hydrogenation for 2 hours in a hydrogen flow. After removal of the catalyst by filtration, the solvent was concentrated and dried. The residue was dissolved in 10 mL of MeCN 10 mL and 152 mg of Fmoc-OSu and 78 µL of DIEA were added to the solution, followed by stirring for 15 hours. After the solvent was distilled off, the residue was dissolved in AcOEt and the solution was washed with 1N HCl aq. solution, satd. NaHCO$_3$ aq. solution and then satd. NaCl aq. solution. After drying over Na$_2$SO$_4$, the solvent was concentrated and diethyl ether-petroleum ether was added to give 127 mg of Fmoc-PheΨ(NHCO)Gly-OBu$^t$ as precipitates (yield 68%). Fmoc-Leu was introduced into 63 mg of Fmoc-Arg(Boc$_2$,Me)Phe-Rink Amide MBHA resin prepared in EXAMPLE 10. Following Fmoc deprotection, Fmoc-PheΨ(NHCO)Gly-OH (prepared by treating 25 mg of Fmoc-PheΨ(NHCO)Gly-OBu$^t$ with TFA for 3 minutes), 300 μL of 0.5M HOAt, 78 mg of PyAOP and 52 μL of DIEA were added to the resin, and the mixture was shaken for 6 hours. After washing the resin, 2 mL of DMF, 9 μL of DIEA and 12 μL of Ac$_2$O were added to the resin, and the mixture was shaken for 30 minutes. After washing the resin, the peptide chain was extended on ABI 433A to give Boc-$_D$-Tyr(Bu$^t$)Asn(Trt)Trp(Boc)Asn(Trt)Ser(Bu$^t$)Phe..(NHCO)GlyLeuArg(Boc$_2$ μM e)Phe-Rink Amide MBHA resin. To 34 mg of the product, 200 μL of TFA/PhSMe/m-cresol/TIS/EDT (85/5/5/2.5/2.5) was added, and the mixture was stirred for 2 hours. Ether was added to the reaction solution. The resulting precipitate was centrifuged and the supernatant was removed. This procedure was repeated for washing. The residue was extracted with an aqueous acetic acid solution and the extract was filtered to remove the resin. Linear density gradient elution (60 minutes) was then performed with eluants A/B:76/24-66/34 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 0.7 mg of white powders.

Mass spectrum (M+H)$^+$1316.3 (Calcd. 1316.7)
Elution time on HPLC: 18.7 mins.
Elution conditions:
Column: Wakosil-II 5C18 HG (4.6×100 mm)
Eluant: linear density gradient elution with eluants A/B=100/0-0/70, using 0.1% TFA in water as eluant A and 0.1% TFA-containing acetonitrile (35 mins.)
Flow rate: 1.0 ml/min.

Example 12

(Synthesis Process L): Preparation of [N((CH$_2$)$_3$Gn)Gly9]-MS10 (Compound No. 218)

Using 192 mg of Fmoc-Phe-Rink Amide MBHA resin, the peptide chain was extended on ABI 433A to give Fmoc-GlyPhe-Rink Amide MBHA resin. After a ¼ volume of the product was subjected to Fmoc deprotection, 2 mL of DMF, 50 μL of AcOH, 5 mg of Boc-β-Ala-H and 16 mg of NaBH$_3$CN were added thereto and the mixture was shaken for 30 minutes. After washing the resin, 71 mg of Fmoc-Leu, 56 mg of CIP, 27 mg of HOAt and 105 mL of DIEA were added to the resin, and the mixture was shaken for 15 hours. After washing the resin, the peptide chain was extended on ABI 433A to give Z-Tyr(Bzl)Asn(Trt)Trp(Boc)Asn(Trt)Ser(Bu$^t$)PheGlyLeuN((CH$_2$)$_3$NHBoc)GlyPhe-Rink Amide MBHA resin (SEQ ID NO: 227). To the product, 1 mL of TFA/PhOH/H$_2$O/TIS/EDT (87.5/5/2.5/2.5/2.5) was added and the mixture was stirred for 2 hours. After the resin was removed by filtration and then concentrated, ether was added to the concentrate. A half volume of the resulting precipitate was dissolved in 500 μL of DMF, and 9 mg of 1H-pyrazole-1-carboxamidine hydrochloride and 22 mL of DIEA were added to the solution. The mixture was then stirred for 15 hours. The solvent was distilled off and ether was added to precipitate. Under ice cooling, 60 μL of PhSMe, 56 μL of m-cresol, 26 μL of EDT, 337 μL of TFA and 65 μL of TMSBr were added to the mixture, followed by stirring for 2 hours. After the solvent was distilled off, ether was added to the residue. The resulting precipitate was centrifuged and the supernatant was removed. This procedure was repeated for washing. The residue was extracted with an aqueous acetic acid solution and the extract was filtered to remove the resin. Linear density gradient elution (60 minutes) was then performed with eluants A/B:74/26-64/36 using: 0.1% TFA in water and eluant B: 0.1% TFA-containing acetonitrile on preparative HPLC using YMC D-ODS-5-ST S-5 120A column (20×150 mm). The fractions containing the product were collected and lyophilized to give 1.8 mg of white powders.

Mass spectrum (M+H)$^+$1302.5 (Calcd. 1302.7)
Elution time on HPLC: 18.6 mins.
Elution conditions:
Column: Wakosil-II 5C18 HG (4.6×100 mm)
Eluant: linear density gradient elution with eluants A/B=100/0-30/70, using 0.1% TFA in water as eluant A and 0.1% TFA-containing acetonitrile (35 mins.)
Flow rate: 1.0 ml/min.

Example 13

(Synthesis Process M): Preparation of MS10 (Compound No. 3)

Commercially available p-methyl BHA resin (0.77 mmol/g resin) was charged in a reaction tank of peptide synthesizer ABI 430A. Boc-Phe, Boc-Arg(Tos), Boc-Leu, Boc-Gly, Boc-Phe, Boc-Ser(Bzl), Boc-Asn, Boc-Trp(For), Boc-Asn, and Boc-Tyr(Br—Z) were introduced into the resin in this order, in accordance with the Boc-strategy (DCC-HOBt) peptide synthesis to give the objective peptide resin protected. This resin, 0.11 g, was stirred at 0° C. for 60 minutes in 10 ml of anhydrous hydrogen fluoride containing 1 ml of p-cresol and 1.2 ml of 1,4-butanediol. The hydrogen fluoride was then distilled off in vacuum. Diethyl ether was added to the residue and the precipitate was filtered. To the precipitate 50% acetic acid aqueous solution was added for extraction to remove insoluble matters. After sufficiently concentrating the extract, the concentrate was applied to Sephadex (trade name) G-25 column (2.0×80 cm) filled with 50% acetic acid aqueous solution followed by development with the same solvent. The main fractions were collected and lyophilized to give 40 mg of white powders. A half volume of the powders was applied to column chromatography (2.6×60 cm) packed with LiChroprep (trade name) RP-18 followed by washing with 200 ml of water containing 0.1% TFA. Linear density gradient elution was performed with 300 ml of 0.1% TFA in water and 300 ml of 0.1% TFA-containing 33% acetonitrile. The main fractions were collected and lyophilized to give 2.2 mg of the desired peptide.

Elemental analysis (M+H) 1302.5 (Calcd. 1302.6)
Elution time on HPLC: 18.7 mins.
Elution conditions:
Column: Wakosil-II 5C18T 4.6×100 mm
Eluant: linear density gradient elution with eluants A/B=95/5-45/55, using 0.1% TFA in water as eluant A and 0.1% TFA-containing acetonitrile (25 mins.)
Flow rate: 1.0 ml/min.

The structures of compounds synthesized as in EXAMPLES 1 to 11 and physicochemical properties of these compounds are shown in TABLES 1 to 11 below.

TABLE 1

| Compd. No. | | M + H+ (obs.) | M + H+ (cal.) | HPLC (min.) | HPLC Mode | Synthesis Process |
|---|---|---|---|---|---|---|
| 1 | Metastin | 5858.35 | 5858.51 | 18.1 | d | N |
| 2 | Lys-Asp-Leu-Pro-Asn-MS10 ('Lys-Asp-Leu-Pro-Asn' disclosed as SEQ ID NO: 228) | 1869.6 | 1869.9 | 18.6 | d | N |
| 3 | MS10 | 1302.5 | 1302.6 | 18.7 | d | N |
| 4 | des(1)-MS10 | 1139.6 | 1139.6 | 18.1 | d | N |
| 17 | [Pya(4)10]MS10 | 1303.6 | 1303.6 | 14.7 | d | N |
| 18 | [Tyr(Me)10]MS10 | 1332.7 | 1332.7 | 17.7 | d | N |
| 19 | [Phe(2F)10]MS10 | 1320.5 | 1320.6 | 17.8 | d | N |
| 23 | [Tyr5]MS10 | 1378.6 | 1378.8 | 18.6 | d | N |
| 24 | [Leu5]MS10 | 1328.7 | 1328.7 | 19.8 | d | N |
| 30 | Acetyl-MS10 | 1344.5 | 1344.6 | 29.2 | b | A |
| 31 | Fmoc-MS10 | 1524.6 | 1524.7 | 23.1 | b | A |
| 38 | [D-Ser5]MS10 | 1302.5 | 1302.6 | 11.8 | c | A |
| 39 | [D-Asn4]MS10 | 1302.5 | 1302.6 | 11.6 | c | A |
| 40 | [D-Trp3]MS10 | 1302.5 | 1302.6 | 11.5 | c | A |
| 41 | [D-Asn2]MS10 | 1302.5 | 1302.6 | 11.7 | c | A |
| 42 | [D-Tyr1]MS10 | 1302.5 | 1302.6 | 11.4 | c | A |
| 44 | [Lys9]MS10 | 1274.6 | 1274.6 | 11.7 | c | A |
| 45 | [Ala8]MS10 | 1260.5 | 1260.6 | 10 | c | A |
| 50 | [Ala7]MS10 | 1316.3 | 1316.7 | 12.2 | c | A |
| 51 | [NMePhe10]MS10 | 1316.3 | 1316.7 | 22.7 | a | A |
| 53 | des(1-3)-Fmoc-MS10 | 1061.2 | 1061.5 | 27.3 | a | A |
| 54 | des(1-2)-Fmoc-MS10 | 1247.4 | 1247.6 | 29.6 | a | A |
| 55 | des(1)-Fmoc-MS10 | 1361.6 | 1361.6 | 28.2 | a | A |
| 56 | [Lys2]MS10 | 1316.6 | 1316.7 | 16.8 | d | N |
| 57 | [Asp2]MS10 | 1303.7 | 1303.6 | 17.7 | d | N |
| 58 | [Tyr2]MS10 | 1351.7 | 1351.7 | 18.2 | d | N |
| 59 | [Leu2]MS10 | 1301.6 | 1301.7 | 19.2 | d | N |
| 60 | [Pya(3)10]MS10 | 1303.6 | 1303.6 | 14.7 | d | N |
| 61 | [Phe(4F)10]MS10 | 1320.6 | 1320.6 | 18.0 | d | N |
| 67 | [Ala3]MS10 | 1187.4 | 1187.6 | 9.3 | c | A |
| 68 | [Leu3]MS10 | 1229.6 | 1229.6 | 11.1 | c | A |
| 69 | [Ser3]MS10 | 1203.5 | 1203.6 | 8.9 | c | A |

TABLE 2

| 70 | [Asp3]MS10 | 1231.6 | 1231.6 | 9 | c | A |
|---|---|---|---|---|---|---|
| 71 | [Lys3]MS10 | 1244.6 | 1244.7 | 8.1 | c | A |
| 72 | [Ala1]MS10 | 1210.5 | 1210.6 | 11.1 | c | A |
| 73 | [Leu1]MS10 | 1252.6 | 1252.7 | 12.5 | c | A |
| 74 | [Ser1]MS10 | 1226.6 | 1226.6 | 10.9 | c | A |
| 75 | [Asp1]MS10 | 1254.4 | 1254.6 | 11 | c | A |
| 76 | [Lys1]MS10 | 1267.6 | 1267.7 | 10 | c | A |
| 77 | [Phe(4CN)10]MS10 | 1327.5 | 1327.6 | 17.2 | d | N |
| 78 | [Trp(For)3, Phe(4CN)10]MS10 | 1355.6 | 1355.6 | 17.4 | d | N |
| 79 | [Hph10]MS10 | 1316.5 | 1316.7 | 20.6 | a | A |
| 81 | [NMeArg9]MS10 | 1316.3 | 1316.7 | 23.3 | a | A |
| 82 | [Arg(Me)9]MS10 | 1316.5 | 1316.7 | 20.1 | a | E |
| 83 | [Arg(asyMe2)9]MS10 | 1330.4 | 1330.7 | 21.3 | a | A |
| 87 | des(4-5)-Boc-MS10 | 1201.6 | 1201.6 | 22.5 | d | A |
| 88 | des(4-5)-MS10 | 1101.5 | 1101.5 | 18.6 | d | A |
| 90 | [9Ψ10,CH2NH]MS10 | 1260.6 | 1260.7 | 19.8 | a | D |
| 91 | [8Ψ9,CH2NH]MS10 | 1288.7 | 1288.7 | 20.5 | a | D |
| 97 | [Har9]MS10 | 1316.3 | 1316.7 | 11.9 | c | A |
| 98 | [Lys(Me2)9]MS10 | 1302.6 | 1302.7 | 11.8 | c | A |
| 101 | [Ser7]MS10 | 1332.6 | 1332.6 | 11.6 | c | A |
| 105 | [Nle8]MS10 | 1302.3 | 1302.6 | 11.9 | c | A |
| 107 | [Val8]MS10 | 1288.5 | 1288.6 | 11 | c | A |
| 109 | [Tyr10]MS10 | 1408.4 | 1408.7 | 10.2 | c | A |
| 110 | [Nal(2)10]MS10 | 1332.4 | 1332.6 | 13.5 | c | A |
| 111 | [Phe(F5)10]MS10 | 1342.4 | 1342.7 | 13.5 | c | A |
| 112 | [Cha10]MS10 | 1360.3 | 1360.6 | 13.4 | c | A |
| 114 | des(1-3)-3-(3-Indolyl)propionyl-MS10 | 1010.5 | 1010.5 | 13.8 | c | A + I |
| 121 | des(1-4)-[Trp5]MS10 | 824.3 | 824.5 | 22.5 | d | N |
| 123 | [NMeLeu8]MS10 | 1316.7 | 1316.7 | 12.7 | c | A |
| 126 | [NMeSer5]MS10 | 1317 | 1316.7 | 11.8 | c | A |
| 127 | [D-Asn4,NMePhe6]MS10 | 1316.7 | 1316.7 | 11.8 | c | A |
| 128 | [10Ψ,CSNH]MS10 | 1318.4 | 1318.6 | 21.8 | a | C |
| 129 | [Arg(symMe2)9]MS10 | 1331.2 | 1330.7 | 20.9 | a | A |

TABLE 3

| 130 | [Phe(4Cl)10]MS10 | 1336.4 | 1336.6 | 13.1 | c | A |
|---|---|---|---|---|---|---|
| 131 | [Phe(4NH2)10]MS10 | 1317.4 | 1317.6 | 8.3 | c | A |
| 132 | [Phe(4NO2)10]MS10 | 1347.4 | 1347.6 | 12.2 | c | A |
| 133 | [Nal(1)10]MS10 | 1352.6 | 1352.7 | 13.5 | c | A |
| 134 | [Trp10]MS10 | 1341.5 | 1341.6 | 12 | c | A |
| 137 | [Nle9]MS10 | 1259.4 | 1259.6 | 15.3 | c | A |
| 138 | [Cit9]MS10 | 1303.6 | 1303.6 | 12.2 | c | A |
| 140 | [Arg(Me)9,NMePhe10]MS10 | 1330.4 | 1330.7 | 21 | a | E |
| 141 | [D-Tyr1,Arg(Me)9]MS10 | 1316.9 | 1316.7 | 20.2 | a | E |
| 142 | [D-Tyr1,D-Trp3,Arg(Me)9]MS10 | 1316.7 | 1316.7 | 20.1 | a | E |
| 143 | [D-Trp3,Arg(Me)9]MS10 | 1316.7 | 1316.7 | 20.3 | a | E |
| 144 | des(1-3)-Fmoc-[Arg(Me)9]MS10 | 1075.2 | 1075.5 | 26 | a | E |
| 145 | des(1-2)-Fmoc-[Arg(Me)9]MS10 | 1261.2 | 1261.6 | 28.6 | a | E |

TABLE 3-continued

| | | | | | | |
|---|---|---|---|---|---|---|
| 146 | [10Ψ,CSNH,D-Tyr1]MS10 | 1318.4 | 1318.6 | 21.4 | a | C |
| 150 | [Tyr6]MS10 | 1318.4 | 1318.6 | 10.2 | c | A |
| 151 | [Nal(1)6]MS10 | 1352.6 | 1352.7 | 13.5 | c | A |
| 152 | [Nal(2)6]MS10 | 1352.6 | 1352.7 | 13.6 | c | A |
| 153 | [Phe(F$_5$)6]MS10 | 1392.5 | 1392.6 | 13.7 | c | A |
| 154 | [Phe(4F)6]MS10 | 1320.8 | 1320.6 | 12.3 | c | A |
| 156 | [Cha6]MS10 | 1308.2 | 1308.5 | 13.2 | c | A |
| 163 | [6Ψ7,CH$_2$NH]MS10 | 1288.7 | 1288.7 | 18.2 | a | D |
| 165 | [Dap(Gly)9]-MS10 | 1289.8 | 1289.6 | 19.2 | a | E |
| 166 | [6Ψ7,CSNH]MS10 | 1318.7 | 1318.6 | 20.8 | a | F |
| 169 | [D-Tyr1,Ala3,Arg(Me)9]MS10 | 1202.1 | 1201.6 | 9 | c | E |
| 170 | [D-Tyr1,Ser3,Arg(Me)9]MS10 | 1218.2 | 1217.6 | 8.8 | c | E |
| 171 | [D-Tyr1,Cha3,Arg(Me)9]MS10 | 1284.2 | 1283.7 | 12.1 | c | E |
| 172 | [D-Tyr1,Cha6,Arg(Me)9]MS10 | 1402.9 | 1322.7 | 13.1 | c | E |
| 173 | [D-Tyr1,Ala7,Arg(Me)9]MS10 | 1410.9 | 1330.7 | 12.2 | c | E |
| 174 | [D-Tyr1,Arg(Me)9,Trp10]MS10 | 1335.3 | 1335.7 | 11.7 | c | E |
| 176 | [AzaGly7]MS10 | 1303.3 | 1303.6 | 18.9 | a | G |
| 181 | [D-Tyr1,Cha3,6,Arg(Me)9]MS10 | 1370.6 | 1370.6 | 13.9 | c | E |
| 182 | [D-Tyr1,Cha3,6,Arg(Me)9,Trp10]MS10 | 1328.2 | 1328.7 | 21.3 | a | E |
| 183 | [Phe(4NH$_2$)9]MS10 | 1328.2 | 1308.6 | 19.4 | a | A |

TABLE 4

| | | | | | | |
|---|---|---|---|---|---|---|
| 184 | [Phe(4-Guanidino)9]MS10 | 1350.4 | 1350.6 | 19.7 | a | E |
| 185 | [Dap(GnGly)9]MS10 | 1331.2 | 1331.6 | 19.1 | a | E |
| 186 | [Trp(For)10]MS10 | 1369.3 | 1369.6 | 19.6 | a | B |
| 187 | [Abu8]MS10 | 1274.4 | 1274.6 | 10.4 | c | A |
| 189 | [Ala(3-Bzt)10]MS10 | 1358.4 | 1358.6 | 13.4 | c | A |
| 190 | [D-Tyr1,Cha3,AzaGly7,Arg(Me)9]MS10 | 1284.5 | 1284.7 | 19.3 | a | H |
| 191 | [D-Tyr1,Ser3,AzaGly7,Arg(Me)9]MS10 | 1218.4 | 1218.6 | 15.9 | a | H |
| 192 | [D-Tyr1,Arg(Et)9]MS10 | 1330.5 | 1330.7 | 18.9 | a | E |
| 193 | [D-Tyr1,Arg(n-Pr)9]MS10 | 1344.8 | 1344.7 | 19.4 | a | E |
| 194 | [D-Tyr1,Arg(Ac)9]MS10 | 1345.1 | 1344.6 | 18.8 | a | E |
| 197 | [Phe(3F)10]MS10 | 1320.6 | 1320.6 | 12.2 | c | A |
| 198 | [Phe(3,4F$_2$)10]MS10 | 1338.7 | 1338.6 | 12.7 | c | A |
| 199 | [Phe(3,4Cl$_2$)10]MS10 | 1370.6 | 1370.6 | 13.1 | c | A |
| 200 | [Phe(3CF$_3$)10]MS10 | 1370.6 | 1370.6 | 13.1 | c | A |
| 201 | [Ala(2-Qui)10]MS10 | 1353.4 | 1353.6 | 9.8 | c | A |
| 203 | [D-Tyr1,Cha6,Arg(Me)9]MS10 | 1322.4 | 1322.7 | 12.9 | c | E |
| 204 | [D-Tyr1,Ala7,Arg(Me)9]MS10 | 1330.4 | 1330.7 | 11.7 | c | E |
| 205 | [D-Tyr1,Thr3,Arg(Me)9]MS10 | 1231.4 | 1231.6 | 9 | c | E |
| 206 | [D-Tyr1,Ile3,Arg(Me)9]MS10 | 1243.6 | 1243.7 | 10.1 | c | E |
| 207 | [D-Tyr1,Ser4,Arg(Me)9]MS10 | 1289.5 | 1289.6 | 11.7 | c | E |
| 208 | [D-Tyr1,Thr4,Arg(Me)9]MS10 | 1303.4 | 1303.7 | 12 | c | E |
| 209 | [D-Tyr1,Gln4,Arg(Me)9]MS10 | 1330.8 | 1330.7 | 11.6 | c | E |
| 210 | [D-Tyr1,Ala4,Arg(Me)9]MS10 | 1273.7 | 1273.6 | 12.3 | c | E |
| 211 | [D-Tyr1,Thr5,Arg(Me)9]MS10 | 1330.7 | 1330.7 | 11.7 | c | E |
| 212 | [D-Tyr1,Ala5,Arg(Me)9]MS10 | 1300.5 | 1300.7 | 12.1 | c | E |
| 213 | [D-Tyr1,Val8,Arg(Me)9]MS10 | 1302.5 | 1302.6 | 10.4 | c | E |
| 214 | [D-Tyr1,Gln2,Arg(Me)9]MS10 | 1330.5 | 1330.7 | 11.4 | c | E |

TABLE 4-continued

| | | | | | | |
|---|---|---|---|---|---|---|
| 215 | [D-Tyr1,Thr2,Arg(Me)9]MS10 | 1303.4 | 1303.7 | 11.9 | c | E |
| 216 | des(1)-[D-Asn2,Arg(Me)9]MS10 | 1153.3 | 1153.6 | 11.1 | c | E |
| 217 | des(1)-[D-Tyr2,Arg(Me)9]MS10 | 1202.4 | 1202.6 | 12.3 | c | E |
| 218 | [N((CH$_2$)3Gn))Gly9]MS10 | 1302.5 | 1302.7 | 18.6 | a | M |
| 220 | [Arg(Et)9]MS10 | 1330.7 | 1330.7 | 19.5 | a | E |

TABLE 5

| | | | | | | |
|---|---|---|---|---|---|---|
| 221 | [D-Tyr1,Thr3,AzaGly7,Arg(Me)9]MS10 | 1232.5 | 1232.6 | 16.1 | a | H |
| 222 | des(1)-[D-Tyr2,AzaGly7,Arg(Me)9]MS10 | 1203.5 | 1203.6 | 19.3 | a | H |
| 223 | des(1-2)-[D-Trp3,Arg(Me)9]MS10 | 1039.5 | 1039.5 | 11 | c | E |
| 224 | des(1)-[D-Tyr2,D-Trp3,Arg(Me)9]MS10 | 1202.4 | 1202.6 | 12.2 | c | E |
| 225 | des(1)-[D-Asn2,D-Trp3,Arg(Me)9]MS10 | 1153.6 | 1153.6 | 11.1 | c | E |
| 226 | des(1)-[D-Tyr2,Ser3,Arg(Me)9]MS10 | 1103.5 | 1103.6 | 9.5 | c | E |
| 227 | des(1)-[D-Tyr2,Thr3,Arg(Me)9]MS10 | 1117.3 | 1117.6 | 9.8 | c | E |
| 228 | des(1)-[D-Tyr2,Ile3,Arg(Me)9]MS10 | 1129.6 | 1129.6 | 11.5 | c | E |
| 229 | [D-Tyr1,Val3,Arg(Me)9]MS10 | 1229.5 | 1229.6 | 9.7 | c | E |
| 230 | [D-Tyr1,D-Asn2,Arg(Me)9]MS10 | 1316.5 | 1316.7 | 11.8 | c | E |
| 231 | [D-Tyr1,D-Asn2,D-Trp3,Arg(Me)9]MS10 | 1316.3 | 1316.7 | 11.7 | c | E |
| 232 | [D-Tyr1,AzaGly7,Arg(Me)9]MS10 | 1317 | 1317.6 | 21 | a | H |
| 233 | [D-Tyr1,Ile3,AzaGly7,Arg(Me)9]MS10 | 1244.1 | 1244.7 | 20.9 | a | H |
| 234 | [D-Tyr1,Val3,AzaGly7,Arg(Me)9]MS10 | 1230.5 | 1230.6 | 20.6 | a | H |
| 235 | [D-Tyr1,Ala3,AzaGly7,Arg(Me)9]MS10 | 1202.5 | 1202.6 | 20.5 | a | H |
| 236 | [D-Tyr1,D-Trp3,AzaGly7,Arg(Me)9]MS10 | 1317.6 | 1317.6 | 20.9 | a | H |
| 237 | [D-Tyr1,D-Asn2,AzaGly7,Arg(Me)9]MS10 | 1317.6 | 1317.6 | 20.9 | a | H |
| 238 | [D-Tyr1,D-Asn2,D-Trp3,AzaGly7,Arg(Me)9]MS10 | 1317.6 | 1317.6 | 20.6 | a | H |
| 239 | des(1)-[D-Tyr2,Ser3,AzaGly7,Arg(Me)9]MS10 | 1104.1 | 1104.6 | 19 | a | H |

TABLE 6

| | | | | | | |
|---|---|---|---|---|---|---|
| 240 | des(1)-[D-Tyr2,Ile3,AzaGly7,Arg(Me)9]MS10 | 1130.1 | 1130.6 | 20.3 | a | H |
| 241 | des(1)-[D-Tyr2,Thr3,AzaGly7,Arg(Me)9]MS10 | 1188 | 1118.6 | 20.3 | a | H |
| 242 | des(1)-[D-Tyr2,D-Trp3,AzaGly7,Arg(Me)9]MS10 | 1202.9 | 1203.6 | 21.2 | a | H |
| 244 | [D-Tyr1,Phe3,AzaGly7,Arg(Me)9]MS10 | 1278.6 | 1278.6 | 10.5 | c | H |
| 245 | [D-Tyr1,Nal(1)3,AzaGly7,Arg(Me)9]MS10 | 1328.5 | 1328.7 | 12.3 | c | H |
| 246 | [D-Tyr1,Nal(2)3,AzaGly7,Arg(Me)9]MS10 | 1328.7 | 1328.7 | 12.3 | c | H |

TABLE 6-continued

| | | | | | | |
|---|---|---|---|---|---|---|
| 247 | [D-Tyr1,Phe(2Cl)3,AzaGly7,Arg(Me)9]MS10 | 1315.6 | 1312.6 | 11.3 | c | H |
| 248 | [D-Tyr1,Phe(3Cl)3,AzaGly7,Arg(Me)9]MS10 | 1312.5 | 1312.6 | 11.6 | c | H |
| 249 | [D-Tyr1,Phe(4Cl)3,AzaGly7,Arg(Me)9]MS10 | 1312.5 | 1312.6 | 11.7 | c | H |
| 250 | [D-Tyr1,Phe(4NH$_2$)3,AzaGly7,Arg(Me)9]MS10 | 1293.4 | 1293.6 | 7.8 | c | H |
| 251 | [D-Tyr1,Pya(3)3,AzaGly7,Arg(Me)9]MS10 | 1279.4 | 1279.6 | 7.8 | c | H |
| 252 | [D-Tyr1,D-Ala3,AzaGly7,Arg(Me)9]MS10 | 1202.4 | 1202.6 | 8.5 | c | H |
| 253 | [D-Tyr1,Pro3,AzaGly7,Arg(Me)9]MS10 | 1228.4 | 1228.6 | 8.6 | c | H |
| 254 | des(1)-[D-Tyr2,Phe3,AzaGly7,Arg(Me)9]MS10 | 1164.4 | 1164.6 | 11.8 | c | H |
| 255 | des(1)-[D-Tyr2,Nal(2)3,AzaGly7,Arg(Me)9]MS10 | 1214.5 | 1214.6 | 13.7 | c | H |
| 256 | des(1)-[D-Pya(3)2,Phe3,AzaGly7,Arg(Me)9]MS10 | 1149.3 | 1149.6 | 9.5 | c | H |

TABLE 7

| | | | | | | |
|---|---|---|---|---|---|---|
| 257 | [D-Tyr1,D-Asn2,Phe3,AzaGly7,Arg(Me)9]MS10 | 1278.5 | 1278.6 | 10.9 | c | H |
| 258 | [D-Pya(3)1,AzaGly7,Arg(Me)9]MS10 | 1302.3 | 1302.6 | 10.1 | c | H |
| 259 | [D-Ala1,AzaGly7,Arg(Me)9]MS10 | 1225.5 | 1225.6 | 10.7 | c | H |
| 260 | des(1-3)-3-(3-Indolyl)propionyl-[AzaGly7,Arg(Me)9]MS10 | 1025.2 | 1025.5 | 13.7 | c | I |
| 261 | [7Ψ8,CH$_2$NH]MS10 | 1288.1 | 1288.7 | 17.2 | a | D |
| 265 | des(1-3)-Indole-3-carbonyl-[AzaGly7,Arg(Me)9]MS10 | 997.3 | 997.5 | 12.6 | c | I |
| 266 | des(1-3)-Indole-3-acetyl-[AzaGly7,Arg(Me)9]MS10 | 1011.3 | 1011.5 | 12.7 | c | I |
| 267 | des(1-3)-4-(3-Indolyl)butyryl-[AzaGly7,Arg(Me)9]MS10 | 1039.3 | 1039.5 | 14.4 | c | I |
| 268 | des(1-3)-Diphenylacetyl-[AzaGly7,Arg(Me)9]MS10 | 1048.5 | 1048.5 | 15.7 | c | I |
| 269 | des(1-3)-3-Phenylpropionyl-[AzaGly7,Arg(Me)9]MS10 | 986.7 | 986.5 | 13.5 | c | I |
| 270 | [D-Tyr1Phe3,Ser-Phe5,AzaGly7,Arg(Me)9]MS10 | 1425.5 | 1425.7 | 13.4 | c | H |
| 271 | des(1-2)-[AzaGly7,Arg(Me)9]MS10 | 1040.2 | 1040.5 | 10.4 | c | H |
| 272 | des(1-2)-Acetyl-[AzaGly7,Arg(Me)9]MS10 | 1082.3 | 1082.6 | 12.8 | c | H |
| 273 | des(1-2)-Amidino-[AzaGly7,Arg(Me)9]MS10 | 1082.3 | 1082.6 | 11.4 | c | J |
| 274 | des(1-2)-Acetyl[Ala3,AzaGly7,Arg(Me)9]MS10 | 967.3 | 967.5 | 9.6 | c | H |
| 275 | des(1-2)-Acetyl[Arg3,AzaGly7,Arg(Me)9]MS10 | 1052.2 | 1052.6 | 8.5 | c | H |

TABLE 7-continued

| | | | | | | |
|---|---|---|---|---|---|---|
| 276 | des(1-2)-Acetyl[Thr3,AzaGly7,Arg(Me)9]MS10 | 997.2 | 997.5 | 9.4 | c | H |
| 277 | des(1-3)-n-Hexanoyl-[AzaGly7,Arg(Me)9]MS10 | 952.2 | 952.5 | 13.4 | c | I |

TABLE 8

| | | | | | | |
|---|---|---|---|---|---|---|
| 278 | des(1-3)-Cyclohexane-carbonyl[AzaGly7,Arg(Me)9]MS10 | 964.3 | 964.5 | 13.2 | c | I |
| 279 | des(1-3)-2-(Indol-3-yl)ethylcarbamoyl-[AzaGly7,Arg(Me)9]MS10 | 1040.2 | 1040.5 | 20.1 | a | J |
| 281 | [D-Tyr1,Pya(2)6,Arg(Me)9]MS10 | 1317.3 | 1317.6 | 7.8 | c | E |
| 282 | [D-Tyr1,Pya(4)6,Arg(Me)9]MS10 | 1317.2 | 1317.6 | 8 | c | E |
| 283 | [D-Tyr1,D-Asn2,Cha3,AzaGly7,Arg(Me)9]MS10 | 1284.3 | 1284.7 | 12.3 | c | H |
| 284 | [D-Tyr1,D-Asn2,Thr3,AzaGly7,Arg(Me)9]MS10 | 1232.2 | 1232.6 | 8.6 | c | H |
| 285 | [D-Tyr1,Pya(2)3,AzaGly7,Arg(Me)9]MS10 | 1279.2 | 1279.6 | 7.9 | c | H |
| 286 | [D-Tyr1,Pya(4)3,AzaGly7,Arg(Me)9]MS10 | 1279.2 | 1279.6 | 7.7 | c | H |
| 287 | [D-Tyr1,D-Ser2,AzaGly7,Arg(Me)9]MS10 | 1290.1 | 1290.6 | 11.4 | c | H |
| 288 | [D-Tyr1,D-His2,AzaGly7,Arg(Me)9]MS10 | 1340.2 | 1340.7 | 10.3 | c | H |
| 289 | des(1)-[D-Pya(3)2,AzaGly7,Arg(Me)9]MS10 | 1188.2 | 1188.6 | 10 | c | H |
| 290 | [D-Pya(3)1,D-Asn2,Cha3,AzaGly7,Arg(Me)9]MS10 | 1269.5 | 1269.7 | 10.9 | c | H |
| 291 | [D-Pya(3)1,D-Tyr2,Cha3,AzaGly7,Arg(Me)9]MS10 | 1317.4 | 1318.7 | 12 | c | H |
| 293 | [4Ψ5,CH$_2$NH]MS10 | 1288.1 | 1288.7 | 18.4 | a | D |
| 294 | [1Ψ2,CH$_2$NH]MS10 | 1288.4 | 1288.7 | 19.2 | a | D |
| 295 | [2Ψ3,CH$_2$NH]MS10 | 1288.1 | 1288.7 | 18.2 | a | D |
| 296 | [6Ψ7,CSNH,D-Tyr1,Arg(Me)9]MS10 | 1332.1 | 1332.6 | 20.5 | a | F |
| 297 | [D-Tyr1,Thr5,AzaGly7,Arg(Me)9]MS10 | 1331.2 | 1330.7 | 11.3 | c | H |
| 298 | [D-Tyr1,D-Asn2,Thr5,AzaGly7,Arg(Me)9]MS10 | 1331.1 | 1330.7 | 11.6 | c | H |

TABLE 9

| | | | | | | |
|---|---|---|---|---|---|---|
| 299 | [1Ψ2,CH$_2$NH,AzaGly7,Arg(Me)9]MS10 | 1303.4 | 1330.7 | 11.3 | c | D + H |
| 300 | [1Ψ2,CH$_2$NH,D-Trp3,AzaGly7,Arg(Me)9]MS10 | 1303.4 | 1303.7 | 10.8 | c | D + H |
| 301 | [D-Tyr1,Ala(2-Qui)3,AzaGly7,Arg(Me)9]MS10 | 1329.4 | 1329.6 | 9 | c | H |
| 302 | [D-Tyr1,D-Pya(4)3,AzaGly7,Arg(Me)9]MS10 | 1279.4 | 1279.6 | 7.6 | c | H |
| 303 | [D-Tyr1,D-Asn2,Pya(4)3,AzaGly7,Arg(Me)9]MS10 | 1279.4 | 1279.6 | 7.6 | c | H |
| 304 | [D-Asn2,Pya(4)3,AzaGly7,Arg(Me)9]MS10 | 1279.4 | 1279.6 | 7.7 | c | H |

TABLE 9-continued

| | | | | | | |
|---|---|---|---|---|---|---|
| 305 | des(1)-[D-Tyr2, D-Pya(4)3,AzaGly7, Arg(Me)9]MS10 | 1165.4 | 1165.6 | 8 | c | H |
| 306 | [D-Pya(4)1,D-Asn2,Cha3,AzaGly7, Arg(Me)9]MS10 | 1269.5 | 1269.5 | 10.8 | c | H |
| 307 | [7Ψ8,CH$_2$NH, D-Tyr1,Arg(Me)9]MS10 | 1302.2 | 1302.7 | 17.9 | a | D + E |
| 308 | [6Ψ7,CH$_2$NH, D-Tyr1,Arg(Me)9]MS10 | 1302.3 | 1302.7 | 18.1 | a | D + E |
| 310 | [Nar9]MS10 | 1288.8 | 1288.6 | 19.4 | a | E |
| 311 | [Nar(Me)9]MS10 | 1302.3 | 1302.6 | 19.5 | a | E |
| 312 | [Har(Me)9]MS10 | 1330.2 | 1330.7 | 19.5 | a | E |
| 313 | [Dab9]MS10 | 1246.1 | 1246.6 | 19.3 | a | A |
| 314 | [Orn9]MS10 | 1260.2 | 1260.6 | 19.3 | a | A |
| 315 | des(1)-[D-Asn2, Cha3,AzaGly7, Arg(Me)9]MS10 | 1121.3 | 1121.6 | 11.4 | c | H |
| 316 | [D-Tyr1,D-Asn2, Thr3,AzaGly7, Arg(Me)9, Phe(4F)10]MS10 | 1250.5 | 1250.6 | 17 | a | H |
| 317 | [D-Tyr1,D-Asn2, Pya(4)3, AzaGly7,Arg(Me)9, Phe(4F)10]MS10 | 1297.4 | 1297.6 | 16.4 | a | H |
| 318 | [D-Tyr1,AzaGly7, Arg(Me)9, Phe(4F)10]MS10 | 1335.4 | 1335.6 | 19 | a | H |

TABLE 10

| | | | | | | |
|---|---|---|---|---|---|---|
| 319 | [6Ψ7,NHCO, D-Tyr1,Arg(Me)9]MS10 | 1316.3 | 1316.7 | 18.7 | a | K |
| 322 | des(1-3)-3-Pyridylpropionyl-[AzaGly7, Arg(Me)9]MS10 | 987.4 | 987.5 | 8.09 | c | I |
| 323 | des(1-3)-4-Imidazoleacetyl-[AzaGly7, Arg(Me)9]MS10 | 962.5 | 962.5 | 7.87 | c | I |
| 324 | des(1-3)-4-Piperidinecarbonyl-[AzaGly7,Arg(Me)9]MS10 | 965.5 | 965.5 | 7.69 | c | I |
| 325 | des(1-3)-1-Piperidineacetyl-[AzaGly7, Arg(Me)9]MS10 | 979.5 | 979.5 | 8.52 | c | I |
| 326 | des(1-3)-1-Methylpiperidinio-1-acetyl-[AzaGly7, Arg(Me)9]MS10 | 993.4 | 993.6 | 8.71 | c | I |
| 327 | des(1-3)-1-Pyridinioacetyl-[AzaGly7, Arg(Me)9]MS10 | 973.4 | 973.5 | 8.09 | c | I |
| 328 | des(1-3)-D-Glucronyl-[AzaGly7, Arg(Me)9]MS10 | 1030.2 | 1030.5 | 7.46 | c | I |
| 375 | H$_2$N(CH$_2$)2Gly-[D-Tyr1, Arg(Me)9]MS10 | 1416.4 | 1416.7 | 17.3 | a | E |
| 385 | des(1)-[D-Tyr2, D-Pya(4)3, AzaGly7,Arg(Me)9, Trp10]MS10 | 1204.4 | 1204.6 | 8.3 | c | H |
| 386 | des(1-3)-3-Pyridylpropionyl-[AzaGly7, Arg(Me)9, Trp10]MS10 | 1026.4 | 1026.2 | 8.5 | c | I |
| 387 | Dap-[D-Tyr1, Arg(Me)9]MS10 | 1402.7 | 1402.7 | 17.0 | a | E |
| 397 | MeNHCS-Sar-[D-Tyr1,Arg(Me)9]MS10 | 1461.2 | 1460.7 | 20.0 | a | E |
| 400 | (S)-1-(Quinolin-8-yl-carbamoyl)-4-thiapentylcarbamoyl-[D-Tyr1, Arg(Me)9]MS10 | 1617.9 | 1617.7 | 21.7 | a | E |

TABLE 10-continued a: 0-70% AcCN/35 min,
flow 1 ml/min,
Wakosil-II 5C18 HG
(4.6 × 100 mm)
b: 0-70% AcCN/35 min,
flow 1 ml/min,
YMC ODSAM-
301 (4.6 × 100 mm)

TABLE 11 c: 20-70%
AcCN/25 min,
flow 1 ml/min,
YMC ODS
AM-301
(4.6 × 100 mm)
d: 5-55%
AcCN/25 min,
flow 1 ml/min,
Wakosil-II
5C18 HG
(4.6 × 100 mm)
Compound No. 1
alone shows M$^+$
value.

Formulation Example 1

| | |
|---|---|
| (1) Compound No. 305 | 10.0 mg |
| (2) Lactose | 60.0 mg |
| (3) Cornstarch | 35.0 mg |
| (4) Gelatin | 3.0 mg |
| (5) Magnesium stearate | 2.0 mg |

A mixture of 10.0 mg of Compound No. 305, 60.0 mg of lactose and 35.0 mg of cornstarch is passed through a sieve of 1 mm mesh for granulation, using 0.03 ml of 10% aqueous gelatin solution (3.0 mg as gelatin). The granules are dried at 40° C. and sieved again. The granules thus obtained are mixed with 2.0 mg of magnesium stearate and compressed. The resulting core tablets are coated with sugar-coating of an aqueous suspension of sucrose, titanium dioxide, talc and gum arabic. The coated tablets are polished with yellow beeswax to obtain coated tablets.

Formulation Example 2

| | |
|---|---|
| (1) Compound No. 305 | 10.0 mg |
| (2) Lactose | 70.0 mg |
| (3) Cornstarch | 50.0 mg |
| (4) Soluble starch | 7.0 mg |
| (5) Magnesium stearate | 3.0 mg |

A mixture of 10.0 mg of Compound 305 and 3.0 mg of magnesium stearate is granulated in 0.07 ml of an aqueous solution of a soluble starch (7.0 mg as soluble starch). The granules are dried, and mixed with 70.0 mg of lactose and 50.0 mg of cornstarch. The mixture is compressed to obtain tablets.

Formulation Example 3

| | | |
|---|---|---|
| (1) Compound No. 305 | 5.0 mg | |
| (2) Table salt | 20.0 mg | |
| (3) Distilled water to make the whole volume | 2 ml | |

After 5.0 mg of Compound No. 305 and 20.0 mg of table salt are dissolved in distilled water, water is added to the solution to make the whole volume 2.0 ml. The solution is filtered and the filtrate is filled in a 2 ml ampoule under aseptic conditions. The ampoule is sterilized and sealed to obtain a solution for injection.

Test Example 1

Assay for hOT7T175 Receptor Binding Activity
(1) Preparation of Cy-5-Labeled Metastin (40-54)

A synthetic peptide having the 40-54 amino acid sequence in the amino acid sequence of the metastin, wherein Cy-5 was introduced via the E-amino group of lysine located at the amino terminus and the carboxyl terminus was further amidated, was prepared in accordance with the synthesis technique of Amersham Bioscience, Inc. Using this synthetic peptide, a test for binding inhibition was carried out.
Sequence:

(Cy-5)-KDLPNYNWNSFGLRF-NH$_2$   (SEQ ID NO: 229)

(2) Test for Binding Inhibition Using a Test Compound, Cy-5-Labeled Metastin (40-54) and hOT7T175-Expressed CHO Cell hOT7T175-Expressed CHO cells were cultured in MEM-cc medium (nucleic acid-free) containing 10% dialyzed serum. The medium was removed and the adherent cells were washed with PBS. Then, PBS containing 5 mM EDTA was added and the cells were scraped from a flask with a cell scraper. After centrifugation, the cells were suspended at $1.11 \times 10^5$ cells/ml in assay buffer (10 mM HEPES pH 7.4, 140 mM NaCl, 2.5 mM CaCl$_2$, 3 mM MgCl$_2$, 0.5% BSA, 0.01% NaN$_3$) and Cy-5-labeled metastin (40-54) was added to the suspension in a final concentration of 1 nM. To each well of a 96-Well Black Clear Bottom Plate (Applied Biosystems, Inc.), 10 μL of assay buffer containing 1% dimethylsulfoxide was added to examine total binding, 10 μL of 10 μM non-labeled peptide (having the same amino acid sequence as that of the labeled one) solution diluted with assay buffer to examine non-specific binding, and 10 μL of a test compound diluted with assay buffer to examine the binding inhibition activity of the test compound, respectively. Furthermore, 90 μL each of the cell suspension was dispensed to each well. An hour after, the level of Cy-5-labeled metastin (40-54) bound to the cells was determined by the FMAT 8100 HTS system (Applied Biosystems, Inc.). The specific binding is a value obtained by subtracting the non-specific binding from the total binding. The binding inhibition activity of each test compound is shown by a ratio of the value obtained by subtracting a value found in the presence of a test compound from the total binding, to the specific binding. The receptor binding activity of each test compound is shown in TABLES 11 through 17.

TABLE 12

| Compd.No. | | IC$_{50}$ (M) |
|---|---|---|
| 1 | Metastin | 1.7E−07 |
| 3 | MS10 | 6.5E−09 |
| 4 | des(1)-MS10 | 2.6E−07 |
| 17 | [Pya(4)10]MS10 | 6.6E−12 |
| 18 | [Tyr(Me)10]MS10 | 7.7E−09 |
| 19 | [Phe(2F)10]MS10 | 8.6E−09 |
| 23 | [Tyr5]MS10 | 4.0E−07 |
| 24 | [Leu5]MS10 | 8.3E−10 |
| 30 | Acetyl-MS10 | 3.1E−08 |
| 31 | Fmoc-MS10 | 9.3E−07 |
| 32 | Leu-Pro-Asn-MS10 | 2.5E−08 |
| 39 | [D-Asn4]MS10 | 8.3E−07 |
| 40 | [D-Trp3]MS10 | 1.9E−08 |
| 41 | [D-Asn2]MS10 | 2.1E−07 |
| 42 | [D-Tyr1]MS10 | 5.7E−08 |
| 44 | [Lys9]MS10 | 1.9E−07 |
| 50 | [Ala7]MS10 | 1.9E−07 |
| 54 | des(1-2)-Fmoc-MS10 | 4.5E−07 |
| 57 | [Asp2]MS10 | 1.0E−07 |
| 58 | [Tyr2]MS10 | 1.6E−08 |
| 59 | [Leu2]MS10 | 3.4E−07 |
| 60 | [Pya(3)10]MS10 | 1.7E−07 |
| 61 | [Phe(4F)10]MS10 | 1.3E−08 |
| 67 | [Ala3]MS10 | 2.7E−08 |
| 68 | [Leu3]MS10 | 7.7E−09 |
| 69 | [Ser3]MS10 | 8.3E−08 |
| 70 | [Asp3]MS10 | 2.0E−07 |
| 71 | [Lys3]MS10 | 6.6E−08 |
| 72 | [Ala1]MS10 | 5.4E−07 |
| 73 | [Leu1]MS10 | 2.2E−07 |
| 75 | [Asp1]MS10 | 8.8E−07 |

TABLE 13

| | | |
|---|---|---|
| 77 | [Phe(4CN)10]MS10 | 7.4E−09 |
| 78 | [Trp(CHO)3, Phe(4CN)10]MS10 | 2.5E−08 |
| 82 | [Arg(Me)9]MS10 | 4.1E−09 |
| 83 | [Arg(Me$_2$)asy9]MS10 | 2.5E−08 |
| 97 | [Har9]MS10 | 3.7E−07 |
| 101 | [Ser7]MS10 | 1.0E−07 |
| 105 | [Nle8]MS10 | 8.8E−07 |
| 107 | [Val8]MS10 | 1.2E−07 |
| 109 | [Tyr10]MS10 | 2.3E−07 |
| 110 | [Nal(2)10]MS10 | 2.4E−08 |
| 111 | [Phe(F$_5$)10]MS10 | 1.4E−07 |
| 112 | [Cha10]MS10 | 3.7E−07 |
| 114 | des(1-3)-3-(3-Indolyl)propionyl-MS10 | 5.5E−07 |
| 128 | [10Ψ,CSNH]MS10 | 5.5E−08 |
| 129 | [Arg(Me$_2$)sy9]MS10 | 8.3E−08 |
| 130 | [Phe(4Cl)10]MS10 | 4.2E−08 |
| 131 | [Phe(4NH$_2$)10]MS10 | 1.2E−07 |
| 132 | [Phe(4NO$_2$)10]MS10 | 9.3E−08 |
| 133 | [Nal(1)10]MS10 | 3.3E−07 |
| 134 | [Trp10]MS10 | 1.1E−07 |
| 141 | [D-Tyr1,Arg(Me)9]MS10 | 5.1E−05 |
| 142 | [D-Tyr1,D-Trp3,Arg(Me)9]MS10 | 2.6E−08 |
| 143 | [D-Trp3,Arg(Me)9]MS10 | 7.7E−09 |
| 145 | des(1-2)-Fmoc-[Arg(Me)9]MS10 | 1.2E−07 |
| 146 | [10Ψ,CSNH,D-Tyr1]MS10 | 3.7E−07 |
| 150 | [Tyr6]MS10 | 3.2E−07 |
| 151 | [Nal(1)6]MS10 | 3.0E−07 |
| 152 | [Nal(2)6]MS10 | 1.8E−07 |
| 153 | [Phe(F$_5$)6]MS10 | 3.9E−07 |
| 154 | [Phe(4F)6]MS10 | 6.0E−08 |
| 156 | [Cha6]MS10 | 4.9E−08 |
| 163 | [6Ψ7,CH$_2$NH]MS10 | 2.5E−07 |
| 166 | [6Ψ7,CSNH]MS10 | 9.4E−09 |
| 169 | [D-Tyr1,Ala3,Arg(Me)9]MS10 | 1.6E−07 |
| 170 | [D-Tyr1,Ser3,Arg(Me)9]MS10 | 2.6E−07 |

TABLE 14

| | | |
|---|---|---|
| 171 | [D-Tyr1,Cha3,Arg(Me)9]MS10 | 1.1E−07 |
| 174 | [D-Tyr1,Arg(Me)9,Trp10]MS10 | 4.2E−07 |
| 176 | [AzaGly7]MS10 | 5.2E−08 |
| 181 | [D-Tyr1,Cha3,6,Arg(Me)9]MS10 | 1.9E−07 |
| 182 | [D-Tyr1,Cha3,6,Arg(Me)9,Trp10]MS10 | 9.8E−08 |
| 186 | [Trp(CHO)10]MS10 | 4.6E−07 |
| 187 | [Abu8]MS10 | 7.2E−07 |
| 189 | [Ala(3-Bzt)10]MS10 | 2.3E−07 |
| 190 | [D-Tyr1,Cha3,AzaGly7,Arg(Me)9]MS10 | 1.2E−08 |
| 191 | [D-Tyr1,Ser3,AzaGly7,Arg(Me)9]MS10 | 3.0E−07 |
| 192 | [D-Tyr1,Arg(Et)9]MS10 | 5.3E−07 |
| 193 | [D-Tyr1,Arg(n-Pr)9]MS10 | 9.2E−07 |
| 194 | [D-Tyr1,Arg(Ac)9]MS10 | 2.1E−07 |
| 197 | [Phe(3F)10]MS10 | 1.7E−07 |
| 198 | [Phe(3,4F$_2$)10]MS10 | 1.7E−07 |
| 199 | [Phe(3,4Cl$_2$)10]MS10 | 4.7E−07 |
| 200 | [Phe(3CF$_3$)10]MS10 | 3.4E−07 |
| 201 | [Ala(2-Qui)10]MS10 | 8.2E−07 |
| 203 | [D-Tyr1,Cha6,Arg(Me)9]MS10 | 3.7E−08 |
| 204 | [D-Tyr1,Ala7,Arg(Me)9]MS10 | 6.8E−07 |
| 205 | [D-Tyr1,Thr3,Arg(Me)9]MS10 | 2.6E−07 |
| 206 | [D-Tyr1,Ile3,Arg(Me)9]MS10 | 8.5E−08 |
| 208 | [D-Tyr1,Thr4,Arg(Me)9]MS10 | 8.3E−07 |
| 210 | [D-Tyr1,Ala4,Arg(Me)9]MS10 | 7.3E−07 |
| 211 | [D-Tyr1,Thr5,Arg(Me)9]MS10 | 4.4E−08 |
| 212 | [D-Tyr1,Ala5,Arg(Me)9]MS10 | 3.6E−08 |
| 213 | [D-Tyr1,Val8,Arg(Me)9]MS10 | 1.9E−07 |
| 214 | [D-Tyr1,Gln2,Arg(Me)9]MS10 | 3.9E−07 |
| 215 | [D-Tyr1,Thr2,Arg(Me)9]MS10 | 2.5E−07 |
| 216 | des(1)-[D-Asn2,Arg(Me)9]MS10 | 7.0E−07 |
| 217 | des(1)-[D-Tyr2,Arg(Me)9]MS10 | 2.5E−07 |
| 220 | [Arg(Et)9]MS10 | 3.3E−07 |
| 221 | [D-Tyr1,Thr3,AzaGly7,Arg(Me)9]MS10 | 9.5E−08 |
| 222 | des(1)-[D-Tyr2,AzaGly7,Arg(Me)9]MS10 | 3.3E−08 |
| 223 | des(1-2)-[D-Trp3,Arg(Me)9]MS10 | 7.6E−07 |

TABLE 15

| | | |
|---|---|---|
| 224 | des(1)-[D-Tyr2,D-Trp3,Arg(Me)9]MS10 | 1.4E−07 |
| 225 | des(1)-[D-Asn2,D-Trp3,Arg(Me)9]MS10 | 4.1E−07 |
| 226 | des(1)-[D-Tyr2,Ser3,Arg(Me)9]MS10 | 1.0E−07 |
| 227 | des(1)-[D-Tyr2,Thr3,Arg(Me)9]MS10 | 4.8E−07 |
| 228 | des(1)-[D-Tyr2,Ile3,Arg(Me)9]MS10 | 4.0E−08 |
| 229 | [D-Tyr1,Val3,Arg(Me)9]MS10 | 1.3E−07 |
| 230 | [D-Tyr1,D-Asn2,Arg(Me)9]MS10 | 2.5E−07 |
| 231 | [D-Tyr1,D-Asn2,D-Trp3,Arg(Me)9]MS10 | 5.5E−08 |
| 232 | [D-Tyr1,AzaGly7,Arg(Me)9]MS10 | 4.9E−08 |
| 233 | [D-Tyr1,Ile3,AzaGly7,Arg(Me)9]MS10 | 2.3E−08 |
| 234 | [D-Tyr1,Val3,AzaGly7,Arg(Me)9]MS10 | 4.7E−08 |
| 235 | [D-Tyr1,Ala3,AzaGly7,Arg(Me)9]MS10 | 1.0E−07 |
| 236 | [D-Tyr1,D-Trp3,AzaGly7,Arg(Me)9]MS10 | 4.2E−08 |
| 237 | [D-Tyr1,D-Asn2,AzaGly7,Arg(Me)9]MS10 | 2.7E−08 |
| 238 | [D-Tyr1,D-Asn2,D-Trp3,AzaGly7,Arg(Me)9]MS10 | 4.9E−08 |
| 239 | des(1)-[D-Tyr2,Ser3,AzaGly7,Arg(Me)9]MS10 | 1.2E−07 |
| 240 | des(1)-[D-Tyr2,Ile3,AzaGly7,Arg(Me)9]MS10 | 1.7E−08 |
| 241 | des(1)-[D-Tyr2,Thr3,AzaGly7,Arg(Me)9]MS10 | 5.6E−08 |
| 242 | des(1)-[D-Tyr2,D-Trp3,AzaGly7,Arg(Me)9]MS10 | 7.0E−08 |
| 244 | [D-Tyr1,Phe3,AzaGly7,Arg(Me)9]MS10 | 7.7E−08 |
| 245 | [D-Tyr1,Nal(1)3,AzaGly7,Arg(Me)9]MS10 | 9.8E−08 |
| 246 | [D-Tyr1,Nal(2)3,AzaGly7,Arg(Me)9]MS10 | 7.1E−09 |
| 247 | [D-Tyr1,Phe(2Cl)3,AzaGly7,Arg(Me)9]MS10 | 4.5E−08 |
| 248 | [D-Tyr1,Phe(3Cl)3,AzaGly7,Arg(Me)9]MS10 | 5.8E−08 |
| 249 | [D-Tyr1,Phe(4Cl)3,AzaGly7,Arg(Me)9]MS10 | 1.5E−07 |
| 250 | [D-Tyr1,Phe(4NH$_2$)3,AzaGly7,Arg(Me)9]MS10 | 3.7E−09 |
| 251 | [D-Tyr1,Pya(3)3,AzaGly7,Arg(Me)9]MS10 | 8.7E−08 |
| 252 | [D-Tyr1,D-Ala3,AzaGly7,Arg(Me)9]MS10 | 5.8E−07 |
| 253 | [D-Tyr1,Pro3,AzaGly7,Arg(Me)9]MS10 | 2.7E−08 |
| 254 | des(1)-[D-Tyr2,Phe3,AzaGly7,Arg(Me)9]MS10 | 1.1E−08 |
| 255 | des(1)-[D-Tyr2,Nal(2)3,AzaGly7,Arg(Me)9]MS10 | 3.3E−08 |
| 256 | des(1)-[D-Pya(3)2,Phe3,AzaGly7,Arg(Me)9]MS10 | 2.2E−08 |
| 257 | [D-Tyr1,D-Asn2,Phe3,AzaGly7,Arg(Me)9]MS10 | 4.0E−08 |
| 258 | [D-Pya(3)1,AzaGly7,Arg(Me)9]MS10 | 9.0E−08 |
| 259 | [D-Ala1,AzaGly7,Arg(Me)9]MS10 | 2.5E−07 |

TABLE 16

| | | |
|---|---|---|
| 260 | des(1-3)-3-(3-Indolyl)propionyl-[AzaGly7,Arg(Me)9]MS10 | 3.2E−07 |
| 261 | [7ψ8,CH$_2$NH]MS10 | 3.9E−07 |
| 265 | des(1-3)-Indole-3-carboxyl-[AzaGly7,Arg(Me)9]MS10 | 9.5E−08 |
| 266 | des(1-3)-Indole-3-acetyl-[AzaGly7,Arg(Me)9]MS10 | 2.3E−07 |
| 267 | des(1-3)-4-(3-Indolyl)butyryl-[AzaGly7,Arg(Me)9]MS10 | 3.6E−07 |
| 268 | des(1-3)-Diphenylacetyl-[AzaGly7,Arg(Me)9]MS10 | 5.5E−07 |
| 269 | des(1-3)-3-Phenylpropionyl-[AzaGly7,Arg(Me)9]MS10 | 4.7E−07 |
| 270 | Endo-Phe5a-[D-Tyr1,Phe3,AzaGly7,Arg(Me)9]MS10 | 1.5E−08 |
| 271 | des(1-2)-[AzaGly7,Arg(Me)9]MS10 | 1.2E−07 |
| 272 | des(1-2)-Acetyl-[AzaGly7,Arg(Me)9]MS10 | 5.4E−07 |
| 273 | des(1-2)-Amidino-[AzaGly7,Arg(Me)9]MS10 | 3.0E−07 |
| 275 | des(1-2)-Acetyl-[Arg3,AzaGly7,Arg(Me)9]MS10 | 4.1E−07 |
| 276 | des(1-2)-Acetyl-[Thr3,AzaGly7,Arg(Me)9]MS10 | 4.8E−07 |
| 277 | des(1-3)-n-Hexanoyl-[AzaGly7,Arg(Me)9]MS10 | 5.4E−08 |
| 278 | des(1-3)-Cyclohexanecarbonyl-[AzaGly7,Arg(Me)9]MS10 | 1.1E−07 |
| 279 | des(1-3)-2-(Indol-3-yl)ethylcarbamoyl-[AzaGly7,Arg(Me)9]MS10 | 2.9E−08 |
| 281 | [D-Tyr1,Pya(2)6,Arg(Me)9]MS10 | 2.3E−07 |
| 283 | [D-Tyr1,D-Asn2,Cha3,AzaGly7,Arg(Me)9]MS10 | 6.9E−10 |
| 284 | [D-Tyr1,D-Asn2,Thr3,AzaGly7,Arg(Me)9]MS10 | 3.4E−10 |
| 285 | [D-Tyr1,Pya(2)3,AzaGly7,Arg(Me)9]MS10 | 4.0E−08 |
| 286 | [D-Tyr1,Pya(4)3,AzaGly7,Arg(Me)9]MS10 | 1.7E−08 |
| 287 | [D-Tyr1,D-Ser2,AzaGly7,Arg(Me)9]MS10 | 2.3E−09 |
| 288 | [D-Tyr1,D-His2,AzaGly7,Arg(Me)9]MS10 | 7.2E−11 |
| 289 | [D-Pya(3)2,AzaGly7,Arg(Me)9]MS10-(2-10) | 8.4E−09 |
| 290 | [D-Pya(3)1,D-Asn2,Cha3,AzaGly7,Arg(Me)9]MS10 | 1.4E−09 |
| 291 | [D-Pya(3)1,D-Tyr2,Cha3,AzaGly7,Arg(Me)9]MS10 | 4.1E−10 |
| 294 | [1y2,CH$_2$NH]MS10 | 3.0E−08 |
| 295 | [2y3,CH$_2$NH]MS10 | 6.8E−07 |
| 296 | [6y7,CSNH,D-Tyr1,Arg(Me)9]MS10 | 1.4E−08 |
| 297 | [D-Tyr1,Thr5,AzaGly7,Arg(Me)9]MS10 | 9.3E−10 |
| 298 | [D-Tyr1,D-Asn2,Thr5,AzaGly7,Arg(Me)9]MS10 | 2.5E−10 |
| 299 | [1Ψ2,CH$_2$NH,AzaGly7,Arg(Me)9]-MS10 | 1.2E−09 |
| 300 | [1Ψ2,CH$_2$NH,D-Trp3,AzaGly7,Arg(Me)9]-MS10 | 3.8E−09 |
| 301 | [D-Tyr1,Ala(2-Qui)3,AzaGly7,Arg(Me)9]MS10 | 1.5E−08 |

TABLE 17

| 302 | [D-Tyr1,D-Pya(4)3,AzaGly7,Arg(Me)9]MS10 | 7.7E−09 |
| 303 | [D-Tyr1,D-Asn2,Pya(4)3,AzaGly7,Arg(Me)9]MS10 | 5.0E−10 |
| 304 | [D-Asn2,Pya(4)3,AzaGly7,Arg(Me)9]MS10 | 5.0E−09 |
| 305 | des(1)-[D-Tyr2,D-Pya(4)3,AzaGly7,Arg(Me)9]MS10 | 1.3E−09 |
| 306 | [D-Pya(4)1,D-Asn2,Cha3,AzaGly7,Arg(Me)9]MS10 | 4.4E−09 |
| 307 | [7Ψ8,CH$_2$NH,D-Tyr1,Arg(Me)9]MS10 | 6.4E−08 |
| 308 | [6Ψ7,CH$_2$NH,D-Tyr1,Arg(Me)9]MS10 | 3.5E−07 |
| 310 | [Nar9]MS10 | 3.1E−07 |
| 311 | [Nar(Me)9]MS10 | 4.7E−07 |
| 312 | [Har(Me)9]MS10 | 1.0E−07 |
| 313 | [Dab9]MS10 | 6.9E−07 |
| 314 | [Orn9]MS10 | 4.7E−07 |
| 316 | [D-Tyr1,D-Asn2,Thr3,AzaGly7,Arg(Me)9,Phe(4F)10]MS10 | 2.6E−08 |
| 317 | [D-Tyr1,D-Asn2,Pya(4)3,AzaGly7,Arg(Me)9,Phe(4F)10]MS10 | 2.1E−09 |
| 318 | [D-Tyr1,AzaGly7,Arg(Me)9,Phe(4F)10]MS10 | 9.9E−10 |
| 319 | [6Ψ7,NHCO,D-Tyr1,Arg(Me)9]MS10 | 9.7E−09 |
| 322 | des(1-3)-3-Pyridylpropionyl-[AzaGly7,Arg(Me)9]MS10 | 5.4E−08 |
| 323 | des(1-3)-4-Imidazoleacetyl-[AzaGly7,Arg(Me)9]MS10 | 2.8E−07 |
| 328 | des(1-3)-D-Glucuronyl-[AzaGly7,Arg(Me)9]MS10 | 4.7E−07 |

Test Example 2

Assay for Intracellular Ca Ion Level-Increasing Activity Using Flipr

In accordance with the method described in JPA 2000-312590, the intracellular Ca ion level-increasing activity was measured using FLIPR.

The stable expression cell line hOT7T175 was acquired by transduction of expression plasmid pAK-rOT175 for animal cells into CHO/dhff cells, using CellPhect Transfection Kit (Amersham Pharmacia Biotech, Inc.). First, 240 μL of Buffer A (attached to CellPhect Transfection Kit) was added to 9.6 μg of plasmid DNA dissolved in 240 μl of distilled water, followed by stirring. After settling the mixture for 10 minutes, 480 μL of Buffer B (attached to CellPhect Transfection Kit) was added to the mixture, which was vigorously stirred to form DNA-containing liposomes. Then, 4×10$^5$ CHO/dhff cells (obtained from ATCC) were inoculated on a 60 mm Petri dish. After culturing the cells in Ham's F-12 medium (Nissui Seiyaku Co., Ltd.) supplemented with 10% fetal bovine serum (BIO WHITTAKER, Inc.) at 37° C. for 2 days in 5% carbon dioxide gas, 480 μL of the liposomes were dropwise added to the cells in the Petri dish. After culturing the cells at 37° C. for 6 hours in 5% carbon dioxide gas, the cells were washed twice with serum-free Ham's F-12 medium and 3 ml of 15% glycerol was added to the cells in the Petri dish to treat for 2 minutes. The cells were again washed twice with serum-free Ham's F-12 medium followed by incubation in Ham's F-12 medium supplemented with 10% fetal bovine serum at 37° C. for 15 hours in 5% carbon dioxide gas. The cells were dispersed by trypsin treatment and recovered from the Petri dish. The recovered cells were inoculated on a 6-well plate in 1.25×10$^4$ cells/well and incubation was initiated at 37° C. in Dulbecco's modified Eagle medium (DMEM) medium (Nissui Seiyaku Co., Ltd.) containing 10% dialyzed fetal bovine serum (JRH BIOSCIENCES, Inc.) under 5% carbon dioxide gas. The plasmid-transfected CHO transformants grew in the medium but the non-transfected cells gradually died. The medium was exchanged on Days 1 and 2 to remove the cells died. Approximately 20 colonies of the CHO transformants that kept growing on Days 8 to 10 after the incubation were isolated. From the cells in these colonies, cells showing high reactivity with the ligand peptide metastin (hereinafter merely referred to as hOT7T175/CHO) were selected to provide for the following experiment.

The intracellular Ca ion level-increasing activity of the synthetic peptide in hOT7T175/CHO was determined using FLIPR (Molecular Devices, Inc.).

hOT7T175/CHO was subcultured in DMEM supplemented with 10% dialyzed fetal bovine serum (hereinafter abbreviated as dFBS) and provided for the experiment (hereinafter abbreviated as 10% dFBS/DMEM). The hOT7T175/CHO was suspended in 10% dFBS-DMEM in 15×10$^4$ cells/ml. The suspension was inoculated on a 96-well plate for FLIPR (Black Plate Clear Bottom, Coster, Inc.) at 200 μL each (3.0×10$^4$ cells/200 μL/well), followed by incubation at 37° C. overnight in a 5% CO$_2$ incubator (hereinafter simply referred to as the cell plate). Then, 21 ml of HANKS/HBSS (9.8 g of HANKS, 0.35 g of sodium hydrogencarbonate, 20 ml of 1M HEPES; after adjusting the pH to 7.4 with 1N sodium hydroxide, the mixture was sterilized by filtration), 210 μl of 250 mM Probenecid and 210 μA of fetal bovine serum (FBS) were mixed (HANKS/HBSS-Probenecid-FBS).

Furthermore, 2 vials of Fluo3-AM (50 μug/vial) were dissolved in 21 μL of dimethylsulfoxide and 21 μL of 20% Pluronic acid. The resulting solution was added to and mixed with 10 ml of HANKS/HBSS-Probenecid-FBS described above. After the culture medium was removed, the mixture was dispensed onto the cell plate in 100 μL each/well, followed by incubation at 37° C. for an hour in a 5% CO$_2$ incubator (pigment loading). The peptide was dissolved in dimethylsulfoxide in 1×10$^{-3}$ M. The peptide solution was diluted with HANKS/HBSS containing 2.5 mM Probenecid, 0.2% BSA and 0.1% CHAPS. The dilution was transferred to a 96-well plate for FLIPR (V-Bottom plate, Coster, Inc.) (hereinafter referred to as a sample plate). After completion of the pigment loading onto the cell plate, the cell plate was washed 4 times with wash buffer, which was obtained by adding 2.5 mM Probenecid to HANKS/HBSS, using a plate washer. After the washing, 100 μL of wash buffer was left. The cell plate and the sample plate were set in FLIPR and 0.05 ml of a sample from the sample plate was automatically transferred to the cell plate with the FLIPR device to promote the cell response. A change in intracellular calcium ion level for 180 seconds was measured with passage of time. Tables 18 through 22 show the intracellular Ca ion level-increasing activity [expressed by a specific activity to metastin (1-54)].

TABLE 18

| Compd. No. | Specific Activity |
|---|---|
| Metastin (1-54) | 1 |
| Metastin (45-54) | 10 |
| 17 | 5 |
| 18 | 1 |
| 19 | 2 |
| 24 | 1 |
| 30 | 10 |
| 31 | 2 |
| 32 | 10 |
| 40 | 30 |
| 41 | 10 |
| 42 | 30 |
| 45 | 1 |
| 50 | 30 |
| 53 | 1 |
| 54 | 5 |
| 55 | 5 |
| 56 | 1 |
| 74 | 1 |
| 75 | 1 |
| 76 | 1 |
| 78 | 10 |
| 79 | 1 |
| 87 | 1 |

TABLE 18-continued

| Compd. No. | Specific Activity |
|---|---|
| 88 | 1 |
| 97 | 10 |
| 98 | ½ |
| 101 | 10 |
| 105 | 1 |
| 109 | 20 |
| 110 | 20 |
| 111 | 3 |
| 112 | 2 |
| 114 | 3 |

TABLE 19

| | |
|---|---|
| 128 | 10 |
| 130 | 10 |
| 131 | 3 |
| 132 | 10 |
| 133 | 3 |
| 134 | 30 |
| 141 | 10 |
| 142 | 2 |
| 143 | 3 |
| 144 | 1 |
| 146 | 10 |
| 151 | 1 |
| 152 | 5 |
| 154 | 5 |
| 156 | 2 |
| 163 | 1 |
| 166 | 5 |
| 169 | 2 |
| 170 | 1 |
| 171 | 10 |
| 172 | 1 |
| 173 | 1 |
| 174 | 10 |
| 176 | 5 |
| 182 | 5 |
| 187 | 1 |
| 189 | 10 |
| 190 | 10 |
| 192 | 1 |
| 193 | 001 |
| 194 | 1 |
| 187 | 10 |
| 198 | 10 |
| 199 | 3 |
| 200 | 10 |

TABLE 20

| | |
|---|---|
| 201 | 1 |
| 203 | 10 |
| 204 | 5 |
| 205 | 10 |
| 206 | 10 |
| 207 | ½ |
| 208 | 1 |
| 209 | ½ |
| 210 | 1 |
| 211 | 10 |
| 212 | 10 |
| 213 | 2 |
| 214 | 10 |
| 215 | 10 |
| 216 | 1 |
| 217 | 20 |
| 220 | 5 |
| 222 | 5 |
| 224 | 2 |
| 224 | 1 |
| 224 | 1 |
| 224 | 1 |

TABLE 20-continued

| | |
|---|---|
| 228 | 5 |
| 229 | 1 |
| 230 | 10 |
| 231 | 1 |
| 232 | 3 |
| 233 | 1 |
| 234 | 1 |
| 235 | 1 |
| 236 | 2 |
| 237 | 3 |
| 238 | 1 |
| 241 | 1 |
| 242 | 2 |

TABLE 21

| | |
|---|---|
| 244 | 1 |
| 245 | 1 |
| 246 | 2 |
| 247 | 1 |
| 248 | 2 |
| 249 | 1 |
| 250 | 1 |
| 254 | 1 |
| 255 | 1 |
| 256 | 1 |
| 257 | 3 |
| 258 | 2 |
| 259 | 1 |
| 260 | 5 |
| 261 | 1 |
| 265 | 3 |
| 266 | 2 |
| 267 | 2 |
| 268 | 1 |
| 269 | 3 |
| 270 | 1 |
| 271 | 1 |
| 272 | 2 |
| 273 | 5 |
| 274 | 1 |
| 277 | 2 |
| 278 | 2 |
| 279 | 5 |
| 281 | ½ |
| 284 | 1 |
| 286 | 2 |
| 287 | 2 |
| 288 | 1 |
| 289 | 1 |
| 290 | 1 |

TABLE 22

| | |
|---|---|
| 291 | 2 |
| 294 | 10 |
| 295 | 1 |
| 296 | 3 |
| 297 | 1 |
| 298 | 5 |
| 299 | 5 |
| 300 | 5 |
| 301 | 1 |
| 302 | 2 |
| 303 | 5 |
| 304 | 3 |
| 305 | 5 |
| 306 | 2 |
| 307 | 1 |
| 308 | 2 |
| 310 | 3 |
| 311 | 1 |
| 312 | 3 |
| 314 | 1 |
| 315 | 1 |

TABLE 22-continued

| | |
|---|---|
| 316 | 1 |
| 317 | 1 |
| 318 | 5 |
| 319 | 3 |
| 322 | 1 |
| 323 | 1 |
| 375 | 2 |
| 385 | 10 |
| 386 | 7 |
| 387 | 1 |
| 397 | 5 |

Test Example 3

Assay for Cell Growth Inhibition Activity in hOT7T175-Expressed Cho Cells hOT7T175-Expressed CHO cells (hereinafter hOT7T175) were cultured in DMEM supplemented with 10% dialyzed FBS (hereinafter 10% dFBS/DMEM), which was used for the following assay. The hOT7T175 was suspended in 10% dFBS/DMEM at 10,000 cells/ml. The cells were plated on a 96 well plate at 100 μL each/well (1,000 cells/well), followed by culturing overnight at 37° C. in a 5% $CO_2$ incubator. On the following day, the medium was removed and 90 μL of 10% dFBS/DMEM supplemented with 0.5% BSA (hereinafter, 0.5% BSA/10% dFBS/DMEM) was added. Subsequently, 10 μL of a solution of metastin or a metastin derivative in 0.5% BSA/10% dFBS/DMEM was added to each well, followed by culturing at 37° C. in a 5% $CO_2$ incubator for 3 days. After 10 μL of Cell Counting Kit-8 solution (Dojin Chemical Laboratory) was added to each well, incubation was performed at 37° C. in a 5% $CO_2$ incubator for 4 hours and absorbance was measured at 450 nm.

The cell inhibition activities of Metastin (1-54), Metastin (45-54) and synthetic compound are shown in Table 23.

TABLE 23

| Compd. No. | $IC_{50}$ (M) |
|---|---|
| 305 | 8.94E−09 |
| 232 | 9.67E−09 |
| 286 | 1.83E−08 |
| 303 | 4.12E−08 |
| 322 | 7.19E−08 |
| 141 | 8.70E−08 |
| 1-54 | 2.12E−07 |
| 45-54 | 8.51E−06 |

* Numerals 1-54 and 45-54 denote Metastin (1-54) and Metastin (45-54), respectively.

Test Example 4

Assay for Chemotaxis Inhibition Activity in hOT7T175-Expressed CHO Cells

Figure 1:
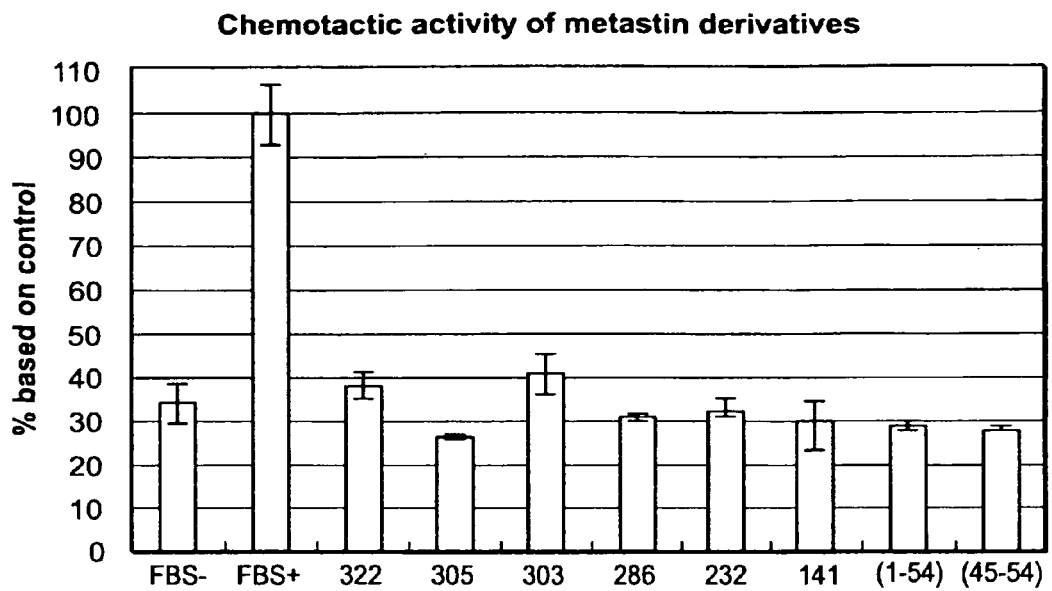
FIG. 1 shows evaluation of the chemotaxis inhibition activity of Compound Nos. 322, 305, 303, 286, 232 and 141 using hOT7T175-expressed CHO cells. On the abscissa, FBS– designates the absence of FBS, FBS+ designates the presence of FBS, 322 designates the addition of Compound No. 322, 305 designates the addition of Compound No. 305, 303 designates the addition of Compound No. 303, 286 designates the addition of Compound No. 286, 232 designates the addition of Compound No. 232, 141 designates the addition of Compound No. 141, (1-54) designates the addition of Metastin (1-54), and (45-54) designates the addition of Metastin 45-54.

The hOT7T175-expressed CHO cells (hereinafter hOT7T175) were cultured in DMEM supplemented with 10% dialyzed FBS (hereinafter 10% dFBS/DMEM), which was provided for assay. Also, a 24-well 6.5 mm Transwell (pore size of 8.0 μm) (COSTAR) was treated with fibronectin by the following method. Specifically, 0.5 ml of 1 μg/ml bovine fibronectin (Yagai Co., Ltd.) was added to the upper and lower chambers of Transwell. After settling the mixture at room temperature for 10 minutes, the fibronectin solution was removed and further air-dried. After washing with DMEM 3 times, hOT7T175 was suspended in DMEM containing 0.5% BSA (hereinafter 0.5% BSA/DMEM) at a density of $2.5 \times 10^6$ cells/ml. Metastin or a metastin derivative was diluted with 0.5% BSA/DMEM. After 600 μL of 0.5% BSA/DMEM supplemented with 20% FBS (or 0.5% BSA/DMEM for negative control) was added to the lower chamber of Transwell, and 50 μL of the cell suspension and 50 μL of the metastin or a metastin derivative dilution (or 0.5% BSA/DMEM for positive control) were added to the upper chamber. After incubation at 37° C. in a 5% $CO_2$ incubator for 7 hours, the culture medium was removed and the upper side of the filter was wiped with a cotton swap wetted with phosphate-buffered saline to remove all cells on the upper side of the filter. The filter was fixed and stained with DifQuick (International Reagents Corporation) and the cells migrated toward the lower side of the filter were counted. The chemotaxis inhibition activity is shown in FIG. 1.

Test Example 5

Evaluation of Tumor Growth Inhibition Activity

The tumor growth inhibition effect of Metastin (1-54) (hereinafter referred to as Metastin) and Compounds (Compound Nos. 305 and 322) in vivo was evaluated using tumor-bearing mice with human colonic carcinoma-derived cell line SW620.

Alza osmotic pump (0.25 μL/hour, 14 days release, Model 1002) filled with 100 μL each of 1 mM Metastin, 0.1 mM and 1 mM Compounds dissolved in distilled water (Otsuka Joryusui K.K.) and distilled water as a vehicle was subcutaneously embedded in the back of BALB/cAnN-nu mice (6 weeks old, female, Charles River Japan, Inc.) under ether anesthesia to initiate continuous administration for 14 days. The number of experiments was n=10 in the Metastin group and the vehicle group and n=11 in the both Compound groups. On the following day, human colonic carcinoma-derived cell line SW620 (ATCC) was dissolved in 20 mM phosphate buffered saline (pH 7.2)(PBS) containing 200 μL of 0.15M NaCl at a density of $2 \times 10^6$ cells. The resulting solution was subcutaneously injected into the left flank of the mice above. The day when the cells were injected was made Day 0. Tumor was measured with an electronic caliper every other or 2 other days during Days 4 to 13 from the cell administration, and tumor size was calculated by the following equation: (shorter diameter)×longer diameter/2. As shown in FIG. 2, the Metastin group (24 nmol/day/mouse×14 days) showed a significant effect of tumor growth inhibition on Day 6, when compared to the vehicle group. On the other hand, the Compound No. 322 group showed a significant tumor growth inhibition activity in a ¹/₁₀ dose (2.4 nmol/day/mouse×14 days) of Metastin from Days 6 to 8. Also, the Compound No. 322 group (24 nmol/day/mouse×14 days) receiving the same dose as that of Metastin showed a significant tumor growth inhibition activity from Days 6 to 11, when compared to the vehicle group and on Day 11, showed a significant tumor growth inhibition activity even when compared with the Metastin group. The foregoing results reveal that Metastin shows the effect of tumor growth inhibition in vivo as well and Compound No. 322 has the effect of tumor growth inhibition by10 times higher than with Metastin.

The results of Compound No. 305 are also shown in FIG. 3. The Metastin group (24 nmol/day/mouse×14 days) showed a significant effect of tumor growth inhibition from Days 5 to 7, when compared to the vehicle group. On the other hand, the Compound No. 305 group (2.4 nmol/day/mouse×14 days) receiving a ¹/₁₀ dose as that of Metastin showed a significant tumor growth inhibition activity from Days 5 to 11, when compared to the vehicle group. Furthermore, the Compound No. 305 group (24 nmol/day/mouse×14 days) receiving the same dose as that of Metastin showed a significant effect of tumor growth inhibition from Days 5 to 9 and on Day 11, when compared to the vehicle group, revealing that Compound No. 305 also shows the in vivo effect of tumor growth inhibition of 10 times higher than with Metastin.

Test Example 6

Hyperglycemic Effect of Metastin

In order to study the effect of Metastin on glucose level by peripheral administration, an operation was performed in free moving animal to collect blood. Mature male Wistar rats (weighing 210-230 g at the time of operation) were anesthetized by intraperitoneal injection of 50 mg/kg pentobarbital. The animal was taped dorsally to the dissection pad and the left jugular vein was exposed. A polyethylene tube SP35 (inner diameter of 0.5 mm, outer diameter of 0.9 mm, Natsume Seisakusho Co., Ltd.) was cut into a length of about 30 cm and filled up with 200 units/ml of heparinated saline. The tube was then inserted into the jugular vein to a depth of about 4.5 cm and fixed. The other end of the tube was subcutaneously inserted into the back to expose at the jugular (back).

After the operation, the animal was maintained overnight. Prior to administration of Metastin, 300 μl of blood was drawn through a 1 ml tuberculin syringe with a 25-gauge needle (both by Terumo Co., Ltd.). To prevent blood clotting, 3 μl of 300 KIU/ml aprotinin solution containing 3 mg/ml EDTA had been previously filled in the syringe. Otsuka saline or 1 mL saline solution of Metastin (17, 80 or 170 nmol) was intravenously injected in a dose of 1 mL/kg through the tube. Blood was collected from the jugular vein by 300 μL each 0, 5, 15, 30 and 60 minutes starting from the intravenous injection. The collected blood was centrifuged (13,000 rpm, 5 minutes) with a high speed refrigerated centrifuge (MR-150, Tomy Seiko Co., Ltd.) to recover the supernatant (plasma). Glucose level in blood was measured using Fuji Drychem 3500 (FUJI FILM). As shown in FIG. 4, the metastin group showed a significant hyperglycemic effect (p<0.005, n=5) in blood dose-dependently (17-170 nmol/kg) from 5 minutes after the intravenous injection, when compared to the control group. In the blood glucose level, a prolonged period of time (30 minutes at maximum) with an increase of the maximum level was noted, as the dose of metastin increased.

Test Example 7

Effect of Promoting Pancreatic Glucagon Secretion by Metastin

In order to study the mechanism of Metastin for the effect of increasing glucose level in blood, effects of metastin on the level of blood glucagon, insulin, corticosterone and thyroid hormone (T3) known as hormones affecting glucose level in blood were examined. An operation was performed in free moving mature Wistar male rats (weighing 260-3000 g at the time of operation) to collect blood. After the operation, the animal was maintained overnight. Prior to administration of Metastin, 300 μl of blood was drawn through a 1 ml tuberculin syringe with a 25-gauge needle (both by Terumo Co., Ltd.). To prevent blood clotting, 3 μl of 300 KIU/ml aprotinin solution containing 3 mg/ml EDTA had been previously filled in the syringe. Otsuka saline or a saline solution of Metastin (80 nmol/mL) was intravenously injected in a dose of 1 mL/kg through the tube. Blood was collected from the jugular vein by 300 μl each 1, 3, 5 and 15 minutes starting from the intravenous injection. The collected blood was centrifuged (13,000 rpm, 5 minutes) with a high speed refrigerated centrifuge (MR-150, Tomy Seiko Co., Ltd.) to recover the supernatant (plasma). Glucagon level in blood was measured using a glucagon kit "Daiichi" (Daiichi Radioisotope Laboratories Ltd.), insulin level in blood using rat insulin [$^{125}$I] assay system (Amersham Biosciences), corticosterone level in blood using rat corticosterone [$^{125}$I] assay system (Amersham Biosciences), thyroid hormone (T3) in blood using T-3.RIA beads (Dinabott Co. Ltd.), and glucose level in blood using Fuji Drychem 3500 (FUJI FILM). As shown in FIG. 5, the Metastin group showed a significant effect of increasing glucagon level in blood 1 minute after the injection, when compared to the control group. The significant effect of increasing glucagon level continued until 5 minutes after the injection. On the other hand, in the blood insulin level (FIG. 6), corticosterone level in blood (FIG. 7) and thyroid hormone (T3) level in blood (FIG. 8), no change was noted by the injection of Metastin. Based on these results and the observed increase in blood glucagon level followed by blood glucose level (FIG. 9), the effect of increasing blood glucose level by intravenous injection of Metastin was considered to be induced by stimulation of glucagon secretion by metastin.

Test Example 8

Hypoglycemic Effect of Metastin Derivatives

The effect of the metastin derivatives KiSS305 (Compound No. 305) and KiSS322 (Compound No. 322) on blood glucose level and blood glucagon level was examined. An operation was performed in free moving mature Wistar male rats (weighing 260-3000 g at the time of operation) in a manner similar to TEST EXAMPLE 1 to collect blood. After the operation, the animal was maintained overnight. Prior to administration of the metastin, 300 μl of blood was drawn through a 1 ml tuberculin syringe with a 25-gauge needle (both by Terumo Co., Ltd.). To prevent blood clotting, 3 μl of 300 KIU/ml aprotinin solution containing 3 mg/ml EDTA had previously been filled in the syringe. Otsuka saline or a saline solution of the metastin (80 nmol/mL) was intravenously injected in a dose of 1 mL/kg through the tube. Blood was collected from the jugular vein by 300 μl each 2, 5, 15, 30, 45 and 60 minutes starting from the intravenous injection. The collected blood was centrifuged (13,000 rpm, 5 minutes) with a high speed refrigerated centrifuge (MR-150, Tomy Seiko Co., Ltd.) to recover the supernatant (plasma). Glucose level in blood was measured using Fuji Drychem 3500 (FUJI FILM) and glucagon level in blood was measured using a glucagon kit "Daiichi" (Daiichi Radioisotope Laboratories Ltd.), as in TEST EXAMPLE 1 or 2. As shown in FIG. 10, both compounds showed an increase in the blood glucose level. Also, both compounds showed an increase in the blood glucagon level, as shown in FIG. 11.

Test Example 9

Induction of Ovulation by Human Metastin in Immature Rats

Equine chorionic gonadotropin (eCG, serotropin, Dainippon Pharmaceutical Co., Ltd.) was dissolved in saline (Otsuka Pharmaceutical Co., Ltd.) in a concentration of 100 IU/mL. Using a 1 mL tuberculin syringe with a 26-gauge needle (both by Terumo Co., Ltd.), eCG was subcutaneously injected into the dorsal area of female Wistar rats of 23 days old after birth (Charles River Japan, Inc.) in a dose of 10 IU/animal, during 9:30 to 10:00 AM. As shown below, the animal was grouped 47 to 48 hours after the eCG injection and the drugs were injected to these groups, respectively.

Group A (5 rats): Human chorionic gonadotropin (hCG, gonadotropin, Dainippon Pharmaceutical Co., Ltd.) was dissolved in saline at 100 IU/mL and the solution was subcutaneously injected into the back in a dose of 20 IU/animal.

Group B (5 rats): Human metastin was dissolved in saline at 100 nmol/mL and the solution was subcutaneously injected into the back in a dose of 20 nmol/animal.

Group C (5 rats): Human metastin was dissolved in saline at 33.3 nmol/mL and the solution was subcutaneously injected into the back in a dose of 6.67 nmol/animal.

Group D (6 rats): Saline was subcutaneously injected into the back in a dose of 200 µL/animal.

After administration of the drugs described above, the animal was sacrificed by decapitation after 24 to 25 hours to recover blood, bilateral oviducts and uterus. In collecting the blood, 90 µL of 10 KIU/mL aprotinin solution (Trasylol, Bayer) containing 3 mg/ml EDTA had been previously filled in a tube for recovery to prevent blood clotting. After blood recovery, the blood was thoroughly blended and the mixture was centrifuged at 2,000 G for 25 minutes. The supernatant was recovered and used as a plasma sample.

The number of oocytes was counted as follows.

Where retained oocytes in the oviducal ampulla were confirmed by stereomicroscopic observation of the oviduct, the ampulla was punctured with a 27-gauge syringe needle (Terumo) to retrieve the oocytes. After granulosa cells surrounding the oocytes were removed by trypsin treatment, the number of oocytes was counted. Where the retained oocytes in the oviducal ampulla were not confirmed by stereomicroscopic observation of the oviduct, a 27-gauge syringe needle with the polished tip was inserted into the tubal ostium and more than 400 µL of saline was flushed into the oviduct and uterine for rinsing. Then, the presence or absence of oocytes in the effluent was observed.

The number of oocytes obtained is shown in TABLE 24.

TABLE 24

|  | Group A | Group B | Group C | Group D |
| --- | --- | --- | --- | --- |
| 1 | 36 | 29 | 29 | 0 |
| 2 | 35 | 56 | 39 | 0 |
| 3 | 40 | 17 | 32 | 0 |
| 4 | 42 | 25 | 22 | 0 |
| 5 | 35 | 32 | 16 | 0 |
| Average number of ova | 37.6 | 31.8 | 27.6 | 0.00 |
| Standard deviation | 3.21 | 14.65 | 8.91 | 0.00 |

In the table, numerals 1 to 5 indicate rat identification number.

In Group A, which is a multipurpose superovulation treatment group, ovulation of 37.6 oocytes in average per rat was confirmed. In Groups B and C receiving the metastin, ovulation of 31.8 and 27.6 oocytes in average, respectively, were confirmed. Turning to Group D receiving saline, the number of oocytes was 0.6 in average, indicating that voluntary ovulation was little observed in the absence of ovulation stimulation.

The level of estradiol contained in the plasma collected from the rats shown in TABLE 22 was determined by radioimmunoassay (DPC-Estradiol Kit; Diagnostic Products Corporation). The results are shown in FIG. 12.

The results reveal that among Groups A, B and C, there is no difference in the level of estradiol contained in plasma, showing that the level of estradiol was extremely high only in Group D receiving saline.

The level of progesterone contained in plasma was determined by radioimmunoassay (DPC.Progesterone; Diagnostic Products Corporation). The results are shown in FIG. 13.

The results reveal that the level of progesterone was highest in Group A and in Groups B and C, the blood level was approximately half that of Group A and that the progesterone level was extremely low in Group D.

In general, the major steroid hormone produced in rat mouse and human ovaries is estrogen in the mature phase of ovarian follicle, whereas the hormone is progesterone after ovulation was induced. It is understood actually from the results in FIG. 12 and FIG. 13 that Group D receiving saline maintained the state where estrogen was highly produced, because of no induction of ovulation; whereas in Group A receiving hCG, production of estrogen increased. In Groups B and C, which are groups receiving the metastin, the plasma estrogen level was very low but the level of progesterone increased, indicating that the metastin induced ovulation in the rat ovary via its normal ovulatory process. It is considered that since the progesterone level in Groups B and C was lower than in Group A, the metastin would have a milder ovarian stimulation, when compared to hCG.

Test Example 10

Gonadotropin-Releasing Effect of Human Metastin in Immature Rats

Human metastin dissolved in saline in a concentration of 33.3 nmol/mL was subcutaneously injected into the dorsal area of female Wistar rats of 25 days old after birth (Charles River Japan, Inc.) in a dose of 200 µL/animal, i.e., 6.67 nmol as human metastin, during 9:00 to 10:00 AM. Prior to the metastin injection and 1, 2 and 4 hours after the injection, the animal was decapitated to recover blood. In recovery of blood, 90 µA of 10 KIU/mL aprotinin solution (Trasylol, Bayer) containing 3 mg/mL EDTA had been previously filled in a centrifuging tube for recovery to prevent blood clotting. After blood recovery, the blood was thoroughly blended and the mixture was centrifuged at 2,000 G for 25 minutes. The supernatant was recovered and used as a plasma sample. The levels of FSH (follicle-stimulating hormone), LH (luteinizing hormone) and progesterone contained in the plasma were determined by radioimmunoassay (Rat Follicle Stimulating Hormone (rFSH) [$^{125}$I] Biotrack Assay System with Magnetic Separation, Rat Luteinizing Hormone (rLH) [$^{125}$I] Biotrack Assay System with Magnetic Separation, both by Amersham Biosciences, and DPC.Progesterone by Diagnostic Products Corporation).

The results obtained by monitoring changes in the FSH level in blood from the immature rat by the metastin injection are shown in FIG. 14. One hour after the metastin injection, the blood FSH level began to significantly increase and reached the maximum after 2 hours. While a decrease in the blood FSH level was noted after 4 hours, the FSH level was still maintained higher than the level prior to the injection.

The results obtained by monitoring changes in the LH level in blood from the immature rat by the metastin injection are shown in FIG. 15. Similarly to the case of FSH, the blood LH level began to significantly increase 1 hour after and reached the maximum after 2 hours. While a decrease in the blood LH level was noted after 4 hours, the LH level was still maintained higher than the level prior to the injection.

The results obtained by monitoring changes in the progesterone level in blood from the immature rat by the metastin injection are shown in FIG. 16. Reflecting the increase of blood LH level, the progesterone level began to increase slowly 1 hour after the metastin injection and showed a significantly higher level than the level prior to the injection 2 hours after.

The results of FIG. 14 and FIG. 15 reveal that peripheral administration of the metastin induces release of gonadotropin such as FSH, LH, etc. The induction of ovulation by the metastin demonstrated in TEST EXAMPLE 9 is considered to be mediated by this gonadotropin release, particularly LH release.

The effect of inducing ovulation demonstrated in TEST EXAMPLE 9 is an action in rats receiving eCG but the effect in this TEST EXAMPLE shows the results obtained using nude rats. No eCG pretreatment is required for the effect of releasing gonadotropin by the metastin.

The results shown in FIG. 16 mean that the release of gonadotropin by the metastin injection imparts physiological stimulation also to the ovary, resulting in increasing the production of progesterone.

Test Example 11

Gonadotropin-Releasing Effect of Human Metastin in Mature Male Rats

Human metastin dissolved in saline in a concentration of 175 nmol/mL was subcutaneously injected into the dorsal area of male Wistar rats of 11 weeks old after birth (Charles River Japan, Inc.) in a dose of 200 μL/animal, i.e., 35 nmol as human metastin, during 10:30 to 11:30 AM. Prior to the metastin injection and 1, 2 and 4 hours after the injection, the animal was decapitated to recover blood. In recovery of blood, 300 μA of 10 KIU/mL aprotinin solution (Trasylol, Bayer) containing 3 mg/mL EDTA had been previously filled in a centrifuging tube for recovery to prevent blood clotting. After blood recovery, the blood was thoroughly blended and the mixture was centrifuged at 2,000 G for 25 minutes. The supernatant was recovered and used as a plasma sample. The levels of FSH (follicle-stimulating hormone), LH (luteinizing hormone) and testosterone contained in the plasma were determined by radioimmunoassay (Rat Follicle Stimulating Hormone (rFSH) [$^{125}$I] Biotrack Assay System with Magnetic Separation, Rat Luteinizing Hormone (rLH) [$^{125}$I] Biotrack Assay System with Magnetic Separation, both by Amersham Biosciences, and DPC.Total Testosterone by Diagnostic Products Corporation).

The results obtained by monitoring changes in the blood FSH level in rats by the metastin injection are shown in FIG. 17. One hour after the metastin injection, the blood FSH level began to significantly increase and reached the maximum after 2 hours, and even after 4 hours, still maintained a higher state.

The results obtained by monitoring changes in the blood LH level in rats by the metastin injection are shown in FIG. 18. Similarly to the case of FSH, the blood LH level began to significantly increase 1 hour after and reached the maximum after 2 hours. While a decrease in the blood LH level was noted after 4 hours, the LH level was still maintained higher than the level prior to the injection.

The results obtained by monitoring changes in the blood testosterone level in rats by the metastin injection are shown in FIG. 19. The testosterone level showed a rapid increase in 1 hour after the metastin injection. While a decrease in the blood testosterone level was noted after 2 and 4 hours, the testosterone level was still maintained at both points of time, which was higher than the level prior to the injection.

The results of FIG. 17 and FIG. 18 reveal that peripheral administration of metastin induces release of gonadotropin such as FSH, LH, etc. in male rats. In view of the results of TEST EXAMPLE 9, the metastin is considered to be an extremely important factor in both female and male rats, in stimulating the release of gonadotropin.

The results shown in FIG. 19 mean that the release of gonadotropin by the metastin injection imparts physiological stimulation also to the testis, resulting in increasing the production of testosterone.

From these results it is considered that administration of metastin would stimulate the testis mediated by release of gonadotropin. This suggests that metastin possibly affects the male reproductive function including seminal maturation, hormone secretion, etc.

Test Example 12

Stability of Compound in Blood

Blood was drawn from Balb/c mice (female) of 8 weeks old, settled at 37° C. for 30 minutes and centrifuged at 13000 rpm for 10 minutes to give the serum as the supernatant. The serum thus obtained was frozen-stored at −80° C.

The stability test was performed by addition of 5 nmol of Compound (5 μL of aqueous solution) to 45 μL of serum and then settlement of the mixture at 37° C. The settlement was made at 3 points of time, including 2, 10 and 30 minutes. The sample after the settlement was boiled for 3 minutes and cooled on an ice bath. After 200 μL of acetonitrile/water (3/1) was added to the sample, the mixture was ultrasonicated for 5 minutes and then centrifuged at 5000 rpm for 1 minute. After 150 μL of the supernatant was diluted with 250 μL of distilled water, insoluble matters were removed by filtration through a filter having a pore size of 0.45 μm and 200 μL of the filtrate was applied on HPLC (220 nm) to determine the peak area of Compound. A ratio of the peak area to the area when Compound was treated for 0 minute under the same conditions was calculated as a mean value in 4 respective runs to determine the residual ratio. Next, by taking the calculated residual ratio on the ordinate and the time on the abscissa, a graph was prepared and approximated by an exponential function. Thus, the time when the residual ratio reached 50% was determined to be a half life.

The preparative HPLC used was the LC-VP series manufactured by Shimadzu Corporation and Wakosil-II 5C18 HG (4.6 mm×100 mm) manufactured by Wako Pure Chemical Industries, Ltd. was used as the column. Eluant A (0.1% TFA-containing water) and eluant B (0.1% TFA-containing acetonitrile) were used as eluants. Analysis was performed by linear density gradient elution (25 minutes) at a flow rate of 1.0 ml/min. using eluants A/B: 100/0-0/50.

The compounds examined in the experiment and the $t_{1/2}$ (min) values are shown in TABLE 25.

TABLE 25

| Compound No. | $t_{1/2}$ (min) |
|---|---|
| 1 | 22.5 |
| 3 | 0.6 |
| 42 | 0.7 |
| 82 | 1.8 |
| 134 | 2.4 |
| 141 | 8.7 |
| 232 | 28.2 |
| 286 | 57.5 |
| 296 | 47.2 |
| 305 | 66.6 |
| 308 | 13.2 |
| 319 | 33.0 |
| 322 | 94.2 |

Test Example 13

Induction of Ovulation in Immature Rat Using Metastin Derivatives

Equine chorionic gonadotropin (eCG, serotropin, Dainippon Pharmaceutical Co., Ltd.) was dissolved in saline (Otsuka Pharmaceutical Co., Ltd.) in a concentration of 100 IU/mL. Using a 1 mL tuberculin syringe with a 26-gauge needle (both by Terumo Co., Ltd.), eCG was subcutaneously injected into the dorsal area of female Wistar rats of 23 days old after birth (Charles River Japan, Inc.) in a dose of 10 IU/animal, during 9:00 to 10:00 AM. As shown below, the animal was grouped 47 to 48 hours after the eCG injection and the drugs were given to these groups, respectively.

Group A (5 rats): Human chorionic gonadotropin (hCG, gonadotropin, Dainippon Pharmaceutical Co., Ltd.) was dissolved in saline at 100 IU/mL and the solution was subcutaneously injected into the back in a dose of 20 IU/animal.

Group B (5 rats): Compound No. 305 was dissolved in saline at 33.3 nmol/mL and the solution was subcutaneously injected into the back in a dose of 6.7 nmol/animal.

Group C (5 rats): Compound No. 305 was dissolved in saline at 10.0 nmol/mL and the solution was subcutaneously injected into the back in a dose of 2.0 nmol/animal.

Group D (5 rats): Compound No. 322 was dissolved in saline at 33.3 nmol/mL and the solution was subcutaneously injected into the back in a dose of 6.7 nmol/animal.

Group E (5 rats): Compound No. 322 was dissolved in saline at 10.0 nmol/mL and the solution was subcutaneously injected into the back in a dose of 2.0 nmol/animal.

Group F (6 rats): Saline was subcutaneously injected into the back in a dose of 200 μL/animal.

After administration of these drugs, the animal was sacrificed by decapitation after 24 to 25 hours to recover blood, bilateral oviducts and uterus. In collecting the blood, 90 μL of 10 KIU/mL aprotinin solution (Trasylol, Bayer) containing 3 mg/ml EDTA had been previously filled in a tube for recovery to prevent blood clotting. After blood recovery, the blood was thoroughly blended and the mixture was centrifuged at 2,000 G for 25 minutes. The supernatant was recovered and used as a plasma sample.

The number of oocytes was counted by referring to the method described in Eur. J. Endocrinol., 138, 594-600 (1998). That is, where retained oocytes in the oviducal ampulla were confirmed by stereomicroscopic observation of the oviduct, the ampulla was punctured with a 27-gauge syringe needle (Terumo) to retrieve the oocytes. After granulosa cells surrounding the oocytes were removed by trypsin treatment, the number of oocytes was counted. Where the retained oocytes in the oviducal ampulla were not confirmed by stereomicroscopic observation of the oviduct, a 27-gauge syringe needle with the polished tip was inserted into the tubal ostium and more than 400 μL of saline was flushed into the oviduct and uterine for rinsing. Then, the presence or absence of oocytes in the effluent was observed.

The number of oocytes thus obtained is shown in FIG. 20. In Group A, which is a multipurpose superovulation treatment group, the number of oocytes was 38.0 in average per rat. In Groups B, C and D, the number of oocytes was 32.6, 29.4 and 29.6 oocytes in average, respectively, indicating that ovulation was substantially equivalent to Group A. Turning to Group E receiving 2.0 nmol of Compound No. 322, 3 out of 5 rats were ovulated and the number of oocytes was 11.6 in average, which was less than Group A. Further in Group A for negative control, no ovulation was observed at all.

The results of FIG. 20 reveal that for induction of ovulation equivalent to hCG, at least 2.0 nmol/animal of Compound No. 305 and at least 6.7 nmol/animal of Compound No. 322 should be administered.

The results obtained by measuring the level of estradiol contained in plasma are shown in FIG. 21. The level of estradiol in blood was measured by radioimmunoassay (DPC.Estradiol Kit, Iatron, Inc.). As shown in FIG. 21, no difference was found among Groups A, B, C and D in terms of estradiol and only Group F showed a higher level. Group E had a tendency to show a higher level in rats with no ovulation induction.

The results obtained by measuring the level of progesterone contained in plasma are shown in FIG. 22. The level of progesterone in blood was measured by radioimmunoassay (DPC.Progesterone, Iatron, Inc.). As shown in FIG. 22, the level of progesterone in blood was the highest in Group A and in Groups B, C and D, the progesterone level showed less than a half of the level in Group A. Groups E and F showed a very low level.

The results of FIG. 21 and FIG. 22 reveal that by administering more than 2.0 nmol/animal of Compound No. 305 and more than 6.7 nmol/animal of Compound No. 322, normal differentiation from estrogen-producing granulosa cells to progesterone-producing luteal cells was induced. Furthermore, when Compound No. 305 or KiSS-322 was administered, the progesterone level was lower than in the hCG administration, suggesting that the stimulating effect of these derivatives on ovary would be milder than that of hCG.

Industrial Applicability

The metastin derivative of the present invention, its salts, or prodrugs thereof have excellent blood stability, in addition to excellent cancer metastasis inhibiting action or cancer growth inhibiting action and are useful as agents for preventing/treating cancers (e.g., lung cancer, gastric cancer, liver cancer, pancreatic cancer, colorectal cancer, rectal cancer, colonic cancer, prostate cancer, ovarian cancer, cervical cancer, breast cancer, etc.). The metastin derivative of the present invention, its salts, or prodrugs thereof have an effect of regulating a function of the pancreas and are useful as drugs for preventing/treating pancreatic diseases (e.g., acute or chronic pancreatitis, pancreatic cancer, etc.). The metastin derivative of the present invention, its salts, or prodrugs thereof have an effect of regulating a function of the regulating a function of the placenta and are useful as drugs for preventing/treating choriocarcinoma, hydatid mole, invasive mole, miscarriage, fetal hypoplasia, abnormal glucose metabolism, abnormal lipid metabolism or labor induction.

The metastin receptor agonist including the metastin derivative of the present invention, its salts, or prodrugs thereof have effects of increasing blood glucose, promoting pancreatic glucagon secretion or promoting urine formation and are useful as drugs for preventing/treating obesity, hyperlipemia, type II diabetes mellitus, hypoglycemia, hypertension, diabetic neuropathy, diabetic nephropathy, diabetic retinopathy, edema, urinary disturbances, insulin resistance, unstable diabetes, fatty atrophy, insulin allergy, insulinoma, arteriosclerosis, thrombotic disorders or lipotoxicity.

In addition, the metastin derivative of the present invention, its salts, or prodrugs thereof have excellent effects of promoting gonadotropic hormone secretion, promoting sex hormone secretion or inducing or promoting ovulation, etc. and are useful as low-toxic and safe drugs, e.g., gonadal function-improving agents, agents for preventing/treating hormone-dependent cancer (e.g., prostate cancer, breast cancer), infertility, endometriosis or myoma of the uterus, ovulation inducers or stimulators, gonadotropic hormone secretagogue agents, sex hormone secretagogue agents, etc.

Moreover, the metastin derivative of the present invention, its salts, or prodrugs thereof are useful as agents for preventing/treating Alzheimer's disease, mild cognitive impairment, etc.

The invention claimed is:

1. A metastin derivative selected from the group consisting of:

(i) D-Tyr-Asn-Pya(4)-Asn-Ser-Phe-AzaGly-Leu-Arg(Me)-Phe-NH$_2$ (Compound No. 286), (ii) D-Tyr-Asn-Trp-Asn-Ser-PheΨ(CSNH)Gly-Leu-Arg(Me)-Phe-NH$_2$ (Compound No. 296), (iii) D-Tyr-D-Pya(4)-Asn-Ser-Phe-AzaGly-Leu-Arg(Me)-Phe-NH$_2$ (Compound No. 305), (iv) D-Tyr-Asn-Trp-Asn-Ser-PheΨ(CH$_2$NH)Gly-Leu-Arg(Me)-Phe-NH$_2$ (Compound No. 308), (v) D-Tyr-Asn-Trp-Asn-Ser-PheΨ(NHCO)Gly-Leu-Arg(Me)-Phe-NH$_2$ (Compound No. 319), and (SEQ ID NO: 203)
(vi) 3-Pyridylpropionyl-Asn-Ser-Phe-AzaGly-Leu-Arg(Me)-Phe-NH$_2$ (Compound No. 322), and a salt thereof.

2. A pharmaceutical comprising the metastin derivative according to claim 1 or a salt thereof.

* * * * *